United States Patent
Bigley et al.

(10) Patent No.: US 12,410,402 B2
(45) Date of Patent: Sep. 9, 2025

(54) METHODS FOR EXPANSION OF NATURAL KILLER (NK) CELL SUBSET AND RELATED COMPOSITIONS AND METHODS

(71) Applicant: Indapta Therapeutics, Inc, Houston, TX (US)

(72) Inventors: Austin Bigley, Houston, TX (US); Ronald Martell, San Francisco, CA (US); Guy Dipierro, Houston, TX (US)

(73) Assignee: INDAPTA THERAPEUTICS, INC., Houston, TX (US)

( * ) Notice: Subject to any disclaimer, the term of this patent is extended or adjusted under 35 U.S.C. 154(b) by 975 days.

(21) Appl. No.: 17/295,849

(22) PCT Filed: Nov. 21, 2019

(86) PCT No.: PCT/US2019/062695
§ 371 (c)(1),
(2) Date: May 20, 2021

(87) PCT Pub. No.: WO2020/107002
PCT Pub. Date: May 28, 2020

(65) Prior Publication Data
US 2022/0008466 A1    Jan. 13, 2022

Related U.S. Application Data

(60) Provisional application No. 62/770,686, filed on Nov. 21, 2018.

(51) Int. Cl.
*A61K 35/17*     (2025.01)
*A61K 40/15*     (2025.01)
*A61K 40/42*     (2025.01)
*C12N 5/0783*    (2010.01)

(52) U.S. Cl.
CPC ............ *C12N 5/0646* (2013.01); *A61K 40/15* (2025.01); *A61K 40/428* (2025.01); *A61K 2239/31* (2023.05); *A61K 2239/38* (2023.05); *A61K 2239/48* (2023.05); *A61K 2239/59* (2023.05); *C12N 2501/2302* (2013.01); *C12N 2501/50* (2013.01); *C12N 2502/11* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,889,818 A | 12/1989 | Gelfand et al. |
| 5,641,870 A | 6/1997 | Rinderknecht et al. |
| 5,716,613 A | 2/1998 | Guber et al. |
| 5,716,826 A | 2/1998 | Gruber et al. |
| 5,851,529 A | 12/1998 | Guber et al. |
| 6,168,991 B1 | 1/2001 | Choi et al. |
| 6,428,968 B1 | 8/2002 | Molnar-Kimber et al. |
| 6,632,670 B1 | 10/2003 | Wadsworth et al. |
| 6,635,472 B1 | 10/2003 | Lauermann |
| 6,653,103 B2 | 11/2003 | Petersen et al. |
| 6,689,871 B1 | 2/2004 | Wolfe et al. |
| 6,723,316 B2 | 4/2004 | Laquerre et al. |
| 6,897,045 B2 | 5/2005 | Engelhardt et al. |
| 7,001,765 B2 | 2/2006 | Maass et al. |
| 7,033,826 B2 | 4/2006 | Perricaudet et al. |
| 7,153,510 B1 | 12/2006 | Rose |
| 7,172,893 B2 | 2/2007 | Rabinowitz et al. |
| 7,238,526 B2 | 7/2007 | Wilson et al. |
| 7,241,447 B1 | 7/2007 | Engelhardt et al. |
| 7,537,924 B2 | 5/2009 | Coffin |
| 7,550,296 B2 | 6/2009 | Hermiston et al. |
| 7,588,767 B2 | 9/2009 | Szalay et al. |
| 7,588,771 B2 | 9/2009 | Szalay et al. |
| 7,662,398 B2 | 2/2010 | Szalay et al. |
| 7,662,627 B2 | 2/2010 | Johnson et al. |
| 7,731,952 B2 | 6/2010 | Mohr et al. |
| 7,731,974 B2 | 6/2010 | Bell et al. |
| 7,754,221 B2 | 7/2010 | Szalay et al. |
| 7,811,814 B2 | 10/2010 | Bohn et al. |
| 7,897,146 B2 | 3/2011 | Brown et al. |

(Continued)

FOREIGN PATENT DOCUMENTS

| | | |
|---|---|---|
| EP | 1385466 | 2/2004 |
| EP | 1520175 | 4/2005 |

(Continued)

OTHER PUBLICATIONS

Bigley et al., "Latent cytomegalovirus infection enhances antitumour cytotoxicity through accumulation of NKG2C+ NK cells in healthy humans," Clin Exp Immunol. (2016) 185(2): 239-51. (Year: 2016).*

Fujisaki, Hiroyuki et al. Expansion of highly cytotoxic human natural killer cells for cancer cell therapy. Cancer Res 2009; 69: (9). pp. 4010-4017. (Year: 2009).*

Allen et al., "Retargeted oncolytic measles strains entering via the EGFRvIII receptor maintain significant antitumor activity against gliomas with increased tumor specificity," Cancer Res. (2006) 66(24): 11840-50.

Amersdorfer et al., "Molecular characterization of murine humoral immune response to botulinum neurotoxin type A binding domain as assessed by using phage antibody libraries," Infect Immun. (1997) 65(9): 3743-52.

(Continued)

Primary Examiner — Nghi V Nguyen
(74) Attorney, Agent, or Firm — MORRISON & FOERSTER LLP

(57) ABSTRACT

Provided herein are methods for ex vivo expansion of a specialized subset of natural killer (NK) cells, and compositions containing such NK cells. Also provided are methods for identifying or detecting a specialized subset of NK cells. Also provided are methods for treating diseases and conditions such as cancer using provided compositions, including in combination with an antibody capable of binding to disease-associated tissues or cells, such as tumor cells or infected cells.

40 Claims, 38 Drawing Sheets

Specification includes a Sequence Listing.

(56) References Cited

U.S. PATENT DOCUMENTS

| | | |
|---|---|---|
| 7,906,111 B2 | 3/2011 | Wilson et al. |
| 7,927,585 B2 | 4/2011 | Snyder |
| 7,943,374 B2 | 5/2011 | Hildinger |
| 7,968,340 B2 | 6/2011 | Hallek et al. |
| 8,007,780 B2 | 8/2011 | Arbetman |
| 10,066,207 B2 | 9/2018 | Kim et al. |
| 11,471,486 B2 * | 10/2022 | Malmberg ............ C12N 5/0646 |
| 2004/0009604 A1 | 1/2004 | Zhang et al. |
| 2004/0063094 A1 | 4/2004 | Coffin et al. |
| 2005/0220818 A1 | 10/2005 | Lorence |
| 2005/0260601 A1 | 11/2005 | Whitt |
| 2006/0039894 A1 | 2/2006 | Mohr et al. |
| 2006/0292156 A1 | 12/2006 | Campbell |
| 2007/0098743 A1 | 5/2007 | Bell et al. |
| 2007/0110720 A1 | 5/2007 | Brown et al. |
| 2007/0202572 A1 | 8/2007 | Szalay et al. |
| 2007/0212727 A1 | 9/2007 | Szalay et al. |
| 2009/0010889 A1 | 1/2009 | Brown et al. |
| 2009/0053244 A1 | 2/2009 | Chen et al. |
| 2009/0098529 A1 | 4/2009 | Chen et al. |
| 2009/0117034 A1 | 5/2009 | Chen et al. |
| 2009/0136917 A1 | 5/2009 | Szalay et al. |
| 2009/0155287 A1 | 6/2009 | Chen et al. |
| 2009/0162288 A1 | 6/2009 | Chen et al. |
| 2009/0215147 A1 | 8/2009 | Zhang et al. |
| 2009/0274728 A1 | 11/2009 | Brown et al. |
| 2009/0285860 A1 | 11/2009 | Martuza et al. |
| 2010/0062016 A1 | 3/2010 | Szalay et al. |
| 2010/0092515 A1 | 4/2010 | Conner et al. |
| 2010/0113567 A1 | 5/2010 | Barber |
| 2010/0172877 A1 | 7/2010 | Van Den Pol |
| 2010/0178684 A1 | 7/2010 | Woo et al. |
| 2010/0196325 A1 | 8/2010 | Szalay et al. |
| 2010/0233078 A1 | 9/2010 | Szalay et al. |
| 2011/0064650 A1 | 3/2011 | Szalay |
| 2011/0158948 A1 | 6/2011 | Brown et al. |
| 2011/0177032 A1 | 7/2011 | Martuza et al. |
| 2011/0212530 A1 | 9/2011 | Baltimore et al. |
| 2013/0295044 A1 | 11/2013 | Kim et al. |
| 2014/0154216 A1 | 6/2014 | Coffin |
| 2016/0339066 A1 | 11/2016 | Szalay et al. |
| 2017/0137784 A1 | 5/2017 | Masuyama |
| 2018/0057795 A1 * | 3/2018 | Childs ................ C12N 15/867 |
| 2019/0376036 A1 | 12/2019 | DiPierro |

FOREIGN PATENT DOCUMENTS

| | | |
|---|---|---|
| EP | 1606411 | 12/2005 |
| EP | 3539553 | 9/2019 |
| JP | 2002504357 A | 2/2002 |
| JP | 2010524500 A | 7/2010 |
| JP | 2011-529341 | 12/2011 |
| JP | 2012521215 A | 9/2012 |
| JP | 2019170176 A | 10/2019 |
| WO | WO 1999/038955 | 8/1999 |
| WO | WO 1999/043208 A1 | 9/1999 |
| WO | WO 2007/052029 | 5/2007 |
| WO | WO 2009/041113 A1 | 4/2009 |
| WO | WO 2010/110734 | 9/2010 |
| WO | WO 2012/061814 | 5/2012 |
| WO | WO 2014/145252 A2 | 9/2014 |
| WO | WO 2014/189628 A1 | 11/2014 |
| WO | WO 2016/011210 A2 | 1/2016 |
| WO | WO 2016/077734 A2 | 5/2016 |
| WO | WO 2016/151741 A1 | 9/2016 |
| WO | WO 2016/201300 A1 | 12/2016 |
| WO | WO 2017/001572 A1 | 1/2017 |
| WO | WO 2017/017184 A1 | 2/2017 |
| WO | WO 2017/048809 A1 | 3/2017 |
| WO | WO 2017/078807 A1 | 5/2017 |
| WO | WO 2017/079673 A1 | 5/2017 |
| WO | WO 2017/127729 A1 | 7/2017 |
| WO | WO 2017/127755 A1 | 7/2017 |
| WO | WO 2018/148462 | 8/2018 |
| WO | WO 2019/222293 | 11/2019 |
| WO | WO 2020/107002 | 5/2020 |

OTHER PUBLICATIONS

Bae et al., "Extracellular matrix for a rechargeable cell delivery system," J Control Release. (1998) 53(1-3): 249-58.
Benecia et al., "HSV oncolytic therapy upregulates interferon-inducible chemokines and recruits immune effector cells in ovarian cancer," Mol Ther. (2005) 12(5): 789-802.
Bhat et al., "Enhancement of NK cell antitumor responses using an oncolytic parvovirus," Int J Cancer. (2011) 128(4): 908-19.
Bhat et al., "NK-cell-dependent killing of colon carcinoma cells is mediated by natural cytotoxicity receptors (NCRs) and stimulated by parvovirus infection of target cells," BMC Cancer. (2013) 13:367.
Bigley et al., "Acute exercise preferentially redeploys NK-cells with a highly-differentiated phenotype and augments cytotoxicity against lymphoma and multiple myeloma target cells," Brain Behav Immun. (2014) 39:160-71.
Bigley et al., "NK cell function is impaired during long-duration spaceflight," J Appl Physiol. (2018) 126:842-853.
Bigley et al., "Latent cytomegalovirus infection enhances anti-tumour cytotoxicity through accumulation of NKG2C+ NK cells in healthy humans," Clin Exp Immunol. (2016) 185(2): 239-51.
Bigley et al., "Cytomegalovirus: an unlikely ally in the fight against blood cancers?," Clin Exp Immunol. (2018) 193(3): 265-274.
Boerner et al., "Production of Antigen-Specific Human Monoclonal Antibodies From in Vitro-Primed Human Splenocytes," J Immunol (1991) 147 (1), 86-95 (Abstract only).
Bottino et al., "NK cell activating receptors and tumor recognition in humans," Curr Top Microbiol Immunol. (2006) 298: 175-182.
Bouhadir et al., "Degradation of partially oxidized alginate and its potential application for tissue engineering," Biotechnol Prog. (2001) 17(5): 945-50.
Bryant et al., "The effects of scaffold thickness on tissue engineered cartilage in photocrosslinked poly(ethylene oxide) hydrogels," Biomaterials. (2001) 22(6): 619-26.
Bryceson et al., "Line of attack: NK cell specificity and integration of signals," Curr Opin Immunol. (2008) 20(3): 344-352.
Caligiuri et al., "Human natural killer cells," Blood. Aug. 1, 2008;112(3):461-469.
Capuano et al., "Tumor-Targeting Anti-CD20 Antibodies Mediate In Vitro Expansion of Memory Natural Killer Cells: Impact of CD16 Affinity Ligation Conditions and In Vivo Priming," Front Immunol. (2018) 9:1031.
Cartron et al., "Therapeutic activity of humanized anti-CD20 monoclonal antibody and polymorphism in IgG Fc receptor FcgammaRIIa gene," Blood. (2002) 99(3): 754-758.
Chen et al., "Antibody mapping to domains of botulinum neurotoxin serotype A in the complexed and uncomplexed forms," Infect Immun. (1997) 65(5):1626-30.
Chomczynski et al., "Single-step method of RNA isolation by acid guanidinium thiocyanate-phenol-chloroform extraction," Anal Biochem. (1987) 162(1):156-159.
Cooley et al., "First-in-human trial of rhIL-15 and haploidentical natural killer cell therapy for advanced acute myeloid leukemia," Blood Adv. (2019) 3(13):1970-1980.
Dempe et al., "Antitumoral activity of parvovirus-mediated IL-2 and MCP-3/CCL7 delivery into human pancreatic cancer: implication of leucocyte recruitment," Cancer Immunol Immunother. (2012) 61(11): 2113-23.
Finnern et al., "Human autoimmune anti-proteinase 3 scFv from a phage display library," Clin Exp Immunol. (1997) 107(2): 269-81.
Fishwild et al., "High-avidity human IgGK monoclonal antibodies from a novel strain of minilocus transgenic mice," Nature Biotechnology (1996) 14:845-851.
Foley et al., "Cytomegalovirus reactivation after allogeneic transplantation promotes a lasting increase in educated NKG2C+ natural killer cells with potent function," Blood. (2012) 119(11): 2665-2674.

(56) References Cited

OTHER PUBLICATIONS

Fujisaki et al., "Expansion of highly cytotoxic human natural killer cells for cancer cell therapy," Cancer Res. (2009) 69(9): 4010-4017.
Gappa et al., "The effect of zinc-crystallized glucagon-like peptide-1 on insulin secretion of macroencapsulated pancreatic islets," Tissue Eng. (2001) 7(1): 35-44.
Garcia et al., "Human T cell receptor-mediated recognition of HLA-E," Eur J Immunol. (2002) 32(4): 936-44.
Garcia-Aragoncillo et al., "Design of virotherapy for effective tumor treatment," Curr Opin Mol Ther. (2010) 12(4): 403-11.
Gujar et al., "Oncolytic virus-initiated protective immunity against prostate cancer," Mol Ther. (2011) 19(4): 797-804.
Hallden et al., "Oncolytic virotherapy with modified adenoviruses and novel therapeutic targets," Expert Opin Ther Targets. (2012) 16(10): 945-58.
Hatjiharissi et al., "Increased natural killer cell expression of CD16, augmented binding and ADCC activity to rituximab among individuals expressing the Fc{gamma}RIIIa-158 V/V and V/F polymorphism," Blood. (2007) 110(7): 2561-2564.
Heiber et al., "Vesicular stomatitis virus expressing tumor suppressor p53 is a highly attenuated, potent oncolytic agent," J Virol. (2011) 85(20):10440-50.
Hoogenboom et al., "Multi-subunit proteins on the surface of filamentous phage: methodologies for displaying antibody (Fab) heavy and light chains," Nucleic Acids Res. (1991) 19(15):4133-4137.
Hwang et al., "Identification of human NK cells that are deficient for signaling adaptor FcRγ and specialized for antibody-dependent immune functions," Int Immunol. (2012) 24(12): 793-802.
Jarahian et al., "Activation of natural killer cells by newcastle disease virus hemagglutinin-neuraminidase," J Virol. (2009) 83(16): 8108-21.
Jeong et al., "Thermogelling biodegradable copolymer aqueous solutions for injectable protein delivery and tissue engineering," Biomacromolecules. (2002) 3(4):865-8.
Jones et al., "Replacing the complementarity-determining regions in a human antibody with those from a mouse," Nature (1986) 321(6069):522-525.
Kim et al., "FCGR3A gene polymorphisms may correlate with response to frontline R-CHOP therapy for diffuse large B-cell lymphoma," Blood. (2006) 108(8) :2720-2725.
Kim et al., "Targeted and armed oncolytic poxviruses: a novel multi-mechanistic therapeutic class for cancer," Nat Rev Cancer. (2009) 9(1): 64-71.
Koene et al., "FcγRIIIa-158V/F Polymorphism Influences the Binding of IgG by Natural Killer Cell FcγRIIIa, Independently of the FcγRIIIa-48L/R/H Phenotype," Blood. (1997) 90(3): 1109-1114.
Lahiji et al., "Chitosan supports the expression of extracellular matrix proteins in human osteoblasts and chondrocytes," J Biomed Mater Res. (2000) 51(4): 586-95.
Lanier, "Up on the tightrope: natural killer cell activation and inhibition," Nat Immunol. (2008) 9(5): 495-502.
Lee et al., "Preparation of poly(vinyl alcohol)-chondroitin sulfate hydrogel as matrices in tissue engineering," Carbohydrate Polymers. (2005) 61: 348.
Lee et al., "The effects of cross-linking of collagen-glycosaminoglycan scaffolds on compressive stiffness, chondrocyte-mediated contraction, proliferation and biosynthesis," Biomaterials. (2001) 22(23): 3145-3154.
Lee et al., "HLA-E surface expression depends on binding of TAP-dependent peptides derived from certain HLA class I signal sequences," J Immunol. (1998) 160(10): 4951-60.
Lonberg et al., "Human antibodies from transgenic mice," Int Rev Immunol. (1995) 13(1): 65-93.
Lonberg et al., "Antigen-specific human antibodies from mice comprising four distinct genetic modifications," Nature (1994) 368(6474):856-859.
Mann et al., "Smooth muscle cell growth in photopolymerized hydrogels with cell adhesive and proteolytically degradable domains: synthetic ECM analogs for tissue engineering," Biomaterials. (2001) 22(22): 3045-51.
Marks et al., "Molecular evolution of proteins on filamentous phage. Mimicking the strategy of the immune system," J Biol Chem. (1992) 267(23): 16007-16010.
Marks et al., "By-passing immunization. Human antibodies from V-gene libraries displayed on phage," J Mol Bio (1991) 222(3):581-597.
McLoughlin et al., "TNFerade, an adenovector carrying the transgene for human tumor necrosis factor alpha, for patients with advanced solid tumors: surgical experience and long-term follow-up," Ann Surg Oncol. (2005) 12(10):825-30.
Mellor et al., "A critical review of the role of Fc gamma receptor polymorphisms in the response to monoclonal antibodies in cancer," J Hematol Oncol. (2013) 6: 1.
Miller et al., "Requirement of an integrated immune response for successful neuroattenuated HSV-1 therapy in an intracranial metastatic melanoma model," Mol Ther. (2003) 7(6):741-7.
Miyamoto et al., "Coxsackievirus B3 is an oncolytic virus with immunostimulatory properties that is active against lung adenocarcinoma," Cancer Res. (2012) 72(10): 2609-21.
Musolino et al., "Immunoglobulin G fragment C receptor polymorphisms and clinical efficacy of trastuzumab-based therapy in patients with HER-2/neu-positive metastatic breast cancer," J Clin Oncol. (2008) 26(11): 1789-1796.
Ogbomo et al., "Tumor cells infected with oncolytic influenza A virus prime natural killer cells for lysis of resistant tumor cells," Med Microbiol Immunol. (2010) 199(2): 93-101.
Ravetch et al. "IgG Fc Receptors," Annu. Rev. Immunol. (2001) 19: 275-290.
Reisfeld and Sell, "Monoclonal antibodies and cancer therapy" (1985) Conference https://www.osti.gov/biblio/6081141.
Reichmann et al. "Reshaping human antibodies for therapy," Nature (1988) 3 32(6162):323-327.
Rintoul et al., "ORFV: a novel oncolytic and immune stimulating parapoxvirus therapeutic," Mol Ther. (2012) 20(6): 1148-57.
Roda et al., "Natural killer cells produce T cell-recruiting chemokines in response to antibody-coated tumor cells," Cancer Res. (2006) 66(1): 517-526.
Saiki et al., "Analysis of enzymatically amplified beta-globin and HLA-DQ alpha DNA with allele-specific oligonucleotide probes," Nature. (1986) 324(6093):163-6.
Schlums et al., "Cytomegalovirus infection drives adaptive epigenetic diversification of NK cells with altered signaling and effector function," Immunity. (2015) 42(3): 443-456.
Shah et al., "Antigen presenting cell-mediated expansion of human umbilical cord blood yields log-scale expansion of natural killer cells with anti-myeloma activity," PLoS One. (2013) 8(10):e76781.
Smidsrød et al., "Alginate as immobilization matrix for cells," Trends Biotechnol. (1990) 8(3): 71-78.
Somboonyosdech et al., "Correlation of FcγRIIIa polymorphisms and responses to rituximab in Thai population," Asian Biomedicine (2012) 6(6):883-889.
Stewart et al., "Strategies of natural killer cell recognition and signaling," Curr Top Microbiol Immunol. (2006) 298: 1-21.
Suggs et al., "Development of poly(propylene fumarate-co-ethylene glycol) as an injectable carrier for endothelial cells," Cell Transplant. (1999) 8(4):345-50.
Suh et al., "Application of chitosan-based polysaccharide biomaterials in cartilage tissue engineering: a review," Biomaterials. (2000) 21(24): 2589-98.
Tai et al., "Attacking Postoperative Metastases using Perioperative Oncolytic Viruses and Viral Vaccines," Front Oncol. (2014) 4: 217.
Tate et al., "Biocompatibility of methylcellulose-based constructs designed for intracerebral gelation following experimental traumatic brain injury," Biomaterials. (2001) 22(10): 1113-23.
Tomasec et al., "Surface expression of HLA-E, an inhibitor of natural killer cells, enhanced by human cytomegalovirus gpUL40," Science. (2000) 287(5455): 1031.
Verhoyen et al., "Reshaping human antibodies: grafting an antilysozyme activity," Science (1998) 239(4847):1534-1536.

(56) References Cited

OTHER PUBLICATIONS

Vivier et al., "Innate or adaptive immunity? The example of natural killer cells," Science. (2011) 331(6013): 44-49.
White et al., "Characterization of the adaptive and innate immune response to intravenous oncolytic reovirus (Dearing type 3) during a phase I clinical trial," Gene Ther. (2008) 15(12): 911-20.
Zapata et al., "Engineering Linear F(ab')2 Fragments For Efficient Production In *Escherichia coli* And Enhanced Antiproliferative Activity," Protein Engineering (1995) 8(10): 1057-1062.
Zhang et al., "Antibody-dependent memory-like NK cells distinguished by FcRγ-deficiency," J Immunol. (2013) 190(4): 1402-1406.
Zhao et al., "A novel oncolytic herpes simplex virus type 2 has potent anti-tumor activity," PLoS One. (2014) 9(3): e93103.
Liu et al., "FcRγ Gene Editing Reprograms Conventional NK Cells to Display Key Features of Adaptive Human NK Cells," iScience (2020) 23, 101709, pp. 1-20.
Fishwild et al., "Human lgG kappa antigen-specific high affinity monoclonal antibodies from transgenic mice," Faseb Journal. (vol. 12. No. 4. pp A309) 9650 Rockville Pike, Bethesda, MD 20814-3998 USA: Federation Amer Soc Exp Biol, 1998.
Fishwild et al., "Human lgG kappa antigen-specific high affinity monoclonal antibodies from transgenic mice." Journal of Allergy and Clinical Immunology. vol. 99. No. 1. pp S186, Abs 753. 11830 Westline Industrial Dr, St Louis, MO 63146-3318: Mosby-Year Book Inc, 1997.
Fishwild et al. "High avidity human lgG monoclonal antibodies from novel strains of minilocus transgenic mice." Antibody Engineering II. New Technology, Application & Commercialization (W. Hori, Ed.) (1997): 187-211.
Presta, "Antibody engineering," Curr Opin Biotechnol. (1992) 3(4):394-8.
Zhongguo et al. "Construction of pcDNA3.1(+)/A2E eukaryotic expression vector and its expression on K562 cell," (2005) 13:464-467. (Article in Chinese), English Abstract only.
Lee et al., "Epigenetic Modification and Antibody-Dependent Expansion of Memory-like NK Cells in Human Cytomegalovirus-Infected Individuals," Immunity (2015) 42:431-442.
Zhang et al., "Cutting Edge: Antibody-Dependent Memory-like NK Cells Distinguished by FcRγ Deficiency," J. Immunol. (2013) 190(4):1402-1406.
Beziat et al., "CMV drives clonal expansion of NKG2C1NK cells expressing self-specific KIRs in chronic hepatitis patients," Eur. J. Immunol. (2012) 42: 447-457.
Binyamin et al., "Blocking NK cell inhibitory self-recognition promotes antibody-dependent cellular cytotoxicity in a model of anti-lymphoma therapy," J Immunol. (2008) 180(9): 6392-401.
Brandt et al., "The B7 family member B7-H6 is a tumor cell ligand for the activating natural killer cell receptor NKp30 in humans," Journal of Experimental Medicine (2009) 206(7): 1495-1503 (2009).
Childs et al., "Bringing Natural Killer Cells to the Clinic: Ex Vivo Manipulation," American Society of Hematology (2013) 2013:234-246.
Cichocki et al., "CD56dimCD57+NKG2C+ NK cell expansion is associated with reduced leukemia relapse after reduced intensity HCT," Leukemia. (2016) 30(2):456-463, 18 pages.
Cichocki et al., "GSK 3 inhibition drives maturation of NK cells and enhances their antitumor activity," Cancer Res. (2017) 77(20): 5664-5675.
Cichocki et al., "The Past, Present, and Future of NK Cells in Hematopoietic Cell Transplantation and Adoptive Transfer," Curr Top Microbiol Immunol. (2016) 395: 225-243, 19 pages.
Costa-Garcia et al., "Antibody-Mediated Response of NKG2Cbright NK Cells against Human Cytomegalovirus," J Immunol (2015) 194(6): 2715-2724.
Dubois et al., "Preassociation of IL-15 with IL-15R alpha-IgG1-Fc enhances its activity on proliferation of NK and CD8+/CD44high T cells and its antitumor action," J Immunol. (2008) 180(4): 2099-106.
Fiegler et al. "Downregulation of the activating NKp30 ligand B7-H6 by HDAC inhibitors impairs tumor cell recognition by NK cells." Blood, The Journal of the American Society of Hematology (2013) 122.5: 684-693.
Kim et al., "HLA alleles determine differences in human natural killer cell responsiveness and potency," PNAS (2008) 105(8): 3053-3058.
Kucuksezer et al., (2021). "The role of natural killer cells in autoimmune diseases." Frontiers in immunology 12:622306, 23 pages.
Lee et al., "Site-specific integration in CHO cells mediated by CRISPR/Cas9 and homology-directed DNA repair path," Sci. Rep, (2015) 5:8572, 11 pages.
Li et al., "Optimization of genome engineering approaches with the CRISPR/Cas9 system," PLoS One (2004) 9:e105779, 10 pages.
Lopez-Verges et al., "Expansion of a unique CD57+NKG2Chi natural killer cell subset during acute human cytomegalovirus infection," PNAS (2011) 108(36): 14725-14732.
Qian et al. "Advancements in the Study of the Immune Molecule NKp46 in Immune System-related Diseases." Clinical reviews in allergy & immunology (2024) 67: 96-110.
Romee et al. "NK cell CD16 surface expression and function is regulated by a disintegrin and metalloprotease-17 (ADAM 17)." Blood (2013) 121(18): 3599-608.
Sivori et al., "NKp46 is the major triggering receptor involved in the natural cytotoxicity of fresh or cultured human NK cells. Correlation between surface density of NKp46 and natural cytotoxicity against autologous, allogeneic or xenogeneic target cells," Eur J Immunol (1999) 29(5):1656-1666.
Takai et al. "FcR gamma chain deletion results in pleiotrophic effector cell defects." Cell. (1994) 76(3):519-29, 12 pages.

* cited by examiner

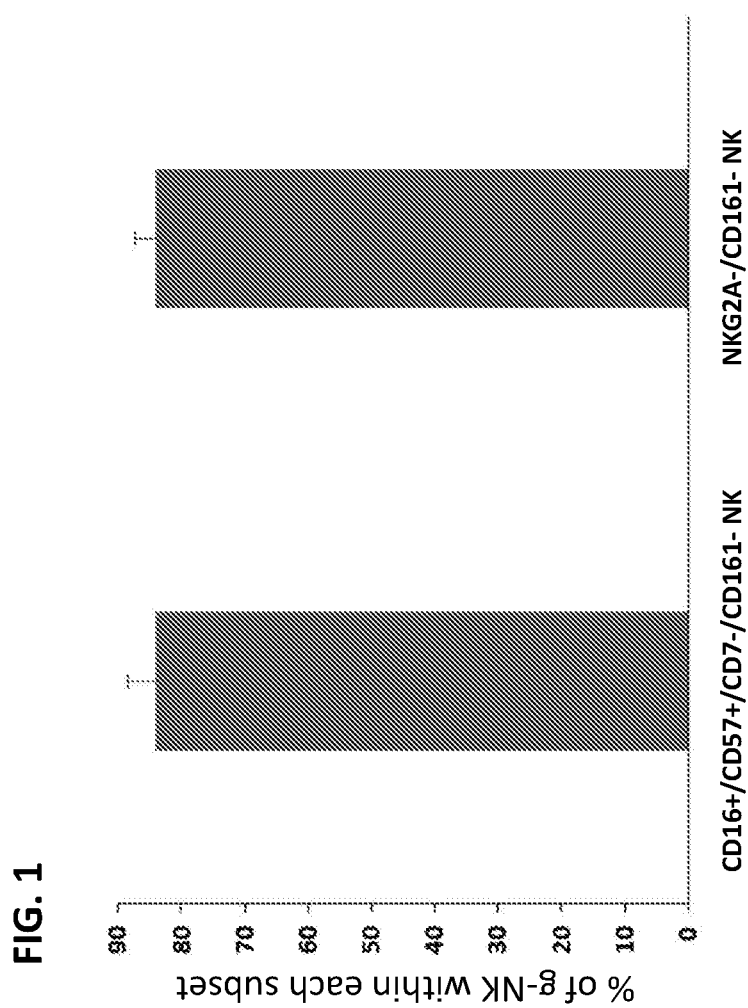

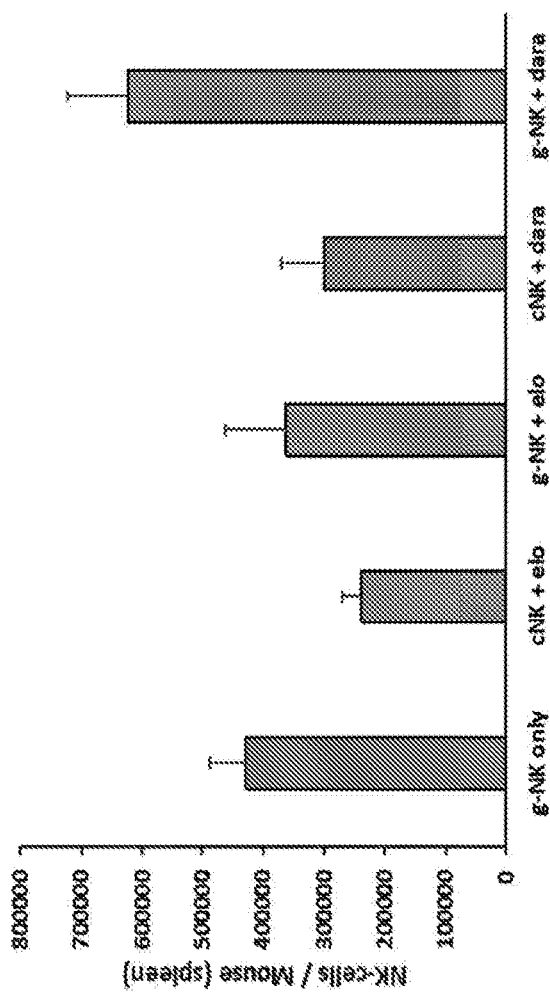
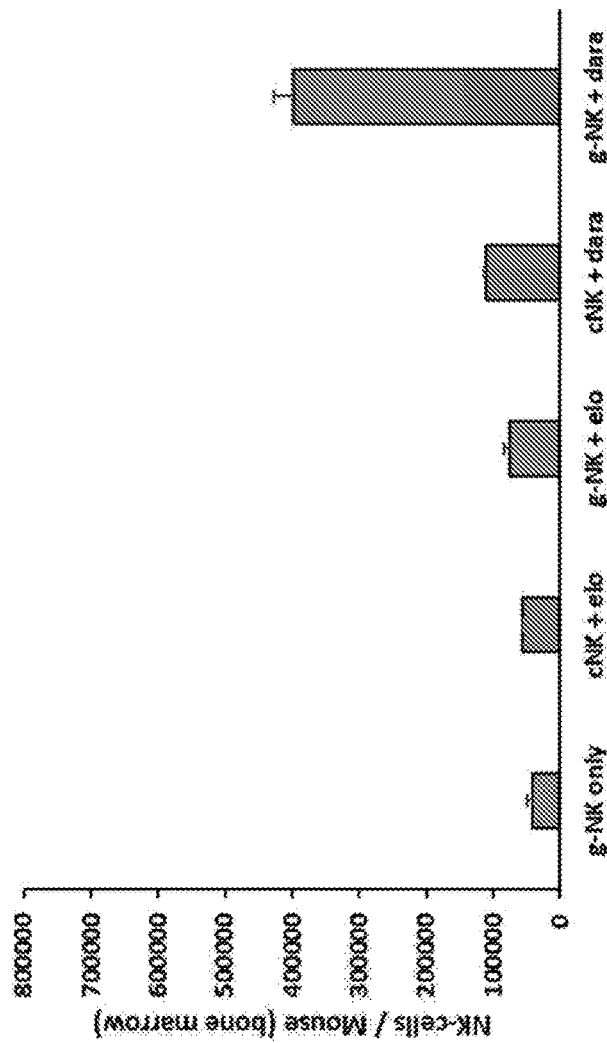
FIG. 12A
FIG. 12B

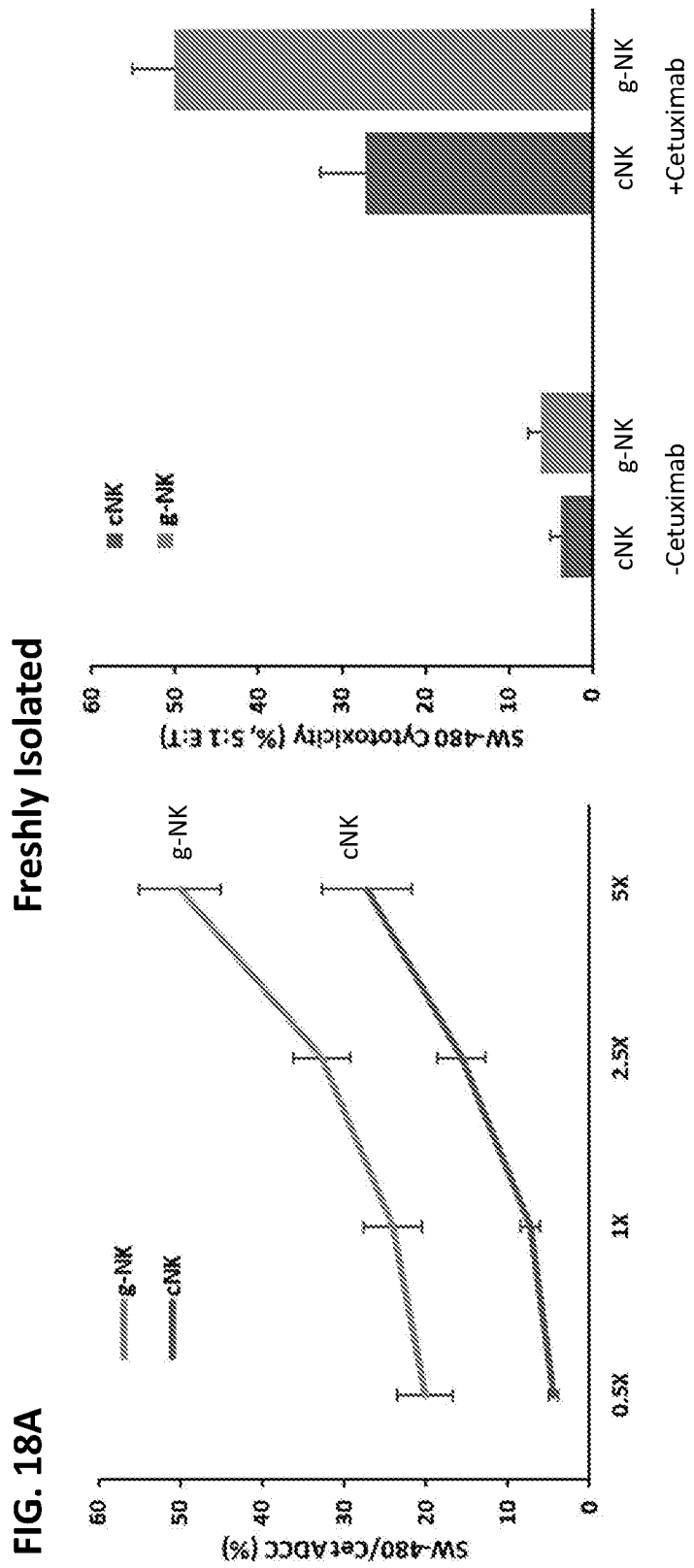

SEQUENCE LISTING

<160> NUMBER OF SEQ ID NOS: 18

<210> SEQ ID NO 1
<211> LENGTH: 86
<212> TYPE: PRT
<213> ORGANISM: Homo sapiens

```
<220> FEATURE:
<223> OTHER INFORMATION: High affinity immunoglobulin gamma Fc receptor
      I

<400> SEQUENCE: 1

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
                35                  40                  45

Gln Val Arg Lys Ala Ala Ile Thr Ser Tyr Glu Lys Ser Asp Gly Val
50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
atatttacag aatggcacag g                                              21

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
gacttggtac ccaggttgaa                                                20

<210> SEQ ID NO 4
<211> LENGTH: 32
<212> TYPE: DNA
<213> ORGANISM: Artificial Sequence
<220> FEATURE:
<223> OTHER INFORMATION: PCR primer

<400> SEQUENCE: 4
atcagattcg atcctacttc tgcagggggc at                                  32

<210> SEQ ID NO 5
<211> LENGTH: 32
<212> TYPE: DNA
<213> ORGANISM: Artificial Sequence
<220> FEATURE:
<223> OTHER INFORMATION: PCR primer

<400> SEQUENCE: 5
acgtgctgag cttgagtgat ggtgatgttc ac                                  32

<210> SEQ ID NO 6
<211> LENGTH: 24
<212> TYPE: DNA
<213> ORGANISM: Artificial Sequence
<220> FEATURE:
<223> OTHER INFORMATION: PCR primer
```

```
<400> SEQUENCE: 6
cccaactcaa cttcccagtg tgat                                              24

<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
gaaatctacc ttttcctcta atagggcaat                                        30

<210> SEQ ID NO 8
<211> LENGTH: 29
<212> TYPE: DNA
<213> ORGANISM: Artificial Sequence
<220> FEATURE:
<223> OTHER INFORMATION: PCR primer

<400> SEQUENCE: 8
gaaatctacc ttttcctcta atagggcaa                                         29

<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
gaaatctacc ttttcctcta atagggca                                          28

<210> SEQ ID NO 10
<211> LENGTH: 21
<212> TYPE: DNA
<213> ORGANISM: Artificial Sequence
<220> FEATURE:
<223> OTHER INFORMATION: CD16 sense primer

<400> SEQUENCE: 10
ccaaaagcca cactcaaaga c                                                 21

<210> SEQ ID NO 11
<211> LENGTH: 21
<212> TYPE: DNA
<213> ORGANISM: Artificial Sequence
<220> FEATURE:
<223> OTHER INFORMATION: CD16 antisense primer

<400> SEQUENCE: 11
acccaggtgg aaagaatgat g                                                 21

<210> SEQ ID NO 12
<211> LENGTH: 25
<212> TYPE: DNA
<213> ORGANISM: Artificial Sequence
<220> FEATURE:
<223> OTHER INFORMATION: TaqMan probe

<400> SEQUENCE: 12
aacatcacca tcactcaagg tttgg                                             25

<210> SEQ ID NO 13
```

```
<211> LENGTH: 25
<212> TYPE: DNA
<213> ORGANISM: Artificial Sequence
<220> FEATURE:
<223> OTHER INFORMATION: V allele forward primer

<400> SEQUENCE: 13
ctgaagacac attttactc ccaaa                                              25

<210> SEQ ID NO 14
<211> LENGTH: 22
<212> TYPE: DNA
<213> ORGANISM: Artificial Sequence
<220> FEATURE:
<223> OTHER INFORMATION: V allele reverse primer

<400> SEQUENCE: 14
tccaaaagcc acactcaaag ac                                                22

<210> SEQ ID NO 15
<211> LENGTH: 25
<212> TYPE: DNA
<213> ORGANISM: Artificial Sequence
<220> FEATURE:
<223> OTHER INFORMATION: F allele forward primer

<400> SEQUENCE: 15
ctgaagacac attttactc ccaac                                              25

<210> SEQ ID NO 16
<211> LENGTH: 238
<212> TYPE: PRT
<213> ORGANISM: Homo sapiens
<220> FEATURE:
<223> OTHER INFORMATION: CD16 (F158)

<400> SEQUENCE: 16
```

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Phe
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

```
Val Ser Phe Cys Leu Val Met Val Leu Leu Phe Ala Val Asp Thr Gly
        195                 200                 205

Leu Tyr Phe Ser Val Lys Thr Asn Ile Arg Ser Ser Thr Arg Asp Trp
        210                 215                 220

Lys Asp His Lys Phe Lys Trp Arg Lys Asp Pro Gln Asp Lys
225                 230                 235

<210> SEQ ID NO 17
<211> LENGTH: 16
<212> TYPE: PRT
<213> ORGANISM: Artificial Sequence
<220> FEATURE:
<223> OTHER INFORMATION: Signal peptide

<400> SEQUENCE: 17

Met Trp Gln Leu Leu Leu Pro Thr Ala Leu Leu Leu Leu Val Ser Ala
1               5                   10                  15

<210> SEQ ID NO 18
<211> LENGTH: 238
<212> TYPE: PRT
<213> ORGANISM: Homo sapiens
<220> FEATURE:
<223> OTHER INFORMATION: CD16 VAR_003960

<400> SEQUENCE: 18

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

Val Ser Phe Cys Leu Val Met Val Leu Leu Phe Ala Val Asp Thr Gly
        195                 200                 205

Leu Tyr Phe Ser Val Lys Thr Asn Ile Arg Ser Ser Thr Arg Asp Trp
        210                 215                 220

Lys Asp His Lys Phe Lys Trp Arg Lys Asp Pro Gln Asp Lys
225                 230                 235
```

METHODS FOR EXPANSION OF NATURAL KILLER (NK) CELL SUBSET AND RELATED COMPOSITIONS AND METHODS

CROSS REFERENCE TO RELATED APPLICATIONS

This application is a national stage application under 35 U.S.C. § 371 of International Application No. PCT/US2019/062695, filed internationally on Nov. 21, 2019, which claims the benefit of priority from U.S. Provisional Application No. 62/770,686, filed Nov. 21, 2018, entitled "METHODS FOR EXPANSION OF NATURAL KILLER (NK) CELL SUBSET AND RELATED COMPOSITIONS AND METHODS," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 776032000500SeqList.txt, created May 17, 2021, which is 7.84 kilobytes in size. The information in the electronic format of the Sequence Listing is incorporated by reference in its entirety.

FIELD

The present disclosure provides methods for ex vivo expansion of a specialized subset of natural killer (NK) cells, and compositions containing such NK cells. Also provided are methods for identifying or detecting a specialized subset of NK cells. Also provided are methods for treating diseases and conditions such as cancer using compositions of the present disclosure, including in combination with an antibody capable of binding to disease-associated tissues or cells, such as tumor cells or infected cells.

BACKGROUND

Antibody-based therapy has become frequently used for treating cancers and other diseases. Responses to antibody therapy have typically focused on the direct inhibitory effects of these antibodies on the tumor cells (e.g. inhibition of growth factor receptors and the subsequent induction of apoptosis), but the in vivo effects of these antibodies may be more complex and may involve the host immune system. Natural killer (NK) cells are immune effector cells that mediate antibody-dependent cellular cytotoxicity when the Fc receptor (CD16; FcγRIII) binds to the Fc portion of antibodies bound to an antigen-bearing cell. NK cells, including specific specialized subsets thereof, can be used in therapeutic methods, including for improving responses to antibody therapy. However, a major obstacle to application of NK cells in cell therapy, such as adoptive cell therapy, is their relative low abundance in human peripheral blood and the lack of surface phenotypic features of particular specialized subsets. Improved methods are needed for obtaining NK cell compositions for therapeutic use. Provided herein are embodiments that meet such needs.

SUMMARY

Provided herein is a method for expanding FcRγ-deficient NK cells (g-NK), said method comprising: (a) isolating a population of primary human cells enriched for natural killer (NK) cells, the isolating comprises selecting from a sample from a human subject: (i) cells negative for CD3 and positive for CD57 ($CD3^{neg}CD57^{pos}$), (ii) cells negative for CD3, positive for CD56, and negative for CD38 ($CD3^{neg}CD56^{pos}CD38^{neg}$); (iii) cells negative for CD3 ($CD3^{neg}$); (iv) cells negative for CD3 ($CD3^{neg}$) and positive for CD56 ($CD3^{neg}CD56^{pos}$); (v) cells negative for CD3 and positive for CD16 ($CD3^{neg}CD16^{pos}$); or (vi) cells negative for CD3, positive for CD56, negative for NKG2A and negative for CD161 ($CD3^{neg}CD56^{pos}NKG2A^{neg}CD161^{neg}$); and (b) culturing the population of enriched NK cells in the presence of (i) irradiated 221.AEH feeder cells, wherein the ratio of irradiated 221.AEH feeder cells to enriched NK cells is from 1:10 to 10:1; and (ii) recombinant IL-2, wherein the method produces an expanded population of g-NK cells.

Provided herein is a method for expanding FcRγ-deficient NK cells (g-NK), said method comprising: (a) isolating a population of primary human cells enriched for natural killer (NK) cells, the isolating comprises selecting from a sample from a human subject: (i) cells negative for CD3 ($CD3^{neg}$), (ii) cells negative for CD3 ($CD3^{neg}$) and positive for CD56 ($CD3^{neg}CD56^{pos}$); (iii) cells negative for CD3 and positive for CD57 ($CD3^{neg}CD57^{pos}$), or (iv) cells negative for CD3 and positive for CD16 ($CD3^{neg}CD16^{pos}$); and (b) culturing the population of enriched NK cells in the presence of (i) irradiated 221.AEH feeder cells, wherein the ratio of irradiated 221.AEH feeder cells to enriched NK cells is from 1:10 to 10:1; and (ii) recombinant IL-2, wherein the method produces an expanded population of g-NK cells.

Provided herein is a method for expanding FcRγ-deficient NK cells (g-NK), said method comprising: (a) isolating a population of primary human cells enriched for natural killer (NK) cells, the isolating comprises selecting from a sample from a human subject: (i) cells negative for CD3 and positive for CD57 ($CD3^{neg}CD57^{pos}$), (ii) cells negative for CD3, positive for CD56, and negative for CD38 ($CD3^{neg}CD56^{pos}CD38^{neg}$); (iii) cells negative for CD3 ($CD3^{neg}$); (iv) cells negative for CD3 ($CD3^{neg}$) and positive for CD56 ($CD3^{neg}CD56^{pos}$); (v) cells negative for CD3 and positive for CD16 ($CD3^{neg}CD16^{pos}$); or (vi) cells negative for CD3, positive for CD56, negative for NKG2A and negative for CD161 ($CD3^{neg}CD56^{pos}NKG2A^{neg}CD161^{neg}$); and (b) combining the population of enriched NK cells with irradiated 221.AEH feeder cells and irradiated peripheral blood mononuclear (PBMC) feeder cells, wherein the ratio of irradiated 221.AEH feeder cells to enriched NK cells is from 1:10 to 10:1 and the ratio of PBMC feeder cells to enriched NK cells is between at or about 1:1 and at or about 5:1, inclusive. Optionally wherein the PBMC feeder cells are autologous to the subject. Said method also involves: (c) culturing the population of (b) in the presence of recombinant IL-2 and an anti-CD3 antibody or antigen-binding fragment, wherein, within 7 days of initiation of the culturing, exchanging the cell culture media with fresh media containing recombinant IL-2, and, optionally, further exchanging the cell culture media with fresh media containing recombinant IL-2 for every 2 or 3 days thereafter for the duration of the culturing, wherein the culturing produces an expanded population of g-NK cells; and (d) collecting the expanded population of cells.

In any of the provided embodiments, prior to isolating or selecting a population of cells enriched in NK cells, the provided methods include harvesting the sample from the human subject. In some of any embodiments, the human subject is CMV seropositive. In some of any embodiments the human subject has the CD16 158V+ NK cell genotype. In embodiments of the provided method, the sample is or comprises peripheral blood mononuclear cells (PBMCs). In some embodiments, the sample is an apheresis or leukaphereis sample.

In any of the provided embodiments, the method includes isolating cells enriched for NK cells from a sample from a subject. In some embodiments, the isolating is by selecting, from the sample, a population of cells enriched for NK cells. In some embodiments, the selecting is by immunoaffinity-based selection. In some of any embodiments, isolating is of (i) and comprises selecting from the sample cells negative for CD3 and positive for CD57 ($CD3^{neg}CD57^{pos}$). In some of any embodiments, isolating is of (ii) and comprises selecting cells from the sample negative for CD3, positive for CD56, and negative for CD38 ($CD3^{neg}CD57^{pos}CD28^{neg}$) In some embodiments, the isolating is of (iii) and comprises selecting from the sample cells negative for CD3 ($CD3^{neg}$). In some embodiments, the isolating is of (iv) and comprises selecting from the sample cells negative for CD3 ($CD3^{neg}$) and positive for CD56 ($CD3^{neg}CD56^{pos}$). In some embodiments, the isolating comprises selecting from the sample cells negative for CD3 and positive for CD57 ($CD3^{neg}CD57^{pos}$). In some embodiments, the isolating is of (v) and comprises selecting from the sample cells negative for CD3 and positive for CD16 ($CD3^{neg}CD16^{pos}$). In some embodiments, the isolating is of (vi) and comprises selecting from the sample cells negative for CD3, positive for CD56, negative for NKG2A and negative for CD161 ($CD3^{neg}CD56^{pos}NKG2A^{neg}CD161^{neg}$).

In some of any of the provided methods, isolating or selecting a population of cells enriched for NK cells, the method can include cryopreserving the isolated population of enriched NK cells, such as prior to carrying out culturing of the cells, such as for expanding the population of cells. In some of any such embodiments, prior to culturing the cells, such as for expanding the population of cell, the provided methods include thawing the cryopreserved sample comprising the enriched NK cells.

Provided herein is a method for expanding FcRγ-deficient NK cells (g-NK), said method comprising: (a) obtaining a population of primary human cells enriched for natural killer (NK) cells, wherein the population of enriched NK cells comprise a phenotype selected from: (i) cells negative for CD3 and positive for CD57 ($CD3^{neg}CD57^{pos}$); (ii) cells negative for CD3, positive for CD56, and negative for CD38 ($CD3^{neg}CD56^{pos}CD38^{neg}$); (iii) cells negative for CD3 ($CD3^{neg}$), (iv) cells negative for CD3 ($CD3^{neg}$) and positive for CD56 ($CD3^{neg}CD56^{pos}$); (v) cells negative for CD3 and positive for CD16 ($CD3^{neg}CD16^{pos}$); or (vi) cells negative for CD3, positive for CD56, negative for NKG2A and negative for CD161 ($CD3^{neg}CD56^{pos}NKG2A^{neg}CD161^{neg}$); and (b) culturing the population of enriched NK cells in the presence of (i) irradiated 221.AEH feeder cells, wherein the ratio of irradiated 221.AEH feeder cells to enriched NK cells is from 1:10 to 10:1; and (ii) recombinant IL-2, wherein the method produces an expanded population of NK cells enriched for g-NK cells. In some embodiments, obtaining the population of cells enriched for NK cells includes thawing a cryopreserved sample comprising the enriched NK cells.

Provided herein is a method for expanding FcRγ-deficient NK cells (g-NK), said method comprising: (a) obtaining a population of primary human cells enriched for natural killer (NK) cells, wherein the population of enriched NK cells comprise a phenotype selected from: (i) cells negative for CD3 ($CD3^{neg}$), (ii) cells negative for CD3 ($CD3^{neg}$) and positive for CD56 ($CD3^{neg}CD56^{pos}$); (iii) cells negative for CD3 and positive for CD57 ($CD3^{neg}CD57^{pos}$), or (iv) cells negative for CD3 and positive for CD16 ($CD3^{neg}CD16^{pos}$); and (b) culturing the population of enriched NK cells in the presence of (i) irradiated 221.AEH feeder cells, wherein the ratio of irradiated 221.AEH feeder cells to enriched NK cells is from 1:10 to 10:1; and (ii) recombinant IL-2, wherein the method produces an expanded population of g-NK cells. In some embodiments, obtaining the population of cells enriched for NK cells includes thawing a cryopreserved sample comprising the enriched NK cells.

In some of any such embodiments, the population of enriched NK cells is of (i) and comprises cells negative for CD3 and positive for CD57 ($CD3^{neg}CD57^{pos}$). In some of any such embodiments, the population of enriched NK cells is of (ii) and comprises cells negative for CD3, positive for CD56, and negative for CD38 ($CD3^{neg}CD56^{pos}CD38^{neg}$). In some of any such embodiments, the population of enriched NK cells is of (iii) and comprises cells negative for CD3 ($CD3^{neg}$). In some of any such embodiments, the population of enriched NK cells is of (iv) and comprises cells negative for CD3 ($CD3^{neg}$) and positive for CD56 ($CD3^{neg}CD56^{pos}$). In some of any such embodiments, the population of enriched NK cells comprises cells negative for CD3 and positive for CD57 ($CD3^{neg}CD57^{pos}$). In some of any such embodiments, the population of enriched NK cells is of (v) and comprises cells negative for CD3 and positive for CD16 ($CD3^{neg}CD16^{pos}$). In some of any such embodiments, the population of enriched NK cells is of (vi) and comprises cells negative for CD3 ($CD3^{neg}$) and positive for CD56, negative for NKG2A and negative for CD161 ($CD3^{neg}CD56^{pos}NKG2A^{neg}CD161^{neg}$).

In some of any such embodiments, the population of enriched NK cells comprises cells negative for CD3 ($CD3^{neg}$). In some of any such embodiments, the population of enriched NK cells comprises cells negative for CD3 ($CD3^{neg}$) and positive for CD56 ($CD3^{neg}CD56^{pos}$). In some of any such embodiments, the population of enriched NK cells comprises cells negative for CD3 and positive for CD57 ($CD3^{neg}CD57^{pos}$). In some of any such embodiments, the population of enriched NK cells comprises cells negative for CD3 and positive for CD16 ($CD3^{neg}CD16^{pos}$).

Provided herein is method for expanding FcRγ-deficient NK cells (g-NK), the method comprising culturing a population of primary human cells enriched for natural killer (NK) cell from a sample from a human subject, the population of enriched NK cells comprising cells negative for CD3 and positive for CD57, wherein the culturing is carried out in the presence of: (i) irradiated 221.AEH feeder cells, wherein the ratio of irradiated 221.AEH feeder cells to enriched NK cells is from 1:10 to 10:1; and (ii) recombinant IL-2; wherein the method produces an expanded population of g-NK cells.

In some of any of the embodiments, prior to the culturing, the method includes isolating the population of enriched NK cells from the sample, the isolating comprising: (1) selecting (a) cells negative for CD3 or (b) cells positive for CD57, thereby enriching a first selected population; and (2) selecting from the first selected population cells for the other of (a) cells negative for CD3 or (b) cells positive for CD57, thereby enriching for cells negative for CD3 and positive for CD57. In some embodiments, the selecting comprises immunoaffinity-based selection.

In some of any of the embodiments, prior to the culturing, the method includes isolating the population of enriched NK cells from the sample, the isolating comprising: (1) selecting from the sample cells negative for CD3 to produce a first selected population; and (2) selecting from the first selected population cells positive for CD57, thereby enriching for cells negative for CD4 and positive for CD57.

Provided herein is a method for expanding FcRγ-deficient NK cells (g-NK), the method comprising culturing a population of primary human cells enriched for natural killer (NK) cells from a sample from a human subject, the population of enriched NK cells comprising cells negative for CD3, positive for CD56, and negative for CD38 wherein the culturing is carried out in the presence of: (i) irradiated 221.AEH feeder cells, wherein the ratio of irradiated 221.AEH feeder cells to enriched NK cells is from 1:10 to 10:1; and (ii) recombinant IL-2, wherein the method produces an expanded population of g-NK cells.

In some of any of the embodiments, prior to the culturing, the method includes isolating the population of enriched NK cells from the sample, the isolating comprising: (1) selecting from the sample cells negative for CD3 thereby enriching a first selected population; (2) selecting from the first selected population (a) cells positive for CD56 or (b) cells negative for CD38, thereby enriching a second selected population; and (3) selecting from the second selected population cells for the other of (a) cells positive for CD56 or (b) cells negative for CD38, thereby enriching for cells negative for CD3 and positive for CD56 and negative for CD38.

In some of any of the embodiments, prior to the culturing, the method includes isolating the population of enriched NK cells from the sample, the isolating comprising: (1) selecting from the sample cells negative for CD3 to produce a first selected population; (2) selecting from the first selected population cells positive for CD56 to produce a second selected population; and (3) selecting from the second selected population cells negative for CD38 thereby enriching for cells negative for CD3 and positive for CD56 and negative for CD38.

Provided herein is a method for expanding FcRγ-deficient NK cells (g-NK), the method comprising culturing a population of primary human cells enriched for natural killer (NK) cells from a sample from a human subject, the population of enriched NK cells comprising cells negative for CD3 and positive for CD16, wherein the culturing is carried out in the presence of: (i) irradiated 221.AEH feeder cells, wherein the ratio of irradiated 221.AEH feeder cells to enriched NK cells is from 1:10 to 10:1; and (ii) recombinant IL-2, wherein the method produces an expanded population of g-NK cells.

In some of any of the embodiments, prior to the culturing, the method includes isolating the population of enriched NK cells from the sample, the isolating comprising: (1) selecting (a) cells negative for CD3 or (b) cells positive for CD16, thereby enriching a first selected population; and (2) selecting from the first enriched selected cells for the other of (a) cells negative for CD3 or (b) cells positive for CD16, thereby enriching for cells negative for CD3 and positive for CD16. In some embodiments, the selecting comprises immunoaffinity-based selection.

In some of any of the embodiments, prior to the culturing, the method includes isolating the population of enriched NK cells from the sample, the isolating comprising: (1) selecting from the sample cells negative for CD3 to produce a first selected population; and (2) selecting from the first selecting from the first selected population cells positive for CD16 thereby enriching for cells negative for CD3 and positive for CD16. In some embodiments, the selecting comprises immunoaffinity-based selection.

Provided herein is a method for expanding FcRγ-deficient NK cells (g-NK), the method comprising culturing a population of primary human cells enriched for natural killer (NK) cells from a sample from a human subject, the population of enriched NK cells comprising cells negative for CD3, positive for CD56, negative for NKG2A and negative for CD161, wherein the culturing is carried out in the presence of: (i) irradiated 221.AEH feeder cells, wherein the ratio of irradiated 221. AEH feeder cells to enriched NK cells is from 1:10 to 10:1; and (ii) recombinant IL-2, wherein the method produces an expanded population of g-NK cells.

In some of any of the embodiments, prior to the culturing, the method includes isolating the population of enriched NK cells from the sample, the isolating comprising: (1) selecting from the sample cells negative for CD3 to produce a first selected population; (2) selecting from the first selected population cells positive for CD56 to produce a second selected population; (3) selecting from the second selected population for (a) cells negative for NKG2A or (b) cells negative for CD161, thereby enriching a third selected population; and (4) selecting from the third selected population cells for the other of (a) cells negative for NKG2A or (b) cells negative for CD161, thereby enriching for cells negative for CD3, positive for CD56, negative for NKG2A and negative for CD161. In some embodiments, the selecting comprises immunoaffinity-based selection.

In some of any of the embodiments, prior to the culturing, the method includes isolating the population of enriched NK cells from the sample, the isolating comprising: (1) selecting from the sample cells negative for CD3 to produce a first selected population; (2) selecting from the first selected population cells positive for CD56 to produce a second selected population; (3) selecting from the second selected population cells negative for NKG2A to produce a third selected population; and (4) selecting from the third selected population cells cells negative for CD161 to enrich for cells negative for CD3, positive for CD56, negative for NKG2A, and negative for CD161. In some embodiments, the selecting comprises immunoaffinity-based selection.

In some of any of the embodiments, prior to the culturing, the method includes isolating the population of enriched NK cells from the sample, the isolating comprising: (1) selecting from the sample cells negative for CD3 to produce a first selected population; (2) selecting from the first selected population cells positive for CD56 to produce a second selected population; (3) selecting from the second selected population cells negative for CD161 to produce a third selected population; and (4) selecting from the third selected population cells cells negative for NKG2A to enrich for cells negative for CD3, positive for CD56, negative for NKG2A, and negative for CD161. In some embodiments, the selecting comprises immunoaffinity-based selection.

In some of any of the provided embodiments, the sample comprises peripheral blood mononuclear cells (PBMCs). In some of any of the provided embodiments, prior to the culturing, the method includes harvesting the sample from the human subject. In some embodiments, the human subject is CMV seropositive. In some embodiments, the human subject has the CD16 158V+ NK cell genotype. In some embodiments, the sample is an apheresis or leukapheresis sample. In some of any of the provided embodiments, the enriched NK cells are from a cryopreserved sample having been previously isolated from the sample from the subject.

In some of any of the provided embodiments, the culturing is further carried out in the presence of (iii) primary human peripheral blood mononuclear cells (PBMCs) feeder cells, wherein the PBMC feeder cells are irradiated. In some of any embodiments, the culturing is carried out subsequent to combining the population of enriched NK cells with irradiated 221.AEH feeder cells and the irradiated PBMC feeder cells. In some such embodiments, the ratio of PBMC feeder cells to enriched NK cells is between at or about 1:1 and at or about 5:1, inclusive. In some of any of the provided embodiments, the PBMC feeder cells are autologous to the subject. In some of any of the provided embodiments, at least a portion of the culturing is carried out in the presence of at least one stimulatory agent that is capable of stimulating the activation of one or more of T cell of the PBMC feeder cells. In some embodiments, the stimulatory agent specifically binds to a member of a TCR complex, optionally wherein the agent specifically binds to a CD3, optionally a CD3epsilon. In some embodiments, the at least one stimulatory agent is an anti-CD3 antibody or antigen-binding fragment thereof. In some embodiments, the anti-CD3 antibody or antigen-binding fragment thereof is an OKT3 antibody or antigen-binding fragment. In some embodiments, the concentration of the anti-CD3 antibody or antigen-binding fragment is between at or about 10 ng/mL and at or about 100 ng/mL. In some embodiments, the concentration of the anti-CD3 antibody or antigen-binding fragment is at or about 50 ng/mL. In some of any of the provided embodiments, the at least one stimulatory agent is added beginning at the initiation of the culturing or at or about the same time as the irradiated PBMC feeder cells. In some of any of the provided embodiments, during at least a portion of the culturing the PBMC feeder cells are activated.

In some of any of the provided embodiments, the ratio of irradiated 221.AEH feeder cells to NK cells is at or about 1:1 or greater. In some of any of the provided embodiments, the ratio of irradiated 221.AEH feeder cells to NK cells is between 1:1 and 5:1, inclusive. In some of any of the provided embodiments, the ratio of irradiated AEH.221 feeder cells to enriched NK cell is between 1:1 and 3:1, inclusive. In some of any of the provided embodiments, the ratio of irradiated AEH.221 feeder cells to enriched NK cells is or is about 2.5:1. In some of any of the provided embodiments the ratio of irradiated AEH.221 feeder cells to enriched NK cells is or is about 1:1. In some of any of the provided embodiments, the ratio of PBMC feeder cells to enriched NK cells is at or about 5:1.

In some of any such embodiments, the NK cells are freshly isolated or have not been frozen or thawed. In some of any such embodiments, the NK cells have been thawed after being frozen.

In some of any of the provided embodiments, the concentration of recombinant IL-2 during at least a portion of the culturing is between at or about 10 IU/mL and at or about 500 IU/mL. In some of any of the provided embodiments, the concentration of recombinant IL-2 during at least a portion of the culturing is at or about 100 IU/mL recombinant IL-2. In some of any of the provided embodiments, the recombinant IL-2 is added beginning at or about the initiation of the culturing.

In some of any of the provided embodiments, the method further comprises exchanging the culture medium one or more times during the culturing. In some of any of the provided embodiments, the exchanging of the culture medium is carried out beginning at or about within 3 to 7 days after the initiation of the culturing, optionally at or about 5 days after the initiation of the culturing. In some of any of the provided embodiments, the exchanging of the culture medium is carried out every two or three days for the remaining duration of the culturing. In some of any of the provided embodiments, the exchanging of the culture medium reduces or removes the at least one stimulatory agent from the culture medium. In some of any of the provided embodiments, at each exchange of the culture medium, the method includes adding fresh media containing recombinant IL-2 to the culture. In some of any such embodiments, the recombinant IL-2 is added at a concentration of between at or about 10 IU/mL and at or about 500 IU/mL, inclusive. In some embodiments, the recombinant IL-2 is added at a concentration of at or about 100 IU/mL recombinant IL-2.

In some of any of the provided embodiments, the population of enriched NK cells comprises at least at or about $0.2 \times 10^6$ enriched NK cells, at least at or about $1.0 \times 10^6$ enriched NK cells, or at or about $10 \times 10^6$ enriched NK cells. In some of any of the provided embodiments, the population of enriched NK cells at the initiation of the culturing is at a concentration of between at or about $0.05 \times 10^6$ enriched NK cells/mL and at or about $1.0 \times 10^6$ enriched NK cells/mL. In some of any of the provided embodiments, the population of enriched NK cells at the initiation of the culturing is at a concentration of between at or about $0.05 \times 10^6$ enriched NK cells/mL and at or about $0.5 \times 10^6$ enriched NK cells/mL. In some of any of the provided embodiments, the population of enriched NK cells at the initiation of the culturing comprises a concentration of at or about $0.2 \times 10^6$ enriched NK cells/mL.

In some of any of the provided embodiments, the culturing is carried out until a time at which the method achieves expansion of at least or at least about $2.50 \times 10^8$ g-NK cells. In some of any of the provided embodiments, the culturing is carried out until a time at which the method achieves expansion of at least or at least about $5.0 \times 10^8$ g-NK cells. In some of any of the provided embodiments, the culturing is carried out until the method achieves expansion of at least or at least about $1.0 \times 10^9$ g-NK cells. In some of any of the provided embodiments, the culturing is carried out until a time at which the method achieves expansion of at least or at least about $5.0 \times 10^9$ g-NK cells.

In some of any of the provided embodiments, the culturing is carried out for at or about or at least at or at least about 5 days, 6 days, 7 days, 8 days, 9 days, 10 days, 11 days, 12 days, 13 days, 14 days, 15 days, 16 days, 17 days, 18 days, 19 days, 20 day, 21 days, 22 days, 23 days, 24 days or 25 days. In some embodiments, the culturing is carried out for at or about or at least at or about 14 days. In some embodiments the culturing is carried out for at or about or at least at or about 21 days.

In some embodiments, the method produces an increased number of g-NK cells at the end of the culturing compared to at the initiation of the culturing. In some of any such embodiments, the increase is greater than or greater than about 100-fold, greater than or greater than about 200-fold, greater than or greater than about 300-fold, greater than or greater than about 400-fold, greater than or greater than about 500-fold, greater than or greater than about 600-fold, greater than or greater than about 700-fold or greater than or greater than about 800-fold. In some of any embodiments, the increase is at or about 1000-fold greater. In some of any embodiments, the increase is at or about 2000-fold greater. In some of any embodiments, the increase is at or about 2500-fold greater.

In some of any of the provided embodiments, the expanded population of g-NK cells produced by the method provided herein is collected after culturing.

In some of any of the provided embodiments, the g-NK cells are $FcR\gamma^{neg}$. In some such embodiments, the g-NK cells further are $CD45^{pos}/CD3^{neg}/CD56^{pos}$. In some embodiments, the g-NK cells have a phenotype $FcR\gamma^{neg//}CD45^{pos}/CD3^{neg}/CD56^{pos}$.

In some of any of the provided embodiments, the g-NK cells are cells having a g-NK surrogate surface marker profile. In some embodiments, the g-NK cell surrogate surface marker profile is CD16$^{pos}$/CD57$^{pos}$/CD7$^{dim/neg}$/CD161$^{neg}$. In some embodiments, the g-NK cell surrogate surface marker profile is NKG2A$^{neg}$/CD161$^{neg}$. In some of any such embodiments, the g-NK cell surrogate surface marker profile is CD38$^{neg}$. In some of any such embodiments, the g-NK cell surrogate surface marker profile further includes CD45$^{pos}$/CD3$^{neg}$/CD56$^{pos}$. In particular embodiments the g-NK cell surrogate surface marker profile includes CD45$^{pos}$/CD3$^{neg}$/CD56$^{pos}$/CD16$^{pos}$/CD57$^{pos}$/CD7$^{dim/neg}$/CD161$^{neg}$. In other particular embodiments, the g-NK cell surrogate surface marker profile includes CD45$^{pos}$/CD3$^{neg}$/CD56$^{pos}$/NKG2A$^{neg}$/CD161$^{neg}$. In other particular embodiments, the g-NK cell surrogate surface marker profile includes CD45$^{pos}$/CD3$^{neg}$/CD56$^{pos}$/CD38$^{neg}$.

In some of any of the provided embodiments, the method further includes, after the culturing, purifying or selecting a population of cells having a g-NK cell surrogate surface marker profile from the expanded population of cells. In some of any such embodiments, the g-NK cell surrogate surface marker profile is CD16$^{pos}$/CD57$^{pos}$/CD7$^{dim/neg}$/CD161$^{neg}$. In some of any such embodiments, the g-NK cell surrogate surface marker profile is NKG2A$^{neg}$/CD161$^{neg}$. In some of any of the embodiments, g-NK cell surrogate surface marker profile further includes the surface phenotype CD45$^{pos}$/CD3$^{neg}$/CD56$^{pos}$.

In some of any of the provided embodiments, the method further includes formulating the expanded population of g-NK cells in a pharmaceutically acceptable excipient. In some of any of the provided embodiments, the method further includes cryopreserving the cells and/or formulating the cells in the presence of a cryoprotectant.

Also provided herein is a composition comprising g-NK cells produced by any of the provided methods. In some embodiments, the composition comprises at least at or about 10$^8$ g-NK cells. In some of any of the provided embodiments, the number of g-NK cells in the composition comprises from at or about 10$^8$ to at or about 10$^{12}$ g-NK cells, from at or about 10$^8$ to at or about 10$^{11}$ g-NK cells, from at or about 10$^8$ to at or about 10$^{10}$ g-NK cells, from at or about 10$^8$ to at or about 10$^9$ g-NK cells, from at or about 10$^9$ to at or about 10$^{12}$ g-NK cells, from at or about 10$^9$ to at or about 10$^{11}$ g-NK cells, from at or about 10$^9$ to at or about 10$^{10}$ g-NK cells, from at or about 10$^{10}$ to at or about 10$^{12}$ g-NK cells, from at or about 10$^{10}$ to at or about 10$^{11}$ g-NK cells, or from at or about 10$^{11}$ to at or about 10$^{12}$ g-NK cells. In some of any of the provided embodiments, the g-NK cells are FcRγ$^{neg}$. In some of any of the provided embodiments, the g-NK cells are cells having a g-NK surrogate surface marker profile. In some embodiments, the g-NK cell surrogate surface marker profile is CD16$^{pos}$/CD57$^{pos}$/CD7$^{dim/neg}$/CD161$^{neg}$. In some embodiments, the g-NK cell surrogate surface marker profile is NKG2A$^{neg}$/CD161$^{neg}$. In some of any of the provided embodiments, the g-NK cells or cells having a g-NK surrogate marker profile further include the surface phenotype CD45$^{pos}$/CD3$^{neg}$/CD56$^{pos}$. In some of any of the provided embodiments, the g-NK cell surrogate surface marker profile is CD38$^{neg}$.

Also provided herein is a composition comprising g-NK cells produced by any of the provided methods. In some embodiments, the composition comprises at least at or about 10$^6$ g-NK cells. In some of any of the provided embodiments, the composition comprises from at or about 10$^6$ to at or about 10$^{10}$ g-NK cells, from at or about 10$^6$ to at or about 10$^9$ g-NK cells, from at or about 10$^6$ to at or about 10$^8$ g-NK cells, from at or about 10$^6$ to at or about 10$^7$ g-NK cells, from at or about 10$^7$ to at or about 10$^{10}$ g-NK cells, from at or about 10$^7$ to at or about 10$^9$ g-NK cells, from at or about 10$^7$ to at or about 10$^8$ g-NK cells, from at or about 10$^8$ to at or about 10$^{10}$ g-NK cells, from at or about 10$^8$ to at or about 10$^9$ g-NK cells, or from at or about 10$^9$ to at or about 10$^{10}$ g-NK cells. In some of any of the provided embodiments, the g-NK cells are FcRγ$^{neg}$. In some of any of the provided embodiments, the g-NK cells are cells having a g-NK surrogate surface marker profile. In some embodiments, the g-NK cell surrogate surface marker profile is CD16$^{pos}$/CD57$^{pos}$/CD7$^{dim/neg}$/CD161$^{neg}$. In some embodiments, the g-NK cell surrogate surface marker profile is NKG2A$^{neg}$/CD161$^{neg}$. In some of any of the provided embodiments, the g-NK cells or cells having a g-NK surrogate marker profile further include the surface phenotype CD45$^{pos}$/CD3$^{neg}$/CD56$^{pos}$.

Provided herein is a composition comprising a natural killer (NK) cell subset, wherein at least at or about 40%, at least at or about 50%, at least at or about 60%, at least at or about 70%, at least at or about 80%, or at least at or about 90% of the cells in the composition have a g-NK cell surrogate marker profile that is CD16$^{pos}$/CD57$^{pos}$/CD7$^{dim/neg}$/CD161$^{neg}$. Provided herein is a composition comprising a natural killer (NK) cell subset, wherein at least at or about 40%, at least at or about 50%, at least at or about 60%, at least at or about 70%, at least at or about 80%, or at least at or about 90% of the cells in the composition have a g-NK cell surrogate marker profile selected from CD16$^{pos}$/CD57$^{pos}$/CD7$^{dim/neg}$/CD161$^{neg}$ and NKG2A$^{neg}$/CD161$^{neg}$. In some embodiments, at least at or about 70% of the cells in the composition comprise a g-NK cell surrogate marker profile that is CD16$^{pos}$/CD57$^{pos}$/CD7$^{dim/neg}$/CD161$^{neg}$. In some embodiments, at least at or about 80% of the cells in the composition comprise a g-NK cell surrogate marker profile that is CD16$^{pos}$/CD57$^{pos}$/CD7$^{dim/neg}$/CD161$^{neg}$. In some embodiments, at least at or about 90% of the cells in the composition comprise a g-NK cell surrogate marker profile that is CD16$^{pos}$/CD57$^{pos}$/CD7$^{dim/neg}$/CD161$^{neg}$.

Provided herein is a composition comprising a natural killer (NK) cell subset, wherein at least at or about 40%, at least at or about 50%, at least at or about 60%, at least at or about 70%, at least at or about 80%, or at least at or about 90% of the cells in the composition have a g-NK cell surrogate marker profile that is NKG2A$^{neg}$/CD161$^{neg}$. In some of any of the provided embodiments, at least at or about 70% of the cells in the composition comprise a g-NK cell surrogate marker profile that is NKG2A$^{neg}$/CD161$^{neg}$. In some of any of the provided embodiments, at least at or about 80% of the cells in the composition comprise a g-NK cell surrogate marker profile that is NKG2A$^{neg}$/CD161$^{neg}$. In some of any of the provided embodiments, at least at or about 90% of the cells in the composition comprise a g-NK cell surrogate marker profile that is NKG2A$^{neg}$/CD161$^{neg}$.

Provided herein is a composition comprising a natural killer (NK) cell subset, wherein at least at or about 40%, at least at or about 50%, at least at or about 60%, at least at or about 70%, at least at or about 80%, or at least at or about 90% of the cells in the composition have a g-NK cell surrogate marker profile that is CD38$^{neg}$. In some of any of the provided embodiments, at least at or about 70% of the cells in the composition comprise a g-NK cell surrogate marker profile that is CD38$^{neg}$. In some of any of the provided embodiments, at least at or about 80% of the cells in the composition comprise a g-NK cell surrogate marker profile that is CD38$^{neg}$. In some of any of the provided embodiments, at least at or about 90% of the cells in the composition comprise a g-NK cell surrogate marker profile that is $CD38^{neg}$. In some embodiments, the g-NK cell surrogate surface marker profile further includes the surface phenotype $CD45^{pos}/CD3^{neg}/CD56^{pos}$. In some of any of the provided embodiments, at least at or about 60% of the cells in the composition comprise a g-NK cell surrogate marker profile selected from $CD16^{pos}/CD57^{pos}/CD7^{dim/neg}/CD161^{neg}$ and $NKG2A^{neg}/CD161^{neg}$. In some of any of the provided embodiments, at least at or about 70% of the cells in the composition comprise a g-NK cell surrogate marker profile selected from $CD16^{pos}/CD57^{pos}/CD7^{dim/neg}/CD161^{neg}$ and $NKG2A^{neg}/CD161^{neg}$. In some of any of the provided embodiments, of the cells that comprise the g-NK cell surrogate marker profile greater than 70% are $FcR\gamma^{neg}$, optionally between at or about 70% and 90% are $FcR\gamma^{neg}$. In some of any of the provided embodiments, the composition comprises at least or about at least $10^8$ cells. In some of any of the provided embodiments, the composition comprises at least or about at least $10^6$ cells. In some of any of the provided embodiments, the composition comprises from at or about $10^8$ to at or about $10^{12}$ cells, from at or about $10^8$ to at or about $10^{11}$ cells, from at or about $10^8$ to at or about $10^{10}$ cells, from at or about $10^8$ to at or about $10^9$ cells, from at or about $10^9$ to at or about $10^{12}$ cells, from at or about $10^9$ to at or about $10^{11}$ cells, from at or about $10^9$ to at or about $10^{10}$ cells, from at or about $10^{10}$ to at or about $10^{12}$ cells, from at or about $10^{10}$ to at or about $10^{11}$ cells, or from at or about $10^{11}$ to at or about $10^{12}$ cells. In some of any of the provided embodiments, the composition comprises from at or about $10^6$ to at or about $10^{10}$ cells, from at or about $10^6$ to at or about $10^9$ cells, from at or about $10^6$ to at or about $10^8$ cells, from at or about $10^6$ to at or about $10^7$ cells, from at or about $10^7$ to at or about $10^{10}$ cells, from at or about $10^7$ to at or about $10^9$ cells, from at or about $10^7$ to at or about $10^8$ cells, from at or about $10^8$ to at or about $10^{10}$ cells, from at or about $10^8$ to at or about $10^9$ cells, or from at or about $10^9$ to at or about $10^{10}$ cells.

In some of any of the provided embodiments, the cells in the composition are from a single donor subject that have been expanded from the same sample. In some of any of the provided embodiments, the composition comprises a pharmaceutically acceptable excipient. In some of any of the provided embodiments, the composition comprises a cryoprotectant. In some of any of the provided embodiments, the composition is sterile.

Provided herein is a kit comprising any of the provided compositions and an additional agent for treatment of a disease. In some of any of the embodiments, the kit further includes instructions for administering the composition and additional agent for treating a disease or condition.

Provided herein is a kit comprising the any of the provided compositions and instructions for administering the composition in a combination therapy with an additional agent for treatment of a disease.

In some of any of the provided embodiments, the additional agent is an antibody or an Fc-fusion protein. In some of any such embodiments, the antibody recognizes or specifically binds a tumor associated antigen. In some of any such embodiments, the antibody recognizes or binds CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, LOXL2, MET, IGF1R, IGLF2, EPHA3, FR-alpha, phosphatidylserine, Syndecan 1, SLAMF7 (CD319), TRAILR1, TRAILR2, RANKL, FAP, vimentin or tenascin. In some of any such embodiments, the antibody is a full length antibody and/or comprises an Fc domain.

In some of any of the provided methods, the additional agent is a cytotoxic agent or cancer drug. In some of any of the provided embodiments, the additional agent is an oncolytic virus.

Provided herein is an article of manufacture, comprising the kit of any of the provided embodiments.

Provided herein is a method of treating a disease or condition comprising administering any of the provided compositions to an individual in need thereof. In some of any such embodiments, the methods include administering from or from about $1\times10^5$ NK cells/kg to at or about $1\times10^7$ NK cells/kg to the individual. In some of any such embodiments, the methods include administering from or from about $5\times10^7$ NK cells to at or about $10\times10^9$ NK cells to the individual. In some of any such embodiments, the methods include administering from or from about $1\times10^8$ to $1\times10^{10}$ cells/m$^2$ to the individual or administering from or from about $1\times10^6$ to $1\times10^{10}$ NK cells/kg.

In some of any of the provided embodiments, the methods further include administering an additional agent to the individual for treating the disease or condition. In some embodiments, the additional agent is an antibody or an Fc-fusion protein. In some embodiments, the disease or condition is a cancer and the antibody recognizes a tumor antigen associated with the cancer. In some of any such embodiments, the antibody recognizes or specifically binds CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, LOXL2, MET, IGF1R, IGLF2, EPHA3, FR-alpha, phosphatidylserine, Syndecan 1, SLAMF7 (CD319), TRAILR1, TRAILR2, RANKL, FAP, vimentin or tenascin. In some of any such embodiments, the antibody comprises an Fc domain and/or is a full-length antibody.

In some of any of the provided embodiments, the methods further include administering a cancer drug or cytotoxic agent to the subject for treating the disease or condition. In some of any of the provided methods, the additional agent is an oncolytic virus.

In some of any of the provided methods, the additional agent and the composition are administered sequentially. In some of any of the provided embodiments the additional agent is administered prior to administration of the composition. In some of any of the provided embodiments, the additional agent and the composition are administered simultaneously.

In some of any of the provided embodiments, the disease or condition is selected from the group consisting of an inflammatory condition, an infection, and cancer. In some of any such embodiments, the disease or condition is an infection and the infection is a viral infection or a bacterial infection. In some of any such embodiments, the disease or condition is a cancer and the cancer is a leukemia, a lymphoma or a myeloma. In some of any such embodiments, the disease or condition is a cancer and the cancer comprises a solid tumor. In some of any such embodiments, the infection is a viral infection or a bacterial infection. In some of any such embodiments, the cancer is a leukemia, a lymphoma or a myeloma. In some of any such embodiments, the cancer comprises a solid tumor.

In some of any of the provided embodiments, the disease or condition is a cancer and the cancer is selected from among an Adenocarcinoma of the stomach or gastroesophageal junction, a bladder cancer, a breast cancer, a brain cancer, a cervical cancer, a colorectal cancer, an endocrine/neuroendocrine cancer, a head and neck cancer, a gastrointestinal stromal cancer, a giant cell tumor of the bone, a kidney cancer, a liver cancer, a lung cancer, a neuroblastoma, an ovarian epithelial/fallopian tube/primary peritoneal cancers, a pancreatic cancer, a prostate cancer, a skin cancer and a soft tissue carcinoma.

In some of any of the provided embodiments, the individual is a human. In some of any of the provided embodiments, the NK cells in the composition is allogenic to the individual. In some of any of the provided embodiments, the NK cells in the composition is autologous to the subject.

Provided herein is a kit comprising a plurality of reagents for detecting a panel of surface markers, said panel of surface markers selected from CD16, CD57 CD7 and CD161 or NKG2A and CD161.

Provided herein is a kit comprising a plurality of reagents for detecting a panel of surface markers, said panel of surface markers comprising NKG2A and CD161.

Provided herein is a kit comprising a plurality of reagents for detecting a panel of surface markers, said panel of surface markers comprising CD3, CD56 and CD38.

In some of any of the provided embodiments, the panel of surface markers further comprises CD3, CD45 and CD56. In some of any of the provided embodiments, the panel further comprises CD45. In some of any of the provided embodiments, each of the plurality of reagents is a binding molecule specific for one marker of the panel of surface markers. In some embodiments, the binding molecule is an antibody or antigen-binding fragment. In some embodiments, the binding molecules are detectably labeled. In some of any of the provided embodiments, the kit further comprises instruction for use of the panel of surface markers as a surrogate marker for detecting the number of g-NK cells in a cell sample.

Provided herein is a method of detecting a g-NK surrogate surface marker profile in a sample comprising natural killer (NK) cells using any of the provided kits.

Provided herein is a method of detecting a g-NK surrogate surface marker profile in a sample, the method comprising: (a) contacting a sample comprising natural killer (NK) cells with reagents for detecting a panel of surface markers comprising CD16, CD57, CD7 and CD161; and (b) detecting the presence or absence of the cells in the sample having the phenotype $CD16^{pos}/CD57^{pos}/CD7^{dim/neg}/CD161^{neg}$.

Provided herein is a method of detecting a g-NK surrogate surface marker profile in a sample, the method comprising: (a) contacting a sample comprising natural killer (NK) cells with reagents for detecting a panel of surface markers selected from CD16, CD57' CD7 and CD161 or NKG2A and CD161; and (b) detecting the presence or absence of the cells in the sample having the phenotype $CD16^{pos}/CD57^{pos}/CD7^{dim/neg}/CD161^{neg}$ or $NKG2A^{neg}/CD161^{neg}$. Provided herein is a method of detecting a g-NK surrogate surface marker profile in a sample, the method comprising: (a) contacting a sample comprising natural killer (NK) cells with reagents for detecting a panel of surface markers comprising NKG2A and CD161; and (b) detecting the presence or absence of the cells in the sample having the phenotype $NKG2A^{neg}/CD161^{neg}$.

In some of any such embodiments, the panel of surface markers further comprises CD45, CD3 and CD56 and wherein the phenotype further comprises $CD45^{pos}/CD3^{neg}/CD56^{pos}$.

Provided herein is a method of detecting a g-NK surrogate surface marker profile in a sample, the method comprising: (a) contacting a sample comprising natural killer (NK) cells with reagents for detecting a panel of surface markers comprising CD3, CD56, and CD38; and (b) detecting the presence or absence of the cells in the sample having the phenotype $CD38^{pos}\ CD56^{pos}/CD38^{neg}$.

In some of any of the provided embodiments, each of the plurality of reagents is a binding molecule specific for one marker of the panel of surface markers. In some of any of the provided embodiments, the binding molecule is an antibody or antigen-binding fragment. In some of any of the provided embodiments, the binding molecules are detectably labeled. In some of any of the provided embodiments, the detecting is by flow cytometry.

BRIEF DESCRIPTION OF THE DRAWINGS

FIG. 1 depicts the percentage of g-NK ($CD45^{pos}/CD3^{neg}/CD56^{pos}/FcR\gamma^{neg}$) within a cell subset having either the surrogate extracellular surface phenotype of $CD45^{pos}/CD3^{neg}/CD56^{pos}/CD16^{pos}/CD57^{pos}/CD7^{dim/neg}/CD161^{neg}$ or $CD45^{pos}/CD3^{neg}/CD56^{pos}/NKG2A^{neg}/CD161^{neg}$. Values are mean±standard error.

FIG. 2B depicts the total number of g-NK cells after expansion by various methods as described in Example 2. FIG. 2C depicts the percentage of g-NK cells before and after expansion by various methods as described in Example 2. Values are mean±standard error.

FIG. 2D depicts the total number of g-NK cells after expansion by various methods as described in Example 2. FIG. 2E depicts the percentage of g-NK cells before and after expansion by various methods as described in Example 2. Values are mean±standard error.

FIG. 4A shows the ADCC activity of g-NK cells expanded by a process starting with enriched $CD3^{neg}CD57^{pos}$ cell in donors with high g-NK compared to donors with low g-NK proportions (n=4). FIG. 4B shows ADCC (1:1 NK-cell to target ratio) activity of g-NK cells, conventional NK cells (cNK) and NKG2C$^{pos}$ (adaptive) NK-cells expanded from fresh or previously frozen (and thawed) NK cells enriched from the same donor (n=4). Values are mean±standard error.

FIG. 5A shows ADCC activity of g-NK and cNK cells in combination with anti-HER2 (Trastuzumab) against the breast cancer cell line SKBR3. FIG. 5B shows ADCC activity of g-NK and cNK cells in combination with anti-EGFR (Cetuximab) against the head and neck cancer cell line CAL27. Values are mean±SE.

FIG. 6A shows ADCC activity of g-NK and cNK cells in combination with anti-EGFR (Cetuximab) against the colorectal cancer cell line HT29. FIG. 6B shows ADCC activity of g-NK and cNK cells in combination with anti-EGFR (Cetuximab) against the colorectal cancer cell line SW480. FIG. 6C shows ADCC activity of g-NK and cNK cells in combination with anti-EGFR (Cetuximab) against the lung cancer cell line A549. Values are mean±SE.

FIG. 7A shows the number of human NK-cells present in whole blood of NSG mice at days 5, 8, 14, 15, and 22 post-infusion. FIG. 7B shows the number of human NK-cells present in the spleen of NSG mice 22 days after NK-cell infusion. FIG. 7C shows the number of human NK-cells present in the bone marrow of NSG mice 22 days after NK-cell infusion. N=3 for all 3 arms. Values are mean±SE.

FIG. 8A shows the effect of treatment with g-NK and rituximab (rituximab+g-NK) on Raji tumor burden as measured by bioluminescence (BLI) in NSG mice relative to untreated mice or mice treated with rituximab only. Values are mean±SE. FIG. 8B shows the effect of treatment with g-NK and rituximab (rituximab+g-NK) on survival in Raji-inoculated NSG mice relative to untreated mice or mice treated with rituximab only. N=8 for all arms.

FIG. 9A shows ADCC activity of freshly isolated g-NK and cNK cells in combination with anti-CD38 (daratumumab; Dara) or anti-SLAMF7 (elotuzumab; Elo) against the multiple myeloma cell line MM.1S (n=16). FIG. 9B shows ADCC activity of expanded g-NK and cNK cells in combination with anti-CD38 (daratumumab; Dara) or anti-SLAMF7 (elotuzumab; Elo) against the multiple myeloma cell line MM.1S (n=5). Values are mean±SE.

FIG. 10A shows the effect of treatment with g-NK and daratumumab (Dara+g-NK) on MM.1S tumor burden (BLI) in NSG mice relative to untreated mice or mice treated with cNK and daratumumab (Dara+cNK), Dara only, vehicle, or g-NK only. FIG. 10B shows the effect of treatment with g-NK and elotuzumab (Elo+g-NK) on MM.1S tumor burden (BLI) in NSG mice relative to untreated mice or mice treated with cNK and elotuzumab (Elo+cNK), Elo only, vehicle, or g-NK only. N=6 for all arms. Values are mean±SE.

FIG. 11A shows the effect of treatment with g-NK and daratumumab (Dara+g-NK) on survival in MM.1S-inoculated NSG mice relative to untreated mice or mice treated with cNK and daratumumab (Dara+cNK), Dara only, vehicle, or g-NK only. FIG. 11B shows the effect of treatment with g-NK and elotuzumab (Elo+g-NK) on survival in MM.1S-inoculated NSG mice relative to untreated mice or mice treated with cNK and elotuzumab (Elo+cNK), Elo only, vehicle, or g-NK only. N=6 for all arms.

FIGS. 12A-12C depict the persistence and homing of g-NK and cNK to bone marrow and spleen when combined with daratumumab (dara) or elotuzumab (elo) in a xenograft model of multiple myeloma. FIG. 12A shows the number of g-NK and cNK in the spleen of MM.1S-inoculated NSG mice treated with daratumumab or elotuzumab. FIG. 12B shows the number of g-NK and cNK in the bone marrow of MM.1S-inoculated NSG mice treated with daratumumab or elotuzumab. FIG. 12C shows the number of g-NK and cNK in the blood of MM.1S-inoculated NSG mice treated with daratumumab or elotuzumab. N=6 for all arms. Values are mean±SE.

FIG. 13A shows the percentage of expanded g-NK cells, unexpanded NK-cells (CD3−/CD56+), and MM.1S cells expressing CD20. FIG. 13B shows the percentage of expanded g-NK cells, unexpanded NK-cells (CD3−/CD56+), and MM.1S cells expressing CD38. FIG. 13C shows the percentage of expanded g-NK cells, unexpanded NK-cells (CD3−/CD56+), and MM.1S cells expressing SLAMF7. FIG. 13D shows the percentage of cNK and g-NK expressing CD38 before and after expansion. N=3 for all arms. Values are mean±SE.

FIG. 14A shows ADCC activity of freshly isolated g-NK and cNK cells in combination with anti-Her2 (trastuzumab; Tras) against the ovarian cancer cell line SKOV3 (n=16). FIG. 14B shows ADCC activity of expanded g-NK and cNK cells in combination with anti-Her2 (trastuzumab; Tras) against the ovarian cancer cell line SKOV3 (n=5). FIG. 14C shows ADCC activity of expanded g-NK and cNK cells in combination with anti-EGFR (cetuximab) against the ovarian cancer cell line SKOV3 (n=4). Values are mean±SE.

FIG. 15A shows the effect of treatment with g-NK and trastuzumab (Tras+g-NK) on SKOV3 tumor burden in NSG mice relative to mice treated with trastuzumab only (Tras only). FIG. 15B shows the effect of treatment with g-NK and trastuzumab (Tras+g-NK) on survival in SKOV3-inoculated NSG mice relative to mice treated with cNK and trastuzumab (Tras+cNK). N=10 for all arms. FIG. 15C shows the effect of treatment with g-NK and trastuzumab (Tras+g-NK) on survival in SKOV3-inoculated NSG mice relative to mice treated with cNK and trastuzumab (Tras+cNK), Tras only, or vehicle.

FIG. 16A shows the number of g-NK and cNK in the blood of SKOV3-inoculated NSG mice treated with trastuzumab. FIG. 16B shows the number of g-NK and cNK in the spleen of SKOV3-inoculated NSG mice treated with trastuzumab. FIG. 16C shows the number of g-NK and cNK in the bone marrow of SKOV3-inoculated NSG mice treated with trastuzumab. N=6 for all arms. Values are mean±SE.

FIG. 17A shows ADCC activity of expanded g-NK and cNK cells in combination with anti-CD38 (daratumumab; Dara) against the multiple myeloma cell line ARH-77 (n=4). FIG. 17B shows ADCC activity of expanded g-NK and cNK cells in combination with anti-CD38 (daratumumab; Dara) against the multiple myeloma cell line MM.1R (n=4). Values are mean±SE.

FIGS. 18A and 18B depict ADCC activity of g-NK cells compared to conventional NK cells (cNK). FIG. 18A shows ADCC activity of freshly isolated g-NK and cNK cells in combination with anti-EGFR (cetuximab; Cet) against the colorectal cancer cell line SW-480 (n=16). FIG. 18B shows ADCC activity of expanded g-NK and cNK cells in combination with anti-EGFR (cetuximab) against the colorectal cancer cell line SW-480 (n=5). Values are mean±SE.

FIG. 20A shows the positive correlation between g-NK CD16 expression and ADCC against MM.1S cells (with daratumumab, Dara). FIG. 20B shows the positive correlation between g-NK CD16 expression and ADCC against MM.1S cells (with elotuzumab, Elo). FIG. 20C shows the positive correlation between g-NK CD16 expression and ADCC against the ovarian cancer SKOV3 (with trastuzumab, Tras). FIG. 20D shows the positive correlation between g-NK CD16 expression and ADCC against the colorectal cancer SW-480 (with cetuximab, Cet) cell lines. N=4 g-NK cell lines.

DETAILED DESCRIPTION

Figure 2A:
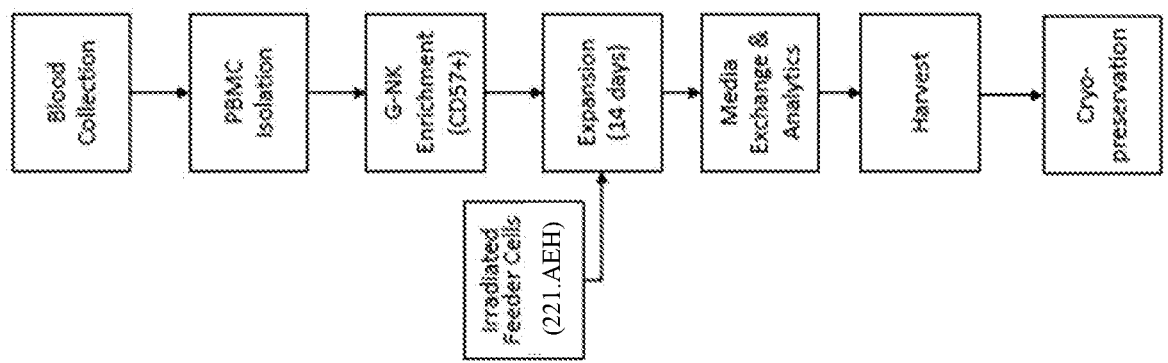
FIG. 2A depicts a flow diagram of an exemplary expansion protocol involving CD3 depletion followed by CD57 enrichment, such as is described in Example 2. In this schematic, irradiated PBMC also can be included as feeder cells, in addition to irradiated 221.AEH cells, during the expansion phase.

Provided herein are methods for the ex vivo expansion of NK cells that are positive for NKG2C (NKG2C$^{pos}$), including a specialized subset of Natural Killer (NK) cells that lack or are deficient in the FceRIγ (FcRγ) chain (referred to as g-NK cells). Also provided herein are kits and methods for detecting a g-NK subset of cells based on a surrogate surface marker profile. Thus, reference to g-NK cells in the present disclosure can, in some cases, include NK cells deficient in the FcRγ chain or cells having a surrogate surface marker profile of such cells.

Natural killer (NK) cells are innate lymphocytes important for mediating anti-viral and anti-cancer immunity through cytokine and chemokine secretion, and through the release of cytotoxic granules (Vivier et al. Science 331 (6013):44-49 (2011); Caligiuri, Blood 112(3):461-469 (2008); Roda et al., Cancer Res. 66(1):517-526 (2006)). NK cells are effector cells that comprise the third largest population of lymphocytes and are important for host immunosurveillance against tumor and pathogen-infected cells. However, unlike T and B lymphocytes, NK cells are thought to have only a limited capacity for target recognition using germline-encoded activation receptors (Bottino et al., Curr Top Microbiol Immunol. 298:175-182 (2006); Stewart et al., Curr Top Microbiol Immunol. 298:1-21 (2006)).

Activation of NK cells can occur through the direct binding of NK cell receptors to ligands on the target cell, as seen with direct tumor cell killing, or through the crosslinking of the Fc receptor (CD16; also known as CD16a or FcγRIIIa) by binding to the Fc portion of antibodies bound to an antigen-bearing cell. Upon activation, NK cells produce cytokines and chemokines abundantly and at the same time exhibit potent cytolytic activity. NK cells are capable of killing tumor cells via antibody dependent cell mediated cytotoxicity (ADCC). In some cases, ADCC is triggered when receptors on the NK cell surface (such as CD16) recognize IgG1 or IgG3 antibodies bound to the surface of a cell. This triggers release of cytoplasmic granules containing perforin and granzymes, leading to target cell death. Because NK cells express the activating Fc receptor CD16, which recognizes IgG-coated target cells, target recognition is broadened (Ravetch & Bolland, Annu Rev Immunol. 19:275-290 (2001); Lanier Nat. Immunol. 9(5):495-502 (2008); Bryceson & Long, Curr Opin Immunol. 20(3):344-352 (2008)). ADCC and antibody-dependent cytokine/chemokine production are primarily mediated by NK cells.

In addition to CD16 expressed on NK cells that is involved in antibody-dependent responses (such as NK cell-mediated ADCC), CD16 also exists in a glycosylphosphatidylinositol-anchored form (also known as FcγRIIIB or CD16B). It is understood that reference to CD16 herein is with reference to the CD16a form that is expressed on NK cells and is not meant to refer to the glycosylphosphatidylinositol-anchored form. The CD16 receptor is able to associate with adaptors, the ξ chain of the TCR-CD3 complex (CD3ξ) and/or the FcRγ chain, to transduce signals through immunoreceptor tyrosine-based activation motifs (ITAMs). In some aspects, CD16 engagement (CD16 crosslinking) initiates NK cell responses via intracellular signals that are generated through one, or both, of the CD16-associated adaptor chains, FcRγ or CD3ξ. Triggering of CD16 leads to phosphorylation of the γ or ξ chain, which in turn recruits tyrosine kinases, syk and ZAP-70, initiating a cascade of signal transduction leading to rapid and potent effector functions. The most well-known effector function is the release of cytoplasmic granules carrying toxic proteins to kill nearby target cells through the process of antibody-dependent cellular cytotoxicity. CD16 crosslinking also results in the production of cytokines and chemokines that, in turn, activate and orchestrate a series of immune responses.

This release of cytokines and chemokines can play a role in the anti-cancer activity of NK cells in vivo. NK cells also have small granules in their cytoplasm containing perforin and proteases (granzymes). Upon release from the NK cell, perforin forms pores in the cell membrane of targeted cells through which the granzymes and associated molecules can enter, inducing apoptosis. The fact that NK cells induce apoptosis rather than necrosis of target cells is significant-necrosis of a virus-infected cell would release the virions, whereas apoptosis leads to destruction of the virus inside the cells.

A specialized subset of NK cells lacking the FcRγ adaptor protein, also known as g-NK cells, are able to mediate robust ADCC responses (see e.g. published Patent Appl. No. US2013/0295044). The mechanism for increased responses may be due to changes in epigenetic modification that influence the expression of the FcRγ. The g-NK cells express the signaling adaptor ξ chain abundantly, but are deficient in the expression of the signaling adaptor γ chain. Compared to conventional NK cells, these γ-deficient g-NK cells exhibit dramatically enhanced activity when activated by antibodies. For example, the g-NK cells can be activated by antibody-mediated crosslinking of CD16 or by antibody-coated tumor cells. In some aspects, the g-NK cells produce greater amounts of cytokines (e.g. IFN-γ or TNF-α) and chemokines (e.g. MIP-1α, MIP-1β, and RANTES) and/or display higher degranulation responses than conventional NK cells expressing the γ chain. The g-NK cells provide high expression of Granzyme B, a component of natural killer cell cytotoxic machinery. Moreover, the g-NK cells have a prolonged lifespan, compared to conventional NK cells, and their presence is maintained long-term. In some embodiments, g-NK cells are functionally and phenotypically stable.

In some embodiments, g-NK cells are more effective in eliciting ADCC responses than conventional NK cells, e.g. NK cells that are not deficient in the γ chain. In some cases, ADCC is a mechanism of action of therapeutic antibodies, including anti-cancer antibodies. In some aspects, cell therapy by administering NK cells can be used in concert with antibodies for therapeutic and related purposes. Provided herein are methods involving combined administration of a composition containing g-NK cells, e.g. as produced by the provided methods, and an antibody, e.g. an anti-cancer antibody. In some embodiments, antibody-directed targeting of g-NK cells leads to improved outcomes for patients due to the improved affinity, cytotoxic and/or cytokine-mediated effect functions of the g-NK cell subset.

In some embodiments, the g-NK cells produce significantly greater amounts of a cytokine than natural killer cells that do express FcRγ. In another embodiment, the cytokine is interferon-gamma (IFN-γ), tumor necrosis factor-α (TNF-α), or a combination thereof. In one embodiment, the g-NK cells produce significantly greater amounts of a chemokine. In one embodiment, the chemokine is MIP-1α, MIP-1β or a combination thereof. In another embodiment, the g-NK cells produce the cytokine or the chemokine upon stimulation through the Fc receptor CD16.

g-NK cells represent a relatively small percentage of NK cells in the peripheral blood, thereby limiting the ability to use these cells in therapeutic methods. In particular, to utilize g-NK cells in the clinic, a high preferential expansion rate is necessary because g-NK cells are generally a rare population. Other methods for expanding NK cells are able to achieve thousand-fold 14-day NK-cell expansion rates, but they yield low differentiation, NKG2C$^{neg}$, FceRIγ$^{pos}$ (FcRγ$^{pos}$) NK-cells (Fujisaki et al. (2009) Cancer Res., 69:4010-4017; Shah et al. (2013) PLoS One, 8:e76781). Further, it is found herein that an expansion optimized for expanding NK cells that phenotypically overlap with g-NK cells does not preferentially expand g-NK cells to amounts that would support therapeutic use. In particular, it has been previously reported that NKG2C$^{pos}$ NK-cells, which exhibit phenotypic overlap with g-NK cells, can be preferentially expanded using HLA-E transfected 221.AEH cells (Bigley et al. (2016) Clin. Exp. Immunol., 185:239-251). Culture with such HLA-expressing cells that constitutively expresses HLA-E pushes the NK-cells in the direction of an NKG2C$^{pos}$/NKG2A$^{neg}$ phenotype (NKG2C is the activating receptor for HLA-E, while NKG2A is the inhibitory receptor for HLA-E). It was thought that because such cells include within it the g-NK, such methods would be sufficient to expand g-NK cells. As shown in the examples herein, however, this method does not achieve robust expansion of g-NK cells.

The provided methods overcome these limitations. The provided methods utilize a greater ratio of 221.AEH cells to NK-cells compared to previous methods. In particular, previous methods have used a lower ratio of 221.AEH cells, such as a ratio of 10:1 NK cell to 221.AEH ratio. It is found herein that a greater ratio of HLA-E-expressing feeder cells, such as 221.AEH cells, results in overall expansion that is greater and more skewed towards the g-NK phenotype. In some embodiments, the greater ratio of 221.AEH cells is possible by irradiating the feeder cells. Moreover, it also is found that inclusion of activated (e.g. anti-CD3-activated) autologous PBMCs, such as irradiated activated PBMCs, can be used as additional feeder cells to supercharge the expansion. In some aspects, the use of irradiated feeder cell lines also is advantageous because it provides for a method that is GMP compatible. The inclusion of recombinant IL-2 during the expansion also is found to support robust expansion.

It also is found that enrichment of NK cells from a cell sample prior to the expansion method, such as by enrichment for CD16 or CD57 cells prior to expansion, further substantially increases the amount of g-NK cell expansion that can be achieved compared to methods that initially enrich NK cells based on CD3 depletion alone. In another embodiment, another enrichment that can be carried out prior to expansion is enriching for NK cells by positive selection for CD56 and negative selection or depletion for CD38. In a further embodiment, another enrichment that can be carried out prior to expansion is enriching for NK cells by positive selection for CD56 followed by negative selection or depletion for NKG2A$^{neg}$ and negative selection or depletion for CD161$^{neg}$. In any of such embodiments, the enriched NK cells can be enriched from a cell sample containing NK cells, such as from peripheral blood mononuclear cells (PBMCs). In some embodiments, prior to the enrichment for NK cells from the cell sample, T cells can be removed by negative selection or depletion for CD3.

Together, the provided approach for expanding g-NK cells can achieve expansion of NK cells that exceeds over 1 billion cells, and in some cases up to 8 billion or more, from an initial 10 million enriched NK cells at the initiation of culture. In particular, the provided methods can result in high-yield (>1000 fold) expansion rates with maintained or, in some cases, increased functionality of the g-NK cells after expansion. Further, it is found that the provided methods are sufficient to expand previously frozen NK cells, which is not commonly achieved by many existing methods that involve rescue of thawed NK cells. In some embodiments, this is achieved by increasing the duration of the expansion protocol. In some embodiments, this is achieved by decreasing the ratio of 221.AEH feeder cells to NK cells, e.g. to about 1:1 221.AEH to NK cells. As shown herein, the provided methods yield g-NK cells that exhibit potent antibody-dependent cell-mediated cytotoxicity (ADCC), supporting the utility of such cells for therapeutic applications.

All references cited herein, including patent applications, patent publications, and scientific literature and databases, are herein incorporated by reference in their entirety for all purposes to the same extent as if each individual reference were specifically and individually indicated to be incorporated by reference.

For clarity of disclosure, and not by way of limitation, the detailed description is divided into the subsections that follow. The section headings used herein are for organizational purposes only and are not to be construed as limiting the subject matter described.

I. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, "antibody" refers to immunoglobulins and immunoglobulin fragments, whether natural or partially or wholly synthetically, such as recombinantly, produced, including any fragment thereof containing at least a portion of the variable heavy chain and/or light chain region of the immunoglobulin molecule that is sufficient to form an antigen binding site and, when assembled, to specifically bind antigen. Hence, an antibody includes any protein having a binding domain that is homologous or substantially homologous to an immunoglobulin antigen-binding domain (antibody combining site). Typically, antibodies minimally include all or at least a portion of the variable heavy ($V_H$) chain and/or the variable light ($V_L$) chain. In general, the pairing of a $V_H$ and $V_L$ together form the antigen-binding site, although, in some cases, a single $V_H$ or $V_L$ domain is sufficient for antigen-binding. The antibody also can include all or a portion of the constant region. Reference to an antibody herein includes full-length antibody and antigen-binding fragments. The term "immunoglobulin" (Ig) is used interchangeably with "antibody" herein.

The terms "full-length antibody," "intact antibody" or "whole antibody" are used interchangeably to refer to an antibody in its substantially intact form, as opposed to an antibody fragment. A full-length antibody is an antibody typically having two full-length heavy chains (e.g., VH-CH1-CH2-CH3 or VH-CH1-CH2-CH3-CH4) and two full-length light chains (VL-CL) and hinge regions, such as antibodies produced from mammalian species (e.g. human, mouse, rat, rabbit, non-human primate, etc.) by antibody secreting B cells and antibodies with the same domains that are produced synthetically. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Antibody fragments, include, but are not limited to, Fab fragments, Fab' fragments, F(ab')$_2$ fragments, Fv fragments, disulfide-linked Fvs (dsFv), Fd fragments, Fd' fragments; diabodies; linear antibodies (see U.S. Pat. No. 5,641,870, Example 2; Zapata et al., *Protein Eng.* 8(10): 1057-1062 [1995]); single-chain antibody molecules, including single-chain Fvs (scFv) or single-chain Fabs (scFab); antigen-binding fragments of any of the above and multispecific antibodies from antibody fragments. For purposes herein, an antibody fragment typically includes one that is sufficient to engage or crosslink CD16 on the surface of an NK cell.

The term "autologous" refers to cells or tissues originating within or taken from an individual's own tissues. For example, in an autologous transfer or transplantation of NK cells, the donor and recipient are the same person.

The term "allogeneic" refers to cells or tissues that belong to or are obtained from the same species but that are genetically different, and which, in some cases, are therefore immunologically incompatible. Typically, the term "allogeneic" is used to define cells that are transplanted from a donor to a recipient of the same species.

The term "enriched" with reference to a cell composition refers to a composition in which there is an increase in the number or percentage of the cell type or population as compared to the number or percentage of the cell type in a starting composition of the same volume, such as a starting composition directly obtained or isolated from a subject. The term does not require complete removal of other cells, cell type, or populations from the composition and does not require that the cells so enriched be present at or even near 100% in the enriched composition.

The term "expression" refers to the process by which a polynucleotide is transcribed from a DNA template (such as into an mRNA or other RNA transcript) and/or the process by which a transcribed mRNA is subsequently translated into peptide, polypeptides or proteins. Transcripts and encoded polypeptides may be collectively referred to as "gene product." If the polynucleotide is derived from genomic DNA, expression may include splicing of the mRNA in a eukaryotic cell.

The term "heterologous" with reference to a protein or nucleic acid refers to a protein or nucleic acid originating from a different genetic source. For example, a protein or nucleic acid that is heterologous to a cell originates from an organism or individual other than the cell in which it is expressed.

As used herein, the term "introducing" encompasses a variety of methods of introducing DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

The term "composition" refers to any mixture of two or more products, substances, or compounds, including cells or antibodies. It may be a solution, a suspension, liquid, powder, a paste, aqueous, non-aqueous or any combination thereof. The preparation is generally in such form as to permit the biological activity of the active ingredient (e.g. antibody) to be effective.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a kit is a packaged combination that optionally includes other elements, such as additional agents and instructions for use of the combination or elements thereof, for a purpose including, but not limited to, therapeutic uses.

As used herein, the term "treatment" or "treating" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disorder (e.g., an eosinophil-mediated disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum dose of cells required to effect a measurable improvement of a particular disorder. In some embodiments, a therapeutically effective amount is the amount of a composition that reduces the severity, the duration and/or the symptoms associated with cancer, viral infection, microbial infection, or septic shock in an animal. A therapeutically effective amount herein may vary according to factors such as the disease state, age, sex, and weight of the patient. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at the earlier stage of disease, the prophylactically effective amount can be less than the therapeutically effective amount.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is human.

II. METHODS FOR EXPANDING NATURAL KILLER CELL SUBSETS

Provided herein is a method for expanding a subset of NK cells from a biological sample from a human subject. In some embodiments, the methods can include expanding a subset of NK cells that are NKG2C$^{pos}$ from a biological sample from a human subject. In some embodiments, the methods can include expanding a subset of cells that are FcRγ-deficient NK cells (g-NK) from a biological sample from a human subject. In some embodiments, the method includes isolating a population of cells enriched for natural killer (NK) cells from a biological sample from a human subject and culturing the cells under conditions in which preferential growth and/or expansion of the g-NK cell subject and/or an NK cell subset that overlaps or shares extracellular surface markers with the g-NK cell subset. For example, the NK cells may be cultured using feeder cells, or in the presence of cytokines to enhance the growth and/or expansion of g-NK cell subject and/or an NK cell subset that overlaps or shares extracellular surface markers with the g-NK cell subset. In some aspects, the provided methods also can expand other subsets of NK cells, such as any NK cell that is NKG2C$^{pos}$.

In some embodiments, the sample, e.g. biological sample, is one containing a plurality of cell populations that includes an NK cell population. In some embodiments, the biological sample is or comprises blood cells, e.g. peripheral blood mononuclear cells. In some aspects, the biological sample is a whole blood sample, an apheresis product or a leukapheresis product. In some embodiments, the sample is a sample of peripheral blood mononuclear cells (PBMCs). Thus, in some embodiments of the provided methods, a population of peripheral blood mononuclear cells (PBMCs) can be obtained. The sample containing a plurality of cell populations that includes an NK cell population can be used as the cells for enriching or selecting an NK cell subset for expansion in accord with the provided methods.

In some embodiments, the biological sample is from a subject that is a healthy subject. In some embodiments, the biological sample is from a subject that has a disease of conditions, e.g. a cancer.

In some embodiments, the cells are isolated or selected from a sample, such as a biological sample, e.g., one obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom. In some aspects, the sample is blood or a blood-derived sample, or is or is derived from an apheresis or leukapheresis product.

In some examples, cells from the circulating blood of a subject are obtained. The samples, in some aspects, contain lymphocytes, including NK cells, T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient, such as by using a Histopaque® density centrifugation.

In some embodiments, the biological sample is from a leukopak enriched leukapheresis product collected from normal peripheral blood. In some embodiments, the leukopak can contain fresh cells. In some embodiments, the leukopak is a cryopreserved sample that is thawed for use in the provided methods.

In some embodiments, the source of biological cells contains from at or about $5\times10^5$ to at or about $5\times10^8$ NK cells or a g-NK cell subset or an NK cell subset that is associated with or includes a surrogate marker for g-NK cells. In some embodiments, the number of NK cells, or a g-NK cell subset or an NK cell subset that is associated with or includes a surrogate marker for g-NK cells, in the biological sample is from at or about $5\times10^5$ to at or about $1\times10^8$, from at or about $5\times10^5$ to at or about $5\times10^7$, from at or about $5\times10^5$ to at or about $1\times10^7$, from at or about $5\times10^5$ to at or about $5\times10^6$, from at or about $5\times10^5$ to at or about $1\times10^6$, from at or about $1\times10^6$ to at or about $1\times10^8$, from at or about $1\times10^6$ to at or about $5\times10^7$, from at or about $1\times10^6$ to at or about $1\times10^7$, from at or about $1\times10^6$ to at or about $5\times10^6$, from at or about $5\times10^6$ to at or about $1\times10^8$, from at or about $5\times10^6$ to at or about $5\times10^7$, from at or about $5\times10^6$ to at or about $1\times10^7$, from at or about $1\times10^7$ to at or about $1\times10^8$, from at or about $1\times10^7$ to at or about $5\times10^7$, or from at or about $5\times10^7$ to at or about $1\times10^8$.

In some embodiments, the biological sample is from a subject that is CMV seropositive. CMV infection can result in phenotypic and functional differentiation of NK cells, including development of high fractions of NK cells expressing NKG2C that exhibit enhanced antiviral activity. CMV-associated NK cells expressing NKG2C display altered DNA methylation patterns and reduced expression of signaling molecules, such as FcRγ (Schlums et al., Immunity (2015) 42:443-56). These NK cells are linked to more potent antibody-dependent activation, expansion, and function relative to conventional NK-cell subsets. In some cases, the biological sample can be from a subject that is CMV seronegative as NK cells with reduced expression of FcRγ can also be detected in CMV seronegative individuals, albeit generally at lower levels. In some cases, the biological sample can be from CMV seropositive individuals.

In some embodiments, NK cells from the subject bear a single nucleotide polymorphism (SNP rs396991) in the CD16 gene, nucleotide 526 [thymidine (T)→guanine (G)] resulting in an amino acid (aa) substitution of valine (V) for phenylalanine (F) at position 158 in the mature (processed) form of the protein (F158V, also called 158V+ herein). It has been found that the CD16 F158V polymorphism is associated with substantially higher affinity for IgG1 antibodies and have the ability to mount more robust NK cell-mediated ADCC responses (Mellor et al. (2013) Journal of Hematology & Oncology, 6:1; Musolino et al. (2008) Journal of Clinical Oncology, 26:1789-1796 and Hatjiharissi et al. (2007) Blood, 110:2561-2564). In some embodiments, antibody-directed targeting of CD16 158V+/g-NK cells leads to improved outcomes for patients due to the improved affinity, cytotoxic and/or cytokine-mediated effect functions of the CD16 158V+/g-NK cell subset.

In some embodiments, the provided methods include enriching or isolating NK cells or a subset thereof from a biological sample of a subject identified as having the CD16 158V+ NK cell genotype. In some embodiments, the method includes screening subjects for the presence of the CD16 158V+ NK cell genotype. In some embodiments, genomic DNA is extracted from a sample from a subject that is or includes NK cells, such as blood sample or bone marrow sample. In some embodiments, the sample is or comprises blood cells, e.g. peripheral blood mononuclear cells. In some embodiments, the sample is or comprises isolated NK cells. In some embodiments, the sample is a sample from a healthy donor subject. Any method for extracting DNA from the sample can be employed. For instance, nucleic acids can be readily isolated from a sample, e.g. cells, using standard techniques such as guanidium thiocyanate-phenol-chloroform extraction (Chomocyznski et al. (1987) Anal. Biochem. 162: 156). Commercially available kits also are readily available for extracting genomic DNA, such as the Wizard genomic DNA purification kit (Promega, Madison, WI).

Genotyping can be performed on any suitable sample. In any of the embodiments described herein, the genotyping reaction can be, for example, a pyrosequencing reaction, DNA sequencing reaction, Mass ARRAY MALDI-TOF, RFLP, allele-specific PCR, real-time allelic discrimination, or microarray. In some embodiments, a PCR-based technique, such as RT-PCR, of genomic DNA is carried out using allele-specific primers for the polymorphism. The PCR method for amplifying target nucleic acid sequences in a sample is well known in the art and has been described in, e.g., Innis et al. (eds.) PCR Protocols (Academic Press, N Y 1990); Taylor (1991) Polymerase chain reaction: basic principles and automation, in PCR: A Practical Approach, McPherson et al. (eds.) IRL Press, Oxford; Saiki et al. (1986) Nature 324: 163; as well as in U.S. Pat. Nos. 4,683,195, 4,683,202 and 4,889,818, all incorporated herein by reference in their entireties.

Primers for detecting the 158V+ polymorphism are known or can be easily designed by a skilled artisan, See. e.g. International published PCT Appl. No. WO2012/061814; Kim et al. (2006) Blood, 108:2720-2725; Cartron et al. (2002) Blood, 99:754-758; Koene et al. (1997) Blood, 90:1109-1114; Hatjiharissi et al. (2007) Blood, 110:2561-2564; Somboonyosdech et al. (2012) Asian Biomedicine, 6:883-889). In some embodiments, PCR can be carried out using nested primers followed by allele-specific restriction enzyme digestion. In some embodiments, the first PCR primers comprise nucleic acid sequences 5'-ATA TTT AC A GAA TGG CAC AGG-3' (SEQ ID NO:2) and 5'-GAC TTG GTA CCC AGG TTG AA-3' (SEQ ID NOG), while the second PCR primers are 5'-ATC AGA TTC GAT CCT ACT TCT GCA GGG GGC AT-3' (SEQ ID NO:4) and 5'-ACG TGC TGA GCT TGA GTG ATG GTG ATG TTC AC-3' (SEQ ID NOG), which, in some cases, generates a 94-bp fragment depending on the nature of allele. In some embodiments, the primer pair comprises the nucleic acid sequences set forth in SEQ ID NOG (CCCAACTCAA CTTCCCAGTG TGAT) and SEQ ID NOG (GAAATC-TACC TTTTCCTCTA ATAGGGCAAT). In some embodiments, the primer pair comprises the nucleic acid sequences set forth in SEQ ID NOG (CCCAACTCAA CTTCCCAGTG TGAT) and SEQ ID NOG (GAAATC-TACC TTTTCCTCTA ATAGGGCAA). In some embodiments, the primer pair comprises the nucleic acid sequences set forth in SEQ ID NOG (CCCAACTCAA CTTCCCAGTG TGAT) and SEQ ID NO:9 (GAAATC-TACC TTTTCCTCTA ATAGGGCA).

In some embodiments, genotyping can be carried out by quantitative real-time RT-PCR following extraction of RNA using primer sequences as follows: CD16 sense set forth in SEQ ID NO: 10 (5'-CCAAAAGCCACACTCAAAGAC-3') and antisense set forth in SEQ ID NO: 11 (5ACCCAGGTG-GAAAGAATGATG-3') and TaqMan probe set forth in SEQ ID NO: 12 (5'-AACATCACCATCACTCAAGGTTTGG-3').

To confirm the genotyping, allele specific amplification can be used with a set of V allele specific primers (e.g. forward primer set forth in SEQ ID NO: 13, 5'-CTG AAG ACA CAT TTT TAC TCC CAAA-3'; and reverse primer set forth in SEQ ID NO:14, 5'-TCC AAA AGC CAC ACT CAA AGA C-3') or a set of F allele specific primers (e.g., forward primer set forth in SEQ ID NO: 15, 5'-CTG AAG ACA CAT TTT TAC TCC CAAC-3'; and reverse primer set forth in SEQ ID NO: 14, 5'-TCC AAA AGC CAC ACT CAA AGA C-3').

The genomic sequence for CD16a is available in the NCBI database at NG_009066.1. The gene ID for CD16A is 2214. Sequence information for CD16, including gene polymorphisms, is available at UniProt Acc. No. P08637. The sequence of CD16 (F158) is set forth in SEQ ID NO: 16 (residue F158 is bold and underlined). In some embodiments, CD16 (F158) further comprises a signal peptide set forth as MWQLLLPTALLLLVSA (SEQ ID NO:17).

(SEQ ID NO: 16)
GMRTEDLPKAVVFLEPQWYRVLEKDSVTLKCQGAYSPEDNSTQWFHNES

LISSQASSYFIDAATVDDSGEYRCQTNLSTLSDPVQLEVHIGWLLLQAP

RWVFKEEDPIHLRCHSWKNTALHKVTYLQNGKGRKLYFHHNSDFYIPKA

TLKDSGSYFCRGL<u>F</u>GSKNVSSETVNITITQGLAVSTISSFFPPGYQVSF

CLVMVLLFAVDTGLYFSVKTNIRSSTRDWKDHKFKWRKDPQDK

The sequence of CD16 158V+(polymorphism resulting in F158V) is known as VAR_003960 and has the sequence set forth in SEQ ID NO: 18 (158V+ polymorphism is in bold and underline). In some embodiments, CD16 (158V+) further comprises a signal peptide set forth as MWQLLLP-TALLLLVSA (SEQ ID NO: 17).

(SEQ ID NO: 18)
GMRTEDLPKAVVFLEPQWYRVLEKDSVTLKCQGAYSPEDNSTQWFHNES

LISSQASSYFIDAATVDDSGEYRCQTNLSTLSDPVQLEVHIGWLLLQAP

RWVFKEEDPIHLRCHSWKNTALHKVTYLQNGKGRKYFHHNSDFYIPKAT

LKDSGSYFCRGL<u>V</u>GSKNVSSETVNITITQGLAVSTISSFFPPGYQVSFC

LVMVLLFAVDTGLYFSVKTNIRSSTRDWKDHKFKWRKDPQDK

In some embodiments, single nucleotide polymorphism (SNP) analysis is employed on genomic deoxyribonucleic acid (DNA) samples using allele-specific probes containing a fluorescent dye label (e.g. FAM or VIC) on the 5' end and a minor groove binder (MGB) and nonfluorescent quencher (NFQ) on the 3' end and an unlabeled PCR primers to detect a specific SNP targets. In some embodiments, the assay measures or detects the presence of an SNP by a change in fluorescence of the dyes associated with the probe. In such embodiments, probes hybridize to the target DNA between the two unlabeled primers and signal from the fluorescent dye on the 5' end is quenched by the NFQ on its 3' end by fluorescence resonance energy transfer (FRET). During PCR, Taq polymerase extends the unlabeled primers using the template as a guide and when the polymerase reaches the labeled probe, it cleaves the molecule separating the dye from the quencher. In some aspects, a qPCR instrument can detect fluorescence from the unquenched label. Exemplary reagents are commercially available SNP Assays, e.g. code C_25815666_10 for rs396991 (Applied Biosystems, Cat No. 4351379 for SNP genotyping of V158F in CD16).

In some embodiments, subjects heterozygous or homozygous for the CD16 158V+(V158F) polymorphism are identified. In some embodiments, subjects homozygous for the CD16 158V+(V158F) polymorphism are identified. In some embodiments, NK cells or an NK cell subset are isolated or enriched from a biological sample from a subject identified as being heterozygous or homozygous for the CD16 158 V+ polymorphism. In some embodiments, NK cells or an NK cell subset are isolated or enriched from a biological sample from a subject identified as being homozygous for the CD16 158 V+ polymorphism.

In some embodiments, the method includes enriching NK cells from the biological sample, such as from a population PBMCs isolated or obtained from the subject. In some embodiments, the population of cells enriched for NK cells is enriched by isolation or selection based on one or more natural killer cell-specific markers. It is within the level of a skilled artisan to choose particular markers or combinations of surface markers. In some embodiments, the surface marker(s) is any one or more of the from the following surface antigens CD11a, CD3, CD7, CD14, CD16, CD19, CD25, CD27, CD56, CD57, CD161, CD226, NKB1, CD62L; CD244, NKG2D, NKp30, NKp44, NKp46, NKG2A, NKG2C, KIR2DL1 and/or KIR2DL3. In some embodiments, the surface marker(s) is any one or more of the from the following surface antigens CD11a, CD3, CD7, CD14, CD16, CD19, CD25, CD27, CD38 CD56, CD57, CD161, CD226, NKB1, CD62L; CD244, NKG2D, NKp30, NKp44, NKp46, NKG2A, NKG2C, SLAMF7 (CD319), KIR2DL1 and/or KIR2DL3. In particular embodiments, the one or more surface antigen includes CD3 and one or more of the following surface antigens CD16, CD56 or CD57. In some embodiments, the one or more surface antigen is CD3 and CD57. In some embodiments, the one or more surface antigen is CD3, CD56 and CD16. In other embodiments, the one or more surface antigen is CD3, CD56 and CD38. In further embodiments, the one or more surface antigen is CD3, CD56, NKG2A and CD161. Reagents, including fluorochrome-conjugated antibodies, for detecting such surface antigens are well known and available to a skilled artisan.

In some embodiments, the NK cell population is enriched, such as by isolation or selection, from a sample by the provided methods are cells that are positive for (marker+) or express high levels (marker$^{high}$) of one or more particular markers, such as surface markers, or that are negative for (marker−) or express relatively low levels (marker$^{low}$) of one or more markers. In some cases, such markers are those that are absent or expressed at relatively low levels on certain populations of NK cells but are present or expressed at relatively higher levels on certain other populations of lymphocytes (such as T cells). In some cases, such markers are those that are present or expressed at relatively higher levels on certain populations of NK cells but are absent or expressed at relatively low levels on certain other populations of lymphocytes (such as T cells or subsets thereof).

In some embodiments, any known method for separation based on such markers may be used. In some embodiments, the separation is affinity- or immunoaffinity-based separation. For example, the isolation in some aspects includes separation of cells and cell populations based on the expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells. For example, in some aspects, a negative selection for CD3 enriches for a population of cells that are CD3$^-$, but also can contain some residual or small percentage of other non-selected cells, which can, in some cases, include a small percentage of cells still being present in the enriched population that are CD3$^+$. In some examples, a positive selection of one of the CD57+ or CD16+ population enriches for said population, either the CD57+ or CD16+ population, but also can contain some residual or small percentage of other non-selected cells, which can, in some cases, include the other of the CD57 or CD16 population still being present in the enriched population.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some aspects, the selection includes positive and/or negative selection steps based on expression of one or more of the surface antigens, such as in cells from a PBMC sample. In some embodiments, the isolation includes positive selection for cells expressing CD56, cells expressing CD16 or cells expressing CD57 and/or negative selection for cells expressing CD38 and/or negative selection for cells expressing non-NK cell markers, such as T cell markers, for example, negative selection for cells expressing CD3 (CD3$^{neg}$). For example, in some embodiments, the isolation includes positive selection for cells expressing CD56, cells expressing CD16 or cells expressing CD57 and/or negative selection for cells expressing non-NK cell markers, such as T cell markers, for example, negative selection for cells expressing CD3 (CD3$^{neg}$). In some embodiments, the isolation includes positive selection for cells expressing CD56, cells expressing CD16 or cells expressing CD57, and/or negative selection for cells expressing CD38 (CD38$^{neg}$), CD161 (CD161$^{neg}$), NKG2A (NKG2A$^{neg}$), and/or negative selection for cells expressing CD3 (CD3$^{neg}$). In some embodiments, the selection includes isolation of cells negative for CD3 (CD3$^{neg}$).

In some embodiments, the isolation includes negative selection for cells expressing CD3 (CD3$^{neg}$) and positive selection for cells expressing CD56 (CD56$^{pos}$). In some embodiments, the selection can further include negative selection for cells expressing CD38 (CD38$^{neg}$). In specific embodiments, the isolated or selected cells are CD3$^{neg}$CD56$^{pos}$CD38$^{neg}$.

In some embodiments, the selection includes negative selection for cells expressing CD3 (CD3$^{neg}$), positive selection for cells expressing CD56 (CD56$^{pos}$), followed by negative selection for cells expressing NKG2A (NKG2A$^{neg}$) and CD161 (CD161$^{neg}$). In specific embodiments, the isolated or selected cells are CD3$^{neg}$CD56$^{pos}$NKG2A$^{neg}$CD161$^{neg}$.

In some embodiments, the selection includes negative selection for cells expressing CD3 (CD3$^{neg}$) and positive selection for cells expressing CD57 (CD57$^{pos}$). In specific embodiments, the isolated or selected cells are CD3$^{neg}$CD57$^{pos}$.

In some embodiments, the selection includes negative selection for cells expressing CD3 (CD3$^{neg}$) and positive for cells expressing CD16 (CD16$^{pos}$). In specific embodiments, the isolated or selected cells are CD3$^{neg}$CD16$^{pos}$. In some of any of the provided embodiments, the g-NK cells are cells having a g-NK surrogate surface marker profile. In some embodiments, the g-NK cell surrogate surface marker profile is CD16$^{pos}$/CD57$^{pos}$/CD7$^{dim/neg}$/CD161$^{neg}$. In some embodiments, the g-NK cell surrogate surface marker profile is NKG2A$^{neg}$/CD161$^{neg}$. In some of any such embodiments, the g-NK cell surrogate surface marker profile is CD38$^{neg}$. In some of any such embodiments, the g-NK cell surrogate surface marker profile further includes CD45$^{pos}$/CD3$^{neg}$/CD56$^{pos}$. In particular embodiments the g-NK cell surrogate surface marker profile includes CD45$^{pos}$/CD3$^{neg}$/CD56$^{pos}$/CD16$^{pos}$/CD57$^{pos}$/CD7$^{dim/neg}$/CD161$^{neg}$. In other particular embodiments, the g-NK cell surrogate surface marker profile includes CD45$^{pos}$/CD3$^{neg}$/CD56$^{pos}$/NKG2A$^{neg}$/CD161$^{neg}$. In other particular embodiments, the g-NK cell surrogate surface marker profile includes CD45$^{pos}$/CD3$^{neg}$/CD56$^{pos}$/CD38$^{neg}$.

In some embodiments, the methods of isolating, selecting and/or enriching for cells, such as by positive or negative selection based on the expression of a cell surface marker or markers, can include immunoaffinity-based selections. In some embodiments, the immunoaffinity-based selections include contacting a sample containing cells, such as PBMCs, with an antibody or binding partner that specifically binds to the cell surface marker or markers. In some embodiments, the antibody or binding partner is bound to a solid support or matrix, such as a sphere or bead, for example microbeads, nanobeads, including agarose, magnetic bead or paramagnetic beads, to allow for separation of cells for positive and/or negative selection. In some embodiments, the spheres or beads can be packed into a column to effect immunoaffinity chromatography, in which a sample containing cells, such as PBMCs, is contacted with the matrix of the column and subsequently eluted or released therefrom.

The incubation generally is carried out under conditions whereby the antibodies or binding partners, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the magnetically responsive particles are left attached to the cells that are to be subsequently incubated and/or cultured; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some of any of such embodiments, the method comprises administering IL-12, IL-15, IL-18, IL-2 and/or CCL5 to the subject prior to enriching, such as selecting and/or isolating, the NK cells or subset thereof.

In embodiments of the provided methods, the enriched NK cells are incubated or cultured in the presence of feeder cells, such as under conditions to support the proliferation and expansion of NK cell subsets, and in particular the g-NK cell subset.

In particular aspects, the feeder cells include cells that stimulate or promote expansion of NKG2C+ and/or inhibit expansion of NKG2A+ cells. In some embodiments, the feeder cells are cells that express or are transfected with HLA-E or a hybrid HLA-E containing the HLA-A2 signal sequence. For example, exemplary of such a hybrid is an AEH hybrid gene containing an MHC class I, such as HLA-A2, promoter and signal sequence and the HLA-E mature protein sequence, which, in some cases, can result in a mature protein identical to that encoded by the HLA-E gene but that can be stably expressed on the cell surface (see e.g. Lee et al. (1998) Journal of Immunology, 160:4951-4960). In some embodiments, the cell is an LCL 721.221, K562 cell or RMA-S cell that is transfected to express an MHC-E molecule stabilized in the presence of an MHC class I, such as HLA-A2, leader sequence. Cells lines that are engineered to express cell surface HLA-E stabilized in the presence of an MHC class I, such as HLA-A2, leader sequence peptide are known in the art (Lee et al. (1998) Journal of Immunology, 160:4951-4960; Zhongguo et al. (2005) 13:464-467; Garcia et al. (2002) Eur J. Immunol., 32:936-944). In some embodiments, irradiated 221.AEH cells can be used as feeder cells or any other HLA-E transfected cell line that is otherwise HLA negative, such as K562. Exemplary of such as cell line for use in the methods provided herein are 221-AEH cells.

In particular embodiments, the HLA-E-expressing feeder cells, e.g. 221.AEH cells, added to the culture are non-dividing, such as by gamma irradiation. In some embodiments, the HLA-E-expressing feeder cells are irradiated with gamma rays in the range of about 1000 to 10000 rad, such as 1000-5000, rads to prevent cell division. In some embodiments, the HLA-E-expressing feeder cells are irradiated with gamma rays in the range of about 10 Gy to 100 Gy, such as 10-50 Gy to prevent cell division.

In some embodiments, the enriched, selected and/or isolated NK cells are incubated or cultured in the presence of HLA-E-expressing feeder cells (e.g. 221.AEH cells), such as an irradiated population thereof, at a ratio of feeder cells to enriched NK cells that is greater than or about 1:10 HLA-E feeder cells (e.g. 221.AEH cells), such as an irradiated population thereof, to enriched NK cells, such as from at or about 1:10 and at or about 10:1 of such feeder cells to enriched NK cells.

In some embodiments, the ratio of HLA-E-expressing feeder cells (e.g. 221.AEH cells), such as an irradiated population thereof, is at a ratio of such feeder cells to enriched NK cells that is between at or about 1:10 and at or about 10:1, between at or about 1:10 and at or about 5:1, between at or about 1:10 and at or about 2.5:1, between at or about 1:10 and at or about 1:1, between at or about 1:10 and at or about 1:2.5, between at or about 1:10 and at or about 1:5, between at or about 1:5 and at or about 10:1, between at or about 1:5 and at or about 5:1, between at or about 1:5 and at or about 2.5:1, between at or about 1:5 and at or about 1:1, between at or about 1:5 and at or about 1:2.5, between at or about 1:2.5 and at or about 10:1, between at or about 1:2.5 and at or about 5:1, between at or about 1:2.5 and at or about 2.5:1, between at or about 1:2.5 and at or about 1:1, between at or about 1:1 and at or about 10:1, between at or about 1:1 and at or about 5:1, between at or about 1:1 and at or about 2.5:1, between at or about 2.5:1 and at or about 10:1, between at or about 2.5:1 and at or about 5:1 or between at or about 5:1 and at or about 10:1, each inclusive.

In some embodiments, the ratio of HLA-expressing feeder cells (e.g. 221.AEH cells), such as an irradiated population thereof, is at a ratio of such feeder cells to enriched NK cells that is at or about 1.25:1, 1.5:1, 1.75:1, 2.0:1, 2.25:1, 2:5:1, 2.75:1, 3.0:1, 3.25:1, 3.5:1, 3.75:1, 4.0:1, 4.25:1, 4.5:1, 4.75:1 or 5:1, or any value between any of the foregoing. In some embodiments, the ratio of HLA-expressing feeder cells (e.g. 221.AEH cells), such as an irradiated population thereof, is at a ratio of such feeder cells to enriched cells that is less than or less than about 5:1. In some embodiments, the ratio of HLA-expressing feeder cells (e.g. 221.AEH cells), such as an irradiated population thereof, is at a ratio between at or about 1:1 and 2.5:1, inclusive. In some embodiments, the ratio of HLA-expressing feeder cells (e.g. 221.AEH cells), such as an irradiated population thereof, is at a ratio of at or about 2.5:1.

In some cases if the starting NK cell population has been cryopreserved prior to expansion, i.e. subject to freeze/thaw, a lower 221.AEH to NK-cell ratio can be employed than for methods using fresh NK cells. It is found here that a ratio of 1:1 221.AEH to freeze/thaw NK-cell resulted in comparable expansion in a culture containing a ration of 2.5:1 221.AEH to fresh NK cells. In some aspects, the lower ratio ensures a higher number of NK cells in the culture to permit more cell-to-cell contact, which may play a role in promoting initial growth and expansion. In some embodiments, if initial enriched population of NK cells from a sample has been subject to freeze/thaw, a ratio of at or about 2:1 to 1:2 221.AEH to freeze/thaw NK-cells is used. In particular embodiments, the ratio is 1:1. It is understood that higher ratio, such as 2.5:1 221.AEH to freeze/thaw NK-cells can be used, but this may require a longer culture, e.g. at or about 21 days, to reach a desired threshold density or number.

In some embodiments, the NK cells are expanded by further adding to the culture non-dividing peripheral blood mononuclear cells (PBMC). In some aspects, the non-dividing feeder cells can comprise gamma-irradiated PBMC feeder cells. In some embodiments, the PBMC are irradiated with gamma rays in the range of about 1000 to 10000 rad, such as 1000-5000, rads to prevent cell division. In some embodiments, the PBMC are irradiated with gamma rays in the range of about 10 Gy to 100 Gy, such as 10-50 Gy to prevent cell division. In some aspects, during at least a portion of the incubation, the irradiated feeder cells are present in the culture medium at the same time as the non-dividing (e.g. irradiated) HLA-E-expressing feeder cells. In some aspects, the non-dividing (e.g. irradiated) PBMC feeder cell, HLA-E-expressing feeder cells and enriched NK cells are added to the culture on the same day, such as on the day of the initiation of the incubation, e.g. at or about or near the same time.

In some embodiments, the incubation or culture is further carried out in the presence of irradiated PBMCs as feeder cells. In some embodiments, the irradiated PBMC feeder cells are autologous to, or from the same subject as, the enriched NK cells were isolated or selected. In particular embodiments, the PBMCs are obtained from the same biological sample, e.g. whole blood or leukapheresis or apheresis product, as used to enrich the NK cells. Once obtained, a portion of the PBMCs are reserved for irradiation prior to enrichment of NK cells as described above.

In some embodiments, irradiated PBMCs are present as feeder cells at a ratio of such feeder cells to enriched NK cells that is from at or about 1:10 to at or about 10:1, from at or about 1:10 to at or about 5:1, from at or about 1:10 to at or about 2.5:1, from at or about 1:10 to at or about 1:1, from at or about 1:10 to at or about 1:2.5, from at or about 1:10 to at or about 1:5, from at or about 1:5 to at or about 10:1, from at or about 1:5 to at or about 5:1, from at or about 1:5 to at or about 2.5:1, from at or about 1:5 to at or about 1:1, from at or about 1:5 to at or about 1:2.5, from at or about 1:2.5 to at or about 10:1, from at or about 1:2.5 to at or about 5:1, from at or about 1:2.5 to at or about 2.5:1, from at or about 1:2.5 to at or about 1:1, from at or about 1:1 to at or about 10:1, from at or about 1:1 to at or about 5:1, from at or about 1:1 to at or about 2.5:1, from at or about 2.5:1 to at or about 10:1, from at or about 2.5:1 to at or about 5:1 or from at or about 5:1 to at or about 10:1.

In some embodiments, the irradiated PBMCs are present as feeder cells at a ratio of such feeder cells to enriched NK cells that is between at or about 1:1 and at or about 5:1, such as at or about 1.25:1, 1.5:1, 1.75:1, 2.0:1, 2.25:1, 2:5:1, 2.75:1, 3.0:1, 3.25:1, 3.5:1, 3.75:1, 4.0:1, 4.25:1, 4.5:1, 4.75:1 or 5:1, or any value between any of the foregoing. In some embodiments, the irradiated PBMCs are present at a ratio of such feeder cells to enriched cells that is or is about 5:1.

In particular embodiments, during at least a portion of the incubation or culture one or more cells or cell types, such as T cells, of the irradiated PBMCs are activated and/or the incubation or culture is carried out in the presence of at least one stimulatory agent that is capable of stimulating the activation of one or more T cells of the PBMC feeder cells. In some embodiments, at least one stimulatory agent specifically binds to a member of a TCR complex. In some embodiments, the at least one stimulatory agent specifically binds to a CD3, optionally a CD3epsilon. In some aspects, the at least one stimulatory agent is an anti-CD3 antibody or antigen binding fragment. An exemplary anti-CD3 antibody includes mouse anti-human CD3 (OKT3).

In some embodiments, the anti-CD3 antibody or antigen-binding fragment is present during at least a portion of the incubation that includes irradiated PBMC feeder cells. In some embodiments, the anti-CD3 antibody or antigen-binding fragment is added to the culture or incubation at or about the same time as the irradiated PBMCs. For example, the anti-CD3 antibody or antigen-binding fragment is added at or about at the initiation of the incubation or culture. In particular aspects, the anti-CD3 antibody or antigen-binding fragment may be removed, or its concentration reduced, during the course of the culture or incubation, such as by exchanging or washing out the culture medium. In particular embodiments, after exchanging or washing, the methods do not include adding back or replenishing the culture media with the anti-CD3 antibody or antigen-binding fragment.

In some embodiments, the anti-CD3 antibody or antigen-binding fragment is added, or is present during at least a portion of the culture or incubation, at a concentration that is between at or about 10 ng/mL and at or about 5 µg/mL, such as between at or about 10 ng/mL and at or about 2 µg/mL, between at or about 10 ng/mL and at or about 1 µg/mL, between at or about 10 ng/mL and at or about 500 ng/mL, between at or about 10 ng/mL and at or about 100 ng/mL, between at or about 10 ng/mL and at or about 50 ng/mL, between at or about 50 ng/mL and at or about 5 µg/mL, such as between at or about 50 ng/mL and at or about 2 µg/mL, between at or about 50 ng/mL and at or about 1 µg/mL, between at or about 50 ng/mL and at or about 500 ng/mL, between at or about 50 ng/mL and at or about 100 ng/mL, between at or about 100 ng/mL and at or about 5 µg/mL, between at or about 100 ng/mL and at or about 2 µg/mL, between at or about 100 ng/mL and at or about 1 µg/mL, between at or about 100 ng/mL and at or about 500 ng/mL, between at or about 500 ng/mL and at or about 5 µg/mL, between at or about 500 ng/mL and at or about 2 µg/mL, between at or about 500 ng/mL and at or about 1 µg/mL, between at or about 1 µg/mL and at or about 5 µg/mL, between at or about 1 µg/mL and at or about 2 µg/mL, or between at or about 2 µg/mL and at or about 5 µg/mL, each inclusive. In some embodiments, the concentration of the anti-CD3 antibody or antigen-binding fragment is at or about 10 ng/mL, 20 ng/mL, 30 ng/mL, 40 ng/mL, 50 ng/mL, 60 ng/mL, 70 ng/mL, 80 ng/mL, 90 ng/mL or 100 ng/mL, or any value between any of the foregoing. In some embodiments, the concentration of the anti-CD3 antibody or antigen-binding fragment is or is about 50 ng/mL.

In some embodiments, the term "antibody" refers to immunoglobulin molecules and antigen-binding portions or fragments of immunoglobulin (Ig) molecules, i.e., molecules that contain an antigen binding site that specifically binds (immunoreacts with) an antigen. The term antibody encompasses not only intact polyclonal or monoclonal antibodies, but also fragments thereof, such as dAb, Fab, Fab', F(ab')$_2$, Fv), single chain (scFv) or single domain antibody (sdAb). Typically, an "antigen-binding fragment" contains at least one CDR of an immunoglobulin heavy and/or light chain that binds to at least one epitope of the antigen of interest. In this regard, an antigen-binding fragment may comprise 1, 2, 3, 4, 5, or all 6 CDRs of a variable heavy chain (VH) and variable light chain (VL) sequence from antibodies that bind the antigen, such as generally six CDRs for an antibody containing a VH and a VL ("CDR1," "CDR2" and "CDR3" for each of a heavy and light chain), or three CDRs for an antibody containing a single variable domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain (V$_H$) regions, single-chain antibody molecules such as scFvs and single-domain V$_H$ single antibodies; and multispecific antibodies formed from antibody fragments. In particular embodiments, the antibodies are single-chain antibody fragments comprising a variable heavy chain region and/or a variable light chain region, such as scFvs In some embodiments, the incubation or culture is initiated in the presence of such enriched NK cells, such as selected and/or isolated NK cells, at a concentration that is at or about, or at least at or about, $0.05\times10^6$ enriched NK cells/mL, at or about $0.1\times10^6$ enriched NK cells/mL, at or about $0.2\times10^6$ enriched NK cells/mL, at or about $0.5\times10^6$ enriched NK cells/mL or at or about $1.0\times10^6$ enriched NK cells/mL. In embodiments of the provided methods, the incubation or culture is initiated in the presence of such enriched NK cells, such as selected and/or isolated NK cells, at a concentration that is between at or about $0.05\times10^6$ enriched NK cells/mL and at or about $1.0\times10^6$ enriched NK cells/mL, such as between at or about $0.05\times10^6$ enriched NK cells/mL and at or about $0.75\times10^6$, between at or about $0.05\times10^6$ enriched NK cells/mL and at or about $0.5\times10^6$, between at or about $0.05\times10^6$ enriched NK cells/mL and at or about $0.20\times10^6$ enriched NK cells/mL, between at or about $0.05\times10^6$ enriched NK cells/mL and at or about $0.1\times10^6$ enriched NK cells/mL, between at or about $0.1\times10^6$ enriched NK cells/mL and at or about $1.0\times10^6$ enriched NK cells/mL, between at or about $0.1\times10^6$ enriched NK cells/mL and at or about $0.75\times10^6$, between at or about $0.1\times10^6$ enriched NK cells/mL and at or about $0.5\times10^6$, between at or about $0.1\times10^6$ enriched NK cells/mL and at or about $0.20\times10^6$ enriched NK cells/mL, between at or about $0.20\times10^6$ enriched NK cells/mL and at or about $1.0\times10^6$ enriched NK cells/mL, between at or about $0.20\times10^6$ enriched NK cells/mL and at or about $0.75\times10^6$, between at or about $0.20\times10^6$ enriched NK cells/mL and at or about $0.5\times10^6$, between at or about $0.5\times10^6$ enriched NK cells/mL and at or about $1.0\times10^6$ enriched NK cells/mL, between at or about $0.5\times10^6$ enriched NK cells/mL and at or about $0.75\times10^6$, between at or about $0.75\times10^6$ enriched NK cells/mL and at or about $1.0\times10^6$ enriched NK cells/mL, each inclusive. In some embodiments, the incubation or culture is initiated in the presence of such enriched NK cells, such as selected and/or isolated NK cells, at a concentration that is at or about $0.2\times10^6$ enriched NK cells/mL. In some of any such embodiments, the amount of enriched NK cells, such as selected or isolated from PBMCs as described above, added or present at the initiation of the incubation or culture is at least or at least about $1\times10^5$ cells, at least or at least about $2\times10^5$ cells, at least or at least about $3\times10^5$ cells, at least or at least about $4\times10^5$ cells, at least or at least about $5\times10^5$ cells, at least or at least about $6\times10^5$ cells, at least or at least about $7\times10^5$ cells, at least or at least about $8\times10^5$ cells, at least or at least about $9\times10^5$ cells, at least or at least about $1\times10^6$ cells or more. In particular embodiments, the amount of enriched NK cells, such as selected or isolated from PBMCs as described above, is at least or about at least or is or is about $1\times10^6$ cells.

In some of these embodiments, the NK cells can be cultured with a growth factor. According to some embodiments, the at least one growth factor comprises a growth factor selected from the group consisting of SCF, GSK3i, FLT3, IL-2, IL-7, IL-15, IL-12, IL-18 and IL-21. According to some embodiments, the at least one growth factor is IL-2 or IL-7 and IL-15. According to some embodiments, the at least one growth factor is IL-2, IL-21 or IL-7 and IL-15. In some embodiments, the growth factor is a recombinant cytokine, such as a recombinant IL-2, recombinant IL-7, recombinant IL-21 or recombinant IL-15.

In particular embodiments, the provided methods include incubation or culture of the enriched NK cells and feeder cells in the presence of recombinant IL-2. In some embodiments, during at least a portion of the incubation the recombinant IL-2 is present at a concentration of between at or about 1 IU/mL and at or about 500 IU/mL, such as between at or about 1 IU/mL and at or about 250 IU/mL, between at or about 1 IU/mL and at or about 100 IU/mL, between at or about 1 IU/mL and at or about 50 IU/mL, between at or about 50 IU/mL and at or about 500 IU/mL, between at or about 50 IU/mL and at or about 250 IU/mL, between at or about 50 IU/mL and at or about 100 IU/mL, between at or about 100 IU/mL and at or about 500 IU/mL, between at or about 100 IU/mL and at or about 250 IU/mL or between at or about 250 IU/mL and at or about 500 IU/mL, each inclusive. In some embodiments, during at least a portion of the incubation the concentration of the IL-2 is at or about 50 IU/mL, 60 IU/mL, 70 IU/mL, 80 IU/mL, 90 IU/mL, 100 IU/mL, 125 IU/mL, 150 IU/mL, 200 IU/mL, or any value between any of the foregoing. In particular embodiments, the concentration of the recombinant IL-2 is or is about 100 IU/mL.

In particular embodiments, the provided methods include incubation or culture of the enriched NK cells and feeder cells in the presence of recombinant IL-21. In some embodiments, during at least a portion of the incubation the recombinant IL-21 is present at a concentration of between at or about 1 IU/mL and at or about 500 IU/mL, such as between at or about 1 IU/mL and at or about 250 IU/mL, between at or about 1 IU/mL and at or about 100 IU/mL, between at or about 1 IU/mL and at or about 50 IU/mL, between at or about 50 IU/mL and at or about 500 IU/mL, between at or about 50 IU/mL and at or about 250 IU/mL, between at or about 50 IU/mL and at or about 100 IU/mL, between at or about 100 IU/mL and at or about 500 IU/mL, between at or about 100 IU/mL and at or about 250 IU/mL or between at or about 250 IU/mL and at or about 500 IU/mL, each inclusive. In some embodiments, during at least a portion of the incubation the concentration of the IL-21 is at or about 50 IU/mL, 60 IU/mL, 70 IU/mL, 80 IU/mL, 90 IU/mL, 100 IU/mL, 125 IU/mL, 150 IU/mL, 200 IU/mL, or any value between any of the foregoing. In particular embodiments, the concentration of the recombinant IL-21 is or is about 100 IU/mL.

In some embodiments, the methods include exchanging the culture medium, which, in some aspects includes washing the cells. For example, during at least a portion of the culture or incubation the culture medium can be exchanged or washed out intermittently, such as daily, every other day, every three days, or once a week. In particular embodiments, the culture medium is exchanged or washed out beginning within or within about 3 days to 7 days after initiation of the culture, such as at or about at day 3, day 4, day 5, day 6 or day 7. In particular embodiments, the culture medium is exchanged or washed out at or about beginning at day 5.

Once the culture medium is removed or washed out, it is replenished. In some embodiments, the replenished culture medium includes the one or more growth factors or cytokines, such as recombinant IL-2. Hence, in some embodiments, the growth factor or cytokine, such as recombinant IL-2, is added intermittently during the incubation or culture. In some such aspects, the growth factor or cytokine, such as recombinant IL-2, is added at or about at the initiation of the culture or incubation, and then is added intermittently during the culture or incubation, such as each time the culture medium is exchanged or washed out. In some embodiments, the growth factor or cytokine, such as recombinant IL-2, is added to the culture or incubation beginning at day 0 (initiation of the incubation) and, at each exchange or wash out of the culture medium, it is further added to replenish the culture or incubation with the growth factor or cytokine, such as recombinant IL-2. In some embodiments, the methods include adding recombinant IL-2 at the initiation of the incubation (day 0), and every two or three days at each wash or exchange of the culture medium for the duration of the incubation, e.g. at or about at day 5, day 7, day 9, day 11, and day 14 of the culture or incubation. In any of such embodiments, the recombinant IL-2 is added to the culture or incubation at a concentration of between at or about 1 IU/mL and at or about 500 IU/mL, such as between at or about 1 IU/mL and at or about 250 IU/mL, between at or about 1 IU/mL and at or about 100 IU/mL, between at or about 1 IU/mL and at or about 50 IU/mL, between at or about 50 IU/mL and at or about 500 IU/mL, between at or about 50 IU/mL and at or about 250 IU/mL, between at or about 50 IU/mL and at or about 100 IU/mL, between at or about 100 IU/mL and at or about 500 IU/mL, between at or about 100 IU/mL and at or about 250 IU/mL or between at or about 250 IU/mL and at or about 500 IU/mL, each inclusive. In some embodiments, the recombinant IL-2 is added to the culture or incubation at a concentration that is at or about 50 IU/mL, 60 IU/mL, 70 IU/mL, 80 IU/mL, 90 IU/mL, 100 IU/mL, 125 IU/mL, 150 IU/mL, 200 IU/mL, or any value between any of the foregoing. In particular embodiments, the concentration of the recombinant IL-2 is or is about 100 IU/mL.

In some embodiments, one or more additional cytokines can be utilized in the expansion of the NK cells, including but not limited to IL-21, IL-18, IL-7, IL-15, and/or IL-12. In some embodiments, one or more additional cytokines can be utilized in the expansion of the NK cells, including but not limited to recombinant IL-21, recombinant IL-18, recombinant IL-7, recombinant IL-15, and/or recombinant IL-12.

In embodiments of the provided methods, culturing or incubating includes providing the chemical and physical conditions (e.g., temperature, gas) which are required or useful for NK cell maintenance. Examples of chemical conditions which may support NK cell proliferation or expansion include but are not limited to buffers, nutrients, serum, vitamins and antibiotics which are typically provided in the growth (i.e., culture) medium. In one embodiment, the NK culture medium includes MEMα comprising 10% FCS or CellGro SCGM (Cell Genix) comprising 5% Human Serum/LiforCell® FBS Replacement (Lifeblood Products). Other media suitable for use with the invention include, but are not limited to Glascow's medium (Gibco Carlsbad Calif.), RPMI medium (Sigma-Aldrich, St Louis Mo.) or DMEM (Sigma-Aldrich, St Louis Mo.). It will be noted that many of the culture media contain nicotinamide as a vitamin supplement for example, MEMα (8.19 μM nicotinamide), RPMI (8.19 μM nicotinamide), DMEM (32.78 μM nicotinamide) and Glascow's medium (16.39 μM nicotinamide).

In some embodiments, such as for applications in which cells are introduced (or reintroduced) into a human subject, culturing is carried out using serum-free formulations, such as AIM V™ serum free medium for lymphocyte culture, MARROWMAX™ bone marrow medium or serum-free stem cell growth medium (SCGM) (e.g. CellGenix® GMP SCGM). Such medium formulations and supplements are available from commercial sources. The cultures can be supplemented with amino acids, antibiotics, and/or with other growth factors cytokines as described to promote optimal viability, proliferation, functionality and/or and survival. In some embodiments, the serum-free media also may be supplemented with a low percentage of human serum, such as 0.5% to 10% human serum, such as at or about 5% human serum. In such embodiments, the human serum can be human serum from human AB plasma (human AB serum) or autologous serum.

In some embodiments, the culturing with feeder cells, and optionally cytokines (e.g. recombinant IL-2) is carried out under conditions that include temperature suitable for the growth or expansion of human NK cells, for example, at least about 25 degrees Celsius, generally at least about 30 degrees, and generally at or about 37 degrees Celsius. In some embodiments, the culturing is carried out at 37° C.±2 in 5% $CO_2$.

In some of any of the provided embodiments, the culturing is carried out until a time at which the method achieves expansion of at least or at least about $2.50 \times 10^8$ g-NK cells. In some of any of the provided embodiments, the culturing is carried out until a time at which the method achieves expansion of at least or at least about $5.0 \times 10^8$ g-NK cells. In some of any of the provided embodiments, the culturing is carried out until the method achieves expansion of at least or at least about $1.0 \times 10^9$ g-NK cells. In some of any of the provided embodiments, the culturing is carried out until a time at which the method achieves expansion of at least or at least about $5.0 \times 10^9$ g-NK cells.

In some of any of the provided embodiments, the culturing is carried out for at or about or at least at or at least about 5 days, 6 days, 7 days, 8 days, 9 days, 10 days, 11 days, 12 days, 13 days, 14 days, 15 days, 16 days, 17 days, 18 days, 19 days, 20 day, 21 days, 22 days, 23 days, 24 days or 25 days. In some embodiments, the culturing is carried out for at or about or at least at or about 14 days. In some embodiments the culturing is carried out for at or about or at least at or about 21 days.

In some embodiments, the provided methods include steps for freezing, e.g., cryopreserving, the cells, either before or after isolation, selection and/or enrichment. In some embodiments, the provided methods include steps for freezing, e.g., cryopreserving, the cells, either before or after incubation and/or culturing. In some embodiments, the method includes cryopreserving the cells in the presence of a cryoprotectant, thereby producing a cryopreserved composition. In some aspects, prior to the incubating and/or prior to administering to a subject, the method includes washing the cryopreserved composition under conditions to reduce or remove the cryoprotectant. Any of a variety of known freezing solutions and parameters in some aspects may be used. In some embodiments, the cells are frozen, e.g., cryofrozen or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryofrozen or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to or to about −80° C. at a rate of or of about 1° per minute and stored in the vapor phase of a liquid nitrogen storage tank.

In some of any of the provided embodiments, the culturing or incubation in accord with any of the provided methods is carried out for at or about or at least at or at least about 5 days, 6 days, 7 days, 8 days, 9 days, 10 days, 11 days, 12 days, 13 days, 14 days, 15 days, 16 days, 17 days, 18 days, 19 days, 20 day, 21 days, 22 days, 23 days, 24 days or 25 days. In some embodiments, the culturing is carried out for at or about or at least at or about 14 days. In some embodiments, the culturing is carried out for at or about or at least at or about 21 days. In certain embodiments, a longer duration of culturing is typically necessary if the enriched NK cells at the initiation of the culturing have been thawed after having been previously frozen or cryopreserved. It is within the level of a skilled artisan to empirically determine the optimal number of days to culture the cells depending on factors such as the state of the cells at the initiation of the culture, the health or viability of the cells that the initiation of the culture or during the culturing and/or the desired number of threshold cells at the end of the culturing depending, for example, on the desired application of the cells, such as the dose of cells to be administered to a subject for therapeutic purposes.

In some of any of the provided methods, the method produces an increased number of NKG2C$^{pos}$ cells at the end of the culturing compared to at the initiation of the culturing. For example, the increase in NKG2C$^{pos}$ cells at the end of culturing compared to at the initiation of the culturing can be greater than or greater than about 100-fold, greater than or greater than about 200-fold, greater than or greater than about 300-fold, greater than or greater than about 400-fold, greater than or greater than about 500-fold, greater than or greater than about 600-fold, greater than or greater than about 700-fold or greater than or greater than about 800-fold. In some of any embodiments, the increase is at or about 1000-fold greater. In some of any embodiments, the increase is at or about 2000-fold greater. In some of any embodiments, the increase is at or about 2500-fold greater. In some embodiments, the culturing or incubation in accord with any of the provided methods is carried out until a time at which the method achieves expansion of at least at or about 2.50×10$^8$ NKG2C$^{pos}$ cells, at least at or about 3.0×10$^8$ NKG2C$^{pos}$ cells, at least at or about 4.0×10$^8$ NKG2C$^{pos}$ cells, at least at or about 5.0×10$^8$ NKG2C$^{pos}$ cells, at least at or about 6.0×10$^8$ NKG2C$^{pos}$ cells, at least at or about 7.0×10$^8$ NKG2C$^{pos}$ cells, at least at or about 8.0×10$^8$ NKG2C$^{pos}$ cells, at least at or about 9.0×10$^8$ NKG2C$^{pos}$ cells, at least at or about 1.0×10$^9$ NKG2C$^{pos}$ cells, at least at or about 1.5×10$^9$ NKG2C$^{pos}$ cells, at least at or about 2.0×10$^9$ NKG2C$^{pos}$ cells, at least at or about 3.0×10$^9$ NKG2C$^{pos}$ cells, at least at or about 4.0×10$^9$ NKG2C$^{pos}$ cells, at least at or about 5.0×10$^9$ NKG2C$^{pos}$ cells, at least at or about 1.0×10$^{10}$ NKG2C$^{pos}$ cells, at least at or about 1.5×10$^{10}$ NKG2C$^{pos}$ cells, at least at or about 2.0×10$^{10}$ NKG2C$^{pos}$ cells, at least at or about 2.5×10$^{10}$ NKG2C$^{pos}$ cells or more.

In some of any of the provided methods, the method produces an increased number of g-NK cells at the end of the culturing compared to at the initiation of the culturing. For example, the increase in g-NK cells at the end of culturing compared to at the initiation of the culturing can be greater than or greater than about 100-fold, greater than or greater than about 200-fold, greater than or greater than about 300-fold, greater than or greater than about 400-fold, greater than or greater than about 500-fold, greater than or greater than about 600-fold, greater than or greater than about 700-fold or greater than or greater than about 800-fold. In some of any embodiments, the increase is at or about 1000-fold greater. In some of any embodiments, the increase is at or about 2000-fold greater. In some of any embodiments, the increase is at or about 2500-fold greater. In some embodiments, the culturing or incubation in accord with any of the provided methods is carried out until a time at which the method achieves expansion of at least at or about 2.50×10$^8$ g-NK cells, at least at or about 3.0×10$^8$ g-NK cells, at least at or about 4.0×10$^8$ g-NK cells, at least at or about 5.0×10$^8$ g-NK cells, at least at or about 6.0×10$^8$ g-NK cells, at least at or about 7.0×10$^8$ g-NK cells, at least at or about 8.0×10$^8$ g-NK cells, at least at or about 9.0×10$^8$ g-NK cells, at least at or about 1.0×10$^9$ g-NK cells, at least at or about 1.5×10$^9$ g-NK cells, at least at or about 2.0×10$^9$ g-NK cells, at least at or about 3.0×10$^9$ g-NK cells, at least at or about 4.0×10$^9$ g-NK cells, at least at or about 5.0×10$^9$ g-NK cells or more, at least at or about 1.0×10$^{10}$ g-NK cells or more, at least at or about 1.5×10$^{10}$ g-NK cells or more, at least at or about 2.0×10$^{10}$ g-NK cells or more, or at least at or about 2.5×10$^{10}$ g-NK cells or more.

In some embodiments, the provided methods result in the preferential expansion of g-NK cells. In some aspects, g-NK cells are identified by the presence, absence or level of surface expression of one or more various marker that distinguishes NK cells from other lymphocytes or immune cells and that distinguishes g-NK cells from conventional NK cells. In embodiments, surface expression can be determined by flow cytometry, for example, by staining with an antibody that specifically bind to the marker and detecting the binding of the antibody to the marker. Similar methods can be carried out to assess expression of intracellular markers, except that such methods typically include methods for fixation and permeabilization before staining to detect intracellular proteins by flow cytometry. In some embodiments, fixation is achieved using formaldehyde (e.g. 0.01%) followed by disruption of membranes using a detergent (e.g. 0.1% to 1% detergent, for example at or about 0.5%), such as Triton, NP-50, Tween 20, Saponin, Digitonin or Leucoperm.

Antibodies and other binding entities can be used to detect expression levels of marker proteins to identify, detect, enrich and/or isolate the g-NK cells. Suitable antibodies may include polyclonal, monoclonal, fragments (such as Fab fragments), single chain antibodies and other forms of specific binding molecules.

In some embodiments, a cell (e.g. NK cell subset) is positive (pos) for a particular marker if there is detectable presence on or in the cell of a particular marker, which can be an intracellular marker or a surface marker. In embodiments, surface expression is positive if staining is detectable at a level substantially above the staining detected carrying out the same procedures with an isotype-matched control under otherwise identical conditions and/or at a level substantially similar to, or in some cases higher than, a cell known to be positive for the marker and/or at a level higher than that for a cell known to be negative for the marker.

In some embodiments, a cell (e.g. NK cell subset) is negative (neg) for a particular marker if there is an absence of detectable presence on or in the cell of a particular marker, which can be an intracellular marker or a surface marker. In embodiments, surface expression is negative if staining is not detectable at a level substantially above the staining detected carrying out the same procedures with an isotype-matched control under otherwise identical conditions and/or at a level substantially lower than a cell known to be positive for the marker and/or at a level substantially similar to a cell known to be negative for the marker.

In some embodiments, a cell (e.g. NK cell subset) is low (lo or min) for a particular marker if there is a lower level of detectable presence on or in the cell of a particular marker compared to a cell known to be positive for the marker. In embodiments, surface expression can be determined by flow cytometry, for example, by staining with an antibody that specifically bind to the marker and detecting the binding of the antibody to the marker, wherein expression, either surface or intracellular depending on the method used, is low if staining is at a level lower than a cell known to be positive for the marker.

In some embodiments, g-NK cells are cells having a phenotype of NK cells (e.g. CD45$^{pos}$, CD3$^{neg}$ and/or CD56$^{pos}$) and express one or more markers that identify or that are associated with a g-NK cell subset.

In some embodiments, g-NK cells are identified as described in published Patent Appl. No. US2013/0295044 or Zhang et al. (2013) J. Immunol., 190:1402-1406.

In some embodiments, g-NK cells are cells that do not express substantial FcRγ but do express at least one marker for natural killer cells. An amino acid sequence for FcRγ chain (Homo sapiens, also called the High affinity immunoglobulin gamma Fc receptor I) is available in the NCBI database as accession number NP-004097.1 (GL4758344), and is reproduced below as SEQ ID NO: 1.

(SEQ ID NO: 1)
MIPAVVLLLLLLVEQAAALGEPQLCYILDAILFLYGIVLTLLYCRLKIQ
VRKAAITSYEKSDGVYTGLSTRNQETYETLKHEKPPQ

In some embodiments, the g-NK cell subset of NK cells can be detected by observing whether FcRγ is expressed by a population of NK cells or a subpopulation of NK cells. In some cases, g-NK cells are identified as cells that do not express FcRγ. FcRγ protein is an intracellular protein. Thus, in some aspects, the presence or absence of FcRγ can be detected after treatment of cells, for example, by fixation and permeabilization, to allow intracellular proteins to be detected. In some embodiments, cells are further assessed for one or more surface markers (CD45, CD3 and/or CD56) prior to the intracellular detection, such as prior to fixation of cells. In some embodiments, g-NK cells are identified, detected, enriched and/or isolated as cells that are CD45$^{pos}$/CD3$^{neg}$/CD56$^{pos}$/FcRγ$^{neg}$.

In some embodiments, it may be useful to detect expression of g-NK cells without employing intracellular staining, such as, for example, if cells of the sample are to be subjected to cell sorting or a functional assay. While treatments, e.g. fixation and permeabilization, to permit intracellular staining of FcRγ can be used to confirm the identity of a substantially pure population of cells, in many cases cell-surface markers can be employed that can be detected without injuring the cells when identifying, detecting or isolating g-NK cells. Thus, in some embodiments, g-NK cells are identified using a surrogate marker profile that correlates with the lack of FcRγ among a subset of NK cells. In some embodiments, a surrogate marker profile is of particular use when the presence or absence of an intracellular protein, such as FcRγ, is difficult or not possible to assess depending on the particular application of the cells.

It is found herein that certain combinations of cell surface marker correlate with the g-NK cell phenotype, i.e. cells that lack or are deficient in intracellular expression of FcRγ, thereby providing a surrogate marker profile to identify or detect g-NK cells in a manner that does not injure the cells. In some embodiments, a surrogate marker profile for g-NK cells provided herein is based on positive surface expression of one or more markers CD16 (CD16$^{pos}$) or CD57 (CD57pos) and/or based on low or negative surface expression of one or more markers CD7 (CD7$^{dim/neg}$), CD161 (CD161$^{neg}$) and/or NKG2A (NKG2A$^{neg}$). In some embodiments, cells are further assessed for one or more surface markers of NK cells, such as CD45, CD3 and/or CD56. In some embodiments, g-NK cells can be identified, detected, enriched and/or isolated with the surrogate marker profile CD45$^{pos}$/CD3$^{neg}$/CD56$^{pos}$/CD16$^{pos}$/CD57$^{pos}$/CD7$^{dim/neg}$/CD161$^{neg}$. In some embodiments, g-NK cells are identified, detected, enriched and/or isolated with the surrogate marker profile CD45$^{pos}$/CD3$^{neg}$/CD56$^{pos}$/NKG2A$^{neg}$/CD161$^{neg}$.

Provided herein are methods for identifying or detecting g-NK cells in a sample containing a population of cells by employing a surrogate marker profile of g-NK cells. In some embodiments, the methods include contacting a sample of cells with a binding molecule, such as an antibody or antigen-binding fragment, that is specific for one or more markers CD16, CD57, CD7, CD161 and/or NKG2A. In some embodiments, the methods further include contacting the sample of cells with a binding molecule, such as an antibody or antigen-binding fragment, that is specific for CD45, CD3 and/or CD56. In some embodiments of the methods, the one or more binding molecules can be contacted with the sample simultaneously. In some embodiments of the methods, the one or more binding molecules can be contacted with the sample sequentially. In some embodiments, following the contact, the methods can include one or more washing under conditions to retain cells that have bound to the one or more binding molecule and/or to separate away unbound binding molecules from the sample.

In some embodiments, each of the one or more binding molecules, e.g. antibody, may be attached directly or indirectly to a label for detection of cells positive or negative for the marker. For example, the binding molecule, e.g. antibody, may be conjugated, coupled or linked to the label. Labels are well known by one of skill in the art. Labels contemplated herein include, but are not limited to, fluorescent dyes, fluorescent proteins, radioisotopes, chromophores, metal ions, gold particles (e.g., colloidal gold particles), silver particles, particles with strong light scattering properties, magnetic particles (e.g., magnetic bead particles such as Dynabeads® magnetic beads), polypeptides (e.g., FLAG™ tag, human influenza hemagglutinin (HA) tag, etc.), enzymes such as peroxidase (e.g., horseradish peroxidase) or a phosphatase (e.g., alkaline phosphatase), streptavidin, biotin, luminescent compounds (e.g., chemiluminescent substrates), oligonucleotides, members of a specific binding pair (e.g., a ligands and its receptor) and other labels well known in the art that are used for visualizing or detecting a binding molecule, e.g. an antibody, when directly or indirectly attached to said antibody.

A number of well-known methods for assessing expression level of surface markers or proteins may be used, such as detection by affinity-based methods, e.g., immunoaffinity-based methods, e.g., in the context of surface markers, such as by flow cytometry. In some embodiments, the label is a fluorophore and the methods for detection or identification of g-NK cells is by flow cytometry. In some embodiments, different labels are used for each of the different markers by multicolor flow cytometry.

In some embodiments, the methods include contacting a sample with a binding molecule specific to CD45, CD3, CD56, CD57, CD7 and CD161. In some such embodiments, g-NK cells are identified or detected as cells having the g-NK cell surrogate marker profile $CD45^{pos}/CD3^{neg}/CD56^{pos}/CD16^{pos}/CD57^{pos}/CD7^{dim/neg}/CD161^{neg}$.

In some embodiments, the methods include contacting a sample with a binding molecule specific to CD45, CD3, CD56, NKG2A and CD161. In some such embodiments, g-NK cells are identified or detected as cells having the g-NK cell surrogate marker profile $CD45^{pos}/CD3^{neg}/CD56^{pos}/NKG2A^{neg}/CD161^{neg}$.

In some embodiments, the provided methods also can include isolating or enriching g-NK, such as g-NK cells preferentially expanded in accord with any of the provided methods. In some such embodiments, a substantially pure population of g-NK cells can be obtained, such as a cell population containing greater than or greater than about 90%, 91%, 92%, 93%, 94%, 95%, 96%, 97%, 98%, 99% or more g-NK cells, such as determined using any of the described panel or combinations of markers. Antibodies and other binding molecules can be used to detect the presence or absence of expression levels of marker proteins, for use in isolating or enriching g-NK cells. In some embodiments, isolation or enrichment is carried out by fluorescence activated cell sorting (FACs). In examples of such methods, g-NK cells are identified or detected by flow cytometry using the methods as described above for staining cells for multiple cell surface markers and stained cells are carried in a fluidic stream for collection of cells that are positive or negative for markers associated with g-NK cells.

III. COMPOSITIONS AND PHARMACEUTICAL FORMULATIONS

Provided herein are compositions containing expanded NK cells such as produced by any of the provided methods. In some embodiments, the compositions contain $NKG2C^{pos}$ cells or a subset thereof. In some embodiments, the compositions contain g-NK cells. In particular, among the provided compositions are compositions of cells that are enriched for g-NK cells.

In some embodiments, the composition comprises about 5-99% $NKG2C^{pos}$ cells or a subset thereof, or any percentage of $NKG2C^{pos}$ cells or a subset thereof between 5 and 99% inclusive. In some embodiments, the composition can include an increased or greater percentages of $NKG2C^{pos}$ cells or a subset thereof relative to total NK cells or total cells compared to the percentage of $NKG2C^{pos}$ cells or the subset thereof relative to total NK cells or total cells naturally present in the subject from which the cells were isolated. In some embodiments, the percentage is increased at least or at least about 2-fold, 3-fold, 4-fold, 5-fold, 10-fold, 20-fold, 30-fold, 40-fold, 50-fold, 60-fold, 70-fold, 80-fold, 90-fold, 100-fold, 150-fold, 200-fold or more.

In some embodiments, the composition can include at least at or about 20%, at least at or about 30%, at least at or about 40%, at least at or about 50%, at least at or about 60%, at least at or about 65%, at least at or about 70%, at least at or about 75%, at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, at least at or about 99%, or substantially 100% $NKG2C^{pos}$ cells or a subset thereof. In some embodiments, the composition comprises more than 50% $NKG2C^{pos}$ cells or a subset thereof. In another embodiment, the composition comprises more than 70% $NKG2C^{pos}$ cells or a subset thereof. In another embodiment, the composition comprises more than 80% $NKG2C^{pos}$ cells or a subset thereof. In some embodiments, the provided compositions include those in which the $NKG2C^{pos}$ cells or a subset thereof make up at least at or about 60%, at least at or about 70%, at least at or about 80%, at least at or about 85%, at least at or about 90%, at least at or about 95% or more of the cells in the composition or of the NK cells in the composition.

In some embodiments, the composition comprises about 5-99% g-NK cells, or any percentage of g-NK cells between 5 and 99% inclusive. In some embodiments, the composition can include an increased or greater percentages of g-NK cells relative to total NK cells or total cells compared to the percentage of g-NK relative to total NK cells or total cells naturally present in the subject from which the cells were isolated. In some embodiments, the percentage is increased at least or at least about 2-fold, 3-fold, 4-fold, 5-fold, 10-fold, 20-fold, 30-fold, 40-fold, 50-fold, 60-fold, 70-fold, 80-fold, 90-fold, 100-fold, 150-fold, 200-fold or more.

In some embodiments, the composition can include at least at or about 20%, at least at or about 30%, at least at or about 40%, at least at or about 50%, at least at or about 60%, at least at or about 65%, at least at or about 70%, at least at or about 75%, at least at or about 80%, at least at or about 81%, at least at or about 82%, at least at or about 83%, at least at or about 84%, at least at or about 85%, at least at or about 86%, at least at or about 87%, at least at or about 88%, at least at or about 89%, at least at or about 90%, at least at or about 91%, at least at or about 92%, at least at or about 93%, at least at or about 94%, at least at or about 95%, at least at or about 96%, at least at or about 97%, at least at or about 98%, at least at or about 99%, or substantially 100% g-NK cells. In some embodiments, the composition comprises more than 50% g-NK cells. In another embodiment, the composition comprises more than 70% g-NK cells. In another embodiment, the composition comprises more than 80% g-NK cells. In some embodiments, the provided compositions include those in which the g-NK cells make up at least at or about 60%, at least at or about 70%, at least at or about 80%, at least at or about 85%, at least at or about 90%, at least at or about 95% or more of the cells in the composition or of the NK cells in the composition.

In some embodiments, the composition includes a population of a natural killer (NK) cell subset, wherein at least at or about 40%, at least at or about 50%, at least at or about 55%, at least at or about 60%, at least at or about 65%, at least at or about 70%, at least at or about 75%, at least at or about 80%, at least at or about 85%, at least at or about 90%, or at least at or about 95% of the cells in the composition have a g-NK cell surrogate marker profile that is CD57$^{pos}$. In some embodiments, from or from about 70% to at or about 90% of the cells in the composition have the phenotype CD57$^{pos}$. In some embodiments, at least at or about 72%, at least at or about 74%, at least at or about 76%, at least at or about 78%, at least at or about 80%, at least at or about 82%, at least at or about 84%, at least at or about 86%, at least at or about 88%, at least at or about 90%, at least at or about 92%, at least at or about 94%, at least at or about 96% or at least at or about 98% of cell in the composition have the phenotype CD57$^{pos}$. In some of any of the provided embodiments, at least at or about 60% of the cells in the composition comprise the phenotype CD57$^{pos}$. In some of any of the provided embodiments, at least at or about 70% of the cells in the composition comprise the phenotype CD57$^{pos}$. In some embodiments, the phenotype further includes the surface phenotype CD3$^{neg}$. In some embodiments, the phenotype further includes the surface phenotype CD45$^{pos}$/CD3$^{neg}$/CD56$^{pos}$. In some of any of the provided embodiments, of the cells that have such a phenotype greater than 50% are FcRγ$^{neg}$, optionally between at or about 50% and 90% are FcRγ$^{neg}$. In some of any of the provided embodiments, of the cells that have such a phenotype greater than 70% are FcRγ$^{neg}$, optionally between at or about 70% and 90% are FcRγ$^{neg}$.

In some embodiments, the composition includes a population of a natural killer (NK) cell subset, wherein at least at or about 40%, at least at or about 50%, at least at or about 55%, at least at or about 60%, at least at or about 65%, at least at or about 70%, at least at or about 75%, at least at least at or about 80%, at least at or about 85%, at least at or about 90%, or at least at or about 95% of the cells in the composition have a g-NK cell surrogate marker profile that is CD16$^{pos}$/CD57$^{pos}$/CD7$^{dim/neg}$/CD161$^{neg}$. In some embodiments, from or from about 70% to at or about 90% of the cells in the composition have the phenotype CD16$^{pos}$/CD57$^{pos}$/CD7$^{dim/neg}$/CD161$^{neg}$. In some embodiments, at least at or about 72%, at least at or about 74%, at least at or about 76%, at least at or about 78%, at least at or about 80%, at least at or about 82%, at least at or about 84%, at least at or about 86%, at least at or about 88%, at least at or about 90%, at least at or about 92%, at least at or about 94%, at least at or about 96% or at least at or about 98% of cell in the composition have the phenotype CD16$^{pos}$/CD57$^{pos}$/CD7$^{dim/neg}$/CD161$^{neg}$. In some of any of the provided embodiments, at least at or about 60% of the cells in the composition comprise the phenotype CD16$^{pos}$/CD57$^{pos}$/CD7$^{dim/neg}$/CD161$^{neg}$. In some of any of the provided embodiments, at least at or about 70% of the cells in the composition comprise the phenotype CD16$^{pos}$/CD57$^{pos}$/CD7$^{dim/neg}$/CD161$^{neg}$. In some embodiments, the phenotype further includes the surface phenotype CD3$^{neg}$. In some embodiments, the phenotype further includes the surface phenotype CD45$^{pos}$/CD3$^{neg}$/CD56$^{pos}$. In some of any of the provided embodiments, of the cells that have such a phenotype greater than 50% are FcRγ$^{neg}$, optionally between at or about 50% and 90% are FcRγ$^{neg}$. In some of any of the provided embodiments, of the cells that have such a phenotype greater than 70% are FcRγ$^{neg}$, optionally between at or about 70% and 90% are FcRγ$^{neg}$.

In some embodiments, the composition includes a population of a natural killer (NK) cell subset, wherein at least at or about 40%, at least at or about 50%, at least at or about 55%, at least at or about 60%, at least at or about 65%, at least at or about 70%, at least at or about 75%, at least at least at or about 80%, at least at or about 85%, at least at or about 90%, or at least at or about 95% of the cells in the composition have a phenotype that is CD38$^{neg}$. In some embodiments, from or from about 70% to at or about 90% of the cells in the composition have the phenotype CD38$^{neg}$. In some embodiments, at least at or about 72%, at least at or about 74%, at least at or about 76%, at least at or about 78%, at least at or about 80%, at least at or about 82%, at least at or about 84%, at least at or about 86%, at least at or about 88%, at least at or about 90%, at least at or about 92%, at least at or about 94%, at least at or about 96% or at least at or about 98% of cell in the composition have the phenotype CD38$^{neg}$. In some of any of the provided embodiments, at least at or about 60% of the cells in the composition comprise the phenotype CD38$^{neg}$. In some of any of the provided embodiments, at least at or about 70% of the cells in the composition comprise the phenotype CD38$^{neg}$. In some embodiments, the phenotype further includes the surface phenotype CD3$^{neg}$. In some embodiments, the phenotype further includes the surface phenotype CD45$^{pos}$/CD3$^{neg}$/CD56$^{pos}$. In some of any of the provided embodiments, of the cells that have such a phenotype greater than 50% are FcRγ$^{neg}$, optionally between at or about 50% and 90% are FcRγ$^{neg}$. In some of any of the provided embodiments, of the cells that have such a phenotype greater than 70% are FcRγ$^{neg}$, optionally between at or about 70% and 90% are FcRγ$^{neg}$.

In some embodiments, the composition includes a population of a natural killer (NK) cell subset, wherein at least at or about 40%, at least at or about 50%, at least at or about 55%, at least at or about 60%, at least at or about 65%, at least at or about 70%, at least at or about 75%, at least at least at or about 80%, at least at or about 85%, at least at or about 90%, or at least at or about 95% of the cells in the composition have a phenotype that is CD16$^{pos}$. In some embodiments, from or from about 70% to at or about 90% of the cells in the composition have the phenotype CD16$^{pos}$. In some embodiments, at least at or about 72%, at least at or about 74%, at least at or about 76%, at least at or about 78%, at least at or about 80%, at least at or about 82%, at least at or about 84%, at least at or about 86%, at least at or about 88%, at least at or about 90%, at least at or about 92%, at least at or about 94%, at least at or about 96% or at least at or about 98% of cell in the composition have the phenotype CD16$^{pos}$. In some of any of the provided embodiments, at least at or about 60% of the cells in the composition comprise the phenotype CD16$^{pos}$. In some of any of the provided embodiments, at least at or about 70% of the cells in the composition comprise the phenotype CD16$^{pos}$. In some embodiments, the phenotype further includes the surface phenotype CD3$^{neg}$. In some embodiments, the phenotype further includes the surface phenotype CD45$^{pos}$/CD3$^{neg}$/CD56$^{pos}$. In some of any of the provided embodiments, of the cells that have such a phenotype greater than 50% are FcRγ$^{neg}$, optionally between at or about 50% and 90% are FcRγ$^{neg}$. In some of any of the provided embodiments, of the cells that have such a phenotype greater than 70% are FcRγ$^{neg}$, optionally between at or about 70% and 90% are FcRγ$^{neg}$.

In some embodiments, the composition includes a population of a natural killer (NK) cell subset, wherein at least at or about 40%, at least at or about 50%, at least at or about 55%, at least at or about 60%, at least at or about 65%, at least at or about 70%, at least at or about 75%, at least at least at or about 80%, at least at or about 85%, at least at or about 90%, or at least at or about 95% of the cells in the composition have a g-NK cell surrogate marker profile that is NKG2A$^{neg}$/CD161$^{neg}$. In some embodiments, from or from about 70% to at or about 90% of the cells in the composition have the phenotype NKG2A$^{neg}$/CD161$^{neg}$. In some embodiments, at least at or about 72%, at least at or about 74%, at least at or about 76%, at least at or about 78%, at least at or about 80%, at least at or about 82%, at least at or about 84%, at least at or about 86%, at least at or about 88%, at least at or about 90%, at least at or about 92%, at least at or about 94%, at least at or about 96% or at least at or about 98% of cell in the composition have the phenotype NKG2A$^{neg}$/CD161$^{neg}$. In some of any of the provided embodiments, at least at or about 60% of the cells in the composition comprise the phenotype NKG2A$^{neg}$/CD161$^{neg}$. In some of any of the provided embodiments, at least at or about 70% of the cells in the composition comprise the phenotype NKG2A$^{neg}$/CD161$^{neg}$. In some embodiments, the phenotype further includes the surface phenotype CD3$^{neg}$. In some embodiments, the phenotype further includes the surface phenotype CD45$^{pos}$/CD3$^{neg}$/CD56$^{pos}$. In some of any of the provided embodiments, of the cells that have such a phenotype greater than 50% are FcRγ$^{neg}$, optionally between at or about 50% and 90% are FcRγ$^{neg}$. In some of any of the provided embodiments, of the cells that have such a phenotype greater than 70% are FcRγ$^{neg}$, optionally between at or about 70% and 90% are FcRγ$^{neg}$.

In some of any of the provided embodiments, the composition comprises from at or about $10^6$ cells to at or about $10^{12}$ cells. In some of any of the provided embodiments, the composition comprises from at or about $10^6$ to at or about $10^{11}$ cells, from at or about $10^6$ to at or about $10^{10}$ cells, from at or about $10^6$ to at or about $10^9$ cells, from at or about $10^6$ to at or about $10^8$ cells, from at or about $10^6$ to at or about $10^7$ cells, from at or about $10^7$ to at or about $10^{12}$ cells, from at or about $10^7$ to at or about $10^{11}$ cells, from at or about $10^7$ to at or about $10^{10}$ cells, from at or about $10^7$ to at or about $10^9$ cells, or from at or about $10^7$ to at or about $10^8$ cells, from at or about $10^8$ to at or about $10^{12}$ cells, from at or about $10^8$ to at or about $10^{11}$ cells, from at or about $10^8$ to at or about $10^{10}$ cells, from at or about $10^8$ to at or about $10^9$ cells, from at or about $10^9$ to at or about $10^{12}$ cells, from at or about $10^9$ to at or about $10^{11}$ cells, from at or about $10^9$ to at or about $10^{10}$ cells, from at or about $10^{10}$ to at or about $10^{12}$ cells, from at or about $10^{10}$ to at or about $10^{11}$ cells, or from at or about $10^{11}$ to at or about $10^{12}$ cells.

In some of any of the provided embodiments, the composition comprises at least or about at least $10^6$ cells. In some of any of the provided embodiments, the composition comprises from at or about $10^6$ to at or about $10^{10}$ cells, from at or about $10^6$ to at or about $10^9$ cells, from at or about $10^6$ to at or about $10^8$ cells, from at or about $10^6$ to at or about $10^7$ cells, from at or about $10^7$ to at or about $10^{10}$ cells, from at or about $10^7$ to at or about $10^9$ cells, from at or about $10^7$ to at or about $10^8$ cells, from at or about $10^8$ to at or about $10^{10}$ cells, from at or about $10^8$ to at or about $10^9$ cells, or from at or about $10^9$ to at or about $10^{10}$ cells.

In some of any of the provided embodiments, the composition comprises at least or about at least $10^8$ cells. In some of any of the provided embodiments, the composition comprises at at least at or about $10^9$ cells. In some of any of the provided embodiments, the composition comprises at at least at or about $10^{10}$ cells. In some of any of the provided embodiments, the composition comprises at at least at or about $10^{11}$ cells. In some of any of the provided embodiments, the composition comprises from at or about $10^8$ to at or about $10^{11}$ cells. In some of any of the provided embodiments, the composition comprises from at or about $10^8$ to at or about $10^{10}$ cells. In some of any of the provided embodiments, the composition comprises from at or about $10^8$ to at or about $10^9$ cells. In some of any of the provided embodiments, the composition comprises from at or about $10^9$ to at or about $10^{11}$ cells. In some of any of the provided embodiments, the composition comprises from at or about $10^9$ to at or about $10^{10}$ cells. In some of any of the provided embodiments, the composition comprises from at or about $10^{10}$ to at or about $10^{11}$ cells.

In some of any of the provided embodiments, the composition comprises at least at or about $10^6$ g-NK cells. In some of any of the provided embodiments, the composition comprises from at or about $10^6$ to at or about $10^{10}$ g-NK cells, from at or about $10^6$ to at or about $10^9$ g-NK cells, from at or about $10^6$ to at or about $10^8$ g-NK cells, from at or about $10^6$ to at or about $10^7$ g-NK cells, from at or about $10^7$ to at or about $10^{10}$ g-NK cells, from at or about $10^7$ to at or about $10^9$ g-NK cells, from at or about $10^7$ to at or about $10^8$ g-NK cells, from at or about $10^8$ to at or about $10^{10}$ g-NK cells, from at or about $10^8$ to at or about $10^9$ g-NK cells, or from at or about $10^9$ to at or about $10^{10}$ g-NK cells. In some of any of the provided embodiments, the g-NK cells are FcRγ$^{neg}$. In some of any of the provided embodiments, the g-NK cells are cells having a g-NK surrogate surface marker profile. In some embodiments, the g-NK cell surrogate surface marker profile is CD16$^{pos}$/CD57$^{pos}$/CD7$^{dim/neg}$/CD161$^{neg}$. In some embodiments, the g-NK cell surrogate surface marker profile is NKG2A$^{neg}$/CD161$^{neg}$. In some of any of the provided embodiments, the g-NK cells or cells having a g-NK surrogate marker profile further include the surface phenotype CD45$^{pos}$/CD3$^{neg}$/CD56$^{pos}$.

In particular embodiments of any of the provided compositions, the cells in the composition are from the same donor. As such, the compositions do not include a mixed population of cells from one or more different donors. As provided here, the methods of expansion result in high yield expansion of at or greater than 500-fold, at or greater than 600-fold, at or greater than 700-fold, at or greater than 800-fold, at or greater than 900-fold, at or greater than 1000-fold or more of certain NK cell subsets, particularly the g-NK cell subset or an NK cell subset that is associated with or includes a surrogate marker for g-NK cells, such as any of the NK cell subsets described above. In some of any embodiments, the increase is at or about 1000-fold greater. In some of any embodiments, the increase is at or about 2000-fold greater. In some of any embodiments, the increase is at or about 2500-fold greater. In particular embodiments, expansion results in at or about 1,000 fold increase in number of certain NK cell subsets, particularly the g-NK cell subset or an NK cell subset that is associated with or includes a surrogate marker for g-NK cells, such as any of the NK cell subsets described above.

In some cases, expansion achieved by the provided methods from an initial source of NK cells obtained from a single donor can produce a composition of cells to provide a plurality of individual doses for administration to a subject in need. As such, the provided methods are particularly suitable for allogeneic methods. In some cases, a single expansion from a starting population of NK cells isolated from one donor in accord with the provided methods can result in greater than or greater than about 20 individual doses for administration to a subject in need, such as at or about 30 individual doses, 40 individual doses, 50 individual doses, 60 individual doses, 70 individual doses, 80 individual doses, 90 individual doses, 100 individual doses, or an individual dose that is a value between any of the foregoing. In some embodiments, the individual dose is from at or about $1 \times 10^5$ cells/kg to at or about $1 \times 10^7$ cells/kg, such as from at or about $1 \times 10^5$ cells/kg to at or about $7.5 \times 10^6$ cells/kg, from at or about $1 \times 10^5$ cells/kg to at or about $5 \times 10^6$ cells/kg, from at or about $1 \times 10^5$ cells/kg to at or about $2.5 \times 10^6$ cells/kg, from at or about $1 \times 10^5$ cells/kg to at or about $1 \times 10^6$ cells/kg, from at or about $1 \times 10^5$ cells/kg to at or about $7.5 \times 10^5$ cells/kg, from at or about $1 \times 10^5$ cells/kg to at or about $5 \times 10^5$ cells/kg, from at or about $1 \times 10^5$ cells/kg to at or about $2.5 \times 10^5$ cells/kg, from at or about $2.5 \times 10^5$ cells/kg to at or about $1 \times 10^7$ cells/kg, from at or about $2.5 \times 10^5$ cells/kg to at or about $7.5 \times 10^6$ cells/kg, from at or about $2.5 \times 10^5$ cells/kg to at or about $5 \times 10^6$ cells/kg, from at or about $2.5 \times 10^5$ cells/kg to at or about $2.5 \times 10^6$ cells/kg, from at or about $2.5 \times 10^5$ cells/kg to at or about $1 \times 10^6$ cells/kg, from at or about $2.5 \times 10^5$ cells/kg to at or about $7.5 \times 10^5$ cells/kg, from at or about $2.5 \times 10^5$ cells/kg to at or about $5 \times 10^5$ cells/kg, from at or about $5 \times 10^5$ cells/kg to at or about $1 \times 10^7$ cells/kg, from at or about $5 \times 10^5$ cells/kg to at or about $7.5 \times 10^6$ cells/kg, from at or about $5 \times 10^5$ cells/kg to at or about $5 \times 10^6$ cells/kg, from at or about $5 \times 10^5$ cells/kg to at or about $2.5 \times 10^6$ cells/kg, from at or about $5 \times 10^5$ cells/kg to at or about $1 \times 10^6$ cells/kg, from at or about $5 \times 10^5$ cells/kg to at or about $7.5 \times 10^5$ cells/kg, from at or about $1 \times 10^6$ cells/kg to at or about $1 \times 10^7$ cells/kg, from at or about $1 \times 10^6$ cells/kg to at or about $7.5 \times 10^6$ cells/kg, from at or about $1 \times 10^6$ cells/kg to at or about $5 \times 10^6$ cells/kg, from at or about $1 \times 10^6$ cells/kg to at or about $2.5 \times 10^6$ cells/kg, from at or about $2.5 \times 10^6$ cells/kg to at or about $1 \times 10^7$ cells/kg, from at or about $2.5 \times 10^6$ cells/kg to at or about $7.5 \times 10^6$ cells/kg, from at or about $2.5 \times 10^6$ cells/kg to at or about $5 \times 10^6$ cells/kg, from at or about $5 \times 10^6$ cells/kg to at or about $1 \times 10^7$ cells/kg, from at or about $5 \times 10^6$ cells/kg to at or about $7.5 \times 10^6$ cells/kg, or from at or about $7.5 \times 10^6$ cells/kg to at or about $1 \times 10^7$ cells/kg. In some embodiments, the individual dose is from at or about $5 \times 10^7$ to at or about $10 \times 10^9$, such as from at or about $5 \times 10^7$ to at or about $5 \times 10^9$, from about or about $5 \times 10^7$ to at or about $1 \times 10^9$, from at or about $5 \times 10^7$ to at or about $5 \times 10^8$, from about or about $5 \times 10^7$ to at or about $1 \times 10^8$, $1 \times 10^8$ to at or about $10 \times 10^9$, from at or about $1 \times 10^8$ to at or about $5 \times 10^9$, from about or about $1 \times 10^8$ to at or about $1 \times 10^9$, from at or about $1 \times 10^9$, from at or about $1 \times 10^8$ to at or about $5 \times 10^8$, from at or about $5 \times 10^8$ to at or about $10 \times 10^9$, from at or about $5 \times 10^8$ to at or about $5 \times 10^9$, from about or about $5 \times 10^8$ to at or about $1 \times 10^9$, from at or about $1 \times 10^9$ to at or about $10 \times 10^9$, from at or about $1 \times 10^9$ to at or about $5 \times 10^9$, or from at or about $5 \times 10^9$ to at or about $10 \times 10^9$. In any of the above embodiments, the dose is given as the number of cells g-NK cells or an NK cell subset that is associated with or includes a surrogate marker for g-NK cells, such as any of the NK cell subsets described above, or a number of viable cells of any of the foregoing. In any of the above embodiments, the dose is given as the number of cells in a composition of expanded cells produced by the method, or a number of viable cells of any of the foregoing.

Among the compositions are pharmaceutical compositions and formulations for administration, such as for adoptive cell therapy. In some embodiments, the engineered cells are formulated with a pharmaceutically acceptable carrier.

A pharmaceutically acceptable carrier can include all solvents, dispersion media, coatings, antibacterial and antifungal agents, isotonic and absorption delaying agents, and the like, compatible with pharmaceutical administration (Gennaro, 2000, Remington: The science and practice of pharmacy, Lippincott, Williams & Wilkins, Philadelphia, PA). Examples of such carriers or diluents include, but are not limited to, water, saline, Ringer's solutions, dextrose solution, and 5% human serum albumin. Liposomes and non-aqueous vehicles such as fixed oils may also be used. Supplementary active compounds can also be incorporated into the compositions. The pharmaceutical carrier should be one that is suitable for NK cells, such as a saline solution, a dextrose solution or a solution comprising human serum albumin.

In some embodiments, the pharmaceutically acceptable carrier or vehicle for such compositions is any non-toxic aqueous solution in which the NK cells can be maintained, or remain viable, for a time sufficient to allow administration of live NK cells. For example, the pharmaceutically acceptable carrier or vehicle can be a saline solution or buffered saline solution. The pharmaceutically acceptable carrier or vehicle can also include various bio materials that may increase the efficiency of NK cells. Cell vehicles and carriers can, for example, include polysaccharides such as methylcellulose (M. C. Tate, D. A. Shear, S. W. Hoffman, D. G. Stein, M. C. LaPlaca, Biomaterials 22, 1113, 2001, which is incorporated herein by reference in its entirety), chitosan (Suh J K F, Matthew H W T. Biomaterials, 21, 2589, 2000; Lahiji A, Sohrabi A, Hungerford D S, et al., J Biomed Mater Res, 51, 586, 2000, each of which is incorporated herein by reference in its entirety), N-isopropylacrylamide copolymer P(NIPAM-co-AA) (Y. H. Bae, B. Vernon, C. K. Han, S. W. Kim, J. Control. Release 53, 249, 1998; H. Gappa, M. Baudys, J. J. Koh, S. W. Kim, Y. H. Bae, Tissue Eng. 7, 35, 2001, each of which is incorporated herein by reference in its entirety), as well as Poly(oxyethylene)/poly(D,L-lactic acid-co-glycolic acid) (B. Jeong, K. M. Lee, A. Gutowska, Y. H. An, Biomacromolecules 3, 865, 2002, which is incorporated herein by reference in its entirety), P(PF-co-EG) (Suggs L J, Mikos A G. Cell Trans, 8, 345, 1999, which is incorporated herein by reference in its entirety), PEO/PEG (Mann B K, Gobin A S, Tsai A T, Schmedlen R H, West J L., Biomaterials, 22, 3045, 2001; Bryant S J, Anseth K S. Biomaterials, 22, 619, 2001, each of which is incorporated herein by reference in its entirety), PVA (Chih-Ta Lee, Po-Han Kung and Yu-Der Lee, Carbohydrate Polymers, 61, 348, 2005, which is incorporated herein by reference in its entirety), collagen (Lee C R, Grodzinsky A J, Spector M., Biomaterials 22, 3145, 2001, which is incorporated herein by reference in its entirety), alginate (Bouhadir K H, Lee K Y, Alsberg E, Damm K L, Anderson K W, Mooney D J. Biotech Prog 17, 945, 2001; Smidsrd O, Skjak-Braek G., Trends Biotech, 8, 71, 1990, each of which is incorporated herein by reference in its entirety).

In some embodiments, the NK cells such as $NKG2C^{pos}$ cells or a subset thereof can be present in the composition in an effective amount. In some embodiments, the composition contains an effective amount of g-NK cells, such as $FcR\gamma^{neg}$ cells or cells having a g-NK surrogate marker profile thereof. An effective amount of cells can vary depending on the patient, as well as the type, severity and extent of disease. Thus, a physician can determine what an effective amount is after considering the health of the subject, the extent and severity of disease, and other variables.

In certain embodiments, the number of such cells in the composition is a therapeutically effective amount. In some embodiments, the amount is an amount that reduces the severity, the duration and/or the symptoms associated with cancer, viral infection, microbial infection, or septic shock in an animal. In some embodiments, a therapeutically effective amount is a dose of cells that results in a reduction of the growth or spread of cancer by at least 2.5%, at least 5%, at least 10%, at least 15%, at least 25%, at least 35%, at least 45%, at least 50%, at least 75%, at least 85%, by at least 90%, at least 95%, or at least 99% in a patient or an animal administered a composition described herein relative to the growth or spread of cancer in a patient (or an animal) or a group of patients (or animals) not administered the composition. In some embodiments, a therapeutically effective amount is an amount to result in cytotoxic activity resulting in activity to inhibit or reduce the growth of cancer, viral and microbial cells.

In some embodiments, the composition comprises an amount of NKG2C$^{pos}$ cells or a subset thereof that is from at or about $10^5$ and at or about $10^{12}$ NKG2C$^{pos}$ cells or a subset thereof, or from at or about $10^5$ to at or about $10^8$ NKG2C$^{pos}$ cells or a subset thereof, or from at or about $10^6$ and at or about $10^{12}$ NKG2C$^{pos}$ cells or a subset thereof, or from at or about $10^8$ and at or about $10^{11}$ NKG2C$^{pos}$ cells or a subset thereof, or from at or about $10^9$ and at or about $10^{10}$ NKG2C$^{pos}$ cells or a subset thereof. In some embodiments, the composition comprises greater than or greater than at or about $10^5$ NKG2C$^{pos}$ cells or a subset thereof, at or about $10^6$ NKG2C$^{pos}$ cells or a subset thereof, at or about $10^7$ NKG2C$^{pos}$ cells or a subset thereof, at or about $10^8$ NKG2C$^{pos}$ cells or a subset thereof, at or about $10^9$ NKG2C$^{pos}$ cells or a subset thereof, at or about $10^{10}$ NKG2C$^{pos}$ cells or a subset thereof, at or about $10^{11}$ NKG2C$^{pos}$ cells or a subset thereof, or at or about $10^{12}$ NKG2C$^{pos}$ cells or a subset thereof. In some embodiments, such an amount can be administered to a subject having a disease or condition, such as to a cancer patient.

In some embodiments, the composition comprises an amount of g-NK cells that is from at or about $10^5$ and at or about $10^{12}$ g-NK cells, or from at or about $10^5$ to at or about $10^8$ g-NK cells, or from at or about $10^6$ and at or about $10^{12}$ g-NK cells, or from at or about $10^8$ and at or about $10^{11}$ g-NK cells, or from at or about $10^9$ and at or about $10^{10}$ g-NK cells. In some embodiments, the composition comprises greater than or greater than at or about $10^5$ g-NK cells, at or about $10^6$ g-NK cells, at or about $10^7$ g-NK cells, at or about $10^8$ g-NK cells, at or about $10^9$ g-NK cells, at or about $10^{10}$ g-NK cells, at or about $10^{11}$ g-NK cells, or at or about $10^{12}$ g-NK cells. In some embodiments, such an amount can be administered to a subject having a disease or condition, such as to a cancer patient.

In some embodiments, the volume of the composition is at least or at least about 10 mL, 50 mL, 100 mL, 200 mL, 300 mL, 400 mL or 500 mL, such as is from or from about 10 mL to 500 mL, 10 mL to 200 mL, 10 mL to 100 mL, 10 mL to 50 mL, 50 mL to 500 mL, 50 mL to 200 mL, 50 mL to 100 mL, 100 mL to 500 mL, 100 mL to 200 mL or 200 mL to 500 mL, each inclusive. In some embodiments, the composition has a cell density of at least or at least about $1\times10^5$ cells/mL, $5\times10^5$ cells/mL, $1\times10^6$ cells/mL, $5\times10^6$ cells/mL, $1\times10^7$ cells/mL, $5\times10^7$ cells/mL or $1\times10^8$ cells/mL. In some embodiments, the cell density of the composition is between or between about $1\times10^5$ cells/mL to $1\times10^8$ cells/mL, $1\times10^5$ cells/mL to $1\times10^7$ cells/mL, $1\times10^5$ cells/mL to $1\times10^6$ cells/mL, $1\times10^6$ cells/mL to $1\times10^7$ cells/mL, $1\times10^6$ cells/mL to $1\times10^8$ cells/mL, $1\times10^6$ cells/mL to $1\times10^7$ cells/mL or $1\times10^7$ cells/mL to $1\times10^8$ cells/mL, each inclusive.

In some embodiments, the composition, including pharmaceutical composition, is sterile. In some embodiments, isolation or enrichment of the cells is carried out in a closed or sterile environment, for example, to minimize error, user handling and/or contamination. In some embodiments, sterility may be readily accomplished, e.g., by filtration through sterile filtration membranes.

Also provided herein are compositions that are suitable for cryopreserving the provided NK cells. In some embodiments, the composition comprises a cryoprotectant. In some embodiments, the cryoprotectant is or comprises DMSO and/or s glycerol. In some embodiments, compositions formulated for cryopreservation can be stored at low temperatures, such as ultra low temperatures, for example, storage with temperature ranges from −40° C. to −150° C., such as or about 80° C.±6.0° C.

In some embodiments, the compositions can be preserved at ultra low temperature before the administration to a patient. In some aspects, NK cell subsets, such as g-NK cells, can be isolated, processed and expanded, such as in accord with the provided methods, and then stored at ultra-low temperature prior to administration to a subject.

A typical method for the preservation at ultra low temperature in small scale is described, for example, in U.S. Pat. No. 6,168,991. For small-scale, cells can be preserved at ultra low temperature by low density suspension (e.g., at a concentration of about 200×106/ml) in 5% human albumin serum (HAS) which is previously cooled. An equivalent amount of 20% DMSO can be added into the HAS solution. Aliquots of the mixture can be placed into vials and frozen overnight inside an ultra low temperature chamber at about −80° C.

In some embodiments, the cryopreserved NK cells are prepared for administration by thawing. In some cases, the NK cells can be administered to a subject immediately after thawing. In such an embodiment, the composition is ready-to-use without any further processing. In other cases, the NK cells are further processed after thawing, such as by resuspension with a pharmaceutically acceptable carrier, incubation with an activating or stimulating agent, or are activated washed and resuspended in a pharmaceutically acceptable buffer prior to administration to a subject.

IV. METHODS OF TREATMENT

Provided herein are compositions and methods relating to the provided cell compositions comprising g-NK cells described herein for use in treating diseases or conditions in a subject. In some embodiments, provided herein is a method of treating a condition in an individual, comprising administering any of the provided compositions, such as compositions comprising g-NK cells, to an individual in need thereof. In particular embodiments, the composition is produced by the methods provided herein. Such methods and uses include therapeutic methods and uses, for example, involving administration of the therapeutic cells, or compositions containing the same, to a subject having a disease, condition, or disorder. In some cases, the disease or disorder is a tumor or cancer. In some embodiments, the cells or pharmaceutical composition thereof is administered in an effective amount to effect treatment of the disease or disorder. Uses include uses of the cells or pharmaceutical compositions thereof in such methods and treatments, and in the preparation of a medicament in order to carry out such therapeutic methods. In some embodiments, the methods thereby treat the disease or condition or disorder in the subject In some embodiments, the methods of treatment or uses involve administration of an effective amount of a composition containing a composition of expanded NK cells produced by the provided method to an individual. In some embodiments, from at or about $10^5$ to at about $10^{12}$, or from at or about $10^5$ and at or about $10^8$, or from at or about $10^6$ and at or about $10^{12}$, or from at or about $10^8$ and at or about $10^{11}$, or from at or about $10^9$ and at or about $10^{10}$ of such expanded NK cells is administered to an individual subject. In some embodiments, a dose of cells containing at or greater than at or about $10^5$, at or greater than at or about $10^6$, at or greater than at or about $10^7$, at or greater than at or about $10^8$, at or greater than at or about $10^9$, at or greater than at or about $10^{10}$, at or greater than at or about $10^{11}$, or at or greater than at or about $10^{12}$ of such expanded NK cells are administered to the individual. In some embodiments, from or from about $10^6$ to $10^{10}$ of such expanded NK cells per kg are administered to the subject.

In some embodiments, the methods of treatment or uses involve administration of an effective amount of any of the provided NK cell compositions, including any as described in Section III, to an individual. In some embodiments, from at or about $10^5$ to at about $10^{12}$, or from at or about $10^5$ and at or about $10^8$, or from at or about $10^6$ and at or about $10^{12}$, or from at or about $10^8$ and at or about $10^{11}$, or from at or about $10^9$ and at or about $10^{10}$ of NK cells from any of the provided compositions is administered to an individual subject. In some embodiments, a dose of cells containing at or greater than at or about $10^5$, at or greater than at or about $10^6$, at or greater than at or about $10^7$, at or greater than at or about $10^8$, at or greater than at or about $10^9$, at or greater than at or about $10^{10}$, at or greater than at or about $10^{11}$, or at or greater than at or about $10^{12}$ of NK cells from any of the provided compositions are administered to the individual. In some embodiments, from or from about $10^6$ to $10^{10}$ of NK cells of any of the provided compositions per kg are administered to the subject.

In some embodiments, the methods of treatment or uses involve administration of an effective amount of a composition containing a population of NKG2C$^{pos}$ cells or a subset thereof to an individual. In some embodiments, from at or about $10^5$ to at about $10^{12}$ NKG2C$^{pos}$ cells or a subset thereof, or from at or about $10^5$ and at or about $10^8$ NKG2C$^{pos}$ cells or a subset thereof, or from at or about $10^6$ and at or about $10^{12}$ NKG2C$^{pos}$ cells or a subset thereof, or from at or about $10^8$ and at or about $10^{11}$ NKG2C$^{pos}$ cells or a subset thereof, or from at or about $10^9$ and at or about $10^{10}$ NKG2C$^{pos}$ cells or a subset thereof. In some embodiments, a dose of cells containing at or greater than at or about $10^5$ NKG2C$^{pos}$ cells or a subset thereof, at or greater than at or about $10^6$ NKG2C$^{pos}$ cells or a subset thereof, at or greater than at or about $10^7$ NKG2C$^{pos}$ cells or a subset thereof, at or greater than at or about $10^8$ NKG2C$^{pos}$ cells or a subset thereof, at or greater than at or about $10^9$ NKG2C$^{pos}$ cells or a subset thereof, at or greater than at or about $10^{10}$ NKG2C$^{pos}$ cells or a subset thereof, at or greater than at or about $10^{11}$ NKG2C$^{pos}$ cells or a subset thereof, or at or greater than at or about $10^{12}$ NKG2C$^{pos}$ cells or a subset thereof are administered to the individual. In some embodiments, from or from about $10^6$ to $10^{10}$ g NKG2C$^{pos}$ cells or a subset thereof per kilogram body weight of a subject are administered to the subject.

In some embodiments, the methods of treatment comprises administering an effective amount of a composition containing g-NK cells to an individual. In some embodiments, from at or about $10^5$ to at about $10^{12}$ g-NK cells, or from at or about $10^5$ and at or about $10^8$ g-NK cells, or from at or about $10^6$ and at or about $10^{12}$ g-NK cells, or from at or about $10^8$ and at or about $10^{11}$ g-NK cells, or from at or about $10^9$ and at or about $10^{10}$ g-NK cells. In some embodiments, a dose of cells containing at or greater than at or about $10^5$ g-NK cells, at or greater than at or about $10^6$ g-NK cells, at or greater than at or about $10^7$ g-NK cells, at or greater than at or about $10^8$ g-NK cells, at or greater than at or about $10^9$ g-NK cells, at or greater than at or about $10^{10}$ g-NK cells, at or greater than at or about $10^{11}$ g-NK cells, or at or greater than at or about $10^{12}$ g-NK cells are administered to the individual. In some embodiments, from or from about $10^6$ to $10^{10}$ g-NK cells/kg are administered to the subject.

In some embodiments, the dose for administration in accord with any of the provided methods of treatment or uses is from at or about $1\times10^5$ cells/kg to at or about $1\times10^7$ cells/kg, such as from at or about $1\times10^5$ cells/kg to at or about $7.5\times10^6$ cells/kg, from at or about $1\times10^5$ cells/kg to at or about $5\times10^6$ cells/kg, from at or about $1\times10^5$ cells/kg to at or about $2.5\times10^6$ cells/kg, from at or about $1\times10^5$ cells/kg to at or about $1\times10^6$ cells/kg, from at or about $1\times10^5$ cells/kg to at or about $7.5\times10^5$ cells/kg, from at or about $1\times10^5$ cells/kg to at or about $5\times10^5$ cells/kg, from at or about $1\times10^5$ cells/kg to at or about $2.5\times10^5$ cells/kg, from at or about $2.5\times10^5$ cells/kg to at or about $1\times10^7$ cells/kg, from at or about $2.5\times10^5$ cells/kg to at or about $7.5\times10^6$ cells/kg, from at or about $2.5\times10^5$ cells/kg to at or about $5\times10^6$ cells/kg, from at or about $2.5\times10^5$ cells/kg to at or about $2.5\times10^6$ cells/kg, from at or about $2.5\times10^5$ cells/kg to at or about $1\times10^6$ cells/kg, from at or about $2.5\times10^5$ cells/kg to at or about $7.5\times10^5$ cells/kg, from at or about $2.5\times10^5$ cells/kg to at or about $5\times10^5$ cells/kg, from at or about $5\times10^5$ cells/kg to at or about $1\times10^7$ cells/kg, from at or about $5\times10^5$ cells/kg to at or about $7.5\times10^6$ cells/kg, from at or about $5\times10^5$ cells/kg to at or about $5\times10^6$ cells/kg, from at or about $5\times10^5$ cells/kg to at or about $2.5\times10^6$ cells/kg, from at or about $5\times10^5$ cells/kg to at or about $1\times10^6$ cells/kg, from at or about $5\times10^5$ cells/kg to at or about $7.5\times10^5$ cells/kg, from at or about $1\times10^6$ cells/kg to at or about $1\times10^7$ cells/kg, from at or about $1\times10^6$ cells/kg to at or about $7.5\times10^6$ cells/kg, from at or about $1\times10^6$ cells/kg to at or about $5\times10^6$ cells/kg, from at or about $1\times10^6$ cells/kg to at or about $2.5\times10^6$ cells/kg, from at or about $2.5\times10^6$ cells/kg to at or about $1\times10^7$ cells/kg, from at or about $2.5\times10^6$ cells/kg to at or about $7.5\times10^6$ cells/kg, from at or about $2.5\times10^6$ cells/kg to at or about $5\times10^6$ cells/kg, from at or about $5\times10^6$ cells/kg to at or about $1\times10^7$ cells/kg, from at or about $5\times10^6$ cells/kg to at or about $7.5\times10^6$ cells/kg, or from at or about $7.5\times10^6$ cells/kg to at or about $1\times10^7$ cells/kg. In some embodiments, the dose is given as the number of g-NK cells or an NK cell subset that is associated with or includes a surrogate marker for g-NK cells, such as any of the NK cell subsets described herein, or a number of viable cells of any of the foregoing. In any of the above embodiments, the dose is given as the number of cells in a composition of expanded cells produced by the provided method, or a number of viable cells of any of the foregoing.

In some embodiments, the dose for administration in accord with any of the methods of treatment or uses is from at or about $5\times10^7$ to at or about $10\times10^9$, such as from at or about $5\times10^7$ to at or about $5\times10^9$, from about or about $5\times10^7$ to at or about $1\times10^9$, from at or about $5\times10^7$ to at or about $5\times10^8$, from about or about $5\times10^7$ to at or about $1\times10^8$, $1\times10^8$ to at or about $10\times10^9$, from at or about $1\times10^8$ to at or about $5\times10^9$, from about or about $1\times10^8$ to at or about $1\times10^9$, from at or about $1\times10^8$ to at or about $5\times10^8$, from at or about $5\times10^8$ to at or about $10\times10^9$, from at or about $5\times10^8$ to at or about $5\times10^9$, from about or about $5\times10^8$ to at or about $1\times10^9$, from at or about $1\times10^9$ to at or about $10\times10^9$, from at or about $1\times10^9$ to at or about $5\times10^9$, or from at or about $5\times10^9$ to at or about $10\times10^9$. In some embodiments, the dose is given as the number of g-NK cells or an NK cell subset that is associated with or includes a surrogate marker for g-NK cells, such as any of the NK cell subsets described herein, or a number of viable cells of any of the foregoing. In any of the above embodiments, the dose is given as the number of cells in a composition of expanded cells produced by the provided method, or a number of viable cells of any of the foregoing.

In some embodiments, the composition containing expanded NK cells are administered to an individual soon after expansion according to the provided methods. In other embodiments, the expanded NK cells are stored or expanded by growth in culture prior to administration, such as by methods described above. For example, the NK cells can be stored for greater than 6, 12, 18, or 24 months prior to administration to the individual.

In some embodiments, the provided compositions containing NK cells and subsets thereof, such as g-NK cells, can be administered to a subject by any convenient route including parenteral routes such as subcutaneous, intramuscular, intravenous, and/or epidural routes of administration.

The provided NK cells and subsets thereof, such as g-NK cells, and compositions can be used in methods of treating an individual with a tumor or hyperproliferative disorders or microbial infection such as a viral infection, yeast infection, fungal infection, protozoan infection and/or bacterial infection. The disclosed methods of treating a subject with the provided NK cells and subsets thereof, such as g-NK cells, and compositions can be in combination with a therapeutic monoclonal antibody, such as an anti-tumor antigen or anti-cancer antibody, anti-viral antibody or anti-bacterial antibody. The provided NK cells and subsets thereof, such as g-NK cells, and compositions can be administered for treatment of animals, such as mammalian animals, for example human subjects.

In some examples, the methods include treating a hyperproliferative disorder, such as a hematological malignancy or a solid tumor. Examples of types of cancer and proliferative disorders that can be treated with the compositions described herein include, but are not limited to, leukemia (e.g., myeloblastic, promyelocytic, myelomonocytic, monocytic, erythroleukemia, chronic myelocytic (granulocytic) leukemia, and chronic lymphocytic leukemia), lymphoma (e.g., Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilm's tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. The treatment and/or prevention of cancer includes, but is not limited to, alleviating one or more symptoms associated with cancer, the inhibition or reduction of the progression of cancer, the promotion of the regression of cancer, and/or the promotion of the immune response.

In some examples, the methods include treating a viral infection, such as an infection caused by the presence of a virus in the body. Viral infections include chronic or persistent viral infections, which are viral infections that are able to infect a host and reproduce within the cells of a host over a prolonged period of time-usually weeks, months or years, before proving fatal. Viruses giving rise to chronic infections that which may be treated in accordance with the present invention include, for example, the human papilloma viruses (HPV), Herpes simplex, and other herpes viruses, the viruses of hepatitis B and C as well as other hepatitis viruses, human immunodeficiency virus, and the measles virus, all of which can produce important clinical diseases. Prolonged infection may ultimately lead to the induction of disease which may be, e.g., in the case of hepatitis C virus liver cancer, fatal to the patient. Other chronic viral infections which may be treated in accordance with the present invention include Epstein Barr virus (EBV), as well as other viruses such as those which may be associated with tumors.

Examples of viral infections which can be treated or prevented with the compositions and methods described herein include, but are limited to, viral infections caused by retroviruses (e.g., human T-cell lymphotrophic virus (HTLV) types I and II and human immunodeficiency virus (HIV)), herpes viruses (e.g., herpes simplex virus (HSV) types I and II, Epstein-Ban virus and cytomegalovirus), arenaviruses (e.g., lassa fever virus), paramyxoviruses (e.g., morbillivirus virus, human respiratory syncytial virus, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., Sendai virus and influenza viruses A, B and C), papovaviruses (e.g., papillomaviruses), picornaviruses (e.g., rhinoviruses, enteroviruses and hepatitis A viruses), poxviruses, reoviruses (e.g., rotaviruses), togaviruses (e.g., rubella virus), and rhabdoviruses (e.g., rabies virus). The treatment and/or prevention of a viral infection includes, but is not limited to, alleviating one or more symptoms associated with said infection, the inhibition, reduction or suppression of viral replication, and/or the enhancement of the immune response.

In some embodiments, the provided NK cells and subsets thereof, such as g-NK cells, and compositions are used in a method of treating a yeast or bacterial infection. For example, the provided g-NK cells and compositions and methods described herein can treat infections relating to *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholera, Escherichia coli, Pseudomonas aeruginosa, Campylobacter* (*Vibrio*) *fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella aborts, Brucella suis, Brucella melitensis, Mycoplasma* spp., *Rickettsia prowazeki, Rickettsia tsutsugumushi, Chlamydia* spp., *Helicobacter pylori* or combinations thereof.

A. Combination Therapy

In some embodiments, compositions containing g-NK cells as provided herein can be administered in a combination therapy with one or more other agents for treating a disease or condition in a subject. In such embodiments, the composition containing g-NK cells as provided herein can be administered prior to, concurrently with or subsequent (after) the administration of one or more other agents. For example, the g-NK cells can be administered simultaneously or sequentially with anti-microbial, anti-viral and other therapeutic agents. Exemplary combination therapies are described in the following subsections.

I. Antibody Combination

In some embodiments, compositions containing g-NK cells as provided herein exhibit enhanced activity when activated by or contacted with antibodies or Fc-containing proteins, such as compared to conventional NK cells. For example, the g-NK cells can be activated by antibody-mediated crosslinking of CD16 or by antibody-coated tumor cells.

In some embodiments, provided herein is a method of treating a condition in an individual comprising administering g-NK cells or composition thereof and an antibody to a subject. One of ordinary skill in the art can select an appropriate therapeutic (e.g., anti-cancer) monoclonal antibody to administer to the subject with the provided g-NK cells and compositions described herein, such as depending on the particular disease or condition of the individual. Suitable antibodies may include polyclonal, monoclonal, fragments (such as Fab fragments), single chain antibodies and other forms of specific binding molecules.

In some embodiments, the antibody may further include humanized or human antibodies. Humanized forms of non-human antibodies are chimeric Igs, Ig chains or fragments (such as Fv, Fab, Fab', F(ab')2 or other antigen-binding subsequences of an antibody) that contain minimal sequence derived from non-human Ig. In some embodiments, the antibody comprises an Fc domain.

Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody (Jones et al., 1986; Riechmann et al., 1988; Verhoeyen et al., 1988). Such "humanized" antibodies are chimeric antibodies (1989), wherein substantially less than an intact human variable domain has been substituted by the corresponding sequence from a non-human species. In practice, humanized antibodies are typically human antibodies in which some CDR residues and possibly some Fc residues are substituted by residues from analogous sites in rodent antibodies. Humanized antibodies include human antibodies (recipient antibody) in which residues from a complementary determining region (CDR) of the recipient are replaced by residues from a CDR of a non-human species (donor antibody) such as mouse, rat or rabbit, having the desired specificity, affinity and capacity. In some instances, corresponding non-human residues replace Fv framework residues of the human antibody. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human antibody consensus sequence. The humanized antibody optimally also comprises at least a portion of an antibody constant region (Fc), typically that of a human antibody (Jones et al., 1986; Presta, 1992; Riechmann et al., 1988).

Human antibodies can also be produced using various techniques, including phage display libraries (Hoogenboom et al., 1991; Marks et al., 1991) and the preparation of human mAbs (Boerner et al., 1991; Reisfeld and Sell, 1985). Similarly, introducing human Ig genes into transgenic animals in which the endogenous antibody genes have been partially or completely inactivated can be exploited to synthesize human Abs. Upon challenge, human antibody production is observed, which closely resembles that seen in humans in all respects, including gene rearrangement, assembly, and antibody repertoire (1997a; 1997b; 1997c; 1997d; 1997; 1997; Fishwild et al., 1996; 1997; 1997; 2001; 1996; 1997; 1997; 1997; Lonberg and Huszar, 1995; Lonberg et al., 1994; Marks et al., 1992; 1997; 1997; 1997).

Specifically, the cells of the present invention can be targeted to tumors by administration with an antibody that recognizes a tumor associated antigen. One of ordinary skill in the art will appreciate that the present g-NK cells are suitable for use with a wide variety of antibodies that recognize tumor associated antigens. Non-limiting examples of a tumor associated antigen includes CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, LOXL2, MET, IGF1R, IGLF2, EPHA3, FR-alpha, phosphatidylserine, Syndecan 1, SLAMF7 (CD319), TRAILR1, TRAILR2, RANKL, FAP, vimentin or tenascin. In some cases, the antibody is an anti-CD20 antibody (e.g. rituximab), an anti-HER2 antibody (e.g. cetuximab), an anti-CD52 antibody, an anti-EGFR antibody and an anti-CD38 antibody (e.g. daratumumab), an anti-SLAMF7 antibody (e.g. elotuzumab).

Non-limiting antibodies that can be used in the provided methods in combination therapy with a cell composition including g-NK cells include Trastuzumab (Herceptin®), Ramucirumab (Cyramza®), Atezolizumab (Tecentriq™), Nivolumab (Opdivo®), Durvalumab (Imfinzi™), Avelumab (Bavencio®), Pembrolizumab (Keytruda®), Bevacizumab (Avastin®), Everolimus (Afinitor®), Pertuzumab (Perjeta®), ado-Trastuzumab emtansine (Kadcyla®), Cetuximab (Erbitux®), Denosumab (Xgeva®), Rituximab (Rituxan®), Alemtuzumab (Campath®), Ofatumumab (Arzerra®), Obinutuzumab (Gazyva®), Necitumumab (Portrazza™), Ibritumomab tiuxetan (Zevalin®), Brentuximab vedotin (Adcetris®), Siltuximab (Sylvant®), Bortezomib (Velcade®), Daratumumab (Darzalex™), Elotuzumab (Empliciti™), Dinutuximab (Unituxin™), Olaratumab (Lartruvo™), Ocrelizumab, Isatuximab, Truxima, Blitzima, Ritemvia, Rituzena, Herzuma, Ruxience, ABP 798, Kanjinti, Ogivry, BI 695500, Novex (RTXM83), Tositumomab or Ontruzant, or a biosimilar thereof. Exemplary antibodies include rituximab, trastuzumab, aletuzumab, certuximab, daratumumab, veltuzumab, ofatumumab, ublituximab, ocaratuzumab or elotuzumab.

In some embodiments, the antibody can be an anti-PD-1 or anti-PD-L1 antibody. Antibodies targeting PD-1 or PD-L1 include, but are not limited to, Nivolumab, Pembrolizumab or Atezolizumab.

Antibodies specific for a selected cancer type can be chosen, and include any antibody approved for treatment of cancer. Examples include trastuzumab (Herceptin) for breast cancer, rituximab (Rituxan) for lymphoma, and cetuximab (Erbitux) for head and neck squamous cell carcinoma. A skilled artisan is familiar with FDA-approved monoclonal antibodies able to bind particular tumor or disease antigens, any of which can be used in accord with the provided methods for treating the tumor or disease.

In some embodiments, the methods are for treating adenocarcinoma of the stomach or gastroesophageal junction and the antibody is Trastuzumab (Herceptin®) or Ramucirumab (Cyramza®).

In some embodiments, the methods are for treating bladder cancer and the antibody is Atezolizumab (Tecentriq™), Nivolumab (Opdivo®), Durvalumab (Imfinzi™), Avelumab (Bavencio®), or Pembrolizumab (Keytruda®).

In some embodiments, the methods are for treating brain cancer and the antibody is Bevacizumab (Avastin®).

In some embodiments, the methods are for treating breast cancer and the antibody is Trastuzumab (Herceptin®).

In some embodiments, the methods are for treating cervical cancer and the antibody is Bevacizumab (Avastin®).

In some embodiments, the methods are for treating colorectal cancer and the antibody is Cetuximab (Erbitux®), Panitumumab (Vectibix®), Bevacizumab (Avastin®) or Ramucirumab (Cyramza®).

In some embodiments, the methods are for treating endocrine/neuroendocrine tumors and the antibody is Avelumab (Bavencio®).

In some embodiments, the methods are for treating head and neck cancer and the antibody is Cetuximab (Erbitux®), Pembrolizumab (Keytruda®), Nivolumab (Opdivo®), Trastuzumab or Ramucirumab.

In some embodiments, the methods are for treating bone cancer and the antibody is Denosumab (Xgeva®).

In some embodiments, the methods are for treating kidney cancer and the antibody is Bevacizumab (Avastin®) or Nivolumab (Opdivo®).

In some embodiments, the methods are for treating leukemia and the antibody is Rituximab (Rituxan®), Alemtuzumab (Campath®), Ofatumumab (Arzerra®), Obinutuzumab (Gazyva®) or Blinatumomab (Blincyto®).

In some embodiments, the methods are for treating lung cancer and the antibody is Bevacizumab (Avastin®), Ramucirumab (Cyramza®), Nivolumab (Opdivo®), Necitumumab (Portrazza™), Pembrolizumab (Keytruda®) or Atezolizumab (Tecentriq™).

In some embodiments, the methods are for treating lymphoma and the antibody is Ibritumomab tiuxetan (Zevalin®), Brentuximab vedotin (Adcetris®), Rituximab (Rituxan®), Siltuximab (Sylvant®), Obinutuzumab (Gazyva®), Nivolumab (Opdivo®) or Pembrolizumab (Keytruda®).

In some embodiments, the methods are for treating multiple myeloma and the antibodies are Bortezomib (Velcade®), Daratumumab (Darzalex™), or Elotuzumab (Empliciti™).

In some embodiments, the methods are for treating neuroblastoma and the antibody is Dinutuximab (Unituxin™).

In some embodiments, the methods are for treating ovarian epithelial/fallopian tube/primary peritoneal cancer and the antibody is Bevacizumab (Avastin®).

In some embodiments, the method is for treating pancreatic cancer and the antibody is Cetuximab (Erbitux®) or Bevacizumab (Avastin®).

In some embodiments, the method is for treating skin cancer and the antibody is Ipilimumab (Yervoy®), Pembrolizumab (Keytruda®), Avelumab (Bavencio®) or Nivolumab (Opdivo®).

In some embodiments, the method is for treating soft tissue sarcoma and the antibody is Olaratumab (Lartruvo™).

The g-NK cells and the additional agent can be administered sequentially or simultaneously. In some embodiments, the additional agent can be administered before administration of the g-NK cells. In some embodiments, the additional agent can be administered after administration of the g-NK cells. For example, the g-NK cells can be administered simultaneously with antibodies specific for a selected cancer type. Alternatively, the g-NK cells can be administered at selected times that are distinct from the times when antibodies specific for a selected cancer type are administered.

In particular examples, the subject is administered an effective dose of an antibody before, after, or substantially simultaneously with the population of g-NK cells. In some examples, the subject is administered about 0.1 mg/kg to about 100 mg/kg of the antibody (such as about 0.5-10 mg/kg, about 1-20 mg/kg, about 10-50 mg/kg, about 20-100 mg/kg, for example, about 0.5 mg/kg, about 1 mg/kg, about 2 mg/kg, about 3 mg/kg, about 4 mg/kg, about 5 mg/kg, about 8 mg/kg, about 10 mg/kg, about 16 mg/kg, about 20 mg/kg, about 24 mg/kg, about 36 mg/kg, about 48 mg/kg, about 60 mg/kg, about 75 mg/kg, or about 100 mg/kg). An effective amount of the antibody can be selected by a skilled clinician, taking into consideration the particular antibody, the particular disease or conditions (e.g. tumor or other disorder), the general condition of the subject, any additional treatments the subject is receiving or has previously received, and other relevant factors. The subject is also administered a population of g-NK cells described herein. Both the antibody and the population of g-NK cells are typically administered parenterally, for example intravenously; however, injection or infusion to a tumor or close to a tumor (local administration) or administration to the peritoneal cavity can also be used. One of skill in the art can determine appropriate routes of administration.

2. Cytokines or Growth Factors

In some embodiments provided herein, the g-NK cells can be administered to an individual in combination with cytokines and/or growth factors. According to some embodiments, the at least one growth factor comprises a growth factor selected from the group consisting of SCF, FLT3, IL-2, IL-7, IL-15, IL-12 and IL-21. In particular embodiments recombinant IL-2 is administered to the subject. In other particular embodiments, recombinant IL-15 is administered to the subject. In some embodiments, the g-NK cells and the cytokines or growth factors are administered sequentially. For example, the g-NK cells may be administered first, followed by administration of the cytokines and/or growth factors. In some embodiments, the g-NK cells are administered simultaneously with the cytokines or growth factors.

In some embodiments, the subject is administered one or more cytokines (such as IL-2, IL-15, IL-21, and/or IL-12) to support survival and/or growth of NK cells. The cytokine(s) can be administered before, after, or substantially simultaneously with the NK cells. In some examples, the cytokine(s) can be administered after the NK cells. In one specific example, the cytokine(s) is administered to the subject within about 1-8 hours (such as within about 1-4 hours, about 2-6 hours, about 4-6 hours, or about 5-8 hours) of the administration of the NK cells.

3. Chemotherapeutic Agents and Multimodality Combination Therapy

In some embodiments, the provided methods also can include administering g-NK cells with a cancer drug or treatment, such as with a chemotherapeutic agent or cytotoxic agent or other treatment.

In some embodiments, the provided methods also can include administering g-NK cells to an individual in combination with a chemotherapeutic agent. In some embodiments, the chemotherapeutic agent may comprise cyclophosphamide, fludarabine, methyl prednasone In some embodiments, the chemotherapeutic agent is selected from the group consisting of: thalidomide, cisplatin (cis-DDP), oxaliplatin, carboplatin, anthracenediones, mitoxantrone; hydroxyurea, methylhydrazine derivatives, procarbazine (N-methylhydrazine, MM), adrenocortical suppressants, mitotane (.omicron..rho.'-DDD), aminoglutethimide, RXR agonists, bexarotene, tyrosine kinase inhibitors, imatinib, mechlorethamine, cyclophosphamide, ifosfamide, melphalan (L-sarcolysin), chlorambucil, ethylenimines, methylmelamines, hexamethylmelamine, thiotepa, busulfan, carmustine (BCNU), semustine (methyl-CCNTJ), lomustine (CCNU), streptozocin (streptozotocin), DNA synthesis antagonists, estramustine phosphate, triazines, dacarbazine (OTIC, dimethyl-triazenoimidazolecarboxamide), temozolomide, folic acid analogs, methotrexate (amethopterin), pyrimidine analogs, fiuorouracin (5-fluorouracil, 5-FU, 5FTJ), floxuridine (fluorodeox>'uridine, FUdR), cytarabine (cytosine arabinoside), gemcitabine, purine analogs, mercaptopurine (6-mercaptopurine, 6-MP), thioguanine (6-thioguanine, TG), pentostatin (2'-deoxycoformycin, deoxycoformycin), cladribine and fludarabine, topoisomerase inhibitors, amsacrine, vinca alkaloids, vinblastine (VLB), vincristine, taxanes, paclitaxel, nab-paclitaxel, (Abraxane), protein bound paclitaxel (Abraxane®), docetaxel (Taxotere®); epipodophyllotoxins, etoposide, teniposide, camptothecins, topotecan, irinotecan, dactinomycin (actinomycin D), daunorubicin (daunomycin, rubidomycin), doxorubicin, Liposomal doxorubicin (Doxil), bleomycin, mitomycin (mitomycin C), idarubicin, epirubicin, buserelin, adrenocorticosteroids, prednisone, progestins, hydroxyprogesterone caproate, medroxyprogesterone acetate, megestrol acetate, diethylstilbestrol, ethinyl estradiol, tamoxifen, anastrozole; testosterone propionate, fluoxymesterone, flutamide, bicalutamide, and leuprolide.

In some embodiments, the cancer drug is a cytotoxic agent, such as a cytotoxic small molecule. In some embodiments, the cancer drug is an immunomodulatory agent, a Bcl2 inhibitor, a P13K inhibitor, a small molecule proteasome inhibitor, a small molecule tyrosine, a small molecule cyclin-dependent kinase inhibitor, an alkylating agent, an antimetabolite, an anthracyline, an anti-tumor antibiotic, a topoisomerase inhibitor, a mitotic inhibitor, a corticosteroid, or a differentiating agent.

In some embodiments, the cancer drug is an immunomodulatory agent. In some embodiments, the cancer drug is thalidomide or its derivatives. For example, in some cases the cancer drug is lenalidomide or Pomalidomide. In some cases, the cancer drug is lenalidomide.

In some embodiments, the cancer drug is a Bcl-2 inhibitor. For example, the cancer drug can be Venetoclax.

In some embodiments, the cancer drug is a P13K inhibitor. For example, the cancer drug can be Idelaisib.

In some embodiments, the cancer drug is a small molecule tyrosine. For example, the cancer drug can be Imatinib mesylate.

In some embodiments, the cancer drug is a cyclin-dependent kinase inhibitor. For example, the cancer drug can be Sekiciclib.

In some embodiments, the cancer drug is an alkylating agent. Examples of alkylating agents include, but are not limited to, Altretamine, Busulfan, Carboplatin, Carmustine, Chlorambucil, Cisplatin, Cyclophosphamide, Dacarbazine, Lomustine, Melphalan, Oxaliplatin, Temozolomide or Thiotepa.

In some embodiments, the cancer drug is an antimetabolite. Antimetabolites interfere with DNA and RNA growth by substituting for the normal building blocks of RNA and DNA. These agents damage cells during the phase when the cell's chromosomes are being copied. They are commonly used to treat leukemias, cancers of the breast, ovary, and the intestinal tract, as well as other types of cancer. Examples of antimetabolites include, but are not limited to, 5-fluorouracil (5-FU), 6-mercaptopurine (6-MP), Capecitabine (Xeloda®), Cytarabine (Ara-C®), Floxuridine, Fludarabine, Gemcitabine (Gemzar®), Hydroxyurea, Methotrexate or Pemetrexed (Alimta®).

In some embodiments, the cancer drug is an antracycline. Anthracyclines drugs work by changing the DNA inside cancer cells to keep them from growing and multiplying. Anthracyclines are anti-tumor antibiotics that interfere with enzymes involved in copying DNA during the cell cycle. They are widely used for a variety of cancers. A major concern when giving anthracyclines drugs is that they can permanently damage the heart if given in high doses. For this reason, lifetime dose limits are often placed on anthracyclines drugs. In some cases, the dose and schedule of these drugs can be reduced when administered in combination with FcεRIγ-deficient NK cells (G-NK). Examples of antracyclines that can be used in the provided combination therapy include, but are not limited to, Daunorubicin, Doxorubicin (Adriamycin®), Epirubicin or Idarubicin.

In some embodiments, the cancer drug is an anti-tumor antibiotic. Examples of anti-tumor antibiotics include, but are not limited to, Actinomycin-D, Bleomycin, Mitomycin-C, or Mitoxantrone.

In some embodiments, the cancer drug is a topoisomerase inhibitor. Topoisomerase drugs interfere with enzymes called topoisomerases, which help separate the strands of DNA so they can be copied. Topoisomerase inhibitors are grouped according to which type of enzyme they affect. Topoisomerase inhibitors are used to treat certain leukemias, as well as lung, ovarian, gastrointestinal, and other cancers. The topoisomerase inhibitor may be a Topoisomerase I inhibitor or a Topoisomerase II inhibitor. Examples of ttopoisomerase I inhibitors include, but are not limited to, Topotecan or Irinotecan (CPT-11). Examples of topoisomerase II inhibitors include, but are not limited to, Etoposide (VP-16), Teniposide, or Mitoxantrone.

In some embodiments, the cancer drug is a mitotic inhibitors. Mitotic inhibitors are compounds that work by stopping cells from dividing to form new cells but can damage cells in all phases by keeping enzymes from making proteins needed for cell reproduction. They are used to treat many different types of cancer including breast, lung, myelomas, lymphomas, and leukemias. These drugs may cause nerve damage, which can limit the amount that can be given. In some cases, the dose and schedule of these drugs can be reduced when administered in combination with FcεRIγ-deficient NK cells (G-NK). Non-limiting examples of mitotic inhibitors include, but are not limited to, Docetaxel, Estramustine, Ixabepilone, Paclitaxel, Vinblastine, Vincristine or Vinorelbine.

In some embodiments, the cancer drug is a corticosteroid. Corticosteroids, often simply called steroids, are natural hormones and hormone-like drugs that are useful in the treatment of many types of cancer, as well as other illnesses. When these drugs are used as part of cancer treatment, they are considered chemotherapy drugs. Non-limiting example of corticosteroids include, but are not limited to, Prednisone, Methylprednisolone (Solumedrol®) or Dexamethasone (Decadron®).

In some embodiments, the cancer drug is a differentiating agent. Non-limiting examples of differentiating agents include, but are not limited to, Retinoids, Tretinoin (ATRA or Atralin®), Bexarotene (Targretin®) or Arsenic trioxide (Arsenox®).

In some embodiments, the cancer drug is selected from the group consisting of cisplatin, carboplatin, and oxaliplatin. In certain embodiments, the cancer drug is selected from the group consisting of paclitaxel, Abraxane®, and Taxotere®. In one embodiment, the chemotherapeutic agent is selected from the group consisting of asparaginase, bevacizumab, bleomycin, doxorubicin, epirubicin, etoposide, 5-fluorouracil, hydroxyurea, streptozocin, and 6-mercaptopurine, cyclophosphamide, paclitaxel, and gemcitabine.

Other non-limiting examples of cancer drugs for use in combination with g-NK cells include, but are not limited to Everolimus (Afinitor®), Toremifene (Fareston®), Fulvestrant (Faslodex®), Anastrozole (Arimidex®), Exemestane (Aromasin®), Fapatinib (Tykerb®), Fetrozole (Femara®), Pertuzumab (Perjeta®), ado-Trastuzumab emtansine (Kadcyla®), Palbociclib (Ibrance®), Ribociclib (Kisqali®), Ziv-aflibercept (Zaltrap®), Regorafenib (Stivarga®), Fanreotide acetate (Somatuline® Depot), Sorafenib (Nexavar®), Sunitinib (Sutent®), Pazopanib (Votrient®), Temsirolimus (Torisel®), Axitinib (Inlyta®), Cabozantinib (Cabometyx™), Fenvatinib mesylate (Fenvima®), Imatinib mesylate (Gleevec®), Dasatinib (Sprycel®), Nilotinib (Tasigna®), Bosutinib (Bosulif®), Tretinoin (Vesanoid®), Ibrutinib (Imbruvica®), Idelalisib (Zydelig®), Venetoclax (Venclexta™), Ponatinib hydrochloride (Iclusig®), Midostaurin (Rydapt®), Crizotinib (Xalkori®), Erlotinib (Tarceva®), Gefitinib (Iressa®), Afatinib dimaleate (Gilotrif®), Ceritinib (FDK378/Zykadia™), Osimertinib (Tagrisso™), Alectinib (Alecensa®), Brigatinib (Alunbrig™), Cyramza, Denileukin diftitox (Ontak®), Vorinostat (Zolinza®), Romidepsin (Istodax®), Bexarotene (Targretin®), Bortezomib (Velcade®), Pralatrexate (Folotyn®), Idelalisib (Zydelig®), Belinostat (Beleodaq®), Bendamustine, Carfilzomib (Kyphosis®), Panobinostat (Farydak®), Ixazomib citrate (Ninlaro®), Olaparib (Fynparza™), Rucaparib camsylate (Rubraca™), Niraparib tosylate monohydrate (Zejula™), Vinorelbine (Navelbine®), Erlotinib (Tarceva®), Sunitinib (Sutent®), Vismodegib (Erivedge®), Sonidegib (Odomzo®), Vemurafenib (Zelboraf®), Trametinib (Mekinist®), Dabrafenib (Tafinlar®), Cobimetinib (Cotellic™), Alitretinoin (Panretin®), Pazopanib (Votrient®), Alitretinoin (Panretin®), Trabectedin (Yondelis®), or Eribulin (Halaven®).

In some embodiments, the composition containing g-NK cells is administered with radiation therapy.

In some embodiments, the combination therapy is a multimodality cancer therapy involving the combinations of a composition containing g-NK cells as provided herein, an antibody such as any described above, plus a cytotoxic small molecule or a cytotoxic radiation therapy. In some embodiments, the cytotoxic small molecule or radiation therapy is administered to the subject separately, such as prior to or after, the administration of the composition containing g-NK cells. In some embodiments, the cytotoxic small molecule or radiation therapy is administered to the subject concurrently with, such as at or about the same time, as the composition containing g-NK cells. In some cases, a multimodality cancer therapy can further include administration of one or more cytokine or growth factor, such as IL-2 or IL-15, to provide further cytokine support.

Multimodality cancer therapy is therapy that combines more than one method of treatment. Multimodality therapy is also called combination therapy. Different and effective modalities are available for various cancers. The differing biology of tumors and the efficacy of various modalities can dictate specific approaches for each. Antibody based therapy has become frequently used for treating cancer and other disease indications. Responses to antibody therapy have focused on the direct inhibitory effects of these antibodies on the tumor cells, but it has been shown that these antibodies have an effect on the host immune system. FcεRIγ-deficient NK cells (G-NK) are immune effector cells that mediate ADCC when bound to the Fc receptor (CD16) of antibodies. Provided embodiments are designed to demonstrate the improved efficacy of the antibody therapy when used in combination with FcεRIγ-deficient NK cells (G-NK) plus the addition of a small molecule and/or radiation therapy.

In some embodiments, multimodality treatment of adenocarcinoma of the stomach or gastroesophageal junction includes administration of a composition of g-NK cells as provided herein in combination with (1) a monoclonal antibody that is Trastuzumab (Herceptin®) or Ramucirumab (Cyramza®) and (2) a cancer drug or cytotoxic agent that is radiation therapy, capecitabine or cisplatin. In particular embodiments, multimodality treatment of adenocarcinoma of the stomach or gastroesophageal junction includes administration of a composition of g-NK cells as provided herein in combination with Trastuzumab (Herceptin®)+Cisplatin.

In some embodiments, multimodality treatment of bladder cancer includes administration of a composition of g-NK cells as provided herein in combination with (1) a monoclonal antibody that is Atezolizumab (Tecentriq™), Nivolumab (Opdivo®), Durvalumab (Imfinzi™), Avelumab (Bavencio®) or Pembrolizumab (Keytruda®) and (2) a cancer drug or cytotoxic agent that is radiation therapy or cisplatin plus fluorouracil. In particular embodiments, multimodality treatment of bladder cancer includes administration of a composition of g-NK cells as provided herein in combination with Atezolizumab (Tecentriq™)+Cisplatin+5-FU.

In some embodiments, multimodality treatment of brain cancer includes administration of a composition of g-NK cells as provided herein in combination with (1) a monoclonal antibody that is Bevacizumab (Avastin®) and (2) a cancer drug or cytotoxic agent that is Everolimus (Afinitor®), Radiation therapy, Carboplatin, Etoposide or Temozolomide. In particular embodiments, multimodality treatment of brain cancer includes administration of a composition of g-NK cells as provided herein in combination with Bevacizumab (Avastin®)+Radiation therapy.

In some embodiments, multimodality treatment of breast cancer includes administration of a composition of g-NK cells as provided herein in combination with (1) a monoclonal antibody that is Trastuzumab (Herceptin®) and (2) a cancer drug or cytotoxic agent that is Tamoxifen (Nolvadex), Toremifene (Fareston®), Everolimus (Afinitor®), Fulvestrant (Faslodex®), Anastrozole (Arimidex®), Exemestane (Aromasin®), Lapatinib (Tykerb®), Letrozole (Femara®), Pertuzumab (Perjeta®), ado-Trastuzumab emtansine (Kadcyla®), Palbociclib (Ibrance®), Ribociclib (Kisqali®), Cisplatin/Paraplatin, Paclitaxel, Doxorubicin or Radiation therapy. In particular embodiments, multimodality treatment of breast cancer includes administration of a composition of g-NK cells as provided herein in combination with Trastuzumab (Herceptin®)+Cisplatin.

In some embodiments, multimodality treatment of colorectal cancer includes administration of a composition of g-NK cells as provided herein in combination with (1) a monoclonal antibody that is Cetuximab (Erbitux®), Panitumumab (Vectibix®), Bevacizumab (Avastin®) or Ramucirumab (Cyramza®) and (2) a cancer drug or cytotoxic agent that is Ziv-aflibercept (Zaltrap®), Regorafenib (Stivarga®), Radiation therapy, 5-Fluorouracil (5-FU), Capecitabine, Irinotecan or Oxaliplatin. In particular embodiments, multimodality treatment of colorectal cancer includes administration of a composition of g-NK cells as provided herein in combination with Cetuximab (Erbitux®)+Oxaliplatin.

In some embodiments, multimodality treatment of endocrine/neuroendocrine tumors includes administration of a composition of g-NK cells as provided herein in combination with (1) a monoclonal antibody that is Avelumab (Bavencio®) and (2) a cancer drug or cytotoxic agent that is Lanreotide acetate (Somatuline® Depot). In particular embodiments, multimodality treatment of endocrine/neuroendocrine tumors includes administration of a composition of g-NK cells as provided herein in combination with Avelumab (Bavencio®)+Oxaliplatin.

In some embodiments, multimodality treatment of head and neck cancer includes administration of a composition of g-NK cells as provided herein in combination with (1) a monoclonal antibody that is Cetuximab (Erbitux®), Pembrolizumab (Keytruda®), Nivolumab (Opdivo®), Trastuzumab or Ramucirumab and (2) a cancer drug or cytotoxic agent that is Radiation therapy, Carboplatin, Cisplatin, Capecitabine, Irinotecan, 5-fluorouracil or Paclitaxel. In particular embodiments, multimodality treatment of head and neck cancer includes administration of a composition of g-NK cells as provided herein in combination with Cetuximab (Erbitux®)+Cisplatin.

In some embodiments, multimodality treatment of giant cell tumor of the bone includes administration of a composition of g-NK cells as provided herein in combination with (1) a monoclonal antibody that is Denosumab (Xgeva®) and (2) a cancer drug or cytotoxic agent that is Radiation therapy, Doxorubicin, Cisplatin, Etoposide, Cyclophosphamide or Methotrexate. In particular embodiments, multimodality treatment of giant cell tumor of the bone includes administration of a composition of g-NK cells as provided herein in combination with Denosumab (Xgeva®)+Doxorubicin.

In some embodiments, multimodality treatment of kidney cancer includes administration of a composition of g-NK cells as provided herein in combination with (1) a monoclonal antibody that is Bevacizumab (Avastin®) or Nivolumab (Opdivo®) and (2) a cancer drug or cytotoxic agent that is Sorafenib (Nexavar®), Sunitinib (Sutent®), Pazopanib (Votrient®), Temsirolimus (Torisel®), Everolimus (Afinitor®), Axitinib (Inlyta®), Cabozantinib (Cabometyx™ Lenvatinib mesylate (Lenvima®), Vinblastine, 5-fluorouracil (5-FU), Capecitabine or Gemcitabine. In particular embodiments, multimodality treatment of kidney cancer includes administration of a composition of g-NK cells as provided herein in combination with Bevacizumab (Avastin®)+Sorafenib (Nexavar®).

In some embodiments, multimodality treatment of leukemia includes administration of a composition of g-NK cells as provided herein in combination with (1) a monoclonal antibody that is Rituximab (Rituxan®), Alemtuzumab (Campath®), Ofatumumab (Arzerra®), Obinutuzumab (Gazyva®) or Blinatumomab (Blincyto®) and (2) a cancer drug or cytotoxic agent that is Imatinib mesylate (Gleevec®), Dasatinib (Sprycel®), Nilotinib (Tasigna®), Bosutinib (Bosulif®), Tretinoin (Vesanoid®), Ibrutinib (Imbruvica®), Idelalisib (Zydelig®), Venetoclax (Venclexta™), Ponatinib hydrochloride (Iclusig®), Midostaurin (Rydapt®), Methotrexate, Cytarabine, Vincristine, Doxorubicin, Daunorubicin or Cyclophosphamide. In particular embodiments, multimodality treatment of leukemia includes administration of a composition of g-NK cells as provided herein in combination with Rituximab (Rituxan®)+Cyclophosphamide.

In some embodiments, multimodality treatment of lung cancer includes administration of a composition of g-NK cells as provided herein in combination with (1) a monoclonal antibody that is Bevacizumab (Avastin®), Ramucirumab (Cyramza®), Nivolumab (Opdivo®), Necitumumab (Portrazza™), Pembrolizumab (Keytruda®), Atezolizumab (Tecentriq™) and (2) a cancer drug or cytotoxic agent that is Crizotinib (Xalkori®), Erlotinib (Tarceva®), Gefitinib (Iressa®), Afatinib dimaleate (Gilotrif®), Ceritinib (LDK378/Zykadia™), Osimertinib (Tagrisso™), Alectinib (Alecensa®), Brigatinib (Alunbrig™), Cyramza, Radiation therapy, Cisplatin, Carboplatin, Paclitaxel (Taxol), nab-paclitaxel, Abraxane), Docetaxel (Taxotere), Gemcitabine (Gemzar), Vinorelbine (Navelbine), Mnotecan (Camptosar), Etoposide (VP-16), Vinblastine or Pemetrexed (Alimta). In particular embodiments, multimodality treatment of lung cancer includes administration of a composition of g-NK cells as provided herein in combination with Necitumumab (Portrazza™)+Carboplatin.

In some embodiments, multimodality treatment of lymphoma includes administration of a composition of g-NK cells as provided herein in combination with (1) a monoclonal antibody that is Ibritumomab tiuxetan (Zevalin®), Brentuximab vedotin (Adcetris®), Rituximab (Rituxan®), Siltuximab (Sylvant®), Obinutuzumab (Gazyva®), Nivolumab (Opdivo®) or Pembrolizumab (Keytruda®) and (2) a cancer drug or cytotoxic agent that is Denileukin diftitox (Ontak®), Vorinostat (Zolinza®), Romidepsin (Istodax®), Bexarotene (Targretin®), Bortezomib (Velcade®), Pralatrexate (Folotyn®), Ibrutinib (Imbruvica®), Idelalisib (Zydelig®), Belinostat (Beleodaq®), Cyclophosphamide, Chlorambucil, Bendamustine, Ifosfamide, Cisplatin, Carboplatin, Oxaliplatin, Fludarabine, Gemcitabine, Methotrexate, Doxorubicin, Vincristine or Etoposide (VP-16). In particular embodiments, multimodality treatment of lymphoma includes administration of a composition of g-NK cells as provided herein in combination with Rituximab (Rituxan®)+Cyclophosphamide.

In some embodiments, multimodality treatment of multiple myeloma includes administration of a composition of g-NK cells as provided herein in combination with (1) a monoclonal antibody that is Bortezomib (Velcade®), Daratumumab (Darzalex™) or Elotuzumab (Empliciti™) and (2) a cancer drug or cytotoxic agent that is Carfilzomib (Kyphosis®), Panobinostat (Farydak®), Ixazomib citrate (Ninlaro®), Melphalan, Vincristine (Oncovin), Cyclophosphamide (Cytoxan), Etoposide (VP-16), Doxorubicin (Adriamycin), Liposomal doxorubicin (Doxil), Bendamustine (Treanda). In particular embodiments, multimodality treatment of multiple myeloma includes administration of a composition of g-NK cells as provided herein in combination with Daratumumab (Darzalex™)+Cyclophosphamide.

In some embodiments, multimodality treatment of neuroblastoma includes administration of a composition of g-NK cells as provided herein in combination with (1) a monoclonal antibody that is Dinutuximab (Unituxin™) and (2) a cancer drug or cytotoxic agent that is radiation therapy, Cyclophosphamide, Cisplatin or carboplatin, Vincristine, Doxorubicin (Adriamycin), Etoposide, Topotecan, Busulfan or Thiotepa. In particular embodiments, multimodality treatment of neuroblastoma includes administration of a composition of g-NK cells as provided herein in combination with Dinutuximab (Unituxin™)+Doxorubicin (Adriamycin).

In some embodiments, multimodality treatment of an ovarian epithelial/fallopian tube/primary peritoneal cancer includes administration of a composition of g-NK cells as provided herein in combination with (1) a monoclonal antibody that is Bevacizumab (Avastin®) and (2) a cancer drug or cytotoxic agent that is Olaparib (Lynparza™), Rucaparib camsylate (Rubraca™), Niraparib tosylate monohydrate (Zejula™), Cisplatin, Carboplatin, Paclitaxel (Taxol®), Docetaxel (Taxotere®), Capecitabine (Xeloda®), Cyclophosphamide (Cytoxan®), Etoposide (VP-16), Gemcitabine (Gemzar®), Ifosfamide (Ifex®), Mnotecan (CPT-11, Camptosar®), Liposomal doxorubicin (Doxil®), Melphalan, Pemetrexed (Alimta®), Topotecan or Vinorelbine (Navelbine®). In particular embodiments, multimodality treatment of an ovarian epithelial/fallopian tube/primary peritoneal cancer includes administration of a composition of g-NK cells as provided herein in combination with Bevacizumab (Avastin®)+Paclitaxel (Taxol®).

In some embodiments, multimodality treatment of pancreatic cancer includes administration of a composition of g-NK cells as provided herein in combination with (1) a monoclonal antibody that is Cetuximab (Erbitux®) or Bevacizumab (Avastin®) and (2) a cancer drug or cytotoxic agent that is Erlotinib (Tarceva®), Everolimus (Afinitor®), Sunitinib (Sutent®), Gemcitabine (Gemzar), 5-fluorouracil (5-FU), Oxaliplatin (Eloxatin), Albumin-bound paclitaxel (Abraxane), Capecitabine (Xeloda), Cisplatin, Irinotecan (Camptosar), Paclitaxel (Taxol), Docetaxel (Taxotere) or Albumin-bound paclitaxel (Abraxane). In particular embodiments, multimodality treatment of pancreatic cancer includes administration of a composition of g-NK cells as provided herein in combination with Erlotinib (Tarceva®)+Oxaliplatin (Eloxatin).

In some embodiments, multimodality treatment of skin cancer includes administration of a composition of g-NK cells as provided herein in combination with (1) a monoclonal antibody that is Ipilimumab (Yervoy®), Pembrolizumab (Keytruda®), Avelumab (Bavencio®) or Nivolumab (Opdivo®) and (2) a cancer drug or cytotoxic agent that is Vismodegib (Erivedge®), Sonidegib (Odomzo®), Vemurafenib (Zelboraf®), Trametinib (Mekinist®), Dabrafenib (Tafinlar®), Cobimetinib (Cotellic™), Alitretinoin (Panretin®), Radiation therapy, Dacarbazine, Temozolomide, Nab-paclitaxel, Paclitaxel, Cisplatin, Carboplatin or Vinblastine. In particular embodiments, multimodality treatment of skin cancer includes administration of a composition of g-NK cells as provided herein in combination with Avelumab (Bavencio®)+Cisplatin.

In some embodiments, multimodality treatment of soft tissue sarcoma includes administration of a composition of g-NK cells as provided herein in combination with (1) a monoclonal antibody that is Olaratumab (Lartruvo™) and (2) a cancer drug or cytotoxic agent that is Pazopanib (Votrient®), Alitretinoin (Panretin®), Radiation therapy, Ifosfamide (Ifex®), Doxorubicin (Adriamycin®), Dacarbazine, Epirubicin, Temozolomide (Temodar®), Docetaxel (Taxotere®), Gemcitabine (Gemzar®), Vinorelbine (Navelbine®), Trabectedin (Yondelis®) or Eribulin (Halaven®). In particular embodiments, multimodality treatment of soft tissue sarcoma includes administration of a composition of g-NK cells as provided herein in combination with Olaratumab (Lartruvo™)+Docetaxel (Taxotere®).

4. Oncolytic Virus

In some embodiments, the provided methods also can include administering g-NK cells with an oncolytic virus. Combination treating of g-NK cells and an oncolytic virus can further include administration of one or more other agents as described, such as an antibody.

It is contemplated that combinations of g-NK cells with oncolytic viruses may promote or increase activity of one or both of the therapies. In some embodiments, the use of oncolytic viruses may sensitive tumor cells to NK cells. Evidence from oncolytic virus therapy indicated oncolytic viruses activate NK-cells (↑IFN-γ) and enhance NK-cell migration to tumors in metastatic melanoma, ovarian cancer, and breast cancer models (Miller et al., 2003 Mol Ther 7:741:747; Benencia et al., 2005 Mol Ther 12:789-802; Zhao et al., 2014 PLoS One 9:e93103). In a phase one clinical trial, oncolytic reovirus was found to increase circulating levels of NK-cells (White et al., 2008 Gene Ther 15:911-920) and NK-cells were found to mediate the antitumor efficacy of oncolytic reovirus and parapoxvirus in animal models of prostate cancer and A549 lung cancer (Gujar et al., 2011 Mol Ther 19:797-804; Rintoul et al., 2012 Mol. Ther. 20:1148-1157). Increased tumor infiltration by NK-cells was also observed with oncolytic Coxsackievirus and Measles virus in animal models of adenocarcinoma and glioblastoma with intratumoral concentrations of NK-cells positively correlating with survival (Miyamoto et al., 2012 Cancer Res. 72:2609-2621; Allen et al., 2006 Cancer res. 66:11840-11850). The mechanism connecting oncolytic virus activity to NK-cell-mediated clearance of tumor cells is enhanced tumor immunogenicity. Specifically, tumors infected with oncolytic viruses are more readily recognized and killed by NK-cells as evidenced by increased cytoxicity mediated by natural cytotoxicity receptors NKp30 and NKp44 as well as enhanced expression of the cytotoxic cytokines IFN-γ, TNF-α, and MIP1α/β (Bhat et al., 2011 Int J Cancer 128:908-919; Dempe et al., 2012 Cancer Immunol Res 61:2113-2123; Bhat et al., 2013 BMC Cancer 13:367). Other oncolytic viruses that have been shown to attract and activate NK-cells in vivo include Influenza virus (Ogbomo et al., 2010 Med Microbiol Immunol 199:93-101), Vesicular stomatitis virus (Heiber et al., 2011 J Virol. 85:10440-10450), and Newcastle disease virus (Jarahian et al., 2009 J Virol. 83:810-821). In a study of post-operative cancer surgery patients, oncolytic vaccinia virus was found to reverse post-operative immunosuppression and prevent metastasis formation (Tai et al., 2014 Front Oncol 4:217). Thus, oncolytic viruses could be able to enhance anti-tumor immunity by NK-cells in otherwise immunocompromised individuals.

In some embodiments, the oncolytic virus targets particular cells, e.g., immune cells. In some embodiments, the oncolytic virus targets a tumor cell and/or cancer cell in the subject. Oncolytic viruses are viruses that accumulate in tumor cells and replicate in tumor cells. By virtue of replication in the cells, tumor cells are lysed, and the tumor shrinks and can be eliminated. Oncolytic viruses can also have a broad host and cell type range. For example, oncolytic viruses can accumulate in immunoprivileged cells or immunoprivileged tissues, including tumors and/or metastases, and also including wounded tissues and cells, thus allowing the delivery and expression of a heterologous protein in a broad range of cell types. Oncolytic viruses can also replicate in a tumor cell specific manner, resulting in tumor cell lysis and efficient tumor regression.

Exemplary oncolytic viruses include adenoviruses, adeno-associated viruses, herpes viruses, Herpes Simplex Virus, Reovirus, Newcastle Disease virus, parvovirus, measles virus, vesicular stomatitis virus (VSV), Coxsackie virus and Vaccinia virus. In some embodiments, oncolytic viruses can specifically colonize solid tumors, while not infecting other organs. In some cases, oncolytic viruses can be used as an infectious agent to deliver heterologous proteins nucleic acids to solid tumors.

Oncolytic viruses can be any of those known to one of skill in the art and include, for example, vesicular stomatitis virus, see, e.g., U.S. Pat. Nos. 7,731,974, 7,153,510, 6,653, 103 and U.S. Pat. Pub. Nos. 2010/0178684, 2010/0172877, 2010/0113567, 2007/0098743, 20050260601, 20050220818 and EP Pat. Nos. 1385466, 1606411 and 1520175; herpes simplex virus, see, e.g., U.S. Pat. Nos. 7,897,146, 7,731,952, 7,550,296, 7,537,924, 6,723,316, 6,428,968 and U.S. Pat. Pub. Nos., 2014/0154216, 2011/0177032, 2011/0158948, 2010/0092515, 2009/0274728, 2009/0285860, 2009/0215147, 2009/0010889, 2007/0110720, 2006/0039894, 2004/0009604, 2004/0063094, International Patent Pub. Nos., WO 2007/052029, WO 1999/038955; retroviruses, see, e.g., U.S. Pat. Nos. 6,689,871, 6,635,472, 5,851,529, 5,716,826, 5,716,613 and U.S. Pat. Pub. No. 20110212530; vaccinia viruses, see, e.g., 2016/0339066, and adeno-associated viruses, see, e.g., U.S. Pat. Nos. 8,007,780, 7,968,340, 7,943,374, 7,906,111, 7,927,585, 7,811,814, 7,662,627, 7,241,447, 7,238,526, 7,172,893, 7,033,826, 7,001,765, 6,897,045, and 6,632,670.

Oncolytic viruses also include viruses that have been genetically altered to attenuate their virulence, to improve their safety profile, enhance their tumor specificity, and they have also been equipped with additional genes, for example cytotoxins, cytokines, prodrug converting enzymes to improve the overall efficacy of the viruses (see, e.g., Kim et al., (2009) Nat Rev Cancer 9:64-71; Garcia-Aragoncillo et al., (2010) Curr Opin Mol Ther 12:403-411; see U.S. Pat. Nos. 7,588,767, 7,588,771, 7,662,398 and 7,754,221 and U.S. Pat. Publ. Nos. 2007/0202572, 2007/0212727, 2010/0062016, 2009/0098529, 2009/0053244, 2009/0155287, 2009/0117034, 2010/0233078, 2009/0162288, 2010/0196325, 2009/0136917 and 2011/0064650). In some embodiments, the oncolytic viruses can be those that have been modified so that they selectively replicate in cancerous cells, and, thus, are oncolytic. For example, the oncolytic virus is an adenovirus that has been engineered to have modified tropism for tumor therapy and also as gene therapy vectors. Exemplary of such is ONYX-015, H101 and Ad5ΔCR (Hallden and Portella (2012) Expert Opin Ther Targets, 16:945-58) and TNFerade (McLoughlin et al. (2005) Ann. Surg. Oncol., 12:825-30), or a conditionally replicative adenovirus Oncorine®.

In some embodiments, the oncolytic virus is a modified herpes simplex virus. In some embodiments, the oncolytic virus is Talimogene laherparepvec (also known as T-Vec, Imlygic or OncoVex GM-CSF). In some embodiments, the infectious agent is a modified herpes simplex virus that is described, e.g., in WO 2007/052029, WO 1999/038955, US 2004/0063094, US 2014/0154216, or, variants thereof.

V. KITS AND ARTICLES OF MANUFACTURE

Provided herein are articles of manufacture and kits comprising the provided compositions containing NK cells enriched for particular subsets, such as g-NK cells. In some embodiments, the compositions are produced by any of the provided methods. In some embodiments, provided herein is a kit comprising any of the provided compositions an additional agent. In some embodiments, the additional agent comprises an Fc domain. In some embodiment the additional agent is an Fc fusion protein or an antibody. In some embodiments, the additional agent is a human, humanized, or chimeric antibody. In some of these embodiments, the additional agent is a full length antibody. Exemplary antibodies included any as described.

Also provided herein are articles of manufacture or kits that comprise a plurality of reagents for detecting a g-NK surrogate surface marker profile, such as described herein. In some embodiments, the reagents include reagents for detecting a panel of surface markers, such as 2, 3, 4, or 5 surface markers, selected from CD16, CD38, CD57, CD7, CD161 and/or NKG2A. In some embodiments, the reagents include reagents for detecting a panel of surface markers from CD16, CD57, CD7 and CD161. In some embodiments, the reagents include reagents for detecting a panel of surface markers from CD161 and NKG2A. In some embodiments, the kits can further include one or more additional reagents for detecting one or more other NK cell surface marker. For example, the kit can include one or more additional reagents, such as 1, 2 or 3 additional reagents, for detecting one or more further surface markers CD45, CD3 and/or CD56. In some embodiments, the reagents include reagents for detecting a panel of surface markers from CD3, CD56 and CD38. In some embodiments, each of the reagents is a binding molecule for detecting a specific surface marker of the panel.

In particular embodiments, the reagents include antibodies or antigen-binding fragments thereof specific for one or more surface markers of the panel. In some cases, the binding molecules, such as antibodies or antigen-binding fragments, can be conjugated directly or indirectly to a moiety that is capable of detection. In some examples, one or more of the antibodies are modified to permit detection of binding. For example, antibodies can be conjugated to a detectable molecule that permits either direct detection or detection via secondary agents. In some embodiments, antibodies are directly labeled, such as with a fluorophore. In some examples, the antibodies can be detected using a secondary reagent, such as by a secondary antibody reagent that binds to the primary antibodies and that is coupled to a detectable protein, such as a fluorescent probe or detectable enzyme, such as horseradish peroxidase. In some such examples, the kit can further include the secondary antibody.

Kits can optionally include one or more components such as instructions for use, devices and additional reagents (e.g., sterilized water or saline solutions for dilution of the compositions and/or reconstitution of lyophilized protein), and components, such as tubes, containers and syringes for practice of the methods. In some embodiments, the kits can further contain reagents for collection of samples, preparation and processing of samples, and/or reagents for quantitating the amount of one or more surface markers in a sample, such as, but not limited to, detection reagents, such as antibodies, buffers, substrates for enzymatic staining, chromagens or other materials, such as slides, containers, microtiter plates, and optionally, instructions for performing the methods. Those of skill in the art will recognize many other possible containers and plates and reagents that can be used in accord with the provided methods.

In some embodiments, the kits can be provided as articles of manufacture that include packing materials for the packaging of the cells, antibodies or reagents, or compositions thereof, or one or more other components. For example, the kits can contain containers, bottles, tubes, vial and any packaging material suitable for separating or organizing the components of the kit. The one or more containers may be formed from a variety of materials such as glass or plastic. In some embodiments, the one or more containers hold a composition comprising cells or an antibody or other reagents for use in the methods. The article of manufacture or kit herein may comprise the cells, antibodies or reagents in separate containers or in the same container.

In some embodiments, the one or more containers holding the composition may be a single-use vial or a multi-use vial, which, in some cases, may allow for repeat use of the composition. In some embodiments, the article of manufacture or kit may further comprise a second container comprising a suitable diluent. The article of manufacture or kit may further include other materials desirable from a commercial, therapeutic, and user standpoint, including other buffers, diluents, filters, needles, syringes, therapeutic agents and/or package inserts with instructions for use.

In some embodiments, the kit can, optionally, include instructions. Instructions typically include a tangible expression describing the cell composition, reagents and/or antibodies and, optionally, other components included in the kit, and methods for using such. In some embodiments, the instructions indicate methods for using the cell compositions and antibodies for administration to a subject for treating a disease or condition, such as in accord with any of the provided embodiments. In some embodiments, the instructions indicated methods for using the reagents, such as antibodies, as a panel for detecting a g-NK surrogate marker phenotype, such as in accord with any of the provided embodiments. In some embodiments, the instructions are provided as a label or a package insert, which is on or associated with the container. In some embodiments, the instructions may indicate directions for reconstitution and/or use of the composition.

VI. EXEMPLARY EMBODIMENTS

Among the provided embodiments are:

1. A method for expanding FcRγ-deficient NK cells (g-NK), said method comprising:
   (a) isolating a population of primary human cells enriched for natural killer (NK) cells, the isolating comprises selecting from a sample from a human subject: (i) cells negative for CD3 ($CD3^{neg}$), (ii) cells negative for CD3 ($CD3^{neg}$) and positive for CD56 ($CD3^{neg}CD56^{pos}$); (iii) cells negative for CD3 and positive for CD57 ($CD3^{neg}CD57^{pos}$), or (iv) cells negative for CD3 and positive for CD16 ($CD3^{neg}CD16^{pos}$); and
   (b) culturing the population of enriched NK cells in the presence of (i) irradiated 221.AEH feeder cells, wherein the ratio of irradiated 221.AEH feeder cells to enriched NK cells is from 1:10 to 10:1; and (ii) recombinant IL-2,
   wherein the method produces an expanded population of g-NK cells.

2. The method of embodiment 1, wherein prior to (a), harvesting the sample from the human subject.

3. The method of embodiment 1 or embodiment 2, wherein the sample is or comprises peripheral blood mononuclear cells (PBMCs).

4. The method of any of embodiments 1-3, wherein the sample is an apheresis or leukaphereis sample.

5. The method of any of embodiments 1-4, wherein the selecting comprises immunoaffinity-based selection.

6. The method of any of embodiments 1-5, wherein the isolating comprises selecting from the sample cells negative for CD3 ($CD3^{neg}$).

7. The method of any of embodiments 1-5, wherein the isolating comprises selecting from the sample cells negative for CD3 ($CD3^{neg}$) and positive for CD56 ($CD3^{neg}CD56^{pos}$).

8. The method of any of embodiments 1-5, wherein the isolating comprises selecting from the sample cells negative for CD3 and positive for CD57 ($CD3^{neg}CD57^{pos}$).

9. The method of any of embodiments 1-5, wherein the isolating comprises selecting from the sample cells negative for CD3 and positive for CD16 ($CD3^{neg}CD16^{pos}$).

10. The method of any of embodiments 1-9, wherein after (a) cryopreserving the isolated population of enriched NK cells and prior to (b) thawing the cryopreserved sample comprising the enriched NK cells.

11. A method for expanding FcRγ-deficient NK cells (g-NK), said method comprising:
    (a) obtaining a population of primary human cells enriched for natural killer (NK) cells, wherein the population of enriched NK cells comprise a phenotype selected from: (i) cells negative for CD3 ($CD3^{neg}$), (ii) cells negative for CD3 ($CD3^{neg}$) and positive for CD56 ($CD3^{neg}CD56^{pos}$); (iii) cells negative for CD3 and positive for CD57 ($CD3^{neg}CD57^{pos}$), or (iv) cells negative for CD3 and positive for CD16 ($CD3^{neg}CD16^{pos}$); and
    (b) culturing the population of enriched NK cells in the presence of (i) irradiated 221.AEH feeder cells, wherein the ratio of irradiated 221.AEH feeder cells to enriched NK cells is from 1:10 to 10:1; and (ii) recombinant IL-2,
    wherein the method produces an expanded population of g-NK cells.

12. The method of embodiment 11, wherein the obtaining comprises thawing a cryopreserved sample comprising the enriched NK cells.

13. The method of embodiment 11 or embodiment 12, wherein the population of enriched NK cells comprises cells negative for CD3 ($CD3^{neg}$).

14. The method of embodiment 11 or embodiment 12, wherein the population of enriched NK cells comprises cells negative for CD3 ($CD3^{neg}$) and positive for CD56 ($CD3^{neg}CD56^{pos}$).

15. The method of embodiment 11 or embodiment 12, wherein the population of enriched NK cells comprises cells negative for CD3 and positive for CD57 ($CD3^{neg}CD57^{pos}$).

16. The method of embodiment 11 or embodiment 12, wherein the population of enriched NK cells comprises cells negative for CD3 and positive for CD16 ($CD3^{neg}CD16^{pos}$).

17. A method for expanding FcRγ-deficient NK cells (g-NK), the method comprising culturing a population of primary human cells enriched for natural killer (NK) cell from a sample from a human subject, the population of enriched NK cells comprising cells negative for CD3 and positive for CD57, wherein the culturing is carried out in the presence of:
    (i) irradiated 221.AEH feeder cells, wherein the ratio of irradiated 221.AEH feeder cells to enriched NK cells is from 1:10 to 10:1; and
    (ii) recombinant IL-2;
    wherein the method produces an expanded population of g-NK cells.

18. The method of embodiment 17, wherein prior to the culturing, isolating the population of enriched NK cells from the sample, the isolating comprising:
    (1) selecting (a) cells negative for CD3 or (b) cells positive for CD57, thereby enriching a first selected population; and
    (2) selecting from the first selected population cells for the other of (a) cells negative for CD3 or (b) cells positive for CD57, thereby enriching for cells negative for CD3 and positive for CD57.

19. A method for expanding FcRγ-deficient NK cells (g-NK), the method comprising culturing a population of primary human cells enriched for natural killer (NK) cells from a sample from a human subject, the population of enriched NK cells comprising cells negative for CD3 and positive for CD16, wherein the culturing is carried out in the presence of:
    (i) irradiated 221.AEH feeder cells, wherein the ratio of irradiated 221.AEH feeder cells to enriched NK cells is from 1:10 to 10:1; and
    (ii) recombinant IL-2,
    wherein the method produces an expanded population of g-NK cells.

20. The method of embodiment 19, wherein prior to the culturing, isolating the population of enriched NK cells from the sample, the isolating comprising:
  (1) selecting (a) cells negative for CD3 or (b) cells positive for CD16, thereby enriching a first selected population; and
  (2) selecting from the first enriched selected cells for the other of (a) cells negative for CD3 or (b) cells positive for CD16, thereby enriching for cells negative for CD3 and positive for CD16.

21. The method of any of embodiments 17-20, wherein the sample comprises peripheral blood mononuclear cells (PBMCs).

22. The method of any of embodiments 17-21, wherein prior to the culturing, harvesting the sample from the human subject.

23. The method of any of embodiments 17-22, wherein the sample is an apheresis or leukaphereis sample.

24. The method of any of embodiments 18 and 19-23, wherein the selecting comprises immunoaffinity-based selection.

25. The method of any of embodiments 18-24, wherein the enriched NK cells are from a cryopreserved sample having been previously isolated from the sample from the subject.

26. The method of any of embodiments 1-25, wherein the culturing is further carried out in the presence of (iii) primary human peripheral blood mononuclear cells (PBMCs) feeder cells, wherein the PBMC feeder cells are irradiated.

27. The method of embodiment 26, wherein the ratio of PBMC feeder cells to enriched NK cells is between at or about 1:1 and at or about 5:1, inclusive.

28. The method of embodiment 26 or embodiment 27, wherein the PBMC feeder cells are autologous to the subject.

29. The method of any of embodiments 26-28, wherein at least a portion of the culturing is carried out in the presence of at least one stimulatory agent that is capable of stimulating the activation of one or more of T cell of the PBMC feeder cells.

30. The method of embodiment 29, wherein the stimulatory agent specifically binds to a member of a TCR complex, optionally wherein the agent specifically binds to a CD3, optionally a CD3epsilon.

31. The method of embodiment 29 or embodiment 30, wherein the at least one stimulatory agent is an anti-CD3 antibody or antigen-binding fragment thereof.

32. The method of embodiment 31, wherein the anti-CD3 antibody or antigen-binding fragment thereof is an OKT3 antibody or antigen-binding fragment.

33. The method of embodiments 31 or embodiment 32, wherein the concentration of the anti-CD3 antibody or antigen-binding fragment is between at or about 10 ng/mL and at or about 100 ng/mL.

34. The method of any of embodiments 31-33, wherein the concentration of the anti-CD3 antibody or antigen-binding fragment is at or about 50 ng/mL.

35. The method of any of embodiments 31-34, wherein the at least one stimulatory agent is added beginning at the initiation of the culturing or at or about the same time as the irradiated PBMC feeder cells.

36. The method of any of embodiments 26-37, wherein during at least a portion of the culturing the PBMC feeder cells are activated.

37. The method of any of embodiments 1-36, wherein the ratio of irradiated 221.AEH feeder cells to NK cells is at or about 1:1 or greater.

38. The method of any of embodiments 1-37, wherein the ratio of irradiated 221.AEH feeder cells to NK cells is between 1:1 and 5:1, inclusive 39. The method of any of embodiments 1-38, wherein the ratio of irradiated AEH.221 feeder cells to enriched NK cell is between 1:1 and 3:1, inclusive.

40. The method of any of embodiments 1-29, wherein the ratio of irradiated AEH.221 feeder cells to enriched NK cells is or is about 2.5:1.

41. The method of any of embodiments 17-40, wherein the ratio of PBMC feeder cells to enriched NK cells is at or about 5:1.

42. The method of any of embodiments 1-41, wherein the concentration of recombinant IL-2 during at least a portion of the culturing is between at or about 10 IU/mL and at or about 500 IU/mL.

43. The method of any of embodiments 1-42, wherein the concentration of recombinant IL-2 during at least a portion of the culturing is at or about 100 IU/mL recombinant IL-2.

44. The method of any of embodiments 1-43, wherein the recombinant IL-2 is added beginning at or about the initiation of the culturing.

45. The method of any of embodiments 1-44, wherein the method further comprises exchanging the culture medium one or more times during the culturing.

46. The method of embodiment 45, wherein the exchanging the culture medium is carried out beginning at or about within 3 to 7 days after the initiation of the culturing, optionally at or about 5 days after the initiation of the culturing.

47. The method of embodiment 46, wherein the exchanging the culture medium is carried out every two or three days for the remaining duration of the culturing.

48. The method of any of embodiments 45-47, wherein the exchanging of the culture medium reduces or removes the at least one stimulatory agent from the culture medium.

49. The method of any of embodiments 45-48, wherein at each exchange of the culture medium, adding the recombinant IL-2 to the culture.

50. The method of any of embodiments 44-49, wherein the recombinant IL-2 is added at a concentration of between at or about 10 IU/mL and at or about 500 IU/mL, inclusive.

51. The method of any of embodiments 44-50, wherein the recombinant IL-2 is added at a concentration of at or about 100 IU/mL recombinant IL-2.

52. The method of any of embodiments 1-51, wherein the population of enriched NK cells comprises at least at or about $0.2\times10^6$ enriched NK cells, at least at or about $1.0\times10^6$ enriched NK cells, or at or about $10\times10^6$ enriched NK cells.

53. The method of any of embodiments 1-52, wherein the population of enriched NK cells at the initiation of the culturing is at a concentration of between at or about $0.05\times10^6$ enriched NK cells/mL and at or about $1.0\times10^6$ enriched NK cells/mL.

54. The method of any of embodiments 1-53, wherein the population of enriched NK cells at the initiation of the culturing is at a concentration of between at or about $0.05\times10^6$ enriched NK cells/mL and at or about $0.5\times10^6$ enriched NK cells/mL 55. The method of any of embodiments 1-54, wherein the population of enriched NK cells at the initiation of the culturing comprises a concentration of at or about $0.2\times10^6$ enriched NK cells/mL.

56. The method of any of embodiments 1-55, wherein the culturing is carried out until a time at which the method achieves expansion of at least or at least about $2.50\times10^8$ g-NK cells.

57. The method of any of embodiments 1-56, wherein the culturing is carried out until a time at which the method achieves expansion of at least or at least about $5.00\times10^8$ g-NK cells.

58. The method of any of embodiments 1-57, wherein the culturing is carried out until the method achieves expansion of at least or at least about $1.0\times10^9$ g-NK cells.

59. The method of any of embodiments 1-58, wherein the culturing is carried out until a time at which the method achieves expansion of at least or at least about $5.0\times10^9$ g-NK cells.

60. The method of any of embodiments 1-59, wherein the culturing is carried out for at or about or at least at or at least about 5 days, 6 days, 7 days, 8 days, 9 days, 10 days, 11 days, 12 days, 13 days, 14 days, 15 days, 16 days, 17 days, 18 days, 19 days, 20 day, 21 days, 22 days, 23 days, 24 days or 25 days.

61. The method of any of embodiments 1-60, wherein the culturing is carried out for at or about or at least at or about 14 days.

62. The method of any of embodiments 1-60, wherein the culturing is carried out for at or about or at least at or about 21 days.

63. The method of any of embodiments 1-62, wherein the method produces an increased number of g-NK cells at the end of the culturing compared to at the initiation of the culturing.

64. The method of embodiment 63, wherein the increase is greater than or greater than about 100-fold, greater than or greater than about 200-fold, greater than or greater than about 300-fold, greater than or greater than about 400-fold, greater than or greater than about 500-fold, greater than or greater than about 600-fold, greater than or greater than about 700-fold or greater than or greater than about 800-fold.

65. The method of any of embodiments 1-64, wherein the g-NK cells are $FcR\gamma^{neg}$.

66. The method of embodiment 65, wherein the g-NK cells further are $CD45^{pos}/CD3^{neg}/CD56^{pos}$.

67. The method of any of embodiments 1-64, wherein the g-NK cells are cells having a g-NK surrogate surface marker profile.

68. The method of any of embodiments 1-70, further comprising purifying or selecting a population of cells having a g-NK cell surrogate surface marker profile from the expanded population of cells.

69. The method of embodiment 67 or embodiment 68, wherein the g-NK cell surrogate surface marker profile is $CD16^{pos}/CD57^{pos}/CD7^{dim/neg}/CD161^{neg}$.

70. The method embodiment 67 or embodiment 68, wherein the g-NK cell surrogate surface marker profile is $NKG2A^{neg}/CD161^{neg}$.

71. The method of embodiment 69 or embodiment 70, wherein the g-NK cell surrogate surface marker profile further is $CD45^{pos}/CD3^{neg}/CD56^{pos}$.

72. The method of any of embodiments 1-71, further comprising formulating the expanded population of g-NK cells in a pharmaceutically acceptable excipient.

73. The method of embodiment 72, further comprising cryopreserving the cells and/or formulating the cells in the presence of a cryoprotectant.

74. A composition comprising g-NK cells produced by the method of any of embodiments 1-73.

75. The composition of any of embodiments 74-78, wherein the composition comprises at least at or about $10^6$ g-NK cells.

76. The composition of embodiment 74 or embodiment 75, wherein the composition comprises from at or about $10^6$ to at or about $10^{10}$ g-NK cells, from at or about $10^6$ to at or about $10^9$ g-NK cells, from at or about $10^6$ to at or about $10^8$ g-NK cells, from at or about $10^6$ to at or about $10^7$ g-NK cells, from at or about $10^7$ to at or about $10^{10}$ g-NK cells, from at or about $10^7$ to at or about $10^9$ g-NK cells, from at or about $10^7$ to at or about $10^8$ g-NK cells, from at or about $10^8$ to at or about $10^{10}$ g-NK cells, from at or about $10^8$ to at or about $10^9$ g-NK cells, or from at or about $10^9$ to at or about $10^{10}$ g-NK cells.

77. The composition of any of embodiments 75-76, wherein the g-NK cells are $FcR\gamma^{neg}$.

78. The composition of embodiment 77, wherein the g-NK cells further are $CD45^{pos}/CD3^{neg}/CD56^{pos}$.

79. The composition of any of embodiments 75-76, wherein the g-NK cells are cells having a g-NK surrogate surface marker profile.

80. The composition of embodiment 79, wherein the g-NK cell surrogate surface marker profile is $CD16^{pos}/CD57^{pos}/CD7^{dim/neg}/CD161^{neg}$.

81. The composition embodiment 79, wherein the g-NK cell surrogate surface marker profile is $NKG2A^{neg}/CD161^{neg}$.

82. A composition comprising a natural killer (NK) cell subset, wherein at least at or about 40%, at least at or about 50%, at least at or about 60%, at least at or about 70%, at least at or about 80%, or at least at or about 90% of the cells in the composition have a g-NK cell surrogate marker profile selected from $CD16^{pos}/CD57^{pos}/CD7^{dim/neg}/CD161^{neg}$ and $NKG2A^{neg}/CD161^{neg}$.

83. The composition of any of embodiments 80-91, wherein the g-NK cell surrogate surface marker profile further comprises $CD45^{pos}/CD3^{neg}/CD56^{pos}$.

84. The composition of embodiment 82 or embodiment 83, wherein at least at or about 60% of the cells in the composition comprise a g-NK cell surrogate marker profile selected from $CD16^{pos}/CD57^{pos}/CD7^{dim/neg}/CD161^{neg}$ and $NKG2A^{neg}/CD161^{neg}$.

85. The composition of any of embodiments 82-84, wherein at least at or about 70% of the cells in the composition comprise a g-NK cell surrogate marker profile selected from $CD16^{pos}/CD57^{pos}/CD7^{dim/neg}/CD161^{neg}$ and $NKG2A^{neg}/CD161^{neg}$.

86. The composition of any of embodiments 83-85, wherein of the cells that comprise the g-NK cell surrogate marker profile greater than 70% are $FcR\gamma^{neg}$, optionally between at or about 70% and 90% are $FcR\gamma^{neg}$.

87. The composition of any of embodiments 83-86, wherein the composition comprises at least or about at least $10^6$ cells.

88. The composition of embodiment any of embodiments 83-87, wherein the composition comprises from at or about $10^6$ to at or about $10^{10}$ cells, from at or about $10^6$ to at or about $10^9$ cells, from at or about $10^6$ to at or about $10^8$ cells, from at or about $10^6$ to at or about $10^7$ cells, from at or about $10^7$ to at or about $10^{10}$ cells, from at or about $10^7$ to at or about $10^9$ cells, from at or about $10^7$ to at or about $10^8$ cells, from at or about $10^8$ to at or about $10^{10}$ cells, from at or about $10^8$ to at or about $10^9$ cells, or from at or about $10^9$ to at or about $10^{10}$ cells.

89. The composition of any of embodiments 74-88, comprising a pharmaceutically acceptable excipient.

90. The composition of any of embodiments 74-89, comprising a cryoprotectant.

91. The composition of any of embodiments 74-90 that is sterile.

92. A kit comprising the composition of any of embodiments 74-91 and an additional agent for treatment of a disease.

93. The kit of embodiment 92, further comprising instructions for administering the composition and additional agent for treating a disease or condition.

94. A kit comprising the composition of any of embodiments 74-91 and instructions for administering the composition in a combination therapy with an additional agent for treatment of a disease.

95. The kit of any of embodiments 92-94, wherein the additional agent is an antibody or an Fc-fusion protein.

96. The kit of embodiment 95, wherein the antibody recognizes or specifically binds a tumor associated antigen.

97. The kit of embodiment 95 or embodiment 96, wherein the antibody recognizes or binds CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, LOXL2, MET, IGF1R, IGLF2, EPHA3, FR-alpha, phosphatidylserine, Syndecan 1, SLAMF7 (CD319), TRAILR1, TRAILR2, RANKL, FAP, vimentin or tenascin.

98. The kit of any one of embodiments 95-97, wherein the antibody is a full length antibody and/or comprises an Fc domain.

99. A method of treating a disease or condition comprising administering the composition of any of embodiments 74-91 to an individual in need thereof.

100. The method of embodiment 99, comprising administering from or from about $1 \times 10^8$ to $1 \times 10^{10}$ cells/m$^2$ to the individual or administering from or from about $1 \times 10^6$ to $1 \times 10^{10}$ NK cells/kg.

101. The method of embodiment 99 or embodiment 100 further comprising administering an additional agent.

102. The method of embodiment 101, wherein the additional agent is an antibody or an Fc-fusion protein.

103. The method of embodiment 102 wherein the antibody recognizes a tumor associated antigen.

104. The method of embodiment 102 or embodiment 103, wherein the antibody recognizes or specifically binds CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, FOXF2, MET, IGF1R, IGFF2, EPHA3, FR-alpha, phosphatidylserine, Syndecan 1, SFAMF7 (CD319), TRAIFR1, TRAIFR2, RANKE, FAP, vimentin or tenascin.

105. The method of any one of embodiments 101-104, wherein the antibody comprises an Fc domain and/or is a full-length antibody.

106. The method of any one of embodiments 101-105, wherein the additional agent and the composition are administered sequentially.

107. The method of embodiment 106, wherein the additional agent is administered prior to administration of the composition.

108. The method of any one of embodiments 101-105, where the additional agent and the composition are administered simultaneously 109. The method of any one of embodiments 101-108, wherein the disease or condition is selected from the group consisting of an inflammatory condition, an infection, and cancer.

110. The method of embodiment 109, wherein the infection is a viral infection or a bacterial infection.

111. The method of embodiment 110, wherein the cancer is a leukemia, a lymphoma or a myeloma.

112. The method of embodiment 110, wherein the cancer comprises a solid tumor.

113. The method of any one of embodiments 101-112, wherein the individual is a human.

114. The method of any one of embodiments 101-113, wherein the NK cells in the composition is allogenic to the individual.

115. The method of any one of embodiments 101-113, wherein the NK cells in the composition is autologous to the subject.

116. A kit comprising a plurality of reagents for detecting a panel of surface markers, said panel of surface markers selected from CD16, CD57' CD7 and CD161 or NKG2A and CD161.

117. The kit of embodiment 116, wherein said panel of surface markers further comprises CD3, CD45 and CD56.

118. The kit of embodiment 116 or embodiment 117, wherein each of the plurality of reagents is a binding molecule specific for one marker of the panel of surface markers.

119. The kit of embodiment 118, wherein the binding molecule is an antibody or antigen-binding fragment.

120. The kit of embodiment 118 or embodiment 119 wherein the binding molecules are detectably labeled.

121. A method of detecting a g-NK surrogate surface marker profile in a sample comprising natural killer (NK) cells using the kit of any of embodiments 116-120.

122. A method of detecting a g-NK surrogate surface marker profile in a sample, the method comprising:
(a) contacting a sample comprising natural killer (NK) cells with reagents for detecting a panel of surface markers selected from CD16, CD57' CD7 and CD161 or NKG2A and CD161; and
(b) detecting the presence or absence of the cells in the sample having the phenotype $CD16^{pos}CD57^{pos}/CD7^{dim/neg}/CD161^{neg}$ or $NKG2A^{neg}/CD161^{neg}$.

123. The method of embodiment 122, wherein the panel of surface markers further comprises CD45, CD3 and CD56 and wherein the phenotype further comprises $CD45^{pos}/CD3^{neg}/CD56^{pos}$.

124. The method of embodiment 122 or embodiment 123, wherein each of the plurality of reagents is a binding molecule specific for one marker of the panel of surface markers.

125. The method of embodiment 124, wherein the binding molecule is an antibody or antigen-binding fragment.

126. The method of embodiment 124 or embodiment 125 wherein the binding molecules are detectably labeled.

127. The method of any of embodiments 122-126, wherein the detecting is by flow cytometry.

VII. EXAMPLES

The following examples are included for illustrative purposes only and are not intended to limit the scope of the invention.

Example 1: Identification of g-NK Surrogate Surface Markers

A study was carried out to identify a combination of extracellular surface markers that could be used as surrogate surface markers to identify g-NK cells, which are negative for the intracellular marker FceRIγ (FcRγ$^{neg}$). The percentage of g-NK cells were determined in a human peripheral blood sample by flow cytometry by intracellular staining for FceRIγ and by extracellular staining for CD45, CD3 and CD56 to identify the g-NK cell subset CD45$^{pos}$/CD3$^{neg}$/CD56$^{pos}$/FcRγ$^{neg}$. As shown in FIG. 1, among g-NK cells in the sample, cells having the NK cell phenotype CD45$^{pos}$/CD3$^{neg}$/CD56$^{pos}$ and that had an extracellular surface phenotype of CD16$^{pos}$/CD57$^{pos}$/CD7$^{dim/neg}$/CD161$^{neg}$ or NKG2A$^{neg}$/CD161$^{neg}$ highly correlated to the presence of g-NK cells in the sample. Specifically, the percentage of g-NK cells within the CD16$^{pos}$/CD57$^{pos}$/CD7$^{dim/neg}$/CD161$^{neg}$ or NKG2A$^{neg}$/CD161$^{neg}$ NK cell subsets were both greater than 80%.

Example 2: Method for Preferential Expansion of FcRγ-Deficient NK Cells (g-NK)

Human peripheral blood mononuclear cells (PBMC) were isolated by Histopaque® density centrifugation from whole blood from a CMV positive human donor, or for comparison a CMV seronegative donor, as per manufacturer's instructions. PBMCs were harvested from buffy coat, washed and assessed by flow cytometry for viable CD45+ cells (to discern PBMCs from residual red blood cells). Approximately ⅔ of the autologous PBMCs were used for enrichment of Natural Killer (NK) cells by immunoaffinity-based magnetic bead separation using Miltenyi MACS™ Microbeads either by depletion of CD3+ cells to remove T cells (CD3 depletion), by CD3 depletion following by positive selection for CD57 to enrich CD57+ NK cells or by positive selection for CD16 (enrich CD16+ NK cells and monocytes). As an alternative, NK enrichment can be carried out by CD3 depletion followed by CD56 enrichment (remove T-cells and enrich NK-cells)

The percentage of isolated g-NK cells was determined by staining the cells with a combination of extracellular surface markers CD45, CD3, CD56, CD16, CD57, CD7, and CD161 or with intracellular staining using an anti-FceRI antibody. The percentage of g-NK cells were identified as viable cells that were CD45$^{pos}$/CD3$^{neg}$/CD56$^{pos}$/FcεRI$^{neg}$ (FcRγ$^{neg}$). If cell sorting is carried out prior to (or after) expansion or a functional assay, only extracellular surface staining can be used and the percentage of g-NK cells is identified using a surrogate surface marker profile as CD45$^{pos}$/CD3$^{neg}$/CD56$^{pos}$/CD16$^{pos}$/CD57$^{pos}$/CD7$^{dim/neg}$/CD161$^{neg}$ lymphocytes or CD45$^{pos}$/CD3$^{neg}$/CD56$^{pos}$/NKG2A$^{neg}$/CD161$^{neg}$, or viable cells thereof.

Freshly isolated NK cells were used immediately for NK cell expansion or were cryopreserved and thawed prior to expansion. The NK cell expansion protocol could be employed for both enriched NK-cells that had been freeze/thawed, and NK cells that were enriched from freeze/thawed PBMCs.

Prior to expansion, HLA-E$^{bright}$ 221.AEH lymphoma cells were prepared as feeder cells by determining the number of viable CD71$^{pos}$ (target cell marker) cells. 221.AEH is a transfectant derived from the 721.221 cell line that highly expresses HLA-E (HLA-E$^{bright}$) (Lee et. Al 1998, J Immunol 160:4951-60). A number of 221.AEH target cells that was about 2.5 times the number of enriched NK cells following post-magnetic bead separation of PBMCs as described above were resuspended to 1×10$^6$ cell/mL in RPMI-1640+10% fetal bovine serum (FBS). The resuspended 221.AEH cells were irradiated at 100 Gy. Additionally, the remaining ⅓ of autologous PBMCs isolated above also were irradiated (100 Gy) for use as feeder cells for the expansion. The use of irradiated PBMCs as feeder cells during the expansion is not required but studies indicated it improved efficacy of NK cell expansion.

Fresh or thawed magnetically enriched NK-cells were seeded at about 10×10$^6$ NK cells at a concentration of 0.2×10$^6$ NK cells/mL in culture media composed of 95% serum-free media (e.g. CellGenix GMP stem cell growth medium (SCGM)) supplemented with 5% human AB (or autologous) serum and 100 IU/mL recombinant IL-2. Beginning at day 0, the seeded NK cells were co-cultured with irradiated autologous PBMCs at a 5:1 PBMC to NK-cell ratio and irradiated 221.AEH feeder cells at a ratio of 2.5:1 221.AEH to NK cells. Optionally, the expansion can be carried out without the irradiated PBMC feeder cells. The co-cultured cells were cultivated for 14 days (fresh cells) or for 21 days (thawed cells) at 37° C. and 5% $CO_2$. In a similar study, thawed NK cells were co-cultured as above, except that the co-culture included irradiated 221.AEH feeder cells at a ratio of 1:1 AEH to NK cells, and were co-cultured for 14 days instead of 21 days.

For the first 5 days of the expansion, the PBMCs serving as feeder cells were activated by adding anti-CD3 monoclonal antibody (OKT3) at 50 ng/mL. For either fresh or thawed cells, the anti-CD3 antibody was washed out after 5 days and 100 IU/mL recombinant IL-2 was replenished every 2-3 days after that (d5, d7, d9, d11, and d14 for fresh cells or thawed cells undergoing 14 day expansion; d5, d7, d9, d11, d14, d16, d18 and d21 for thawed cells undergoing 21 day expansion). In some cases, for the 14 day expansion, the media with fresh recombinant IL-2 was replenished on days 5, 7 and 10. Cells were counted every time the media was changed or replenished. The percentage of g-NK was assessed by flow cytometry at d7 and d14.

An exemplary summary of a 14 day expansion process is shown in FIG. 2A.

For comparison, NK cells were expanded by an alternative method designed to expand NKG2C$^{pos}$ NK cells (described in Bigley et al. 2016, Clin Exp Immunol 185:239-251). In the alternative method, NK cells were enriched by CD3 depletion followed by positive selection using CD56 MicroBeads (Miltenyi Biotec) (but did not include CD16 or CD57 magnetic enrichment prior to the expansion as described above). The enriched NK cells were cultured for 14 days at 37° C. with 30 ng/ml recombinant IL-15 and non-irradiated feeder cells, either 721.221 (HLA-E$^{neg}$ lymphoma) or 221.AEH (HLA-E$^{high}$ lymphoma) target cells, at a 10:1 NK cell to target cell ratio. The alternative method did not include anti-CD3 activated autologous PBMCs as feeder cells. The alternative method also included culture media containing fetal bovine serum.

The percentage of g-NK (CD45$^{pos}$/CD3$^{neg}$/CD56$^{pos}$/FcεRI$^{neg}$) was determined by flow cytometry at day 0 and at the end of expansion (day 14 or day 21). Specifically, the g-NK percentage was determined by intracellular flow cytometry using an FcRγ antibody purchased from Millipore (Burlington, MA, USA).

Figures 2B, 2C:
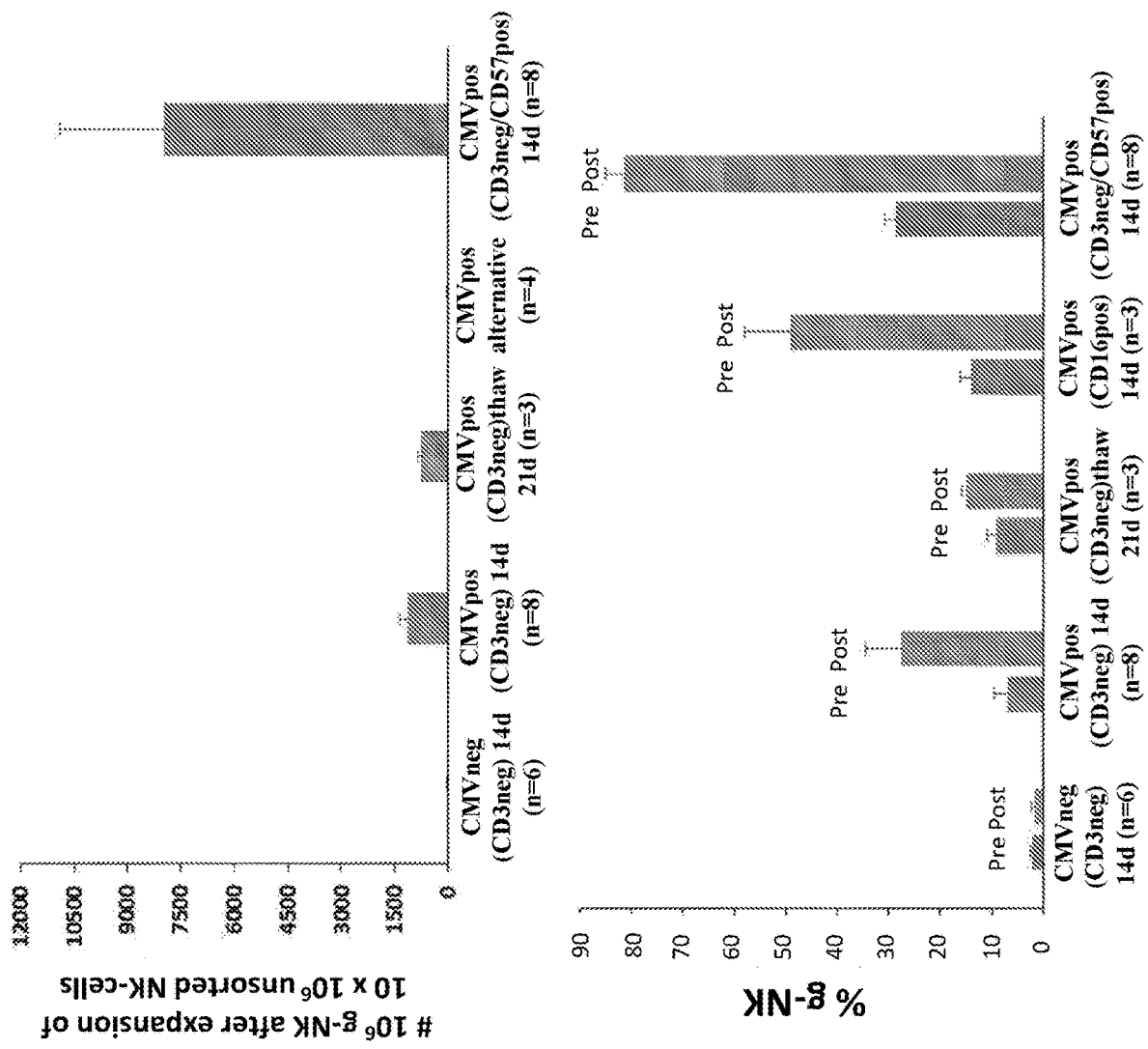
FIGS. 2B and 2C depict the expansion of g-NK from enriched NK cells isolated from peripheral blood mononuclear cells from CMV+ donors. All results shown are from a 14 day expansion from fresh NK cells enriched by the various methods, except that a 21 day expansion was carried out on thawed NK cells that were enriched by CD3 depletion.
Figures 2D, 2E:
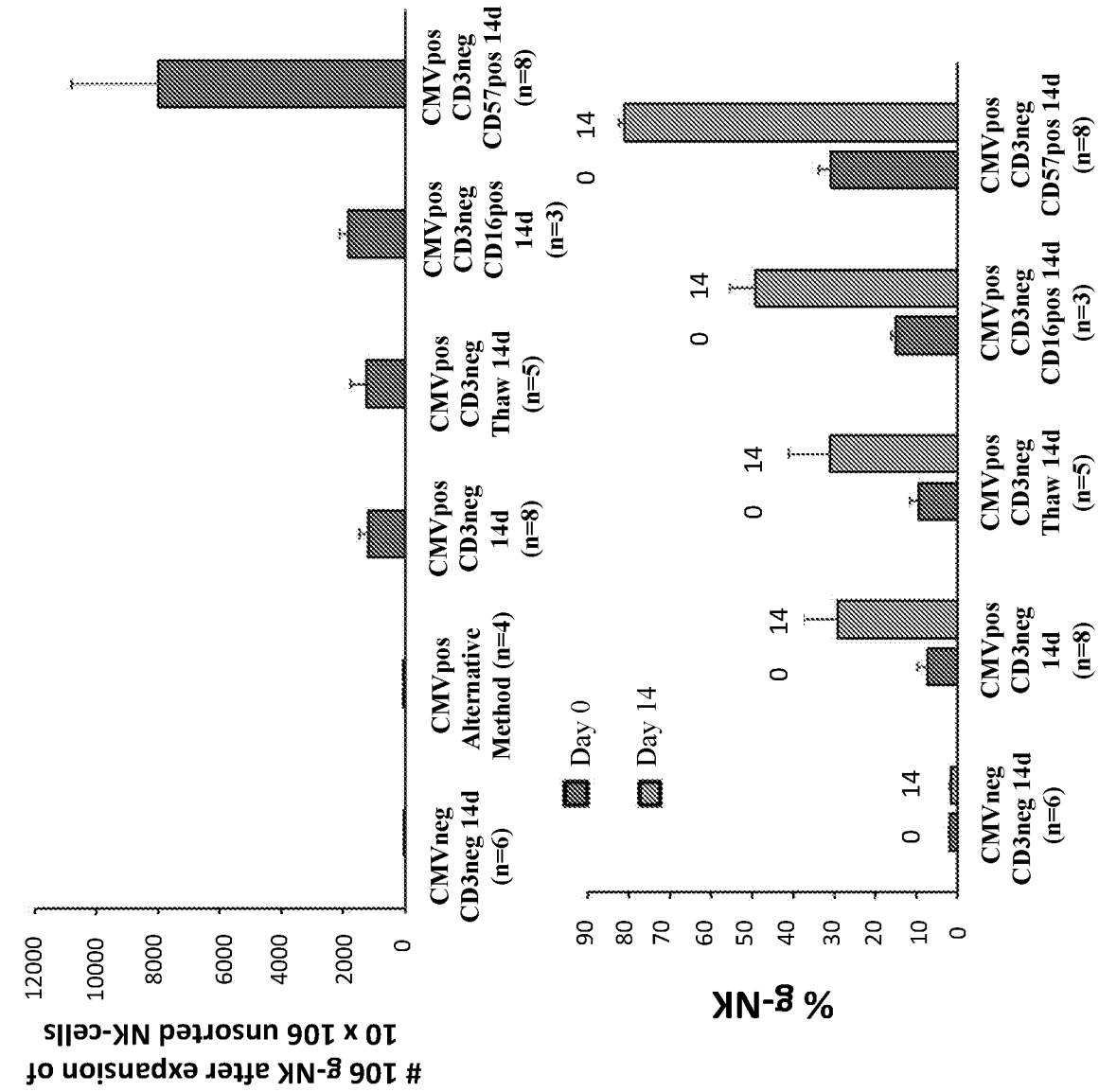
FIGS. 2D and 2E depict the expansion of g-NK from enriched NK cells isolated from peripheral blood mononuclear cells from CMV+ donors. All results shown are from a 14 day expansion of fresh NK cells enriched by the various methods or thawed NK cells that were enriched by CD3 depletion.

FIGS. 2B and 2C depicts the NK cell expansion observed by the above methods at the end of expansion, for the 14 day expansion (fresh cells) and 21 day expansion of thawed cells. FIGS. 2D and E depicts similar results, except that it also depicts results for the process involving CD3 depletion followed by CD16 enrichment (CD3negCD16pos) and also depicts results for a 14 day expansion from thawed cells. When expansion was carried out by the provided methods starting with NK cells enriched only by CD3 depletion (CD3$^{neg}$), an average expansion of 1.2 billion g-NK cells from 10 million NK cells was achieved after 14 days, which represented a subset of 2.1 billion NKG2C$^{pos}$ that were expanded by this method. The observed expansion was similar whether the method was carried out with freshly enriched NK cells (14 days) or with NK cells that had been previously frozen and thawed, as shown in FIG. 2B for 21 day expansion (compare CMVpos CD3neg 14 d vs. CMVpos CD3neg thaw 21d), or as shown in FIG. 2D for 14 day expansion (compare CMVpos CD3neg 14 d vs. CMVpos CD3neg thaw 14d)). The expansion of the thawed NK-cells was superior for the data set depicted in FIG. 2D because a lower 221.AEH to NK-cell ratio was used (1:1 vs. 2.5:1 for the expansion of thawed NK-cells in FIG. 2B). Specifically, in one experiment, for NK cells initially enriched by CD3 depletion alone, about 1.2 billion g-NK were expanded from fresh NK-cells vs. 0.7 billion g-NK for frozen NK-cells. As shown in FIG. 2D, when the provided method was carried out by initially enriching for CD3−CD16+ cells prior to expansion, the average yield was somewhat increased compared to only CD3 depletion. When the provided method was carried out by initially enriching for CD3−/CD57+ cells prior to expansion, the average yield was substantially increased to about 8.0 billion g-NK cells starting from an initial 10 million enriched NK cells after 14 days. In contrast, the alternative method (Bigley et al. 2016) yielded only about 23 million g-NK (or about 45 million NKG2C$^{pos}$ NK cells) from the same starting population.

As shown in FIG. 2C and FIG. 2E, the percentage of g-NK cells post-expansion from CMV$^{pos}$ donors was increased compared to the percentage of g-NK cells in the enriched NK cell population prior to expansion. When the co-culture was carried out with the same ratio of 2.5:1 221.AEH to NK cells, the enrichment was greater for fresh NK-cells that were not previously frozen and expanded for 14 days than for NK cells that had been previously frozen and expanded for 21 days (FIG. 2C, compare CMVpos CD3neg 14 d vs. CMVpos CD3neg thaw 21d). As shown in FIG. 2E, when the co-culture was carried out with a higher ratio of NK cells that had been frozen (1:1 ratio of 221.AEH to NK cells), the percentage of g-NK cells at the end of expansion was similar among starting NK cells whether they were fresh or had been frozen. These results demonstrate that, on average, the thawed PBMCs can achieve similar expansion to fresh samples after 14 days.

Among NK cells enriched by CD3 depletion pre-expansion, the percentage of g-NK increased from 6% of NK-cells initially to 28% post-expansion. A greater increase was observed in cells that were initially enriched for NK cells by CD3 depletion followed by CD16 selection. However, the proportional increase was particularly large when the initial NK cells were enriched for CD3$^{neg}$/CD57$^{pos}$ cells prior to expansion, as opposed to enriching NK cells by CD3 depletion alone or enrichment of CD16$^{pos}$ cells. Specifically, an increase in the percentage of g-NK from 28% of NK-cells initially to 82% post-expansion was observed when NK cells were enriched by CD3 depletion followed by CD57 positive selection. These results support that the provided process can result in a high yield with greater than 1000-fold expansion rates.

In this study, a 'super donor' was identified that had a significantly higher yield of g-NK than other donors. In this 'super donor', 10 million NK cells yielded 27.6 billion g-NK after 14 days and the percentage of g-NK increased from 31% at rest to 85% post-expansion when enriching NK cells by CD3 depletion following by CD57 positive selection pre-expansion.

In CMV-seronegative donors, a much smaller expansion of g-NK was observed, with an average yield of 26 million g-NK beginning with 10 million NK-cells from CMV-seronegative donors (FIGS. 2B and 2D). In CMV-seronegative donors, no preferential expansion was seen for the g-NK subset (2.1% at day 0 vs. 1.7% at day 14) (FIGS. 2C and 2E). These results suggest that the g-NK have memory-like properties in those infected with CMV and that this property is activated by the 221.AEH cells. CMV-infected cells have upregulated HLA-E like the 221.AEH cells (Tomasec et al. (2000) Science, 287:1031). Furthermore, these findings are in line with prior studies that showed g-NK to be "memory-like" NK-cells (Zhang et al., 2013, J Immunol 190:1402-1406) and that NKG2C$^{pos}$ NK-cells (from CMV-seropositive donors) expand in response to CMV reactivation in allogeneic HSCT recipients, but those from CMV-seronegative donors do not (Foley et al., 2012, Blood 119:2665-2674).

The presence of EBV was determined by genomic analysis as described below. Briefly, cells were thawed in a 37° C. water bath and transferred to 5 ml warm medium, then centrifuged and resuspended in fresh medium. 4×10$^6$ cells from each sample were aliquoted into 2 ml tubes and the remaining cells were frozen down in 90% FBS+10% DMSO and stored at −80° C. Genomic DNA (gDNA) was extracted from the cells using Pure Link genomic DNA mini kit (Cat #K1820-00 Invitrogen) and quantified using Qubit (DNA BR) and the quality confirmed using TapeStation (gDNA tape). 50 ng of gDNA was used per reaction in the qPCR (Brilliant III Ultra-Fast SYBR® Green mastermix, Cat #600883, Agilent). Primers for EBNA1 and GAPDH (IDT) were used to detect and quantify EBV. The results showed that no EBV was found in cells expanded with irradiated 221.AEH feeder cells.

Example 3: Assessment of Cytotoxic Activity of Expanded NK Cells

Functional activity of NK cells expanded by the method described in Example 2, compared to the alternative method, was assessed by evaluating target-specific cytotoxic activity.

Figure 3:
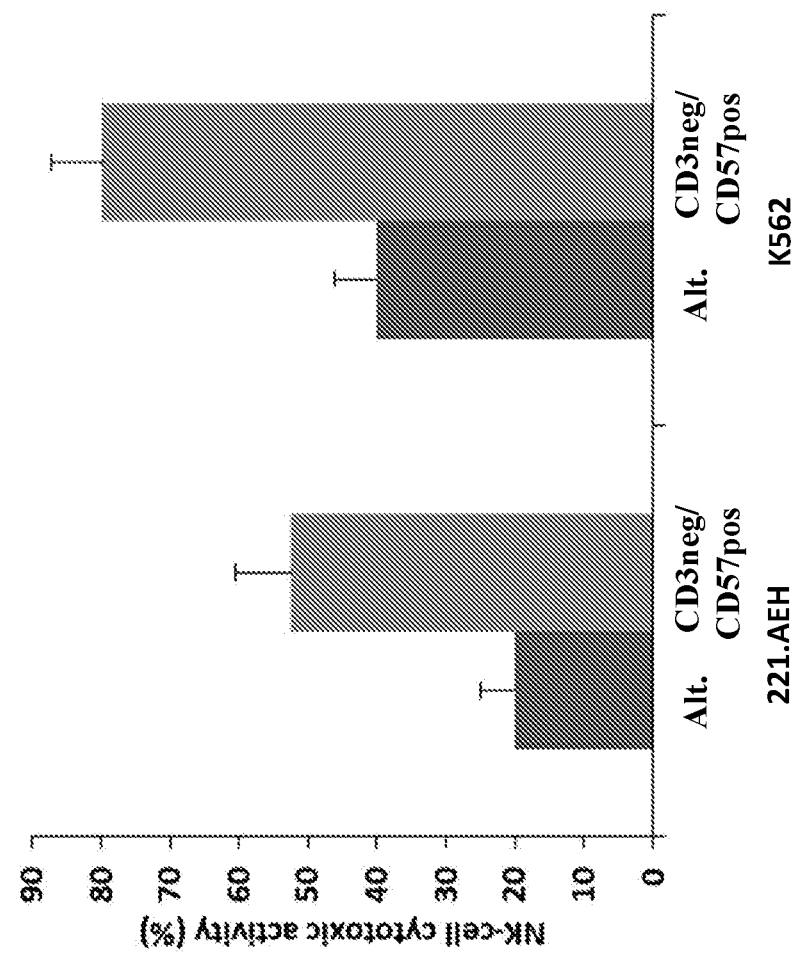
FIG. 3 depicts NK-cell cytotoxic activity (5:1 NK-cell to target ratio) against the 221.AEH and K562 cell lines (n=8) of NK cells expanded by the method described in Example 2 involving enrichment of $CD3^{neg}CD57^{pos}$ NK-cells or by the alternative method. Values are mean±standard error.

Frozen NK-cells from expansions described in Example 1 were thawed and NK cell cytotoxicity was evaluated by co-culture of day 14 expanded NK cells with HLA-deficient K562 and HLA-E$^{bright}$ 221.AEH cell lines at an effector to target cell ratio of 1:1. After a 4-h incubation at 37° C., propidium iodide (PI) was added and the numbers of NK cells, live target cells and dead target cells were resolved using four-color flow cytometry. NK cell cytotoxicity was quantified as the percentage of specific lysis (% total lysis—% spontaneous cell death). As shown in FIG. 3, NK cells expanded by the alternative method described in Example 1 were able to enhance (vs. unexpanded cells) NK-cell killing of the HLA-deficient K562 and HLA-gbnght 221.AEH cell lines from 15% to 40% and 5% to 20%, respectively. However, the method described in Example 1 starting from enriched CD3$^{neg}$CD57$^{pos}$ NK cells resulted in expanded NK cells that were able to kill 80% (vs. 40% for alternative method) and 53% (vs. 20% for alternative method) of K562 and 221.AEH cells, respectively (see FIG. 3).

Example 4: Assessment of Antibody Dependent Cell Mediated Cytotoxicity (ADCC) of Expanded NK Cells in Combination with an Anti-CD20 Antibody Functional activity of NK cells expanded by the method described in Example 2 was assessed by evaluating antibody dependent cell mediated cytotoxicity (ADCC) in combination with an anti-CD20 antibody.

Figure 4A:
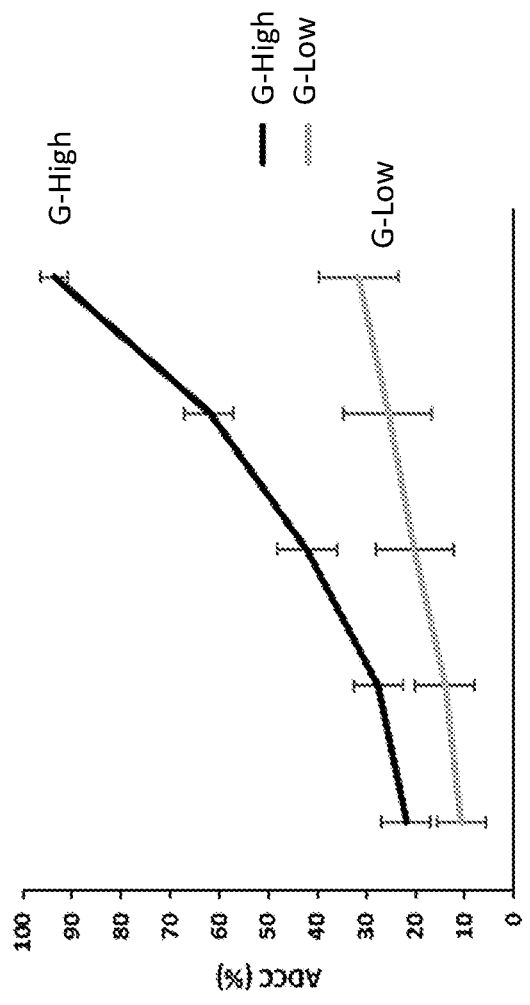
FIGS. 4A and 4B depict ADCC activity of g-NK cells compared to conventional NK cells in combination with anti-CD20 antibody (Rituximab) against the lymphoma cell line RAJI.

For the ADCC cytotoxicity assays, frozen NK cells from expansions described in Example 2 were thawed and incubated in 10% FBS-supplemented RPMI-1640 media for 1 hour at 37° C. NK cells were then incubated with RAJI target cells ($1.0\times10^4$ cells, CD20+ B-cell tumor cell line) at 0.5:1, 1:1, 2.5:1, 5:1, and 10:1 NK cell to target cell ratios in 10% FBS-supplemented RPMI-1640 media in the presence of 10 µg/mL Rituximab (anti-CD20). ADCC was determined by flow cytometry based on staining with an anti-CD71 antibody to identify the tumor target cells and propidium iodide (PI) as a marker of cell death (Bigley et al., (2014) Brain Behav Immun., 39:160-71). As shown in FIG. 4A, ADCC was substantially higher (94% killing at 10:1 ratio) in g-NK high subjects [g-NKmean=24% pre-expansion, n=4] than in g-NK low subjects (31% killing at 10:1 ratio) [g-NKmean=2% pre-expansion, n=4].

Figure 4B:
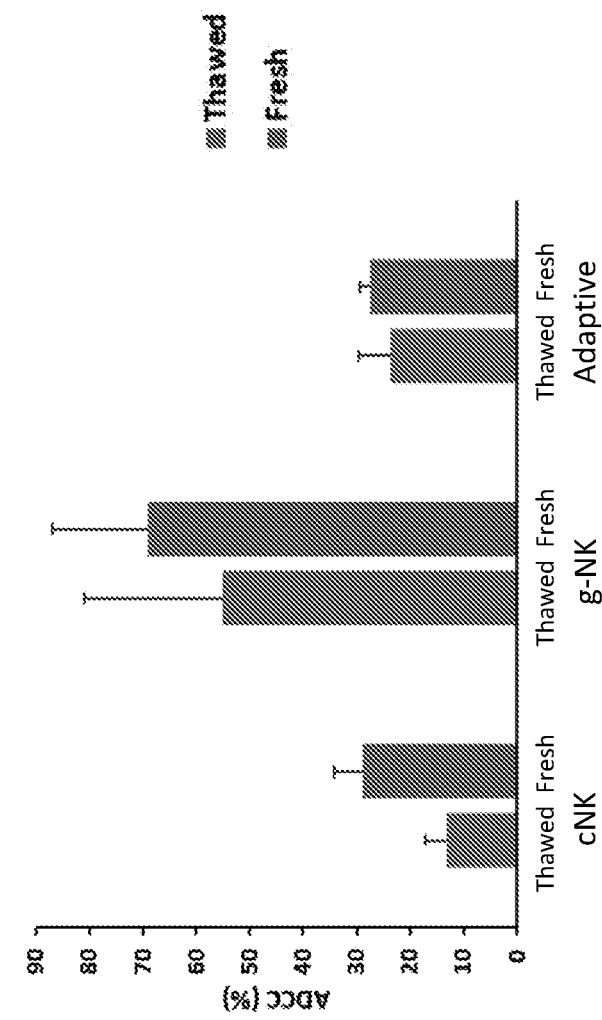

To compare activity of different subsets, expanded NK cells were sorted into 3 categories by flow cytometry for viable NK cells and extracellular surface markers: conventional [cNK; CD45+/CD3−/CD56+/NKG2C−], adaptive (NKG2C+) [CD45+/CD3−/CD56+/NKG2C+/NKG2A−], and g-NK [CD45+/CD3−/CD56+/CD16+/CD57+/CD7−/CD161−], The g-NK could also be sorted using the extracellular phenotype [CD45+/CD3−/CD56+/CD161−/NKG2A−]. In this experiment, conventional, adaptive (NKG2C$^{pos}$), and g-NK were obtained from the four subjects with the highest g-NK cells (g-NK$_{mean}$=25.3±8.5%). As shown in FIG. 4B, g-NK had much better ADCC killing (76%) at a 1:1 NK-cell target cell ratio than NKG2C$^{pos}$ or conventional NK cells (30% or 24%, respectively). Furthermore, the function of the g-NK was similar whether they were derived from fresh or previously frozen NK-cells (FIG. 4B). The 'super donor' described above had expanded g-NK that killed much better (97%) at a 1:1 NK-cell target cell ratio than their NKG2C$^{pos}$ or conventional NK-cells (55% or 38%, respectively).

These results demonstrate that the provided method is capable of generating billions of g-NK in only 2 weeks that are far superior ADCC killers than NKG2C$^{pos}$ or conventional NK-cells.

Example 5: Assessment of Antibody Dependent Cell Mediated Cytotoxicity (ADCC) of Expanded NK Cells in Combination with an ERBB Family-Specific Antibody Functional activity of NK cells expanded by the method described in Example 2, compared to the alternative method, was assessed by evaluating antibody dependent cell mediated cytotoxicity (ADCC) in combination with an anti-HER2 antibody.

Donors were CMV-seropositive (n=4) and magnetically sorted NK-cells (pre-expansion g-NK percentage=18.3±2.9%) were expanded using the method described in Example 2. Expanded NK-cells were then magnetically sorted using CD57 microbeads into CD57+'g-NK' and CD57−'cNK' fractions and cryopreserved for later ADCC assays. The actual g-NK percentages of the CD57+ and CD57-fractions were 82.2±1.6% and 2.4±0.7%, respectively. The g-NK percentages within the CD57+ and CD57− fractions were determined by intracellular flow cytometry using an FcRγ antibody purchased from Millipore (Burlington, MA, USA). For the ADCC cytotoxicity assays, frozen NK-cells from prior expansions were thawed and incubated in 10% FBS-supplemented RPMI-1640 media for 1 hour at 37° C. ADCC assays were performed using the breast cancer cell line SKBR3 and head/neck cancer cell line CAL27 as targets. As we have described previously (Bigley et al., 2014), expanded NK-cells were co-cultured with CD71-labeled SKBR3 and CAL27 target cells ($1.0\times10^4$ cells) at 1:1, 5:1, 10:1, and 20:1 NK-cell: target cell ratios in a final volume of 2.2 mL of target cell-specific media. The media used for the SKBR3 assay was 10% FBS-supplemented McCoy's 5A media with 2.5 µg/mL trastuzumab (anti-HER2) and the media used for the CAL27 assay was 10% FBS-supplemented DMEM with 10 µg/mL cetuximab (anti-EGFR). In each case, basal cytotoxicity was also measured without the treating antibody present. Target cell only tubes were used to control for spontaneous cell death (less than 10% for all assays). There was also a target cell+antibody tube (no NK-cells added) to account for cell death attributed to the antibody alone. After a 4 h incubation at 37° C., the cells were washed and stained with anti-CD3 and CD56 antibodies to quantify the number of NK-cells in the tube. After a final wash, propidium iodide (PI) was added and the number of NK-cells, live target cells, and dead target cells were resolved using 4-color flow cytometry (Bigley et al., 2018). Cytotoxicity was determined by subtracting % spontaneous cell death from % total death at each NK-cell dose (basal cytotoxicity=% total death−% spontaneous cell death). The SKBR3 and CAL27 cell lines were purchased from ATCC (Manassas, VA, USA).

Figure 5A:
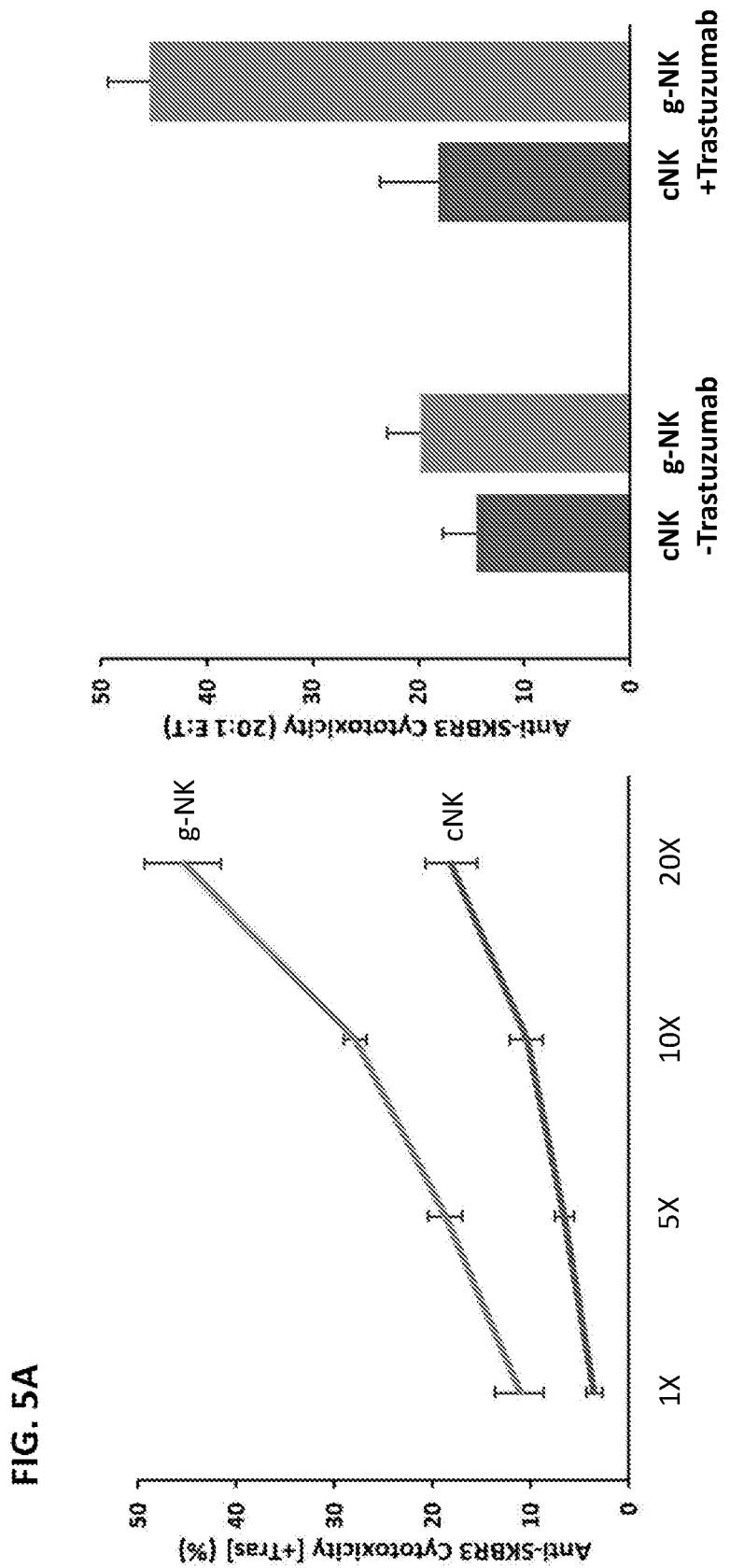
FIGS. 5A and 5B depict ADCC activity of g-NK cells compared to conventional (cNK) NK cells.
Figure 5B:
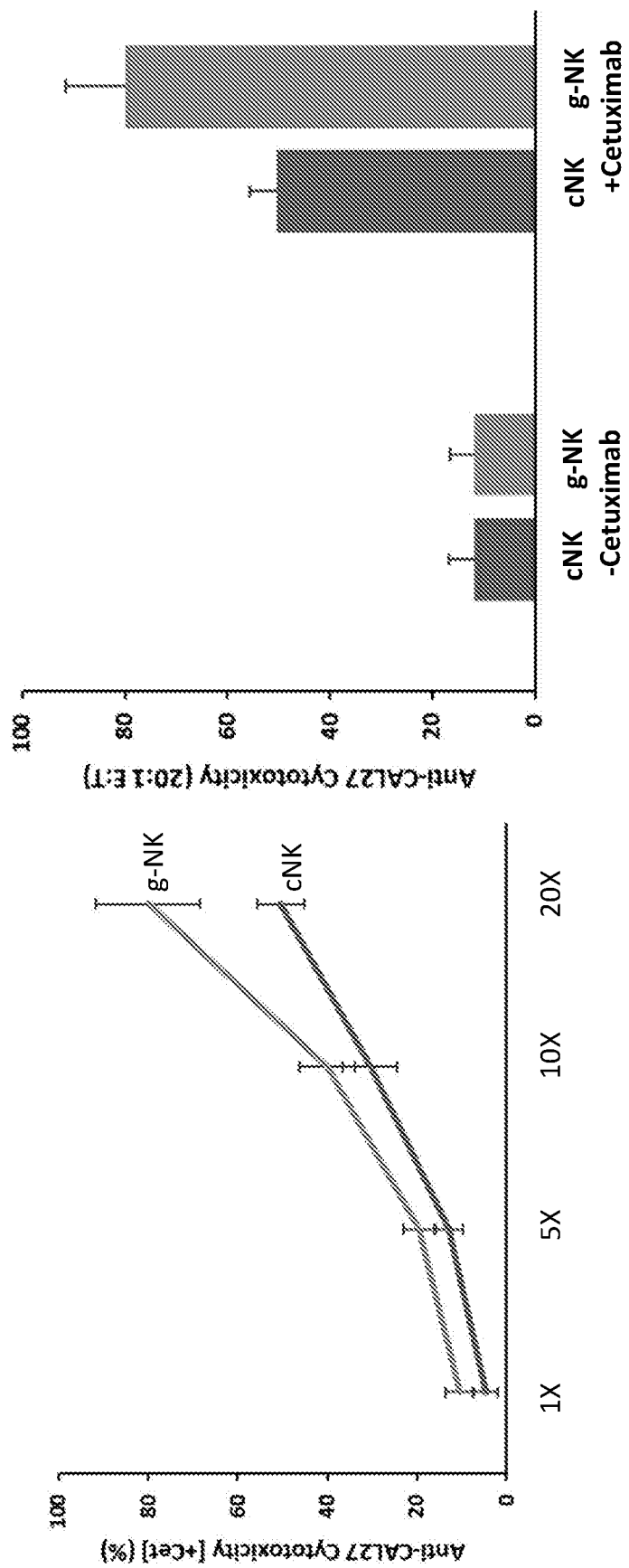

As shown in FIGS. 5A and 5B, g-NK were found to kill SKBR3 and CAL27 targets far better than conventional NK-cells. Specifically, g-NK killed 46% of SKBR3 cells at a 20:1 NK:target ratio when trastuzumab was present, which was far greater than the 18% of SKBR3 cells killed by cNK at the same ratio (n=4) (FIG. 5A). Basal cytotoxicity (without trastuzumab) was 18% for g-NK and 14% for cNK at a 20:1 NK:target ratio. The ADCC of conventional NK-cells was the same as the basal cytotoxicity of g-NK cells. Similarly, FIG. 5B depicts results showing g-NK killed 80% of CAL27 cells at a 20:1 NK:target ratio when cetuximab was present, which was far greater than the 50% of CAL27 cells killed by cNK at the same ratio (n=4). Basal cytotoxicity (without cetuximab) was 12% for both g-NK and cNK at a 20:1 NK:target ratio.

In another series of experiments using the same donor NK-cells as above, NK cells were incubated with colorectal cancer cell lines HT-29 and SW-480 or lung cancer cell line A-549 target cells at 1:1, 5:1, 10:1, and 20:1 NK cell to target cell ratios. The media used for the HT-29 assay was 10% FBS-supplemented McCoy's 5A media with 5 µg/mL cetuximab; the media used for the SW-480 assay was 10% FBS-supplemented Leibovitz's L-15 Medium with 5 µg/mL cetuximab; and the media used for the A-549 assay was 10% FBS-supplemented F-12K Medium with 5 µg/mL cetuximab. ADCC was determined by flow cytometry based on staining with an anti-CD71 antibody to identify the tumor target cells and PI as a marker of cell death. Basal cytotoxicity was also measured without the treating antibody present.

Figure 6A:
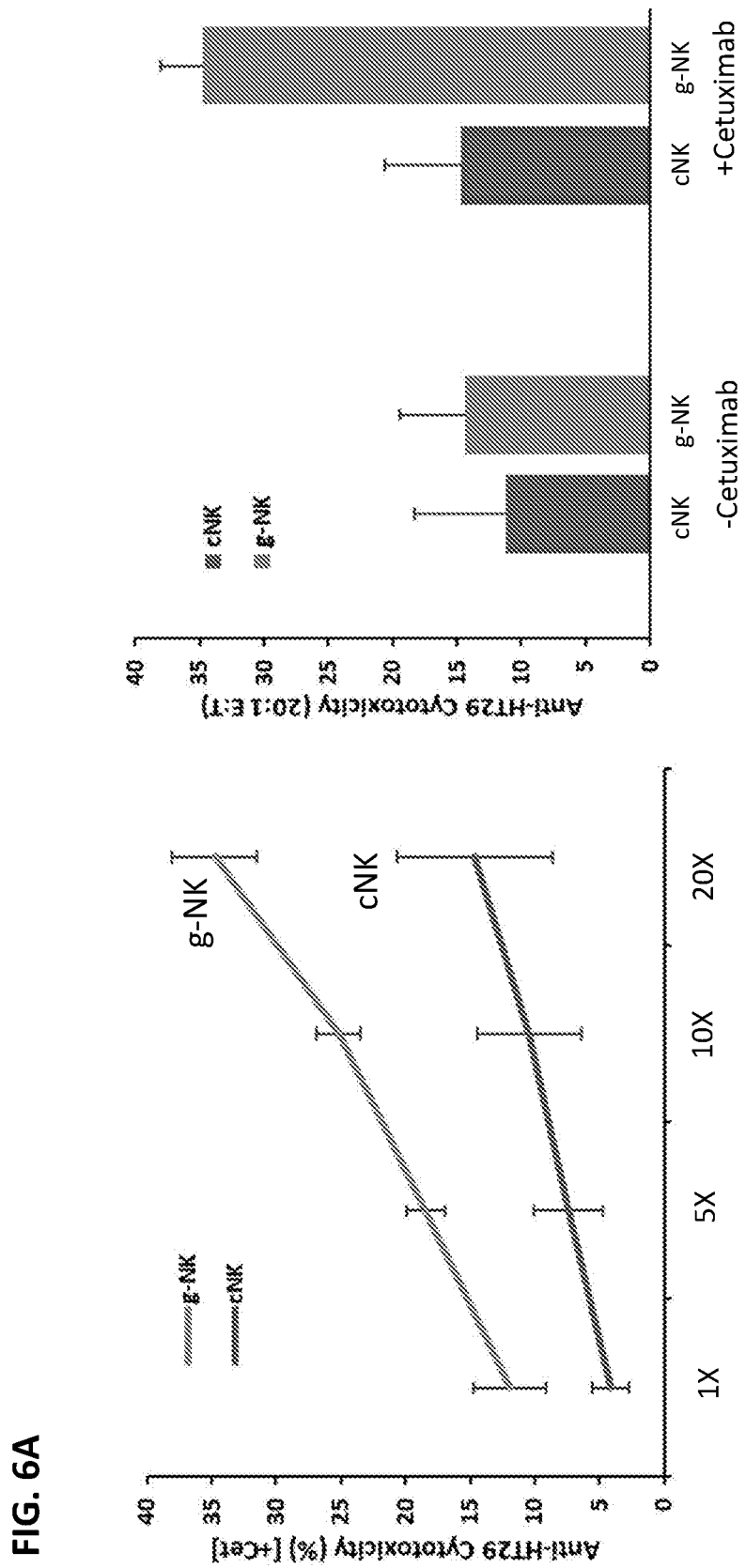
FIGS. 6A-6C depict ADCC activity of g-NK cells compared to conventional NK cells (cNK).
Figure 6B:
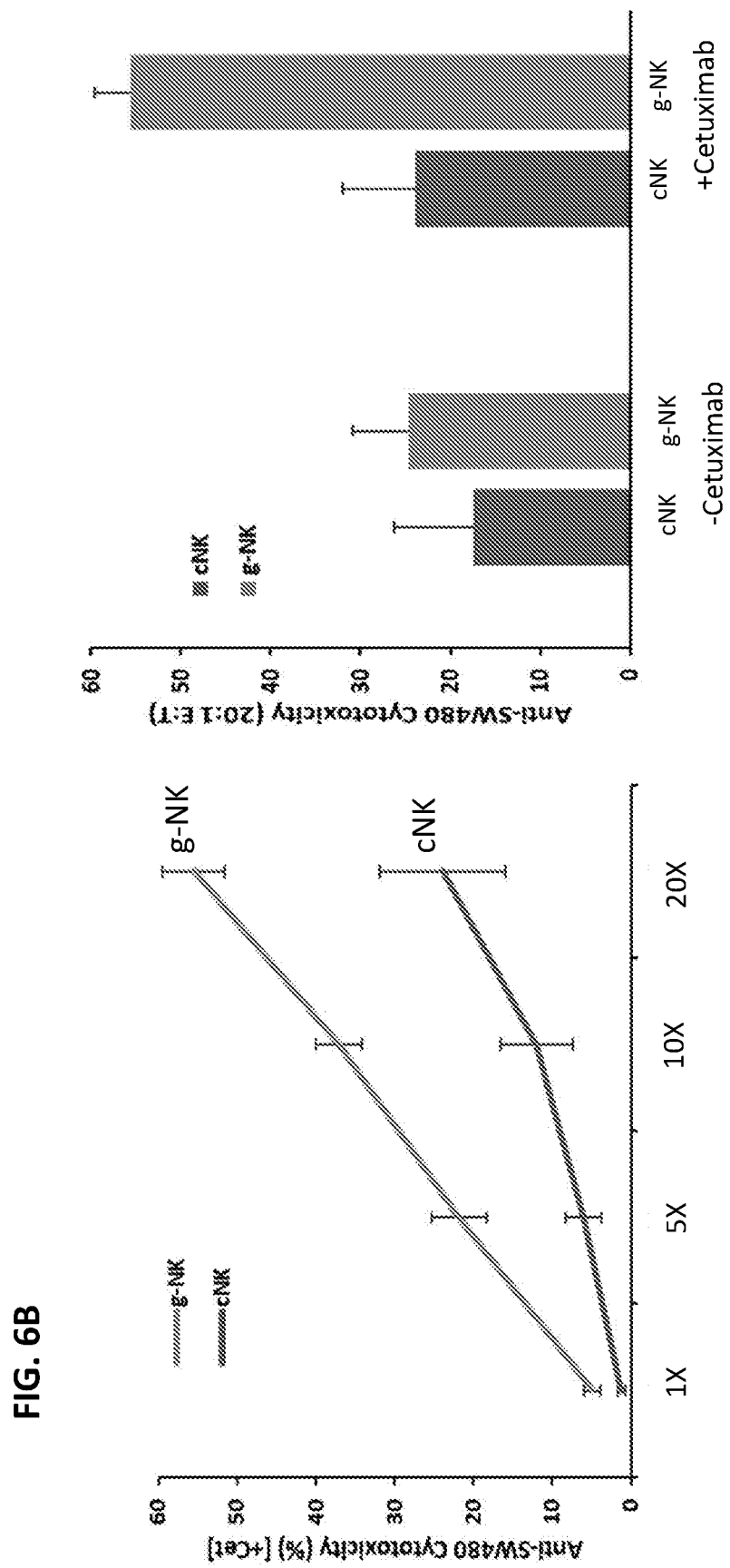
Figure 6C:
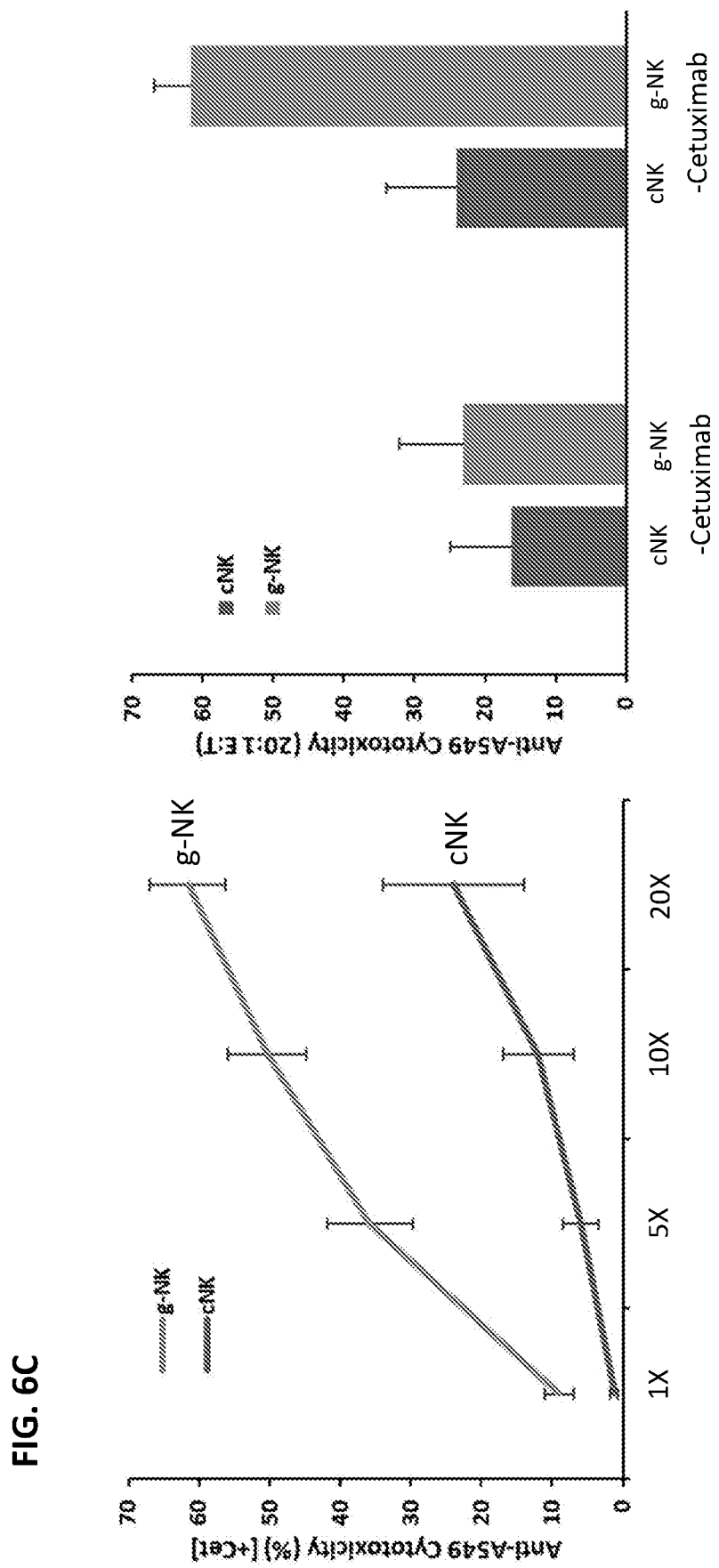

Results in FIGS. 6A-6C show that g-NK were found to kill HT-29, SW-480, and A-549 targets far better than cNK (using the same donor NK-cells as above). Specifically, as shown in FIG. 6A, g-NK killed 35% of HT-29 cells at a 20:1 NK:target ratio when cetuximab was present, which was superior to the 14% of HT-29 cells killed by cNK at the same ratio (n=4). Basal cytotoxicity (without cetuximab) was 14% for g-NK and 11% for conventional NK-cells at a 20:1 NK:target ratio. Similarly, FIG. 6B depicts results showing g-NK killed 56% of SW-480 cells at a 20:1 NK:target ratio when cetuximab was present, which was far greater than the 23% of SW-480 cells killed by cNK at the same ratio (n=4). Basal cytotoxicity (without cetuximab) was 24% for g-NK and 18% for cNK at a 20:1 NK:target ratio. Furthermore, FIG. 6C shows that g-NK killed 62% of A-549 at a 20:1 NK:target ratio when cetuximab was present, which was markedly superior to the 23% of A-549 cells killed by cNK at the same ratio (n=4). Basal cytotoxicity (without cetuximab) was 23% for g-NK and 17% for conventional NK-cells at a 20:1 NK:target ratio. The ADCC of cNK was the same as the basal cytotoxicity of g-NK cells for all 3 cell lines.

Together, the results show that the expanded g-NK are able to enhance ADCC against liquid and solid tumors alike, as well as tumors that are either highly or mildly susceptible to NK-cell ADCC.

Example 6: Assessment of In Vivo Persistence of Expanded NK Cells

NK-cells were expanded as described in Example 2. After 1 week of acclimation, a single dose of $1 \times 10^7$ expanded g-NK (fresh or freeze/thawed) or cNK (freeze/thawed) was injected into female NOD scid gamma (NSG) mice with IL-15 supplement (2 µg I.P. every 3 days) (see Table E1). The g-NK were expanded from a single CMV-seropositive donor (percentage of g-NK was 61% pre-expansion and 90% post-expansion), while the cNK were expanded from a single CMV-seronegative donor (percentage of g-NK was 0% pre-expansion and post-expansion). The percentage of g-NK was confirmed using intracellular flow cytometry. For cells that have been frozen after expansion and thawed for use in this study, the freeze media for the frozen cells was 90% FBS and 10% DMSO. Frozen cell products were thawed rapidly in a hot water bath prior to being administered to the mice (37° C.).

Figure 7A:
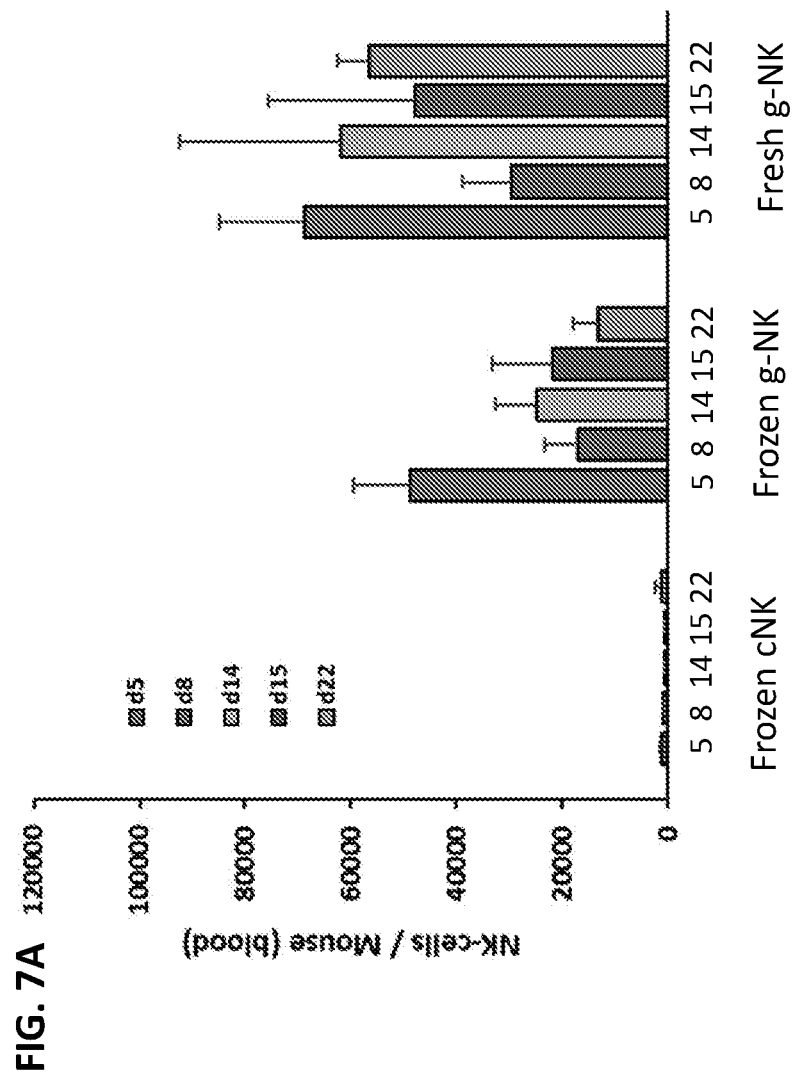
FIGS. 7A-7C depict the persistence of g-NK (fresh or frozen) and cNK (frozen) in NSG mice after infusion of 1×10$^7$ g-NK or cNK cells.
Figure 7B:
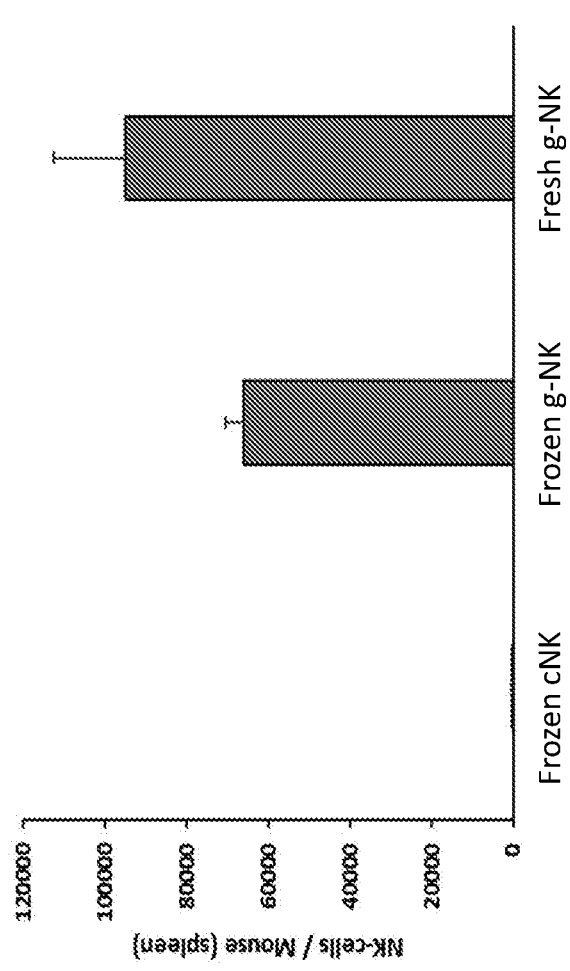

Blood samples were collected from respective mice to determine in vivo persistence of the respective NK cells. For blood collection, 50 µL blood draws were obtained using EDTA vacutainers and frozen (10% DMSO added) at days 5, 8, 14, 15, and 22 post-infusion for later flow cytometry (FIG. 7A). At Day 22, all mice were sacrificed and bone marrow and spleen were viably frozen (90% FBS and 10% DMSO) (FIG. 7B, C respectively).

TABLE E1

Persistence Study Design

| Group Number | Arm | Number of Mice | Day of NK dose | Days of blood collection |
|---|---|---|---|---|
| 1 | IL-15 + Fresh g-NK | 3 | 1 | 1, 5, 8, 14, 15, 22 (sac) |
| 2 | IL-15 + Frozen g-NK | 3 | 1 | 1, 5, 8, 14, 15, 22 (sac) |
| 3 | IL-15 + Frozen cNK | 3 | 1 | 1, 5, 8, 14, 15, 22 (sac) |

Figure 7C:
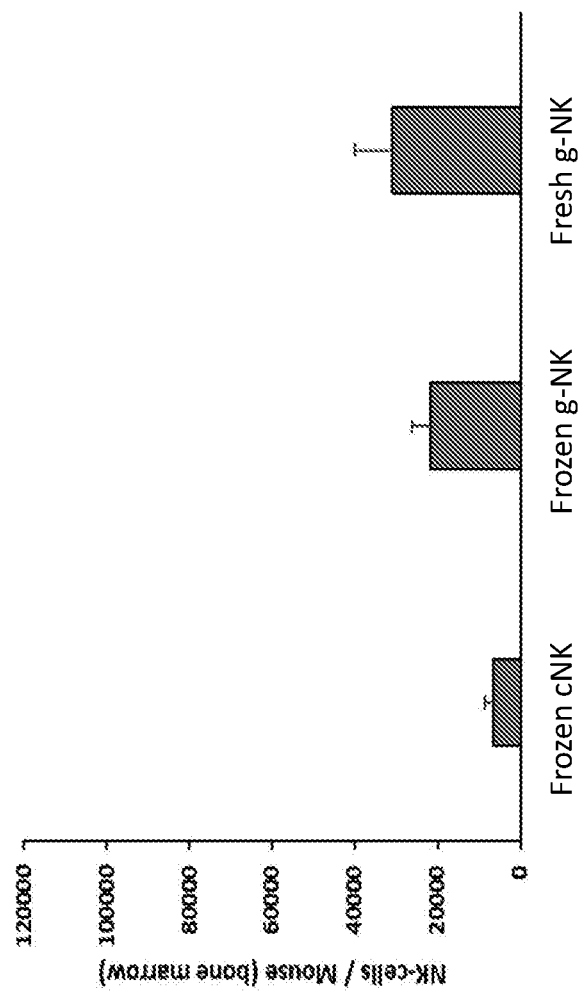

As shown in FIG. 7A, both freshly isolated or freeze-thawed g-NK persisted substantially longer than freeze-thawed cNK in bloodstream of NSG mice, as observed for all time points (days 5, 8, 14, 15, and 22). In particular, almost no cNK were found to have persisted in the spleen after 22 days, whereas a substantial number of g-NK were detected (FIG. 7B). The persistence of g-NK was also superior to that of cNK in the bone marrow (FIG. 7C).

Example 7: Assessment of Anti-Tumor Activity by of Expanded NK Cells in Combination with an Anti-CD20 Antibody Functional activity of NK cells expanded by the method described in Example 2 was assessed by evaluating inhibition on tumor in vivo when injected in combination with an anti-CD20 antibody.

$5 \times 10^5$ Luciferase-labeled Raji human lymphoma cell lines were injected intravenously into female NOD scid gamma (NSG) mice and allowed to grow for 2 days. The monoclonal antibody rituximab was administered I.P. to mice, either alone or in combination with $15 \times 10^6$ expanded g-NK cells (Example 2) that were administered I.V. for 3 doses over 21 days (see Table E2). Bioluminescent imaging was used to monitor tumor burden on a weekly basis, and survival was recorded every 2 or 3 days. The g-NK were expanded from a single CMV-seropositive donor (percentage of g-NK was 61% pre-expansion and 90% post-expansion), while the cNK were expanded from a single CMV-seronegative donor (percentage of g-NK was 0% pre-expansion and post-expansion). The percentage of g-NK was confirmed using intracellular flow cytometry.

TABLE E2

Raji Efficacy Study Design

| Group Number | Arm | Number of Mice | Days of Antibody Administration | Days of NK cell administration |
|---|---|---|---|---|
| 1 | No Treatment | 8 | N/A | N/A |
| 2 | Rituximab 200 µg I.P. | 8 | 1, 8, 15 | N/A |
| 3 | 15e6 Fresh g-NK I.V. + 200 µg rituximab I.P. | 8 | 1, 8, 15 | 1, 8, 15 |

Figure 8A:
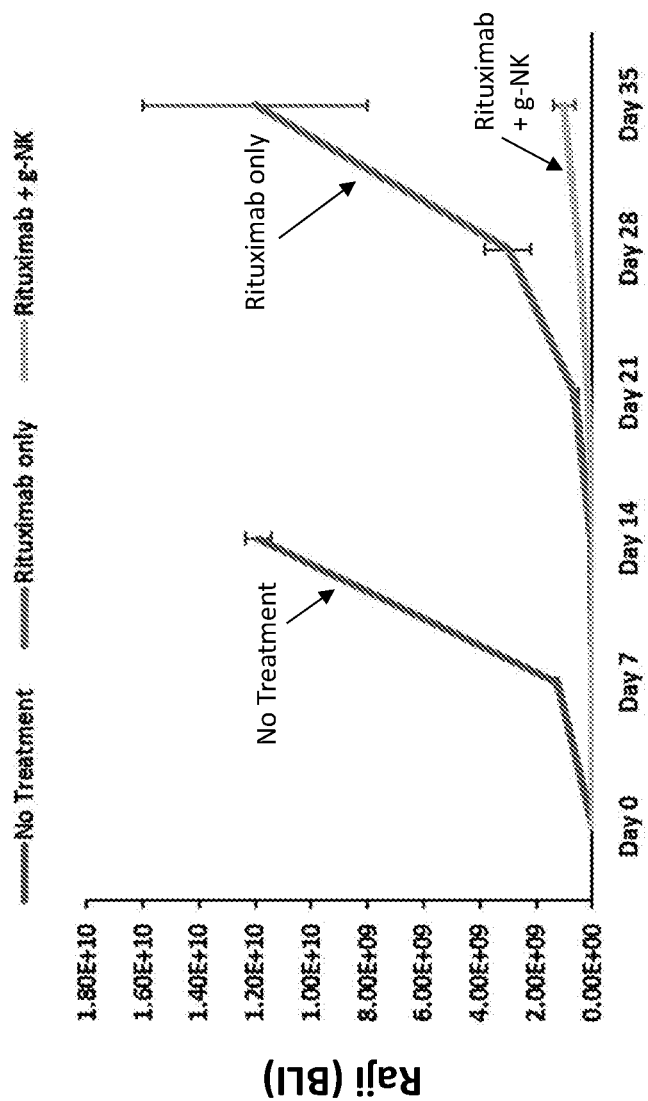
FIGS. 8A and 8B depict the effect of g-NK and rituximab on tumor burden and survival in a xenograft model of lymphoma.
Figure 8B:
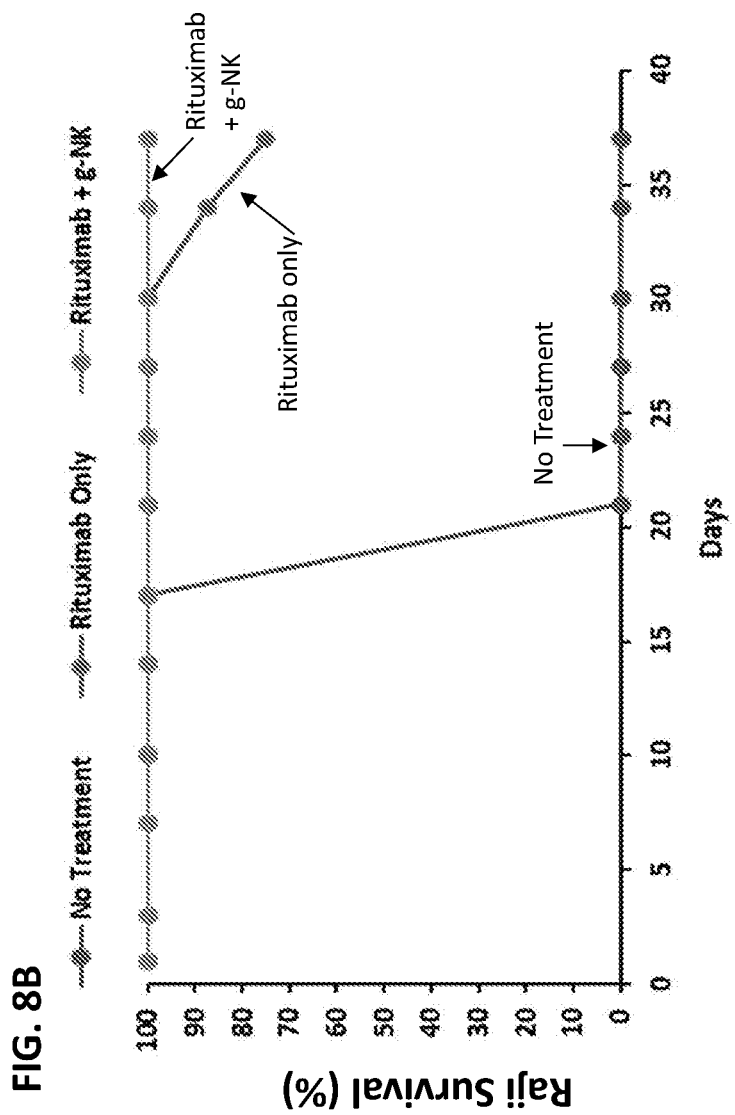

Adoptive transfer of g-NK greatly enhanced the efficacy of rituximab in a xenograft model of Raji lymphoma, and infusion of g-NK was able to enhance survival of NSG mice relative to untreated mice or mice treated with rituximab alone. As shown in FIGS. 8A and 8B, mice receiving no treatment exhibited rapid tumor growth 7 days after injection and all untreated mice expired before Day 25. Mice receiving only rituximab showed a delayed yet still rapid tumor growth after Day 28, and survival began to decline after Day 30. Mice receiving administration of g-NK in conjunction with Rituximab only exhibited slight tumor growth after Day 28, and all mice survived up to Day 35.

These results demonstrate the anti-lymphoma effect of g-NK can be harnessed in vivo when combined with monoclonal antibodies.

Example 8: Assessment of Antibody Dependent Cell Mediated Cytotoxicity (ADCC) of Expanded NK Cells in Combination with an Anti-CD38 Antibody or an Anti-CD319 Antibody Functional activity of NK cells expanded by the method described in Example 2, compared to the alternative method, was assessed by evaluating antibody dependent cell mediated cytotoxicity (ADCC) in combination with Daratumamab (anti-CD38) or Elotuzamab (anti-CD319).

Pre-expansion (freshly isolated) ADCC: Donors were CMV-seropositive (n=14) and CMV-seronegative (n=2). All donors were pre-screened for the percentage of g-NK cells and categorized as either 'g-NK' donors (n=10 CMV+) or 'conventional' donors (n=4 CMV+, n=2 CMV−) based on the proportion of g-NK cells. The proportion of g-NK in the 'g-NK' donors was 30.0±2.1%, while the proportion of g-NK was only 1.6±0.4% in the 'conventional' donors. CD57+ NK-cells were magnetically sorted from the 'g-NK' donors and bulk NK-cells (CD3−/CD56+) were magnetically sorted from the 'conventional' donors. The actual g-NK percentages of the magnetically sorted fractions from the 'g-NK' and 'conventional' donors were 84.3±2.4% and 1.6±0.4%, respectively. The g-NK percentages within each fraction were determined by intracellular flow cytometry using an FcRγ antibody purchased from Millipore (Burlington, MA, USA).

For the ADCC cytotoxicity assays, frozen PBMCs were thawed and incubated in 10% FBS-supplemented RPMI-1640 media for 1 hour at 37° C. Magnetic bead separations were then performed to isolate CD57+ NK-cells and bulk NK-cells from 'g-NK' and 'conventional' donors, respectively. ADCC assays were performed using the multiple myeloma cell line MM.1S (ATCC, Manassas, VA) as targets, NK-cells were co-cultured with CD71-labeled MM.1S target cells ($1.0 \times 10^4$ cells) at 0.5:1, 1:1, 2.5:1, and 5:1 NK-cell:target cell ratios in a final volume of 2.2 mL of target cell-specific media, similar to method described in Bigley et al. 2014. The media used for the ADCC assay was 10% FBS-supplemented RPMI-1640 media with 1 µg/mL daratumumab (anti-CD38) or 1 µg/mL elotuzumab (anti-CD319). In each case, basal cytotoxicity was also measured without the treating antibody present. Target cell only tubes were used to control for spontaneous cell death (less than 10% for all assays). After a 4 h incubation at 37° C., the cells were washed and stained with anti-CD3 and CD56 antibodies to quantify the number of NK-cells in the tube. After a final wash, propidium iodide (PI) was added and the number of NK-cells, live target cells, and dead target cells were resolved using 4-color flow cytometry (Bigley et al., 2018).

Post-expansion (expanded) ADCC: Five donors were pre-screened for the percentage of g-NK cells and categorized as either 'g-NK' donors (n=3) or 'conventional' donors (n=2) based on the proportion of g-NK cells. The proportion of g-NK in the 'g-NK' donors was 30.3±2.0%, while the proportion of g-NK was only 1.6±0.4% in the 'conventional' donors. CD57+ NK-cells were magnetically sorted from the 'g-NK' donors and bulk NK-cells (CD3−/CD56+) were magnetically sorted from the 'conventional' donors. The actual g-NK percentages of the magnetically sorted fractions from the 'g-NK' and 'conventional' donors were 84.0±2.5% and 1.6±0.4%, respectively. The g-NK and cNK fractions were then expanded as described in Example 2 and cryopreserved for later ADCC assays as described above.

Figure 9A:
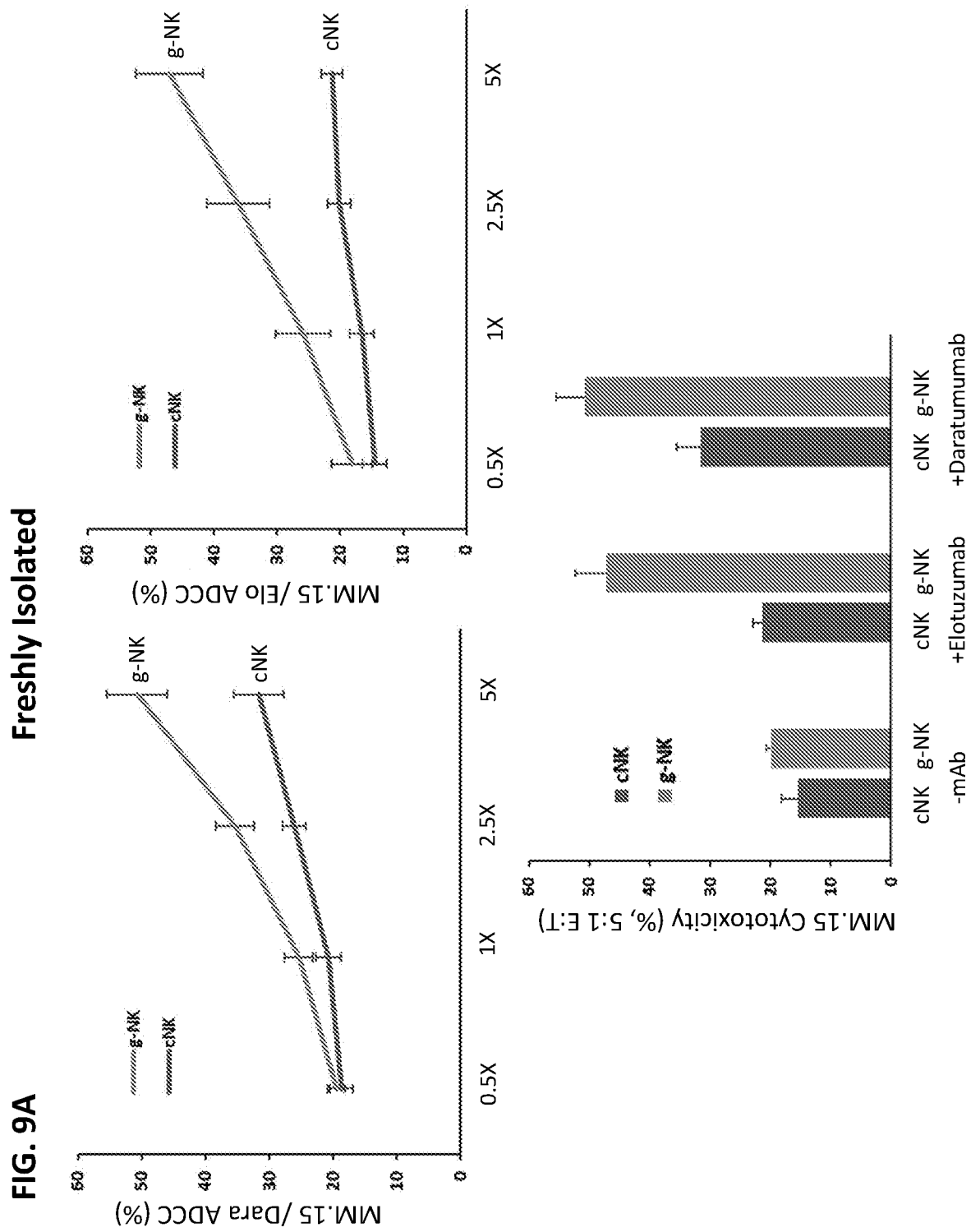
FIGS. 9A and 9B depict ADCC activity of g-NK cells compared to conventional NK cells (cNK).
Figure 9B:
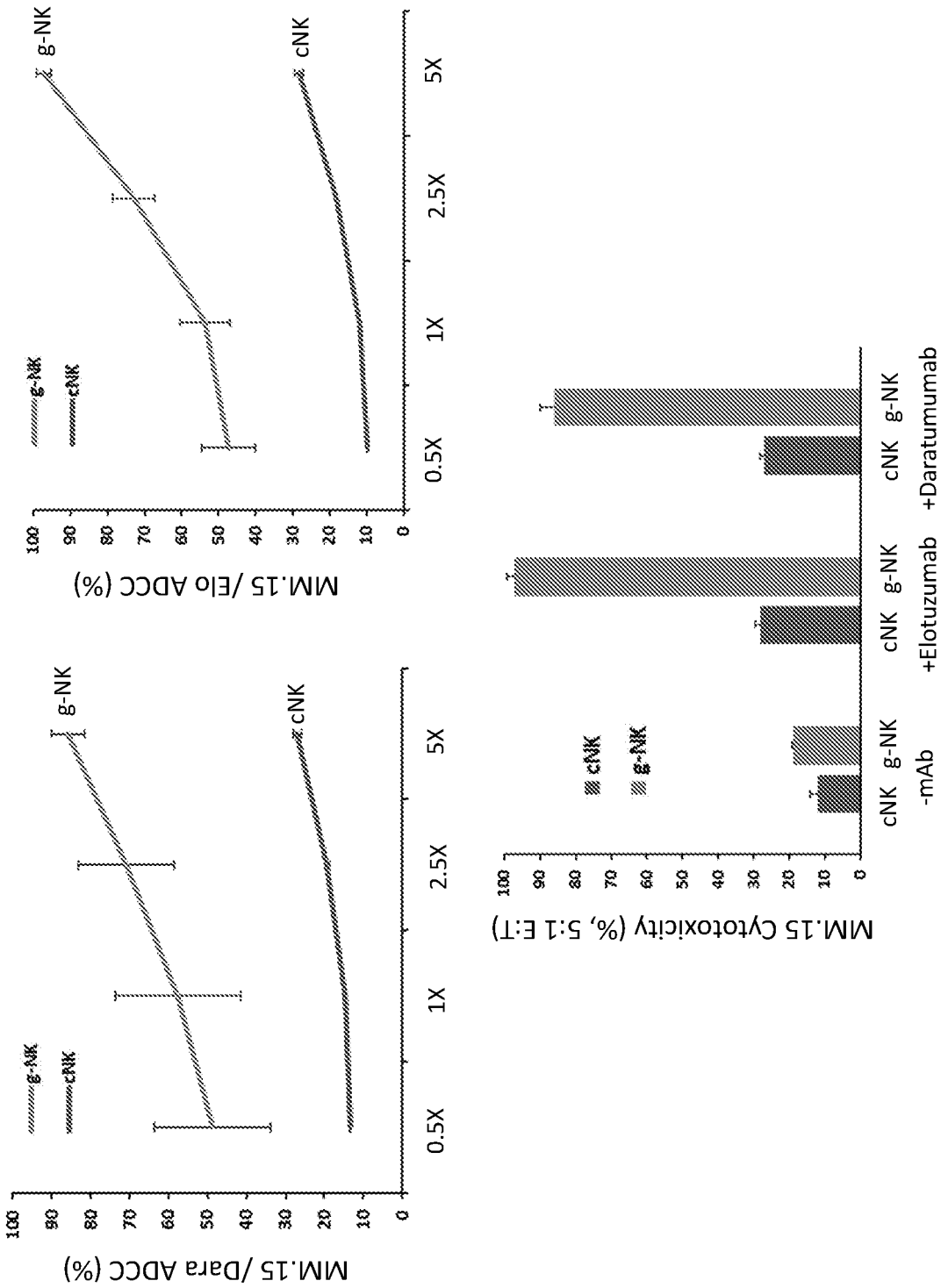

The g-NK have greater ADCC against MM.1S multiple myeloma cells than cNK when combined with daratumumab or elotuzumab. Specifically, freshly isolated g-NK had markedly higher cytotoxicity against MM.1S cells than cNK at all 4 NK-cell doses when daratumumab or elotuzumab were present (see FIG. 9A). Similarly, expanded g-NK had greater anti-myeloma ADCC than expanded cNK when combined with daratumumab or elotuzumab (see FIG. 9B). There was no difference between the cytotoxicity of g-NK and cNK (unexpanded or expanded) against MM.1S cells when antibody was not present (see FIGS. 9A and 9B).

Overall, this data shows that g-NK have strong antibody-dependent cytotoxic activity against multiple myeloma.

Example 9: Assessment of Anti-Tumor Activity by Expanded NK Cells in Combination with an Anti-CD38 Antibody or an Anti-CD319 Antibody Functional activity of NK cells expanded by the method described in Example 2 was assessed by evaluating inhibition on tumor in vivo when injected in combination with an anti-CD38 Antibody or an anti-CD319 antibody.

$1 \times 10^6$ Luciferase-labeled MM.1S human myeloma cell lines were injected intravenously into female NOD scid gamma (NSG) mice and allowed to grow for 7 days. Monoclonal antibodies daratumumab or elotuzumab were administered I.P. to mice, either alone or in combination with expanded g-NK cells or physiological levels of comparator cNK cells, that were administered I.V., for 6 doses over 31 days (see Table E3). Bioluminescent imaging was used to monitor tumor burden on a weekly basis. At study completion, bone marrow and spleen samples were harvested and viably frozen from 3 mice each in g-NK and cNK arms for later flow cytometry analysis, to determine persistence of respective NK populations. The g-NK were expanded from a single CMV-seropositive donor (percentage of g-NK was 61% pre-expansion and 90% post-expansion), while the cNK were expanded from a single CMV-seronegative donor (percentage of g-NK was 0% pre-expansion and post-expansion). The percentage of g-NK was confirmed using intracellular flow cytometry.

g-NK cells were expanded as described in Example 2 and administered at $2 \times 10^7$ cells at each dose, while unexpanded cNK were adminstered at $3 \times 10^5$ cells at each dose. The cNK dose is equivalent to physiological levels of NK-cells/kg in humans (Cooley et al., 2019).

TABLE E3

MM Efficacy Study Design

| Group Number | Arm | Number of Mice | Days of Antibody Administration | Days of NK cell administration |
|---|---|---|---|---|
| 1 | Vehicle control | 6 | N/A | N/A |
| 2 | Daratumumab 10 ug I.P. | 6 | 1, 7, 13, 19, 25, 31 | N/A |
| 3 | 2e7 Fresh g- NK I.V. + 10 ug Daratumumab I.P. | 6 | 1, 7, 13, 19, 25, 31 | 1, 7, 13, 19, 25, 31 |
| 4 | 3e5 Fresh cNK I.V. + 10 ug Daratumumab I.P. | 6 | 1, 7, 13, 19, 25, 31 | 1, 7, 13, 19, 25, 31 |
| 5 | Elotuzumab 10 ug i.p. | 6 | 1, 7, 13, 19, 25, 31 | N/A |
| 6 | 2e7 Frozen g- NK I.V. + 10 ug Elotuzumab I.P. | 6 | 1, 7, 13, 19, 25, 31 | 1, 7, 13, 19, 25, 31 |
| 7 | 3e5 Frozen cNK I.V. + 10 ug Elotuzumab I.P. | 6 | 1, 7, 13, 19, 25, 31 | 1, 7, 13, 19, 25, 31 |
| 8 | 2e7 Frozen g- NK alone I.V. | 6 | N/A | 1, 7, 13, 19, 25, 31 |

Figure 10A:
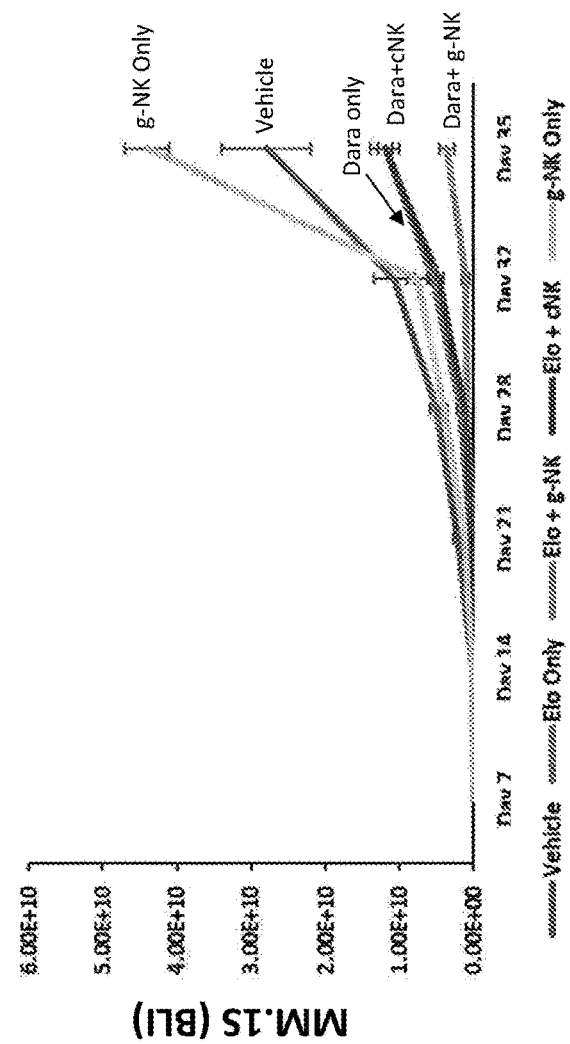
FIGS. 10A and 10B depict the effect of g-NK on in vivo efficacy of daratumumab (Dara) and elotozumab (Elo), respectively, in a xenograft model of multiple myeloma.
Figure 10B:
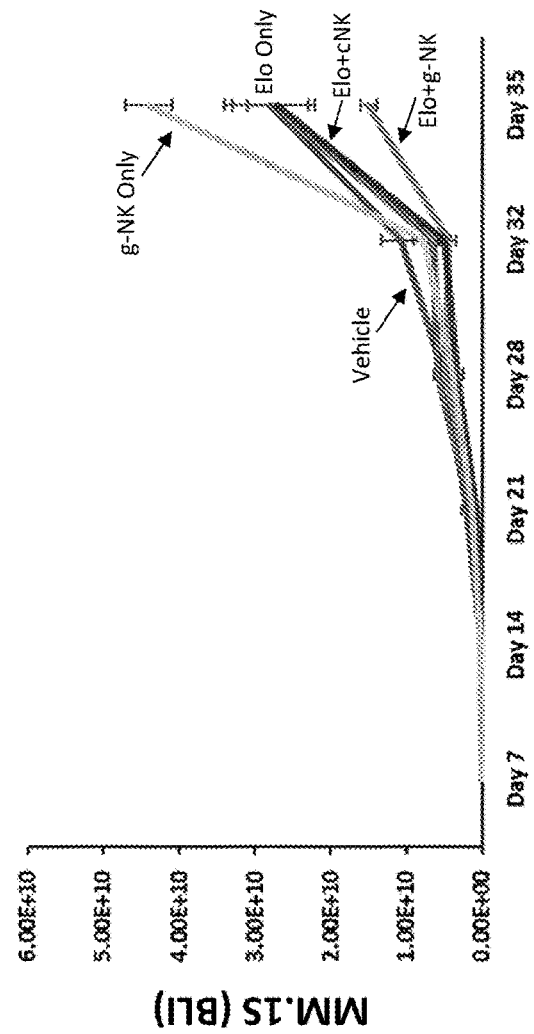
Figure 11A:
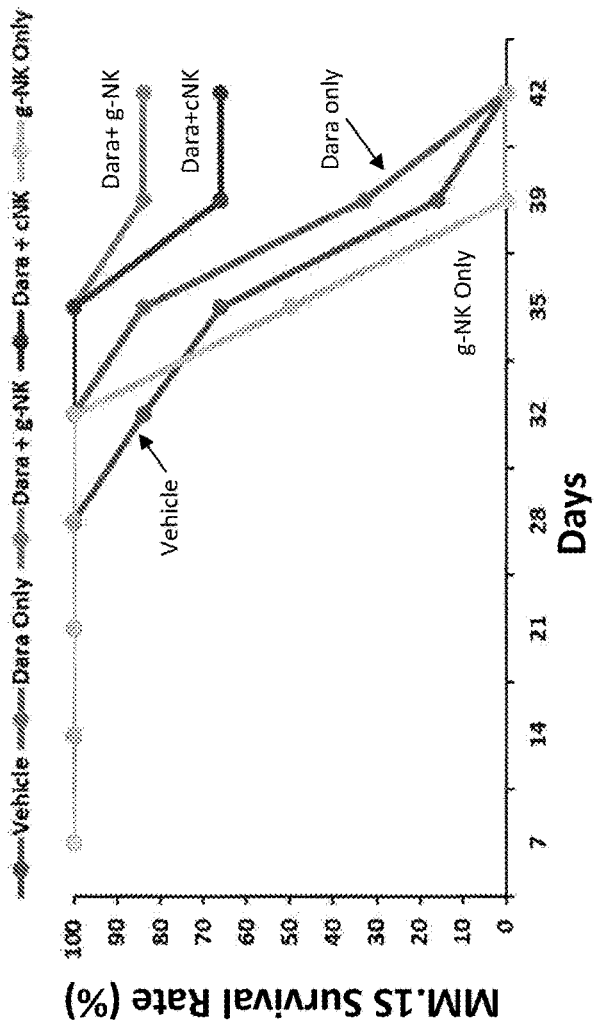
FIGS. 11A and 11B depict the effect of g-NK on survival of MM.1S-inoculated NSG mice treated with daratumumab (Dara) or elotuzumab (Elo).
Figure 11B:
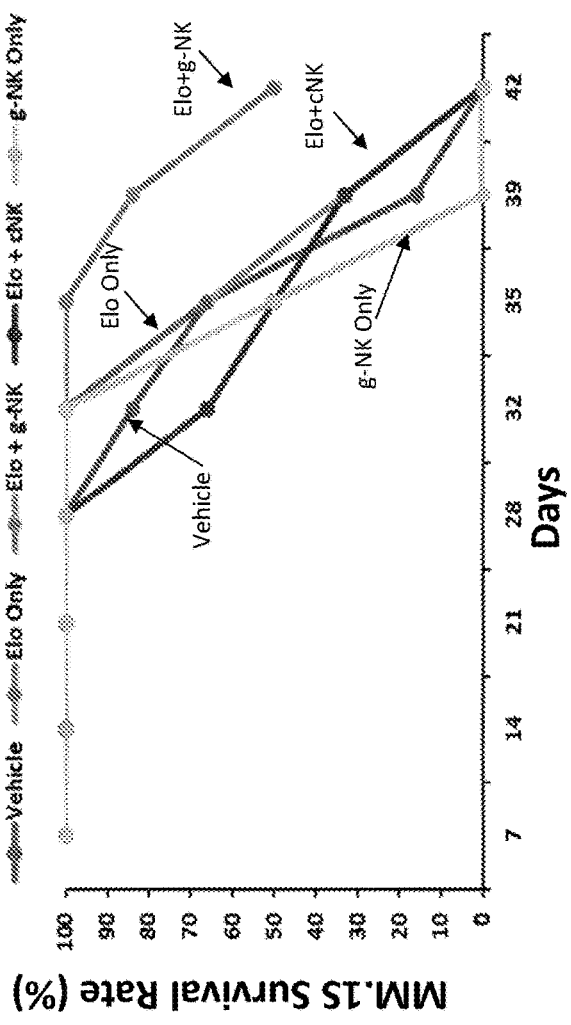

The benefit of adoptively transferred g-NK on tumor burden and survival in NSG mice inoculated with MM.1S and treated with either daratumumab or elotuzumab is described in FIGS. 10 and 11. Mice treated with daratumumab and g-NK had markedly lower tumor burden (BLI) than mice treated with daratumumab alone or daratumumab plus physiological levels of cNK cells (see FIG. 10A). In addition, mice treated with elotuzumab and g-NK had lower tumor burden than mice treated with elotuzumab alone or elotuzumab plus physiological levels of cNK cells (see FIG. 10B). Moreover, the combination of g-NK with daratumumab or elotuzumab resulted in superior survival when compared to mice treated with vehicle, mAb alone, g-NK alone, or mAb plus physiological levels of cNK, as shown in FIG. 11A (daratumumab) and FIG. 11B (elotuzumab)). Overall, this data shows that the anti-myeloma effect of g-NK can be harnessed in vivo when combined with monoclonal antibodies.

Example 10: Assessment of Cell Surface Marker for g-NK Cells

This example demonstrates, in part, the protection of g-NK cells from antibody due to lack of target surface markers.

Approximately $2.0 \times 10^5$ NK-cells and/or MM.1S or Raji cells were aliquoted into flow tubes and stained with 2 μL of 7-AAD viability dye and 2 μL of anti-CD45, 2 μL of anti-CD20, 2 μL of anti-CD38, 2 μL of anti-CD3, 10 μL of anti-SLAMF7, and 2 μL of anti-CD56 antibodies as described in Table E4. After a 10-minute incubation at 4° C., the cells were washed and intracellular staining was performed using an anti-FcεRI antibody (Millipore). After completion of the staining process, the percentages of CD20, CD38, and SLAMF7 expressing g-NK, cNK, and MM.1S or Raji cells were assessed by 8-color flow cytometry (Miltenyi MACS Quant Analyzer 10).

TABLE E4

Flow cytometry panel to determine CD20, CD38, and SLAMF7 expression on NK, MM, and Raji cells.

| Condition | V1 | V2 | B1 | B2 | B3 | B4 | R1 | R2 |
|---|---|---|---|---|---|---|---|---|
| NK Only | CD45 | CD20 | *FcRg | CD38 | 7-AAD | CD3 | SLAMF7 | CD56 |
| NK Only CD20 FMO | CD45 | | *FcRg | CD38 | 7-AAD | CD3 | SLAMF7 | CD56 |
| NK Only CD38 FMO | CD45 | CD20 | *FcRg | | 7-AAD | CD3 | SLAMF7 | CD56 |
| NK Only SLAMF7 FMO | CD45 | CD20 | *FcRg | CD38 | 7-AAD | CD3 | | CD56 |
| NK + MM | CD45 | CD20 | *FcRg | CD38 | 7-AAD | CD3 | SLAMF7 | CD56 |
| NK + MM CD38 FMO | CD45 | CD20 | *FcRg | | 7-AAD | CD3 | SLAMF7 | CD56 |
| NK + MM SLAMF7 FMO | CD45 | CD20 | *FcRg | CD38 | 7-AAD | CD3 | | CD56 |
| MM Only | CD45 | CD20 | | CD38 | 7-AAD | | SLAMF7 | |
| MM Only CD38 FMO | CD45 | CD20 | | | 7-AAD | | SLAMF7 | |
| MM Only SLAMF7 FMO | CD45 | CD20 | | CD38 | 7-AAD | | | |
| NK + Raji | CD45 | CD20 | *FcRg | CD38 | 7-AAD | CD3 | SLAMF7 | CD56 |
| NK + Raji CD20 FMO | CD45 | | *FcRg | CD38 | 7-AAD | CD3 | SLAMF7 | CD56 |
| Raji Only | CD45 | CD20 | | | 7-AAD | | | |
| Raji Only CD20 FMO | CD45 | | | | 7-AAD | | | |

*FcRg is an intracellular epitope

Figure 12C:
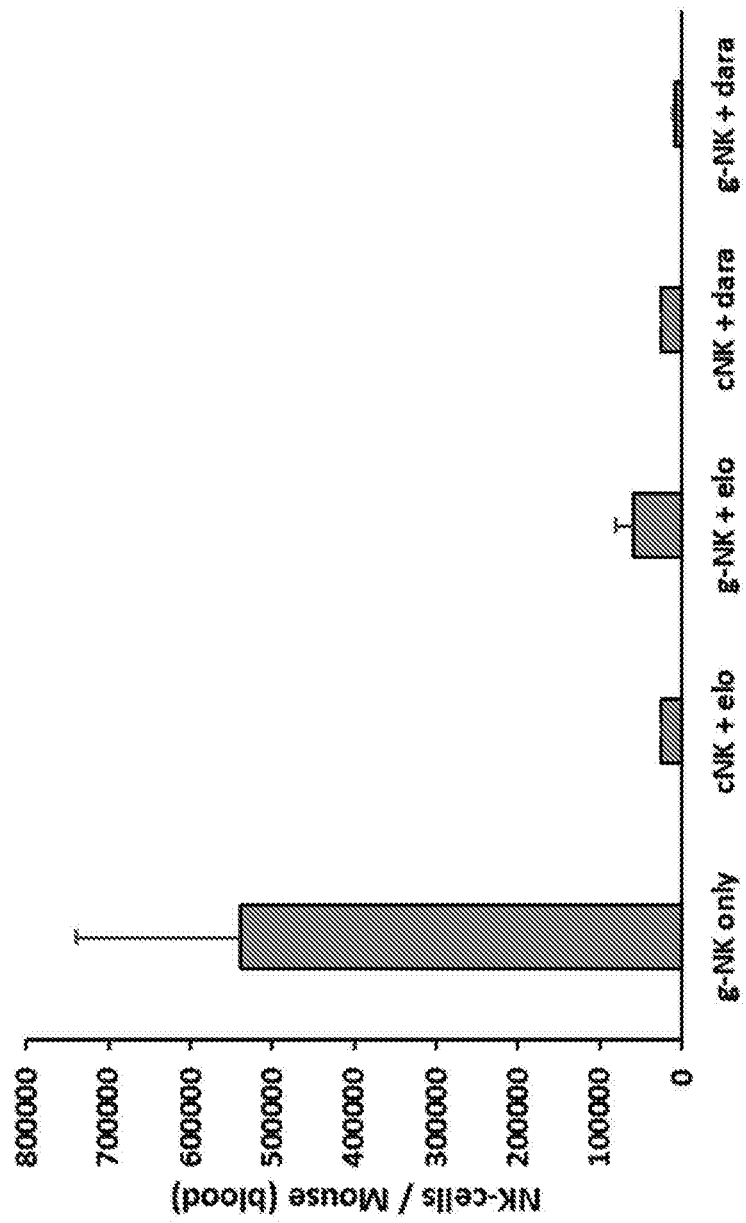

The superior persistence of g-NK in NSG mice inoculated with MM.1S and treated with either daratumumab or elotozumab is described in FIG. 12A-C. g-NK persisted at higher levels in the spleen and bone marrow of daratumumab-treated mice than cNK (see FIGS. 12A and 12B), while there was no difference between g-NK and cNK persistence in blood (see FIG. 12C). Furthermore, the number of g-NK in the bone marrow and spleen of daratumumab-treated mice was higher than for all other groups (see FIGS. 12A and 12B). g-NK persist at higher levels in the spleen and blood of elotuzumab-treated mice than cNK (FIGS. 12A and 12C), while there was no difference between g-NK and cNK persistence in bone marrow (see FIG. 12B). The number of g-NK in the blood of mice treated with g-NK only (no daratumumab or elotuzumab) was markedly higher than for all other groups (see FIG. 12C).

Figure 13A:
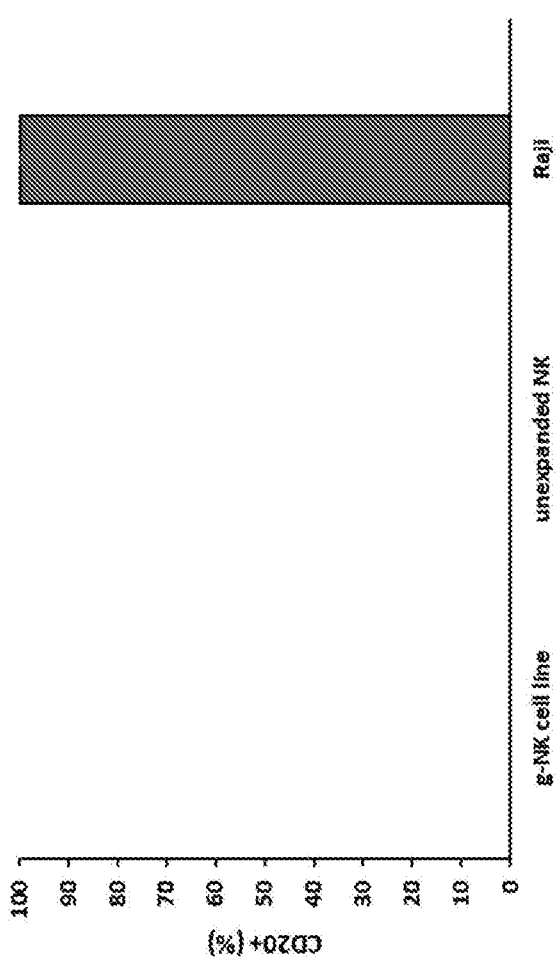
FIGS. 13A-13D depict the expression of CD20 (the target for rituximab), CD38 (the target for daratumumab), and SLAMF7 (the target for elotuzumab) on g-NK and cNK.
Figure 13B:
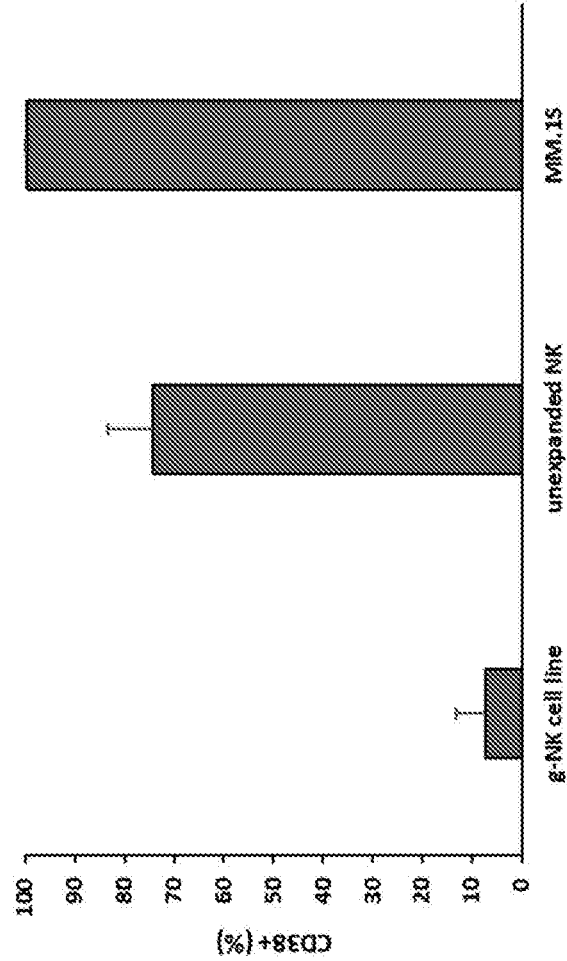
Figure 13C:
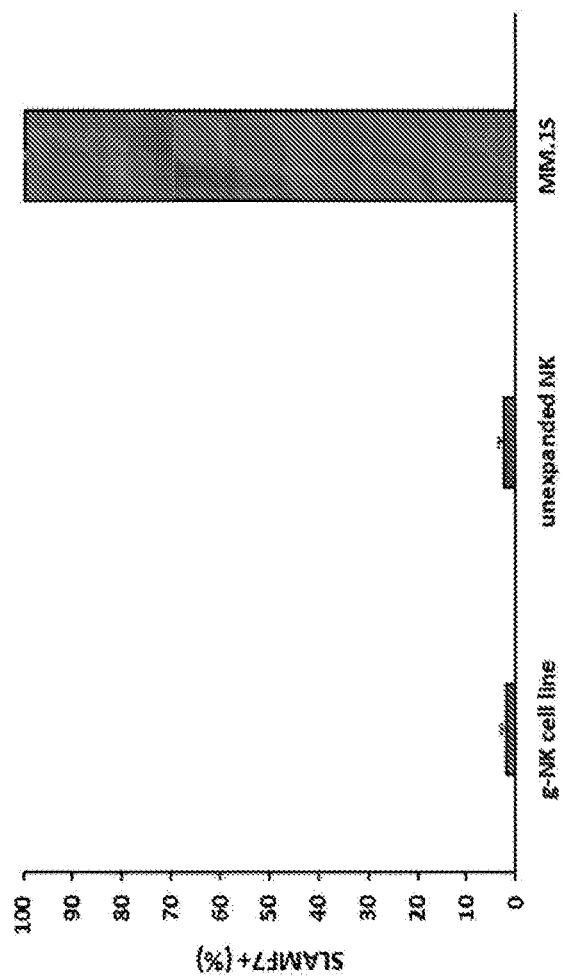
Figure 13D:
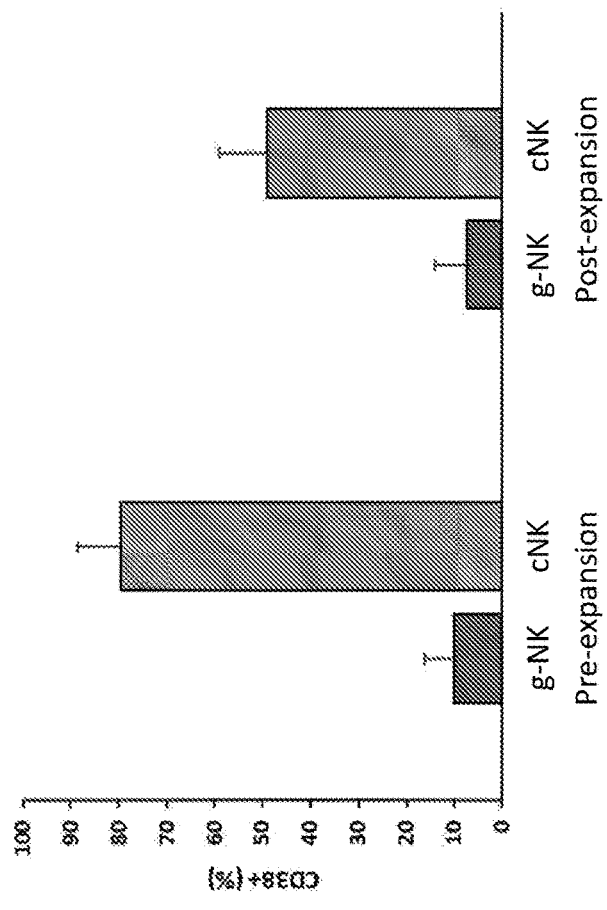

Expression of CD20, CD38, and SLAMF7 on g-NK, cNK, and MM.1S cells is presented in FIG. 13A-13D. Both g-NK and cNK lacked expression of CD20, which was highly expressed on Raji lymphoma cells (FIG. 13A). The expression of CD38 by g-NK was far less than for cNK and MM.1S cells (see FIG. 13B). Expression of SLAMF7 was not different between g-NK and cNK, but both g-NK and cNK exhibited far lower expression of SLAMF7 than MM.1S cells (see FIG. 13C). Reduced expression of CD38 was also seen on expanded g-NK when compared to expanded cNK (see FIG. 13D). The lack of CD20, CD38, or SLAMF7 expression by g-NK afforded protection from mAb-induced fratricide by rituximab (anti-CD20), daratumumab (anti-CD38), or elotuzumab (anti-SLAMF7). Overall, this data further illustrates how g-NK have a persistence advantage when compared to cNK, especially when in the presence of therapeutic antibodies such as daratumamab.

The observations that CD38 expression is decreased or lower on g-NK cells compared to conventional NK cells supports a strategy in which CD38 can be used as a marker for enrichment of g-NK cells. The inverse association of CD38 and the g-NK cell phenotype is consistent with an alternative strategy to CD57 enrichment in the expansion method described in Example 2. These findings support a method for expansion of g-NK cells in which NK cells are enriched from PBMCs by immunoaffinity-based separation by depletion of CD3+ cells to remove T cells (CD3 depletion), followed by CD56 selection to enrich for CD56+ NK cells, followed by negative selection against CD38 to remove or deplete CD38+ cells, i.e. CD3−CD56+CD38−. Following isolation and enrichment of this NK cell subset, the CD3−CD56+CD38−NK cell subset can be frozen or used fresh and then expanded in accord with the method described in Example 2 or FIG. 2, e.g. by culture with irradiated 221.AEH target cells (e.g. 2.5:1 221.AEH to NK cells), and optionally irradiated PBMC feeder cells (e.g. 5:1 PBMC to NK cells) in the presence of recombinant IL-2 (e.g. 100 IU/mL) for about 14 days. If irradiated PBMC feeder cells are used in the expansion, at least a portion of the expansion includes incubation with anti-CD3 monoclonal antibody (OKT3) to activate cells as described in Example 2.

Example 11: Assessment of Antibody Dependent Cell Mediated Cytotoxicity (ADCC) on Ovarian Cancer Cells by Expanded NK Cells in Combination with Trastuzumab or Cetuximab Functional activity of NK cells expanded by the method described in Example 2, compared to the alternative method, was assessed by evaluating antibody dependent cell mediated cytotoxicity (ADCC) in combination with trastuzumab or cetuximab.

Pre-expansion (freshly isolated) ADCC: Donors were CMV-seropositive (n=14) and CMV-seronegative (n=2). All donors were pre-screened for the percentage of g-NK cells and categorized as either 'g-NK' donors (n=10 CMV+) or 'conventional' donors (n=4 CMV+, n=2 CMV−) based on the proportion of g-NK cells. The proportion of g-NK in the 'g-NK' donors was 30.0±2.1%, while the proportion of g-NK was only 1.6±0.4% in the 'conventional' donors. CD57+ NK-cells were magnetically sorted from the 'g-NK' donors and bulk NK-cells (CD3−/CD56+) were magnetically sorted from the 'conventional' donors. The actual g-NK percentages of the magnetically sorted fractions from the 'g-NK' and 'conventional' donors were 84.3±2.4% and 1.6±0.4%, respectively. The g-NK percentages within each fraction were determined by intracellular flow cytometry using an FcRγ antibody purchased from Millipore (Burlington, MA, USA).

For the ADCC cytotoxicity assays, frozen PBMCs were thawed and incubated in 10% FBS-supplemented RPMI-1640 media for 1 hour at 37° C. Magnetic bead separations were then performed to isolate CD57+ NK-cells and bulk NK-cells from 'g-NK' and 'conventional' donors, respectively. ADCC assays were performed using the ovarian cancer cell line SKOV3 (ATCC) as targets. NK-cells were co-cultured with CD71-labeled SKOV3 target cells ($1.0 \times 10^4$ cells) at 0.5:1, 1:1, 2.5:1, and 5:1 NK-cell: target cell ratios in a final volume of 2.2 mL of target cell-specific media, using methods as described in Bigley et al. 2014. The media used for the ADCC assay was 10% McCoy's 5A media with 1 µg/mL trastuzumab (anti-Her2). In each case, basal cytotoxicity was also measured without the treating antibody present. Target cell only tubes were used to control for spontaneous cell death (less than 10% for all assays). After a 4 h incubation at 37° C., the cells were washed and stained with anti-CD3 and CD56 antibodies to quantify the number of NK-cells in the tube. After a final wash, propidium iodide (PI) was added and the number of NK-cells, live target cells, and dead target cells were resolved using 4-color flow cytometry (Bigley et al., 2018).

Figure 14A:
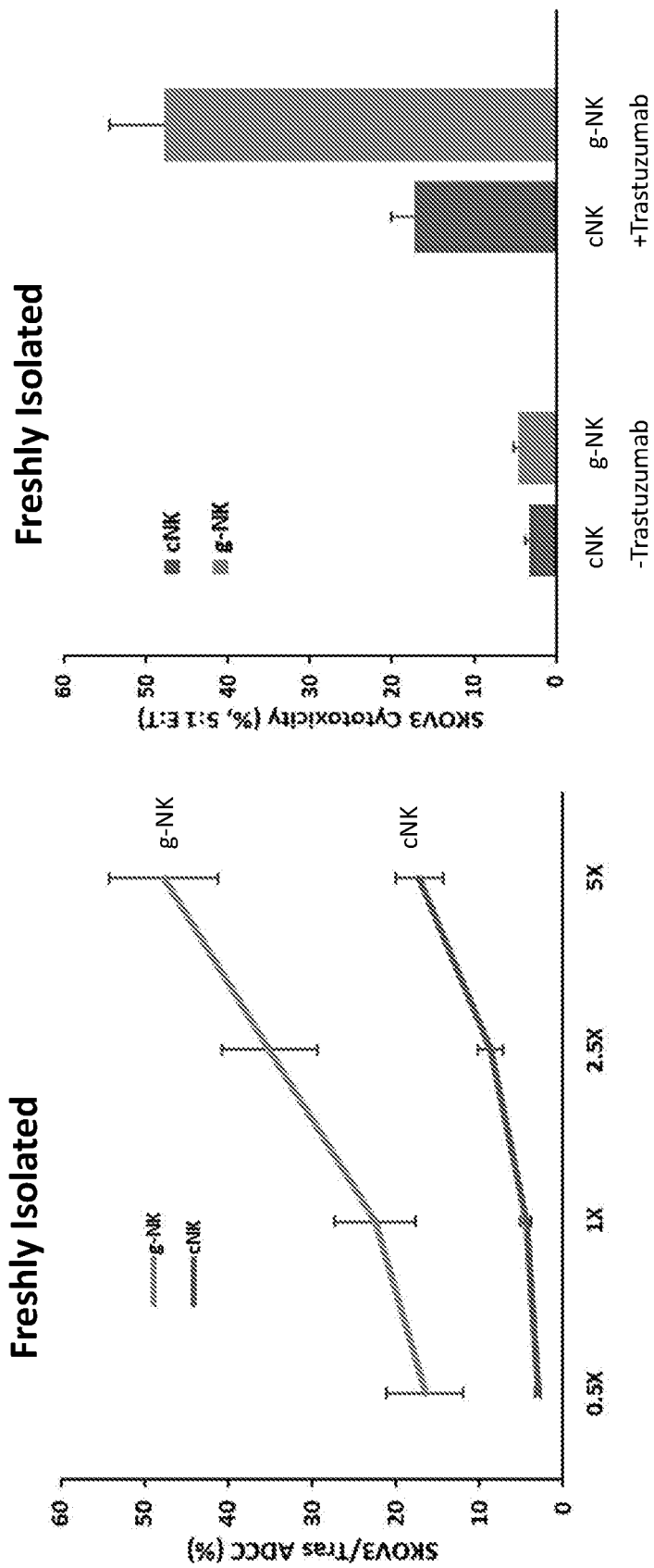
FIGS. 14A-14C depict ADCC activity of g-NK cells compared to conventional NK cells (cNK).
Figure 14B:
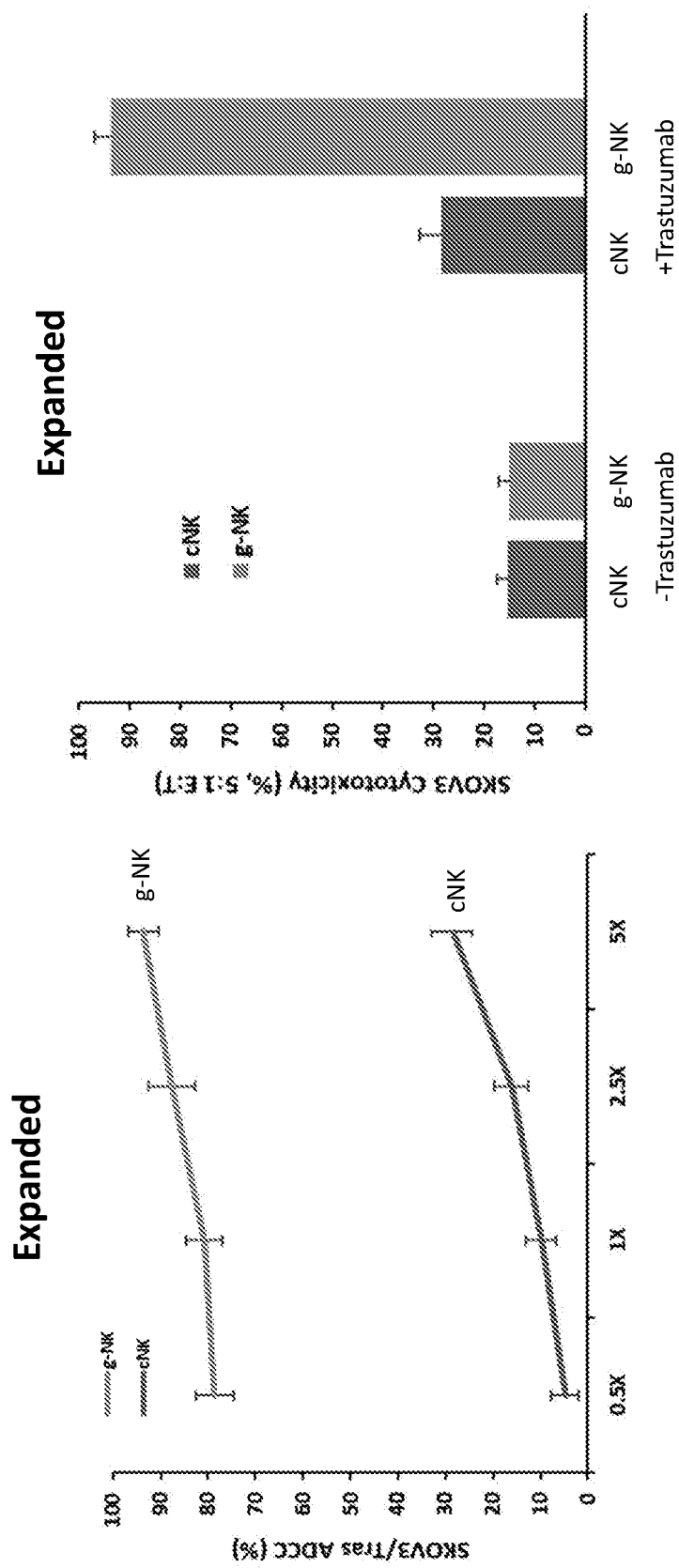
Figure 14C:
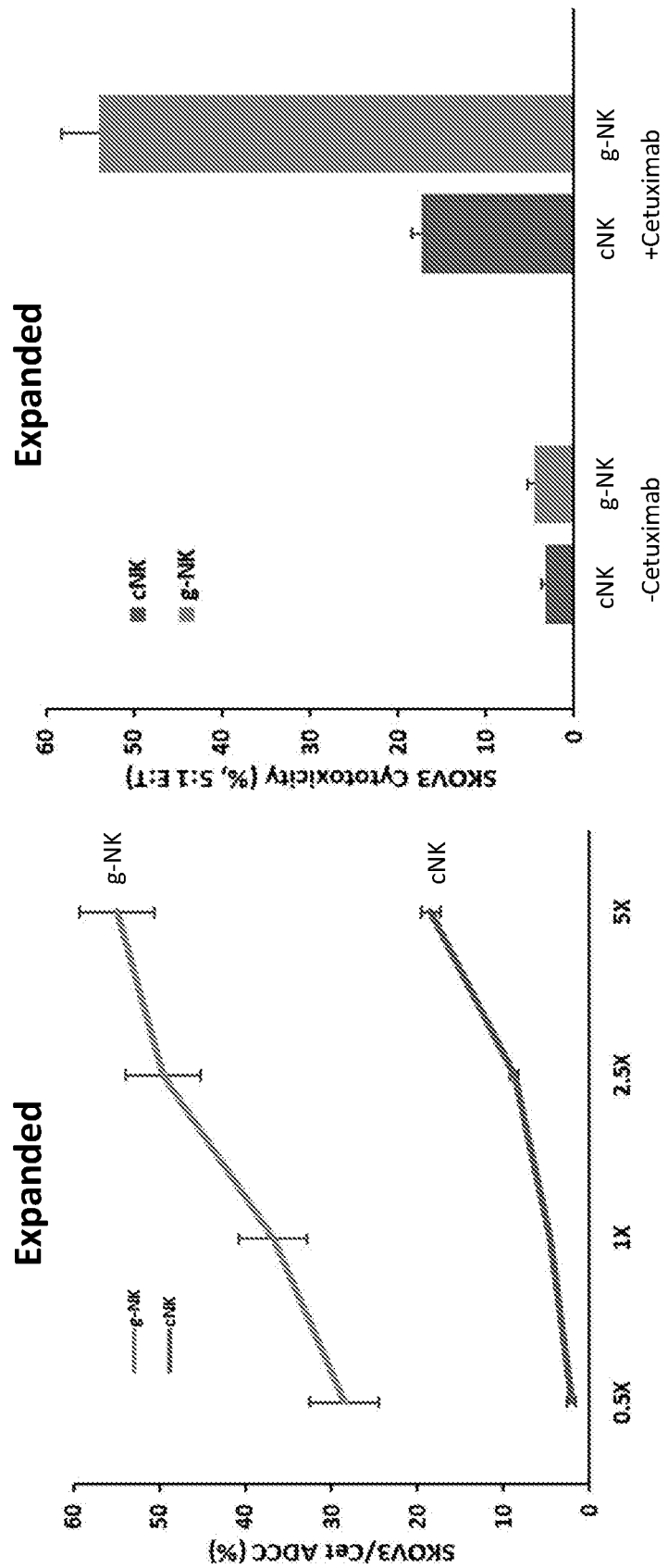

Post-expansion (expanded) ADCC: 5 donors were pre-screened for the percentage of g-NK cells and categorized as either 'g-NK' donors (n=3) or 'conventional' donors (n=2) based on the proportion of g-NK cells. The proportion of g-NK in the 'g-NK' donors was 30.3±2.0%, while the proportion of g-NK was only 1.6±0.4% in the 'conventional' donors. CD57+ NK-cells were magnetically sorted from the 'g-NK' donors and bulk NK-cells (CD3−/CD56+) were magnetically sorted from the 'conventional' donors. The actual g-NK percentages of the magnetically sorted fractions from the 'g-NK' and 'conventional' donors were 84.0±2.5% and 1.6±0.4%, respectively. The g-NK and cNK fractions were then expanded as described in Example 2 and cryopreserved for later ADCC assays as described above.

g-NK have greater ADCC against SKOV3 ovarian cancer cells than cNK when combined with trastuzumab or cetuximab. Specifically, freshly isolated g-NK had markedly higher cytotoxicity against SKOV3 cells than cNK at all 4 NK-cell doses when trastuzumab was present (see FIG. 14A). Similarly, expanded g-NK had far greater anti-SKOV3 ADCC than expanded cNK when combined with trastuzumab or cetuximab (see FIGS. 14B and 14C). There was no difference between the cytotoxicity of g-NK and cNK (unexpanded or expanded) against SKOV3 cells when antibody was not present (see FIGS. 14A and 14B). Overall, this data shows that g-NK have strong antibody-dependent cytotoxic activity against solid tumor malignancies like ovarian cancer.

Example 12: Assessment of Anti-Tumor Activity and Persistence of Expanded NK Cells in Combination with an Anti-HER2 Antibody Functional activity of NK cells expanded by the method described in Example 2 was assessed by evaluating inhibition on tumor in vivo when injected in combination with an anti-HER2 antibody (trastuzumab).

$5 \times 10^6$ SKOV3 human ovarian cancer cell lines were injected intravenously into female NOD scid gamma (NSG) mice and allowed to grow for 30 days. The monoclonal antibody trastuzumab was administered I.P. to mice, either alone or in combination with expanded g-NK or cNK cells, that were administered I.V., for 3-6 doses over 72 days (see Table E5). Caliper measurements were used to monitor tumor burden on a weekly basis. At study completion, bone marrow and spleen samples were harvested and viably frozen from mice in g-NK and cNK arms for later flow cytometry analysis. The g-NK were expanded from a single CMV-seropositive donor (percentage of g-NK was 61% pre-expansion and 90% post-expansion), while the cNK were expanded from a single CMV-seronegative donor (percentage of g-NK was 0% pre-expansion and post-expansion). The percentage of g-NK was confirmed using intracellular flow cytometry.

TABLE E5

SKOV3 Efficacy Study Design

| Group Number | Arm | Number of Mice | Days of Antibody Administration | Days of NK cell administration |
|---|---|---|---|---|
| 1 | Vehicle control | 6 | N/A | N/A |
| 2 | Trastuzumab 10 mg/kg I.P. | 6 | 1, 7, 13, 19 | N/A |
| 3 | 2e7 Fresh g-NK I.V. + Trastuzumab 10 mg/kg I.P. | 6 | 1, 7, 13, 19 | 1, 7, 13, 19, 22, 25, 28, 31, 34, 37, 43, 46, 52, 55, 61, 64, 70 |
| 4 | 2e7 Fresh cNK I.V. + Trastuzumab 10 mg/kg I.P. | 6 | 1, 7, 13, 19 | 1, 7, 13, 19, 22, 25, 28, 31, 34, 37, 43, 46, 52, 55, 61, 64, 70 |

Figure 15A:
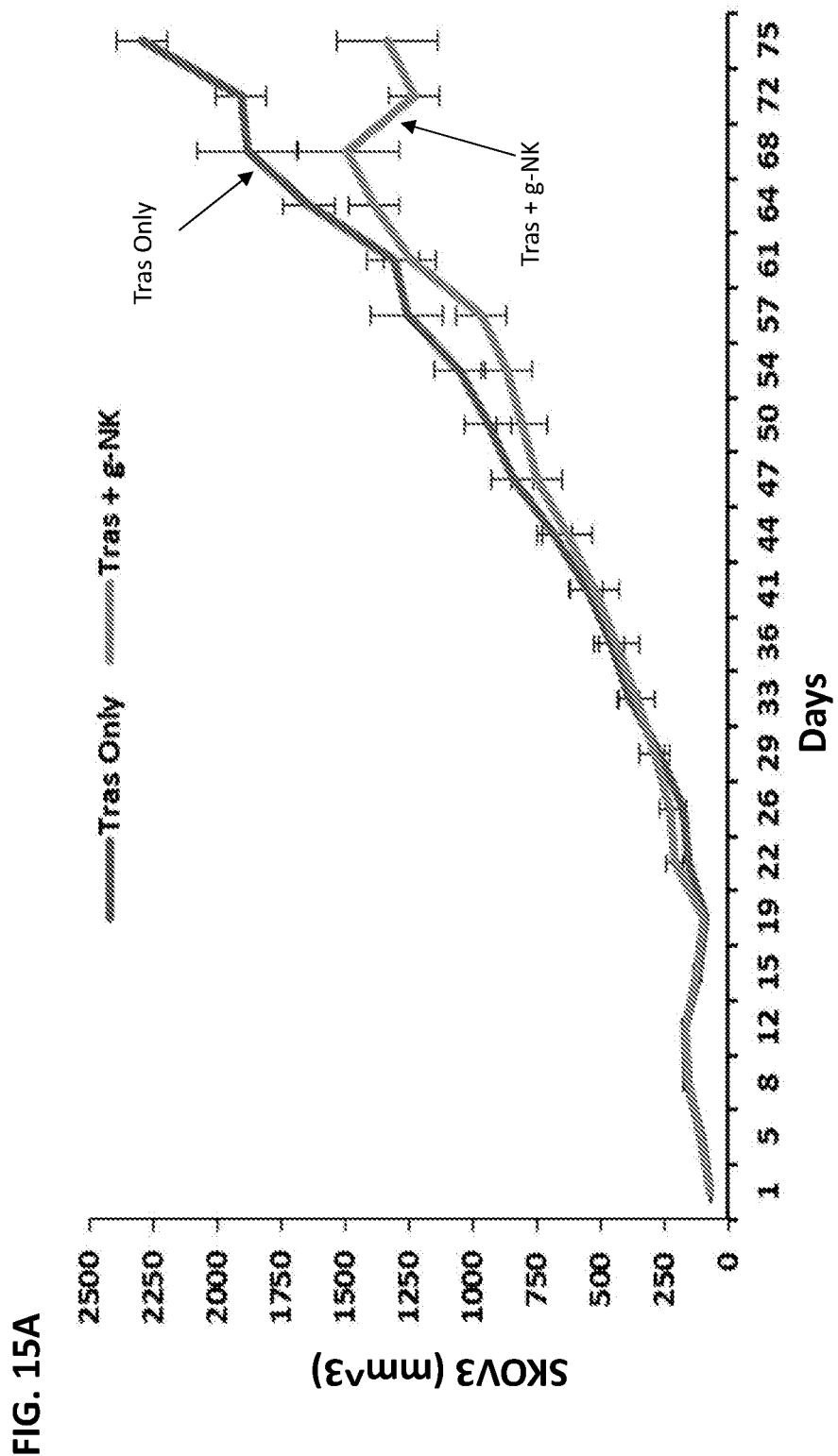
FIGS. 15A-15C depict the effect of g-NK on in vivo efficacy of trastuzumab (Tras) in a xenograft model of ovarian cancer.
Figure 15B:
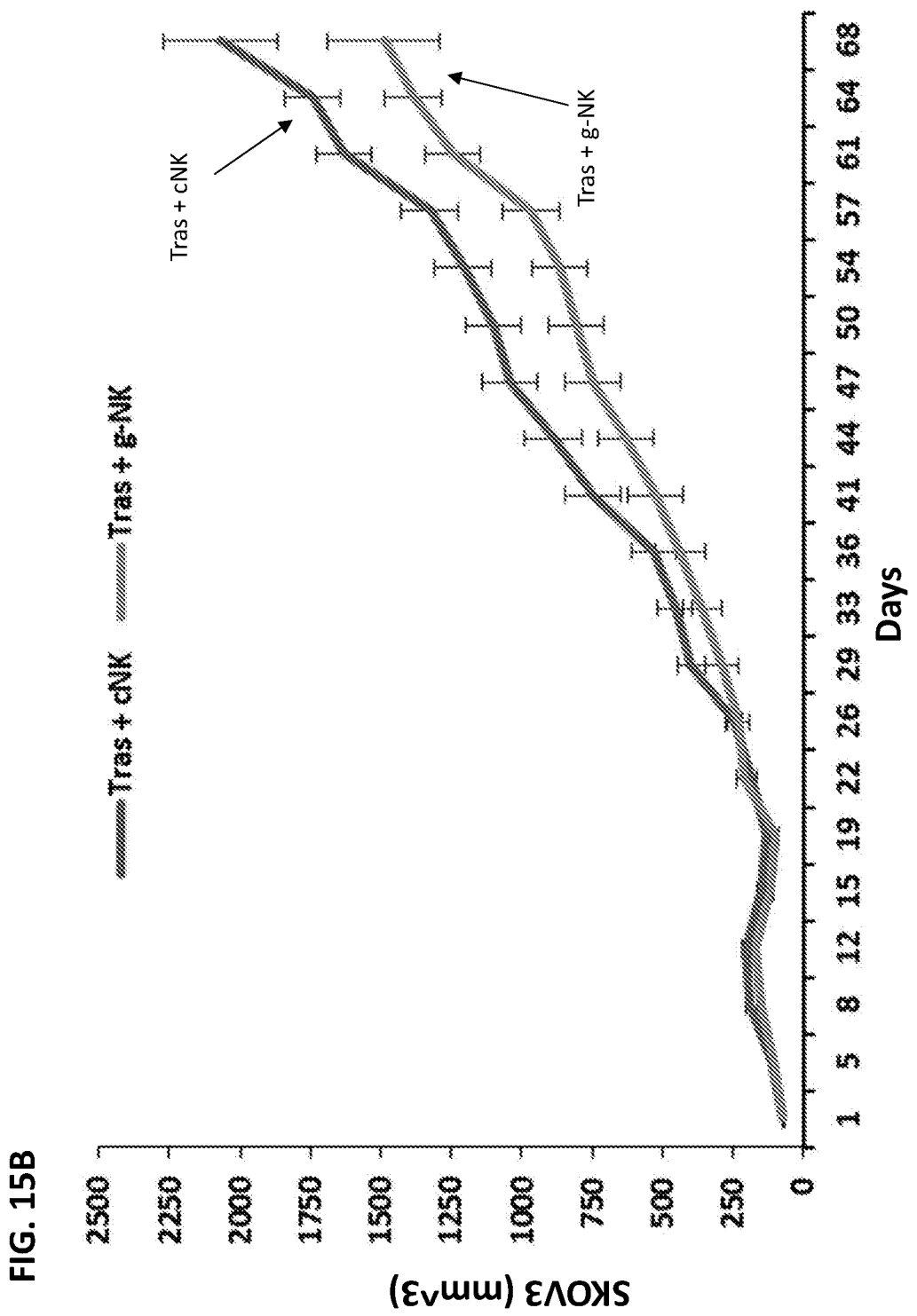
Figure 15C:
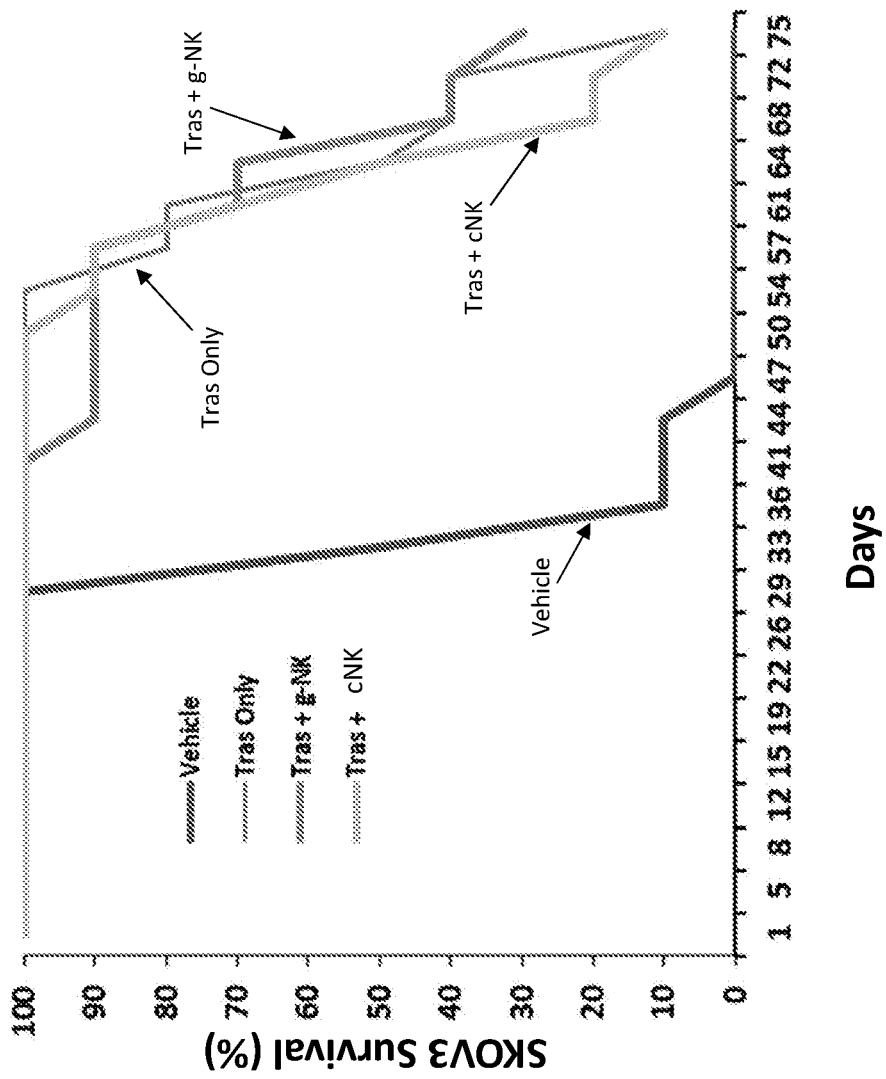

The benefit of adoptively transferred g-NK on tumor burden and survival in NSG mice inoculated with SKOV3 and treated with trastuzumab is described in FIG. 15A-B. Mice treated with trastuzumab and g-NK had smaller tumor size than mice treated with trastuzumab alone or trastuzumab plus equal numbers of cNK cells (see FIG. 15A). In addition, the combination of g-NK with trastuzumab resulted in a trend towards increased survival when compared to mice treated with vehicle, trastuzumab alone, or trastuzumab plus cNK (see FIG. 15B). Overall, this data shows that the anti-tumor effect of g-NK can be harnessed in vivo against solid malignancies when combined with monoclonal antibodies.

Figure 16A:
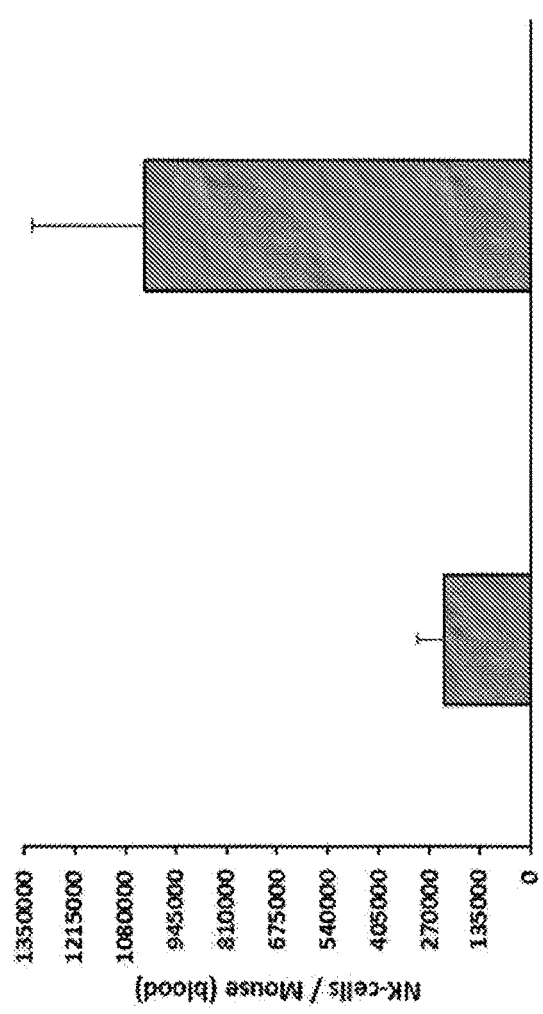
FIGS. 16A-16C depict the persistence of g-NK and cNK when combined with trastuzumab in a xenograft model of ovarian cancer.
Figure 16B:
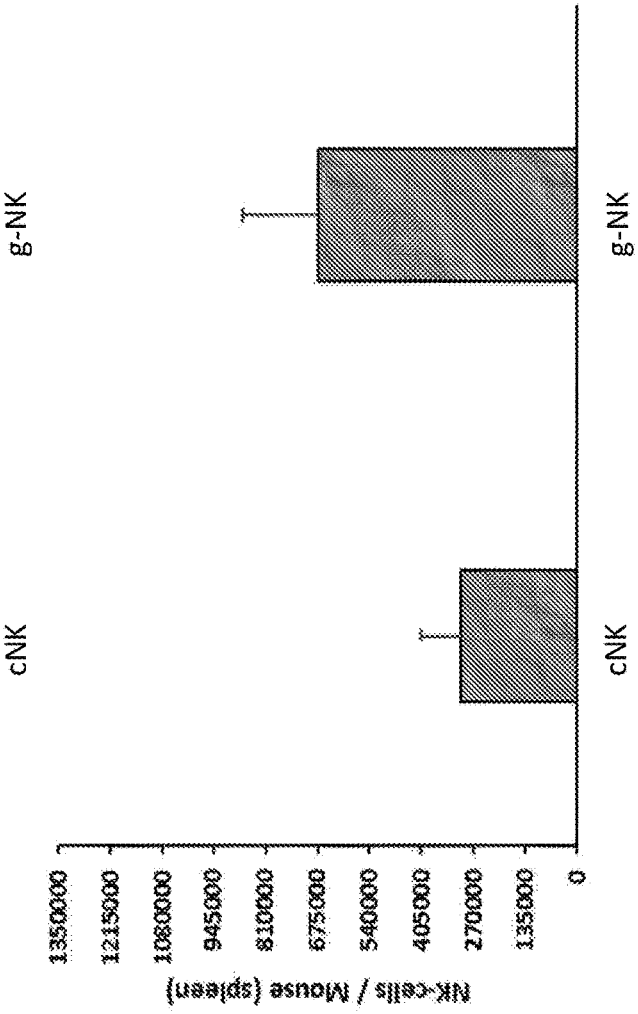
Figure 16C:
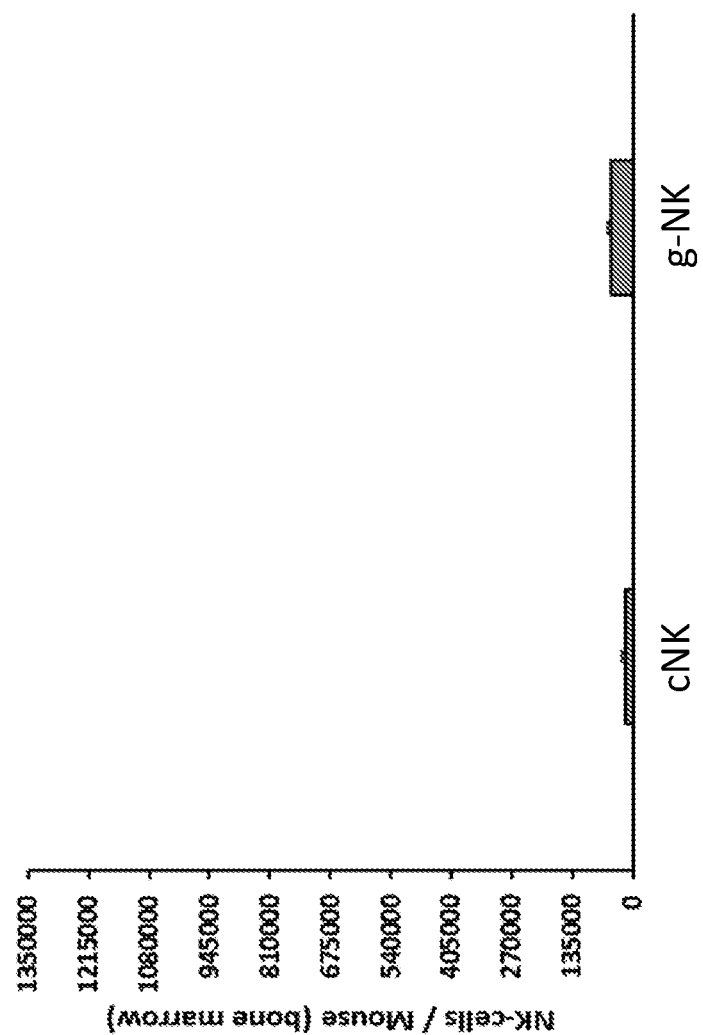

The blood samples, bone marrow and spleen samples showed the superior persistence of g-NK in NSG mice inoculated with SKOV3 and treated with trastuzumab. g-NK persisted at higher levels in the blood (see FIG. 16A), spleen (see FIG. 16B), and bone marrow (see FIG. 16C) of trastuzumab-treated mice than cNK.

Example 13: Assessment of Antibody Dependent Cell Mediated Cytotoxicity (ADCC) on Multiple Myeloma Cells by Expanded NK Cells in Combination with Daratumamab Functional activity of NK cells expanded by the method described in Example 2, compared to the alternative method, was assessed by evaluating antibody dependent cell mediated cytotoxicity (ADCC) in combination with daratumumab or Elotuzamab.

Donors were CMV-seropositive (n=5) and magnetically sorted NK-cells (pre-expansion g-NK percentage=34.6±12.6%) were expanded using the method described in Example 2. Expanded NK-cells were then magnetically sorted using CD57 microbeads into CD57+'g-NK' and CD57-'cNK' fractions and cryopreserved for later ADCC assays. The actual g-NK percentages of the CD57+ and CD57-fractions were 83.1±1.6% and 1.8±0.5%, respectively. The g-NK percentages within the CD57+ and CD57-fractions were determined by intracellular flow cytometry using an FcRγ antibody purchased from Millipore (Burlington, MA, USA).

Figure 17A:
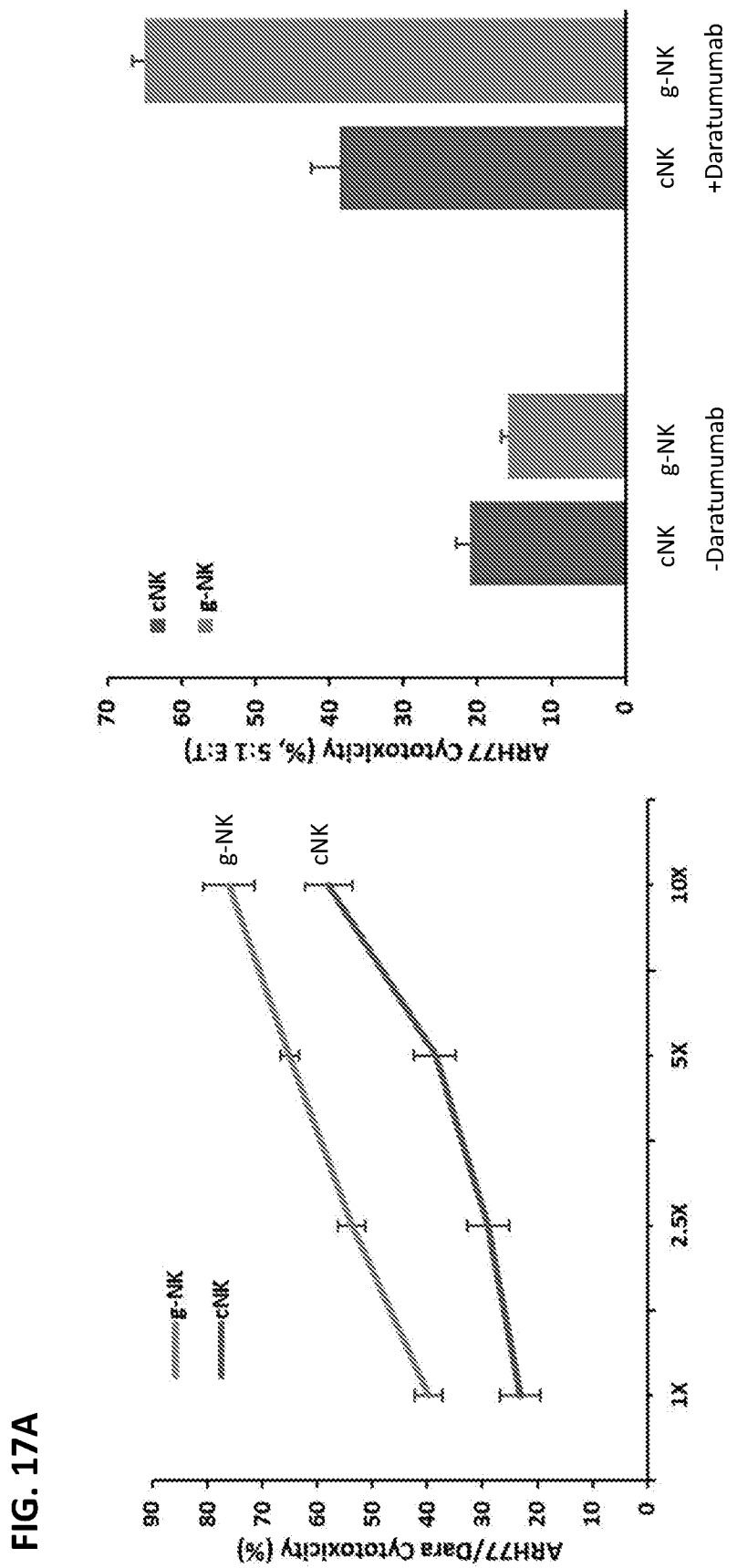
FIGS. 17A and 17B depict ADCC activity of g-NK cells compared to conventional NK cells (cNK).
Figure 17B:
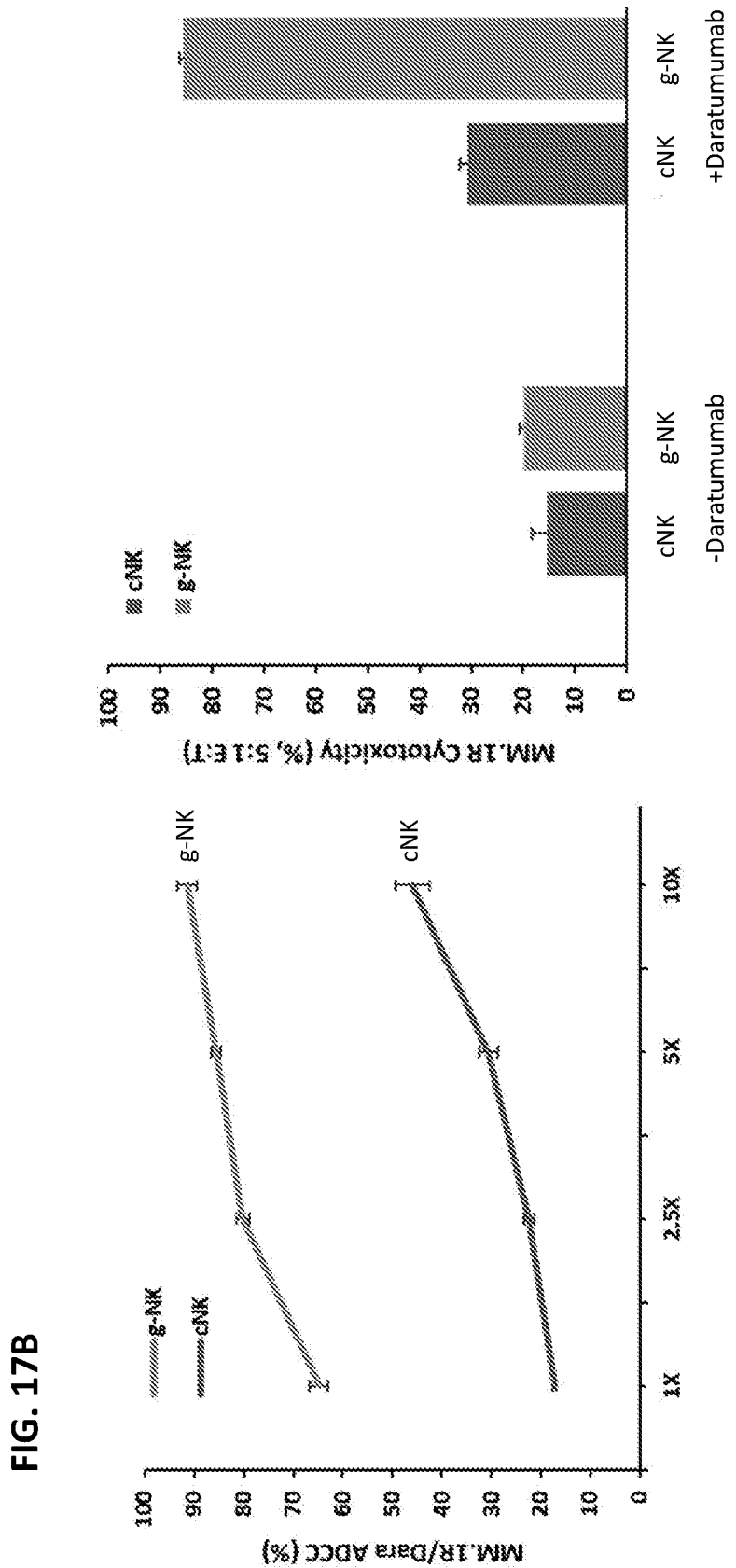

For the ADCC cytotoxicity assays, frozen NK-cells from prior expansions were thawed and incubated in 10% FBS-supplemented RPMI-1640 media for 1 hour at 37° C. ADCC assays were performed using the multiple myeloma cell lines ARH-77 and MM.1R as targets (each from ATCC). Expanded NK-cells were co-cultured with CD71-labeled ARH-77 and MM.1R target cells ($1.0 \times 10^4$ cells) at 1:1, 2.5:1, 5:1, and 10:1 NK-cell: target cell ratios in a final volume of 2.2 mL of target cell-specific media, using the method as described in Bigley et al. 2014. The media used for the assays was 10% FBS supplemented RPMI-1640 media with 1 µg/mL daratumumab (anti-CD38). In each case, basal cytotoxicity was also measured without the treating antibody present. Target cell only tubes were used to control for spontaneous cell death (less than 10% for all assays). After a 4 h incubation at 37° C., the cells were washed and stained with anti-CD3 and CD56 antibodies to quantify the number of NK-cells in the tube. After a final wash, propidium iodide (PI) was added and the number of NK-cells, live target cells, and dead target cells were resolved using 4-color flow cytometry (Bigley et al., 2018).

g-NK have greater ADCC against multiple myeloma cell lines when combined with daratumumab. Specifically, expanded g-NK had markedly higher cytotoxicity against ARH-77 cells than expanded cNK at all 4 NK-cell doses when daratumumab was present (see FIG. 17A). Expanded g-NK also had higher cytotoxicity against MM.1R cells than expanded cNK at all 4 NK-cell doses when daratumumab was present (see FIG. 17B). Overall, this data shows that g-NK have strong antibody-dependent cytotoxic activity against multiple myeloma cell lines beyond MM.1S.

Example 14: Assessment of Antibody Dependent Cell Mediated Cytotoxicity (ADCC) on Multiple Myeloma Cells by Expanded g-NK Cells in Combination with Cetuximab Functional activity of NK cells expanded by the method described in Example 2, compared to the alternative method, was assessed by evaluating antibody dependent cell mediated cytotoxicity (ADCC) in combination with Centuximab.

Pre-expansion (freshly isolated) ADCC: Donors were CMV-seropositive (n=14) and CMV-seronegative (n=2). All donors were pre-screened for the percentage of g-NK cells and categorized as either 'g-NK' donors (n=10 CMV+) or 'conventional' donors (n=4 CMV+, n=2 CMV-) based on the proportion of g-NK cells. The proportion of g-NK in the 'g-NK' donors was 30.0±2.1%, while the proportion of g-NK was only 1.6±0.4% in the 'conventional' donors. CD57+ NK-cells were magnetically sorted from the 'g-NK' donors and bulk NK-cells (CD3-/CD56+) were magnetically sorted from the 'conventional' donors. The actual g-NK percentages of the magnetically sorted fractions from the 'g-NK' and 'conventional' donors were 82.2±1.6% and 2.4±0.7%, respectively. The g-NK percentages within each fraction were determined by intracellular flow cytometry using an FcRγ antibody purchased from Millipore (Burlington, MA, USA).

For the ADCC cytotoxicity assays, frozen PBMCs were thawed and incubated in 10% FBS-supplemented RPMI-1640 media for 1 hour at 37° C. Magnetic bead separations were then performed to isolate CD57+ NK-cells and bulk NK-cells from 'g-NK' and 'conventional' donors, respectively. ADCC assays were performed using the colorectal cancer cell line SW-480 as targets. NK-cells were co-cultured with CD71-labeled SW-480 (ATCC) target cells ($1.0 \times 10^4$ cells) at 0.5:1, 1:1, 2.5:1, and 5:1 NK-cell: target cell ratios in a final volume of 2.2 mL of target cell-specific media, using methods as described in Bigley et al. 2014. The media used for the SW-480 assay was 10% FBS-supplemented Leibovitz's L-15 Medium with 5 µg/mL cetuximab (anti-EGFR). In each case, basal cytotoxicity was also measured without the treating antibody present. Target cell only tubes were used to control for spontaneous cell death (less than 10% for all assays). After a 4 h incubation at 37°

C., the cells were washed and stained with anti-CD3 and anti-CD56 antibodies to quantify the number of NK-cells in the tube. After a final wash, propidium iodide (PI) was added and the number of NK-cells, live target cells, and dead target cells were resolved using 4-color flow cytometry (Bigley et al., 2018).

Figure 18B:
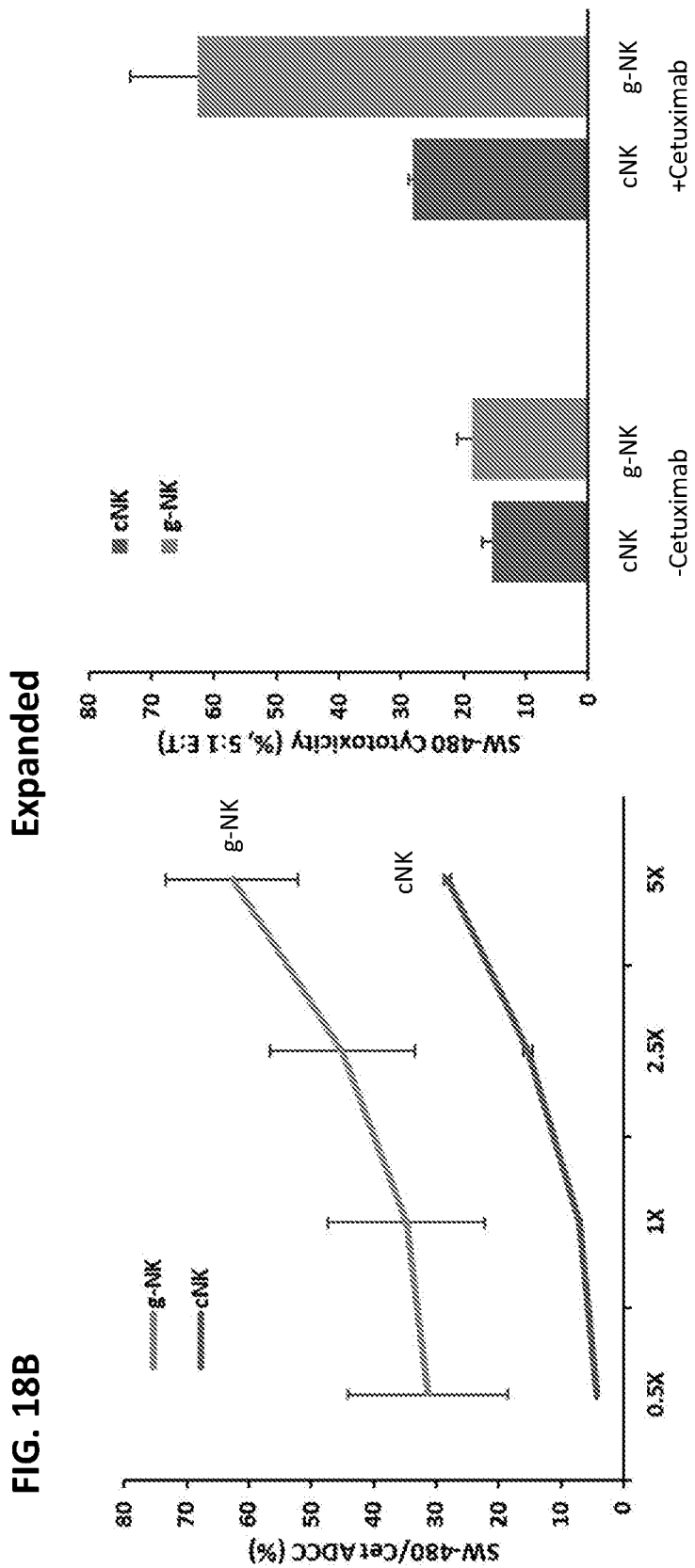

Post-expansion (expanded) ADCC: 5 donors were pre-screened for the percentage of g-NK cells and categorized as either 'g-NK' donors (n=3) or 'conventional' donors (n=2) based on the proportion of g-NK cells. The proportion of g-NK in the 'g-NK' donors was 30.3±2.0%, while the proportion of g-NK was only 1.6±0.4% in the 'conventional' donors. CD57+ NK-cells were magnetically sorted from the 'g-NK' donors and bulk NK-cells (CD3−/CD56+) were magnetically sorted from the 'conventional' donors. The actual g-NK percentages of the magnetically sorted fractions from the 'g-NK' and 'conventional' donors were 84.0±2.5% and 1.6±0.4%, respectively. The g-NK and cNK fractions were then expanded as described in Example 2 and cryopreserved for later ADCC assays as described above.

g-NK have greater ADCC against SW-480 colorectal cancer cells than cNK when combined with cetuximab (see FIGS. 18A and 18B). Freshly isolated g-NK had markedly higher cytotoxicity against SW-480 cells than cNK at all 4 NK-cell doses when cetuximab was present (see FIG. 18A). Similarly, expanded g-NK had far greater anti-SW480 ADCC than expanded cNK when combined with cetuximab (see FIG. 18B). There was no difference between the cytotoxicity of g-NK and cNK (unexpanded or expanded) against SW-480 cells when antibody was not present (see FIGS. 18A and 18B). Overall, this data shows that g-NK have strong antibody-dependent cytotoxic activity against solid tumor malignancies like colorectal cancer.

Example 15: Assessment of CD16 158V Polymorphism on the Efficacy of g-NK Mediated ADCC 158V is a genetic polymorphism of CD16 where the amino acid valine (V) is present at the 158th amino acid position of the protein instead of the more common phenylalanine (F) (Koene et al., 1997). This leads to greater expression and antibody affinity of CD16, which results in enhanced ADCC by CD16 158V+ NK-cells (Hatjiharissi et al., 2007). It has been observed that NK cells from 158 V/V and 158 V/F donors kill ARH-77 myeloma and Daudi lymphoma cells via ADCC far better than that from 158 F/F donors with 158 V/V donors performing the best (Hatjiharissi et al., 2007). This example, at least in part, demonstrates the correlation of ADCC efficacy for g-NK carrying the 158V polymorphism.

40 CMV-seropositive donors were screened to determine the 12 donors with the highest proportion of g-NK. The g-NK of these donors were enriched through magnetic bead separation (CD3−/CD57+) and were tested for ADCC against the following tumor/antibody combinations: 1) SW-480/cetuximab; 2) SKOV3/trastuzumab; 3) SKOV3/cetuximab; 4) MM.1S/daratumumab; and 5) MM.1S/elotuzumab. The ADCC of the g-NK was compared to conventional NK-cells (cNK) from donors who had no g-NK (n=4). Of these 12 donors, 5 donors were categorized as 'super donors' for the consistently high ADCC activity by NK cells.

NK cells from all donors were subjected to polymorphism testing and binning to determine which subgroup each donor belonged to with regards to the 158V polymorphism of CD16 (V/V, V/F, and F/F). The expected distribution was 35% V/V, 25% V/F, and 40% F/F (Hatjiharissi et al., 2007; Somboonyosdech et al., 2012), thus any deviation from this expectation may suggest that the 158V polymorphism may play a role in the high ADCC seen with these donors. For polymorphism testing, frozen NK-cells were thawed and washed with PBS and centrifuged at 100 g. NK cell suspension was collected into a flow tube and stained with 2 µL of a fluorescent antibody for CD45 (to discern leukocytes from residual red blood cells) and 2 µL of 7-AAD (a viability dye). Following a 10-minute incubation at room temperature in the dark, the cells were diluted with 500 µL of PBS and the number of 7-AAD$^{neg}$/CD45$^{pos}$ leukocytes was quantified by flow cytometry. Following the cell count, a magnetic bead separation (Miltenyi MACS™ CD16 Microbeads) was conducted to isolate a population of CD16$^{pos}$ NK-cells. Following the magnetic bead separation, 10× Genomics single cell RNA sequencing was used to determine which CD16 polymorphic group each donor belong to (V/V, V/F, or F/F). For the ADCC assays, the actual g-NK percentage for 158V g-NK and g-NK lacking the polymorphism was 82.2±2.1% and 82.8%±1.9%, respectively. The percentage of g-NK was determined by intracellular flow cytometry.

Figure 19:
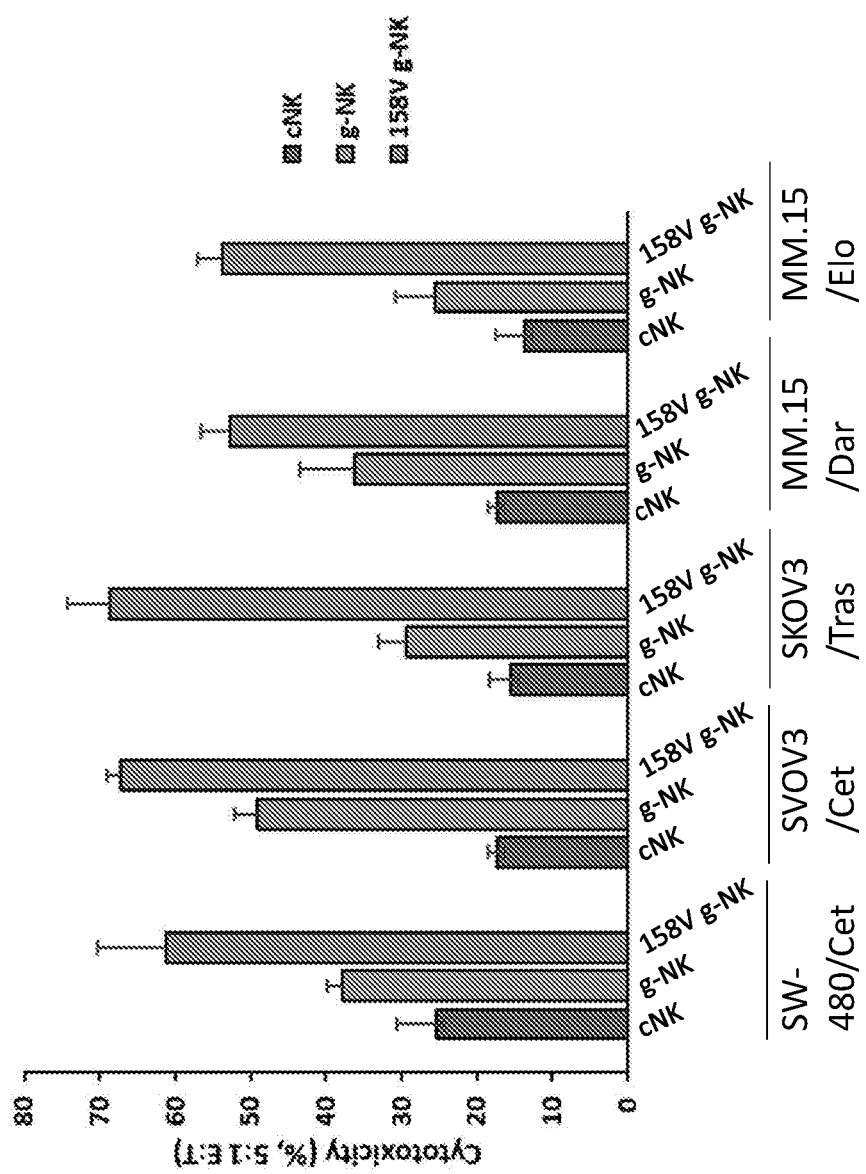
FIG. 19 compares ADCC against SW-480 (with cetuximab; Cet), SKOV3 (with trastuzumab, Tras or cetuximab, Cet), and MM.1S cells (with daratumumab, Dara or elotuzumab, Elo) between cNK (n=4), g-NK (n=7), and CD16 158V g-NK cells (n=5). Values are mean±SE.
Figure 20A:
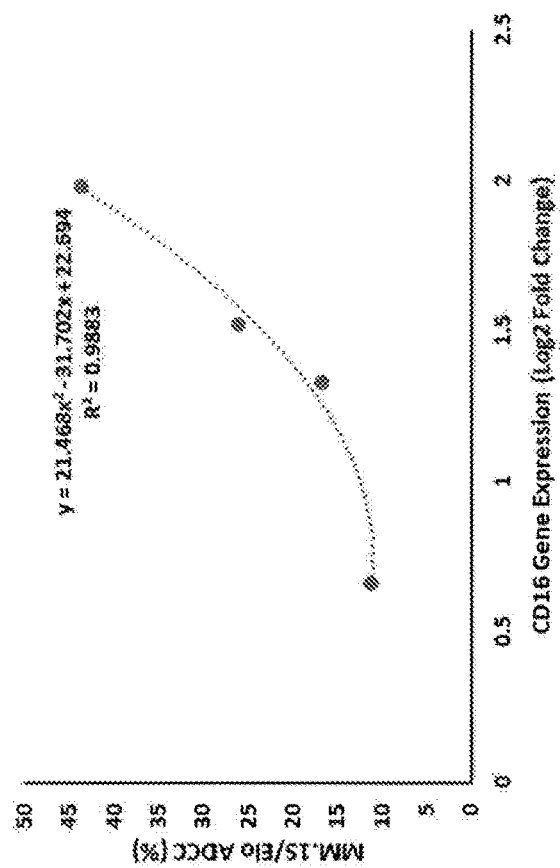
FIGS. 20A-20D depict the relationship between g-NK cell expression of the CD16 gene and ADCC against multiple myeloma and solid tumor cell lines.
Figure 20B:
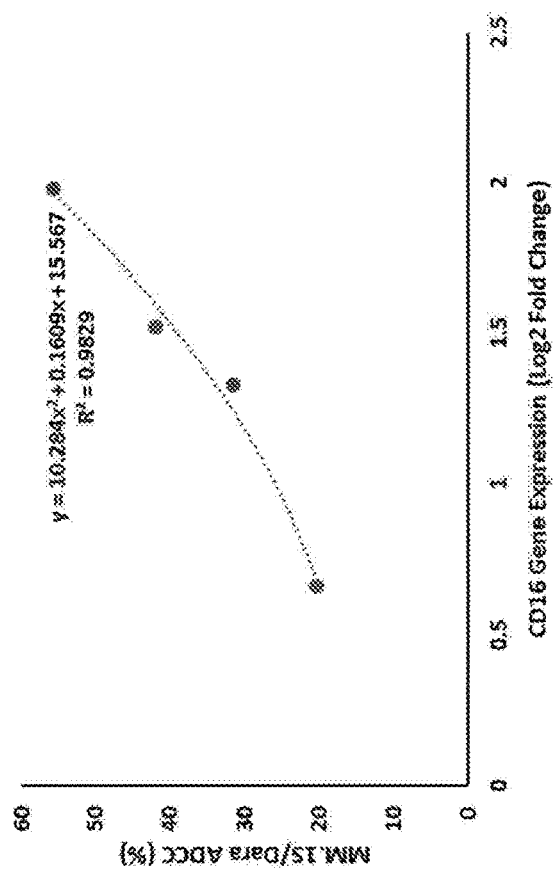
Figure 20D:
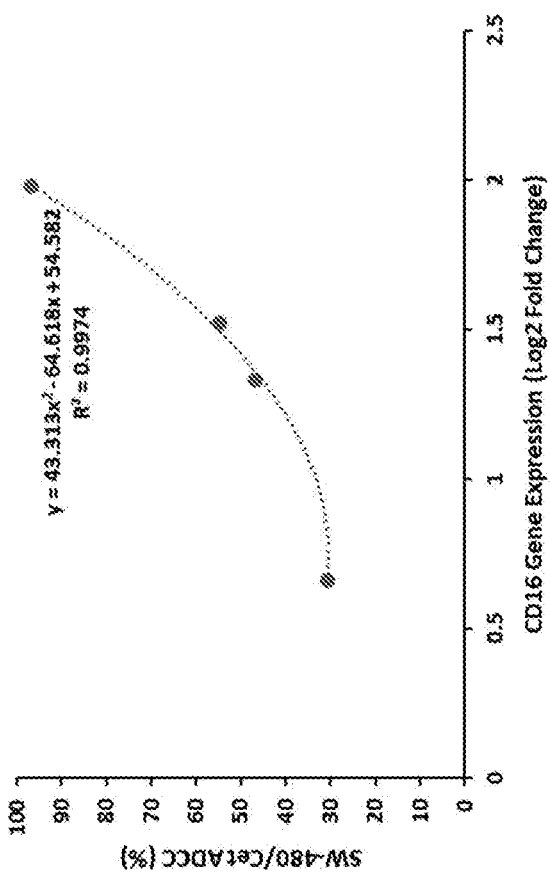
Figure 20C:
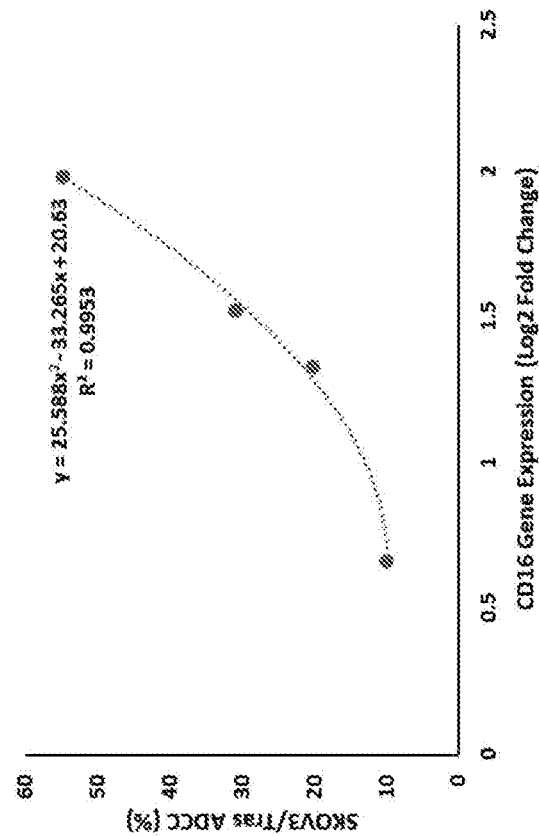

The results indicated that all 5 "super donors" with g-NK cells displaying consistently high ADCC activity exhibited CD16 158V polymorphism. Furthermore, as shown in FIG. 19, 158V g-NK also showed on average significantly higher ADCC activity across a panel of representative cancers (Colorectal: SW-480; ovarian: SVOV3, SKOV3; and multiple myeloma: MM.1S) when respective antibodies were present. In addition, expression of CD16 gene also correlated positively with ADCC efficacy against all hematologic and solid tumor cell lines tested (FIG. 20). Taken together, these results are consistent with an observation that g-NK carrying the 158V genotype are more efficacious in eliminating both hematologic and solid tumors due to the enhanced expression and affinity of CD16, the primary mediator of ADCC for g-NK cells.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

What is claimed:

1. A method for expanding FcRγ-deficient NK cells (g-NK), said method comprising:
   (a) isolating a population of primary human cells enriched for natural killer (NK) cells, the isolating comprises selecting from a sample from a human subject: (i) cells negative for CD3 and positive for CD57 ($CD3^{neg}CD57^{pos}$); (ii) cells negative for CD3, positive for CD56, and negative for CD38 ($CD3^{neg}CD56^{pos}CD38^{neg}$); (iii) cells negative for CD3 ($CD3^{neg}$); (iv) cells negative for CD3 ($CD3^{neg}$) and positive for CD56 ($CD3^{neg}CD56^{pos}$); (v) cells negative for CD3 and positive for CD16 ($CD3^{neg}CD16^{pos}$); or (vi) cells negative for CD3, positive for CD56, negative for NKG2A and negative for CD161 ($CD3^{neg}CD56^{pos}NKG2A^{neg}CD161^{neg}$); and
   (b) culturing the population of enriched NK cells in the presence of (i) irradiated 221.AEH feeder cells, wherein the ratio of irradiated 221.AEH feeder cells to enriched NK cells is between at or about 1:2.5 and at or about 5:1, inclusive; and (ii) recombinant IL-2, wherein the method produces an expanded population of g-NK cells.

2. The method of claim 1, wherein the human subject is CMV seropositive.

3. The method of claim 1, wherein the human subject has the CD16 158V+ NK cell genotype.

4. The method of claim 1, wherein the sample is or comprises peripheral blood mononuclear cells (PBMCs).

5. The method of claim 1, wherein the sample is an apheresis or leukaphereis sample.

6. The method of claim 1, wherein the isolating is of (i) and comprises selecting from the sample cells negative for CD3 and positive for CD57 ($CD3^{neg}CD57^{pos}$).

7. The method of claim 1, wherein after (a) cryopreserving the isolated population of enriched NK cells and prior to (b) thawing the cryopreserved sample comprising the enriched NK cells.

8. The method of claim 1, wherein the culturing is further carried out in the presence of (iii) primary human peripheral blood mononuclear cells (PBMCs) feeder cells, wherein the PBMC feeder cells are irradiated.

9. The method of claim 8, wherein at least a portion of the culturing is carried out in the presence of at least one stimulatory agent that is capable of stimulating the activation of one or more T cell of the PBMC feeder cells.

10. The method of claim 1, wherein the ratio of irradiated AEH.221 feeder cells to enriched NK cell is between 1:1 and 3:1, inclusive.

11. The method of claim 1, wherein the concentration of recombinant IL-2 during at least a portion of the culturing is between at or about 10 IU/mL and at or about 500 IU/mL.

12. The method of claim 1, wherein the population of enriched NK cells at the initiation of the culturing is at a concentration of between at or about $0.05 \times 10^6$ enriched NK cells/mL and at or about $1.0 \times 10^6$ enriched NK cells/mL.

13. The method of claim 1, wherein the population of enriched NK cells at the initiation of the culturing is at a concentration of between at or about $0.05 \times 10^6$ enriched NK cells/mL and at or about $0.5 \times 10^6$ enriched NK cells/mL.

14. The method of claim 1, wherein the culturing is carried out for at or about or at least at or about 14 days.

15. The method of claim 1, wherein the culturing is carried out for at or about or at least at or about 21 days.

16. The method of claim 1, wherein the method produces an increased number of g-NK cells at the end of the culturing compared to at the initiation of the culturing, and wherein the increase is greater than or greater than about 100-fold.

17. The method of claim 1, wherein after the culturing collecting the expanded population of g-NK cells produced by the method.

18. The method of claim 17, further comprising formulating the collected expanded population of g-NK cells in a pharmaceutically acceptable excipient.

19. The method of claim 17, further comprising formulating the collected expanded population of g-NK cells in the presence of a cryoprotectant.

20. The method of claim 1, wherein the culturing the NK cells comprises one or more additional cytokines for the expansion of the NK cells, wherein the one or more additional cytokines is recombinant IL-21, recombinant IL-18, recombinant IL-7, recombinant IL-15, and/or recombinant IL-12.

21. The method of claim 1, wherein the isolating is of (iv) and comprises selecting from the sample cells negative for CD3 and positive for CD56 ($CD3^{neg}CD56^{pos}$).

22. The method of claim 19, further comprising cryopreserving the cells.

23. A method for expanding FcRγ-deficient NK cells (g-NK), said method comprising:
   (a) isolating a population of primary human cells enriched for natural killer (NK) cells, the isolating comprises selecting from a sample from a human subject: (i) cells negative for CD3 and positive for CD57 ($CD3^{neg}CD57^{pos}$); (ii) cells negative for CD3, positive for CD56, and negative for CD38 ($CD3^{neg}CD56^{pos}CD38^{neg}$); (iii) cells negative for CD3 ($CD3^{neg}$); (iv) cells negative for CD3 ($CD3^{neg}$) and positive for CD56 ($CD3^{neg}CD56^{pos}$); (v) cells negative for CD3 and positive for CD16 ($CD3^{neg}CD16^{pos}$); or (vi) cells negative for CD3, positive for CD56, negative for NKG2A and negative for CD161 ($CD3^{neg}CD56^{pos}NKG2A^{neg}CD161^{neg}$);
   (b) combining the population of enriched NK cells with irradiated 221.AEH feeder cells and irradiated peripheral blood mononuclear (PBMC) feeder cells, wherein the ratio of irradiated 221.AEH feeder cells to enriched NK cells is between at or about 1:2.5 and at or about 5:1, inclusive and the ratio of PBMC feeder cells to enriched NK cells is between at or about 1:1 and at or about 5:1, inclusive;
   (c) culturing the population of (b) in the presence of recombinant IL-2 and an anti-CD3 antibody or antigen-binding fragment, wherein, within 7 days of initiation of the culturing, exchanging the cell culture media with fresh media containing recombinant IL-2; and
   (d) collecting the expanded population of cells.

24. The method of claim 23, wherein the human subject is CMV seropositive.

25. A method for expanding FcRγ-deficient NK cells (g-NK), said method comprising:
   (a) obtaining a population of primary human cells enriched for natural killer (NK) cells that have been selected from a sample from a human subject for cells that comprise a phenotype selected from: (i) cells negative for CD3 and positive for CD57 ($CD3^{neg}CD57^{pos}$); (ii) cells negative for CD3, positive for CD56, and negative for CD38 ($CD3^{neg}CD56^{pos}CD38^{neg}$); (iii) cells negative for CD3 ($CD3^{neg}$); (iv) cells negative for CD3 ($CD3^{neg}$) and positive for CD56 ($CD3^{neg}CD56^{pos}$); (v) cells negative for CD3 and positive for CD16 ($CD3^{neg}CD16^{pos}$) or (vi) cells negative for CD3, positive for CD56, negative for NKG2A and negative for CD161 (CD3$^{neg}$CD56$^{pos}$NKG2A$^{neg}$CD161$^{neg}$); and
(b) culturing the population of enriched NK cells in the presence of (i) irradiated 221.AEH feeder cells, wherein the ratio of irradiated 221.AEH feeder cells to enriched NK cells is between at or about 1:2.5 and at or about 5:1, inclusive; and (ii) recombinant IL-2,
wherein the method produces an expanded population of NK cells enriched for g-NK cells.

26. The method of claim 25, wherein the human subject is CMV seropositive.

27. The method of claim 25, wherein the population of enriched NK cells have been selected for cells negative for CD3 and positive for CD56 (CD3$^{neg}$CD56$^{pos}$).

28. The method of claim 25, wherein the human subject has the CD16 158V+ NK cell genotype.

29. The method of claim 25, wherein the sample is or comprises peripheral blood mononuclear cells (PBMCs).

30. The method of claim 25, wherein the culturing the NK cells comprises one or more additional cytokines for the expansion of the NK cells, wherein the one or more additional cytokines is recombinant IL-21, recombinant IL-18, recombinant IL-7, recombinant IL-15, and/or recombinant IL-12.

31. The method of claim 25, wherein the ratio of irradiated AEH.221 feeder cells to enriched NK cell is between 1:1 and 3:1, inclusive.

32. A method for expanding FcRγ-deficient NK cells (g-NK), the method comprising culturing a population of primary human cells enriched for natural killer (NK) cell from a sample from a CMV seropositive human subject, the population of enriched NK cells having been selected from a sample from a human subject for cells negative for CD3 and positive for CD57, wherein the culturing is carried out in the presence of:
(i) irradiated 221.AEH feeder cells, wherein the ratio of irradiated 221.AEH feeder cells to enriched NK cells is between at or about 1:2.5 and at or about 5:1, inclusive; and
(ii) recombinant IL-2;
wherein the method produces an expanded population of g-NK cells.

33. A method for expanding FcRγ-deficient NK cells (g-NK), the method comprising culturing a population of primary human cells enriched for natural killer (NK) cell from a sample from a CMV seropositive human subject, the population of enriched NK cells having been selected from a sample from a human subject for cells negative for CD3, positive for CD56, and negative for CD38, wherein the culturing is carried out in the presence of:
(i) irradiated 221.AEH feeder cells, wherein the ratio of irradiated 221.AEH feeder cells to enriched NK cells is between at or about 1:2.5 and at or about 5:1, inclusive; and
(ii) recombinant IL-2;
wherein the method produces an expanded population of g-NK cells.

34. A method for expanding FcRγ-deficient NK cells (g-NK), the method comprising culturing a population of primary human cells enriched for natural killer (NK) cells from a sample from a CMV seropositive human subject, the population of enriched NK cells having been selected from a sample from a human subject for cells negative for CD3 and positive for CD16, wherein the culturing is carried out in the presence of:
(i) irradiated 221.AEH feeder cells, wherein the ratio of irradiated 221.AEH feeder cells to enriched NK cells is between at or about 1:2.5 and at or about 5:1, inclusive; and
(ii) recombinant IL-2,
wherein the method produces an expanded population of g-NK cells.

35. A method for expanding FcRγ-deficient NK cells (g-NK), the method comprising culturing a population of primary human cells enriched for natural killer (NK) cells from a sample from a CMV seropositive human subject, the population of enriched NK cells having been selected from a sample from a human subject for cells negative for CD3, positive for CD56, negative for NKG2A and negative for CD161, wherein the culturing is carried out in the presence of:
(i) irradiated 221.AEH feeder cells, wherein the ratio of irradiated 221.AEH feeder cells to enriched NK cells is between at or about 1:2.5 and at or about 5:1, inclusive; and
(ii) recombinant IL-2,
wherein the method produces an expanded population of g-NK cells.

36. A method for expanding FcRγ-deficient NK cells (g-NK), the method comprising culturing a population of primary human cells enriched for natural killer (NK) cell from a sample from a CMV seropositive human subject, the population of enriched NK cells having been selected from a sample from a human subject for cells negative for CD3 and positive for CD56, wherein the culturing is carried out in the presence of:
(i) irradiated 221.AEH feeder cells, wherein the ratio of irradiated 221.AEH feeder cells to enriched NK cells is from 1:2.5 and at or about 5:1; and
(ii) recombinant IL-2;
wherein the method produces an expanded population of g-NK cells.

37. The method of claim 36, wherein the human subject has the CD16 158V+ NK cell genotype.

38. The method of claim 36, wherein the sample is or comprises peripheral blood mononuclear cells (PBMCs).

39. The method of claim 36, wherein the culturing the NK cells comprises one or more additional cytokines for the expansion of the NK cells, wherein the one or more additional cytokines is recombinant IL-21, recombinant IL-18, recombinant IL-7, recombinant IL-15, and/or recombinant IL-12.

40. The method of claim 36, wherein the ratio of irradiated AEH.221 feeder cells to enriched NK cell is between 1:1 and 3:1, inclusive.

* * * * *